US009101609B2

(12) United States Patent
Tan et al.

(10) Patent No.: US 9,101,609 B2
(45) Date of Patent: *Aug. 11, 2015

(54) CD37 IMMUNOTHERAPEUTIC AND COMBINATION WITH BIFUNCTIONAL CHEMOTHERAPEUTIC THEREOF

(75) Inventors: Philip Tan, Edmonds, WA (US); Sandy A Simon, Seattle, WA (US); Charles G Cerveny, Seattle, WA (US); Christy Anne Nilsson, Sammamish, WA (US); William Brady, Bothell, WA (US); Jeffrey A Ledbetter, Shoreline, WA (US); Martha S Hayden-Ledbetter, Shoreline, WA (US); Peter A Thompson, Bellevue, WA (US); Cecile Morales, Seattle, WA (US)

(73) Assignee: EMERGENT PRODUCT DEVELOPMENT SEATTLE, LLC, Seattle, WA (US)

( * ) Notice: Subject to any disclaimer, the term of this patent is extended or adjusted under 35 U.S.C. 154(b) by 959 days.

This patent is subject to a terminal disclaimer.

(21) Appl. No.: 12/422,780

(22) Filed: Apr. 13, 2009

(65) Prior Publication Data

US 2009/0274692 A1     Nov. 5, 2009

Related U.S. Application Data

(60) Provisional application No. 61/190,067, filed on Apr. 11, 2008.

(51) Int. Cl.
| *A61K 39/395* | (2006.01) |
| *C07K 16/30* | (2006.01) |
| *C07K 16/28* | (2006.01) |
| *A61K 31/4184* | (2006.01) |
| *C07K 16/46* | (2006.01) |
| *A61K 38/16* | (2006.01) |
| *A61K 39/00* | (2006.01) |

(52) U.S. Cl.
CPC ....... *A61K 39/39541* (2013.01); *A61K 31/4184* (2013.01); *A61K 38/16* (2013.01); *A61K 39/39558* (2013.01); *C07K 16/2896* (2013.01); *C07K 16/3061* (2013.01); *C07K 16/461* (2013.01); *A61K 2039/505* (2013.01); *C07K 2317/24* (2013.01); *C07K 2317/50* (2013.01)

(58) Field of Classification Search
None
See application file for complete search history.

(56) References Cited

U.S. PATENT DOCUMENTS

| 3,927,193 A | 12/1975 | Hansen et al. |
| 3,929,992 A | 12/1975 | Sehgal et al. |
| 4,179,337 A | 12/1979 | Davis et al. |
| 4,301,144 A | 11/1981 | Iwashita et al. |
| 4,316,885 A | 2/1982 | Rakhit |
| 4,331,647 A | 5/1982 | Goldenberg |
| 4,348,376 A | 9/1982 | Goldenberg |
| 4,361,544 A | 11/1982 | Goldenberg |
| 4,444,744 A | 4/1984 | Goldenberg |
| 4,460,459 A | 7/1984 | Shaw et al. |
| 4,460,559 A | 7/1984 | Goldenberg |
| 4,460,561 A | 7/1984 | Goldenberg |
| 4,468,457 A | 8/1984 | Goldenberg et al. |
| 4,496,689 A | 1/1985 | Mitra |
| 4,624,846 A | 11/1986 | Goldenberg |
| 4,640,835 A | 2/1987 | Shimizu et al. |
| 4,650,803 A | 3/1987 | Stella et al. |
| 4,670,417 A | 6/1987 | Iwasaki et al. |
| 4,704,692 A | 11/1987 | Ladner ......................... 364/496 |
| 4,769,330 A | 9/1988 | Paoletti et al. |
| 4,782,840 A | 11/1988 | Martin, Jr. et al. |
| 4,791,192 A | 12/1988 | Nakagawa et al. |
| 4,816,567 A | 3/1989 | Cabilly et al. ................ 530/387 |
| 4,818,709 A | 4/1989 | Primus et al. |
| 4,861,579 A | 8/1989 | Meyer, Jr. et al. ............ 424/1.1 |
| 4,897,268 A | 1/1990 | Tice et al. |
| 4,906,562 A | 3/1990 | Hellstrom et al. ................ 435/7 |
| 4,932,412 A | 6/1990 | Goldenberg |
| 4,935,495 A | 6/1990 | Hellström et al. ............ 530/387 |
| 4,946,778 A | 8/1990 | Ladner et al. ................ 435/69.6 |
| 5,017,487 A | 5/1991 | Stunnenberg et al. |
| 5,023,263 A | 6/1991 | Von Burg |
| 5,023,264 A | 6/1991 | Caufield et al. |
| 5,075,109 A | 12/1991 | Tice et al. |
| 5,091,177 A | 2/1992 | Hellström et al. ........... 424/85.8 |
| 5,098,833 A | 3/1992 | Lasky et al. ................ 435/69.1 |

(Continued)

FOREIGN PATENT DOCUMENTS

| CA | 2 379 586 A1 | 10/2003 |
| CA | 2 414 148 A1 | 6/2004 |

(Continued)

OTHER PUBLICATIONS

Barone, D. et al., "Prolonged Depletion of Circulating B Cells in Cynomolgus Monkeys After a Single Dose of TRU-015, a Novel CD20 Directed Therapeutic," *Ann Rheum Dis*, 64(Suppl. III):159, Jun. 9, 2005.

Batra, J. et al., "Single-Chain Immunotoxins Directed at the Human Transferrin Receptor Containing *Pseudomonas* Exotoxin A or Diptheria Toxin: Anti TFR(Fv)-PE40 and DT388-Anti-TFR(Fv)," *Molecular and Cellular Biology*, 11(4):220-2205, Apr. 1991.

Belov, L. et al., "Immunophenotyping of Leukemias Using a Cluster of Differentiation Antibody Microarray," *Cancer Research*, 61: 4483-4489, Jun. 1, 2001.

(Continued)

*Primary Examiner* — Ronald Schwadron
(74) *Attorney, Agent, or Firm* — Cooley LLP

(57) ABSTRACT

The present disclosure provides a humanized anti-CD37 small modular immunopharmaceutical (SMIP) molecule, as well as synergistic combination therapies of CD37-specific binding molecules (such as anti-CD37 SMIP proteins or antibodies) with bifunctional chemotherapeutics (such as bendamustine) that can be administered concurrently or sequentially, for use in treating or preventing B-cell related autoimmune, inflammatory, or hyperproliferative diseases.

5 Claims, 25 Drawing Sheets

(56) References Cited

U.S. PATENT DOCUMENTS

| | | |
|---|---|---|
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,141,736 A | 8/1992 | Iwasa et al. |
| 5,151,413 A | 9/1992 | Caufield et al. |
| 5,162,333 A | 11/1992 | Failli et al. |
| 5,177,203 A | 1/1993 | Failli et al. |
| 5,217,713 A | 6/1993 | Iwasa et al. |
| 5,221,670 A | 6/1993 | Caufield |
| 5,225,539 A | 7/1993 | Winter ............... 530/387.3 |
| 5,233,036 A | 8/1993 | Hughes |
| 5,256,790 A | 10/1993 | Nelson |
| 5,258,389 A | 11/1993 | Goulet et al. |
| 5,260,203 A | 11/1993 | Ladner et al. ........ 435/172.3 |
| 5,260,300 A | 11/1993 | Hu |
| 5,262,423 A | 11/1993 | Kao |
| 5,302,584 A | 4/1994 | Kao et al. |
| 5,362,718 A | 11/1994 | Skotnicki et al. |
| 5,373,014 A | 12/1994 | Failli et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,411,967 A | 5/1995 | Kao et al. |
| 5,434,131 A | 7/1995 | Linsley et al. ............. 514/2 |
| 5,434,260 A | 7/1995 | Skotnicki et al. |
| 5,455,030 A | 10/1995 | Ladner et al. ............ 424/435.1 |
| 5,463,048 A | 10/1995 | Skotnicki et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,500,362 A | 3/1996 | Robinson et al. ........... 435/7.23 |
| 5,504,091 A | 4/1996 | Molnar-Kimber et al. |
| 5,521,288 A | 5/1996 | Linsley et al. ............ 530/387.3 |
| 5,530,101 A | 6/1996 | Queen et al. ............. 530/387.3 |
| 5,563,145 A | 10/1996 | Failli et al. |
| 5,580,756 A | 12/1996 | Linsley et al. ............. 435/69.7 |
| 5,585,089 A | 12/1996 | Queen et al. ............. 424/133.1 |
| 5,591,828 A | 1/1997 | Bosslet et al. |
| 5,595,721 A | 1/1997 | Kaminski et al. ........... 424/1.49 |
| 5,597,707 A | 1/1997 | Marken et al. ............. 435/69.3 |
| 5,601,819 A | 2/1997 | Wong et al. |
| 5,605,690 A | 2/1997 | Jacobs et al. ............. 424/134.1 |
| 5,637,481 A | 6/1997 | Ledbetter et al. .......... 435/69.6 |
| 5,645,835 A | 7/1997 | Fell, Jr. et al. ........... 424/134.1 |
| 5,665,772 A | 9/1997 | Cottens et al. |
| 5,677,180 A | 10/1997 | Robinson et al. ............. 435/328 |
| 5,677,425 A | 10/1997 | Bodmer et al. ............ 530/387.1 |
| 5,693,762 A | 12/1997 | Queen et al. ............. 530/387.3 |
| 5,709,859 A | 1/1998 | Aruffo et al. ............. 424/134.1 |
| 5,714,147 A | 2/1998 | Capon et al. .............. 424/178.1 |
| 5,721,108 A | 2/1998 | Robinson et al. ............. 435/7.23 |
| 5,736,137 A | 4/1998 | Anderson et al. .......... 424/133.1 |
| 5,770,197 A | 6/1998 | Linsley et al. ............. 424/134.1 |
| 5,773,253 A | 6/1998 | Linsley et al. ............. 435/69.7 |
| 5,776,456 A | 7/1998 | Anderson et al. .......... 424/133.1 |
| 5,780,462 A | 7/1998 | Lee et al. |
| 5,795,572 A | 8/1998 | Diegel et al. ............. 424/135.1 |
| 5,807,734 A | 9/1998 | Diegel et al. ............. 435/252.33 |
| 5,837,243 A | 11/1998 | Deo et al. |
| 5,843,398 A | 12/1998 | Kaminski et al. ........... 424/1.49 |
| 5,843,439 A | 12/1998 | Anderson et al. .......... 424/133.1 |
| 5,844,093 A | 12/1998 | Kettleborough et al. ... 530/387.3 |
| 5,844,095 A | 12/1998 | Linsley et al. ............ 530/387.3 |
| 5,849,898 A | 12/1998 | Seed et al. ............... 536/23.5 |
| 5,858,753 A | 1/1999 | Chantry et al. |
| 5,869,049 A | 2/1999 | Noelle et al. ............. 424/154.1 |
| 5,869,620 A | 2/1999 | Whitlow et al. ........... 530/387.3 |
| 5,876,718 A | 3/1999 | Noelle et al. ............. 424/154.1 |
| 5,876,950 A | 3/1999 | Siadak et al. ............. 435/7.23 |
| 5,882,910 A | 3/1999 | Chantry et al. |
| 5,885,793 A | 3/1999 | Griffiths et al. |
| 5,888,773 A | 3/1999 | Jost et al. ............... 435/69.6 |
| 5,892,019 A | 4/1999 | Schlom et al. ............ 536/23.53 |
| 5,897,861 A | 4/1999 | Fanger et al. |
| 5,916,560 A | 6/1999 | Larsen et al. ............. 424/154.1 |
| 5,922,845 A | 7/1999 | Deo et al. |
| 5,955,315 A | 9/1999 | Lee et al. ............... 435/69.52 |
| 5,959,083 A | 9/1999 | Bosslet et al. |
| 5,980,896 A | 11/1999 | Hellstrom et al. |
| 5,985,589 A | 11/1999 | Chantry et al. |
| 6,015,542 A | 1/2000 | Kaminski et al. ........... 424/1.49 |
| 6,015,695 A | 1/2000 | Casterman et al. .......... 435/69.6 |
| 6,072,035 A | 6/2000 | Hardman et al. |
| 6,074,644 A | 6/2000 | Pastan et al. ............. 424/178.1 |
| 6,074,655 A | 6/2000 | Fowler et al. |
| 6,087,329 A | 7/2000 | Armitage et al. ............. 514/8 |
| 6,090,365 A | 7/2000 | Kaminski et al. ........... 424/1.49 |
| 6,090,914 A | 7/2000 | Linsley et al. ............. 530/350 |
| 6,120,767 A | 9/2000 | Robinson et al. .......... 424/133.1 |
| 6,129,914 A | 10/2000 | Weiner et al. |
| 6,132,992 A | 10/2000 | Ledbetter et al. |
| 6,133,426 A | 10/2000 | Gonzalez et al. |
| 6,136,313 A | 10/2000 | Stevenson |
| 6,147,203 A | 11/2000 | Pastan et al. ............. 536/23.53 |
| 6,150,584 A | 11/2000 | Kucherlapati et al. ........ 800/18 |
| 6,171,586 B1 | 1/2001 | Lam et al. ............... 424/130.1 |
| 6,180,370 B1 | 1/2001 | Queen et al. .............. 435/69.6 |
| 6,193,966 B1 | 2/2001 | Deo et al. |
| 6,194,551 B1 | 2/2001 | Idusogie et al. ........... 530/387.1 |
| 6,197,294 B1 | 3/2001 | Tao et al. |
| 6,224,866 B1 | 5/2001 | Barbera-Guillem ...... 424/130.1 |
| 6,242,195 B1 | 6/2001 | Idusogie et al. .............. 435/7.1 |
| 6,262,244 B1 | 7/2001 | Houchins et al. |
| 6,264,951 B1 | 7/2001 | Armitage et al. .......... 424/184.1 |
| 6,270,765 B1 | 8/2001 | Deo et al. |
| 6,284,536 B1 | 9/2001 | Morrison et al. ............. 435/328 |
| 6,287,537 B1 | 9/2001 | Kaminski et al. ........... 424/1.49 |
| 6,303,755 B1 | 10/2001 | Deo et al. |
| 6,306,393 B1 | 10/2001 | Goldenberg ............... 424/141.1 |
| 6,312,692 B1 | 11/2001 | Noelle et al. ............. 424/154.1 |
| 6,312,694 B1 | 11/2001 | Thorpe et al. |
| 6,352,694 B1 | 3/2002 | June et al. ............... 424/93.71 |
| 6,368,596 B1 | 4/2002 | Ghetie et al. ............ 424/141.1 |
| 6,376,459 B1 | 4/2002 | Aruffo et al. .............. 514/2 |
| 6,379,966 B2 | 4/2002 | Monahan et al. |
| 6,379,967 B1 | 4/2002 | Meredith et al. |
| 6,380,169 B1 | 4/2002 | Adams et al. |
| 6,380,170 B1 | 4/2002 | Muller et al. |
| 6,380,362 B1 | 4/2002 | Watson et al. |
| 6,380,369 B1 | 4/2002 | Adams et al. |
| 6,380,371 B1 | 4/2002 | Sassetti et al. |
| 6,380,382 B1 | 4/2002 | Khodadoust |
| 6,383,138 B1 | 5/2002 | Sen et al. |
| 6,383,478 B1 | 5/2002 | Prokop et al. |
| 6,383,481 B1 | 5/2002 | Ikehara et al. |
| 6,383,512 B1 | 5/2002 | Ciccarelli et al. |
| 6,383,522 B1 | 5/2002 | Dupont |
| 6,383,733 B1 | 5/2002 | Beug et al. |
| 6,383,737 B2 | 5/2002 | Olsen et al. |
| 6,383,738 B1 | 5/2002 | Bruni et al. |
| 6,383,743 B1 | 5/2002 | Kinzler et al. |
| 6,383,746 B1 | 5/2002 | Guignard et al. |
| 6,383,753 B1 | 5/2002 | Thiele et al. |
| 6,383,785 B1 | 5/2002 | Mueller et al. |
| 6,383,794 B1 | 5/2002 | Mountz et al. |
| 6,383,795 B1 | 5/2002 | Carrion et al. |
| 6,383,811 B2 | 5/2002 | Wolff et al. |
| 6,383,814 B1 | 5/2002 | Lee et al. |
| 6,384,018 B1 | 5/2002 | Content et al. |
| 6,384,198 B1 | 5/2002 | Diegel et al. ............. 530/390.1 |
| 6,384,202 B1 | 5/2002 | Sedlacek et al. |
| 6,384,203 B1 | 5/2002 | Anderson et al. |
| 6,384,210 B1 | 5/2002 | Blanchard |
| 6,395,272 B1 | 5/2002 | Deo et al. |
| 6,399,061 B1 | 6/2002 | Anderson et al. .......... 424/133.1 |
| 6,403,769 B1 | 6/2002 | Larochelle et al. ........ 530/387.3 |
| 6,410,319 B1 | 6/2002 | Raubitschek et al. ..... 435/343.1 |
| 6,410,391 B1 | 6/2002 | Zelsacher |
| 6,410,690 B1 | 6/2002 | Deo et al. |

(56) References Cited

U.S. PATENT DOCUMENTS

| | | | |
|---|---|---|---|
| 6,444,792 B1 | 9/2002 | Gray et al. | 530/387.3 |
| 6,455,043 B1 | 9/2002 | Grillo-Lopez | 424/155.1 |
| 6,472,179 B2 | 10/2002 | Stahl et al. | |
| 6,472,510 B1 | 10/2002 | Aruffo et al. | 530/387.3 |
| 6,476,198 B1 | 11/2002 | Kang | |
| 6,482,919 B2 | 11/2002 | Ledbetter et al. | 530/324 |
| 6,515,110 B1 | 2/2003 | Whitlow et al. | 530/387.3 |
| 6,518,277 B1 | 2/2003 | Sadhu et al. | 514/266.1 |
| 6,528,624 B1 | 3/2003 | Idusogie et al. | 530/387.3 |
| 6,538,124 B1 | 3/2003 | Idusogie et al. | 536/23.53 |
| 6,586,428 B2 | 7/2003 | Geroni et al. | 514/231.5 |
| 6,589,527 B1 | 7/2003 | Winter et al. | |
| 6,623,940 B1 | 9/2003 | Ledbetter et al. | 435/69.1 |
| 6,641,809 B1 | 11/2003 | Linsley et al. | 424/134.1 |
| 6,696,290 B2 | 2/2004 | Fitzpatrick et al. | 435/325 |
| 6,761,889 B2 | 7/2004 | Lowman et al. | 424/133.1 |
| 6,800,620 B2 | 10/2004 | Sadhu et al. | 514/183 |
| 6,809,185 B1 | 10/2004 | Schoonjans et al. | |
| 6,815,540 B1 | 11/2004 | Plückthun et al. | 536/23.53 |
| 6,818,213 B1 | 11/2004 | Thorpe et al. | |
| 6,881,557 B2 | 4/2005 | Foote | 435/69.6 |
| 6,893,625 B1 | 5/2005 | Robinson et al. | 424/1.49 |
| 6,896,885 B2 | 5/2005 | Hanna | 424/156.1 |
| 7,052,872 B1 | 5/2006 | Hansen et al. | |
| 7,074,403 B1 | 7/2006 | Goldenberg et al. | 424/130.1 |
| 7,122,646 B2 | 10/2006 | Holliger et al. | |
| 7,129,330 B1 | 10/2006 | Little et al. | |
| 7,148,321 B2 | 12/2006 | Gillies et al. | 530/300 |
| 7,166,707 B2 | 1/2007 | Feige | 530/397.1 |
| 7,183,076 B2 | 2/2007 | Arathoon et al. | |
| 7,612,181 B2 | 11/2009 | Wu et al. | |
| 7,754,208 B2 | 7/2010 | Ledbetter et al. | 424/133.1 |
| 7,754,209 B2 | 7/2010 | Ledbetter et al. | 424/133.1 |
| 7,829,056 B2 | 11/2010 | Lee | |
| 7,829,084 B2 | 11/2010 | Ledbetter et al. | 424/133.1 |
| 8,106,161 B2 | 1/2012 | Ledbetter et al. | |
| 8,147,835 B2 | 4/2012 | Ledbetter et al. | |
| 8,188,237 B2 | 5/2012 | Ledbetter et al. | |
| 8,197,810 B2 | 6/2012 | Ledbetter et al. | |
| 8,333,966 B2 | 12/2012 | Tan et al. | |
| 8,409,577 B2 | 4/2013 | Thompson et al. | |
| 2001/0044135 A1 | 11/2001 | Stahi et al. | 435/69.7 |
| 2002/0004587 A1 | 1/2002 | Miller et al. | 538/388.8 |
| 2002/0006404 A1 | 1/2002 | Hanna et al. | 424/142.1 |
| 2002/0009444 A1 | 1/2002 | Grillo-Lopez | 424/142.1 |
| 2002/0012665 A1 | 1/2002 | Hanna | 424/145.1 |
| 2002/0031510 A1 | 3/2002 | Larsen et al. | 424/131.1 |
| 2002/0039557 A1 | 4/2002 | White | 424/1.49 |
| 2002/0041847 A1 | 4/2002 | Goldenberg | 424/1.49 |
| 2002/0103345 A1 | 8/2002 | Zhu | |
| 2002/0128448 A1 | 9/2002 | Reff | 530/387.3 |
| 2002/0128488 A1 | 9/2002 | Yamakawa et al. | 548/262.4 |
| 2002/0155604 A1 | 10/2002 | Ledbetter et al. | 435/372.3 |
| 2002/0192223 A1 | 12/2002 | Hellstrom et al. | |
| 2002/0197255 A1 | 12/2002 | Anderson et al. | 424/144.1 |
| 2002/0197256 A1 | 12/2002 | Grewal | 424/144.1 |
| 2003/0008923 A1 | 1/2003 | Dukart et al. | |
| 2003/0021781 A1 | 1/2003 | Anderson et al. | 424/144.1 |
| 2003/0026780 A1 | 2/2003 | Hood et al. | |
| 2003/0026801 A1 | 2/2003 | Weiner et al. | 424/144.1 |
| 2003/0031667 A1 | 2/2003 | Deo et al. | |
| 2003/0044423 A1 | 3/2003 | Gillies et al. | 424/192.1 |
| 2003/0078385 A1 | 4/2003 | Arathoon et al. | |
| 2003/0088074 A1 | 5/2003 | Hamers et al. | 530/387.1 |
| 2003/0115614 A1 | 6/2003 | Kanda et al. | |
| 2003/0118592 A1 | 6/2003 | Ledbetter et al. | 424/178.1 |
| 2003/0133930 A1 | 7/2003 | Goldenberg et al. | 424/141.1 |
| 2003/0133939 A1 | 7/2003 | Ledbetter et al. | 424/178.1 |
| 2003/0166868 A1 | 9/2003 | Presta et al. | |
| 2003/0219433 A1 | 11/2003 | Hansen et al. | 424/141.1 |
| 2003/0219436 A1 | 11/2003 | Ledbetter et al. | 424/144.1 |
| 2003/0219446 A1 | 11/2003 | Linsley et al. | 424/178.1 |
| 2003/0219876 A1 | 11/2003 | Ledbetter et al. | 435/69.7 |
| 2004/0018557 A1 | 1/2004 | Qu et al. | |
| 2004/0043029 A1 | 3/2004 | Hellstrom et al. | |
| 2004/0058445 A1 | 3/2004 | Ledbetter et al. | 435/372 |
| 2004/0071696 A1 | 4/2004 | Adams et al. | |
| 2004/0191248 A1 | 9/2004 | Goldenberg et al. | |
| 2005/0012665 A1 | 1/2005 | Runyon et al. | |
| 2005/0031617 A1 | 2/2005 | Ma et al. | |
| 2005/0054000 A1 | 3/2005 | Dubel | |
| 2005/0084933 A1 | 4/2005 | Schilling et al. | 435/69.1 |
| 2005/0123540 A1 | 6/2005 | Hanna et al. | |
| 2005/0136049 A1 | 6/2005 | Ledbetter et al. | 424/132.1 |
| 2005/0158829 A1 | 7/2005 | Fandl et al. | |
| 2005/0163782 A1 | 7/2005 | Glaser et al. | |
| 2005/0164307 A1 | 7/2005 | Kojima et al. | |
| 2005/0175614 A1 | 8/2005 | Ledbetter et al. | 424/145.1 |
| 2005/0180970 A1 | 8/2005 | Ledbetter et al. | 424/143.1 |
| 2005/0186203 A1 | 8/2005 | Singh et al. | |
| 2005/0186216 A1 | 8/2005 | Ledbetter et al. | 424/155.1 |
| 2005/0202012 A1 | 9/2005 | Ledbetter et al. | 424/144.1 |
| 2005/0202023 A1 | 9/2005 | Ledbetter et al. | 424/155.1 |
| 2005/0202028 A1 | 9/2005 | Ledbetter et al. | 424/178.1 |
| 2005/0202534 A1 | 9/2005 | Ledbetter et al. | 435/69.1 |
| 2005/0238646 A1 | 10/2005 | Ledbetter et al. | 424/144.1 |
| 2005/0261317 A1 | 11/2005 | Sadhu et al. | 514/263.21 |
| 2005/0272758 A1 | 12/2005 | Bayever et al. | |
| 2006/0008415 A1 | 1/2006 | Kaisheva et al. | |
| 2006/0051844 A1 | 3/2006 | Heavner et al. | 435/69.7 |
| 2006/0063715 A1 | 3/2006 | Whitlow et al. | |
| 2006/0088529 A1 | 4/2006 | Leung et al. | |
| 2006/0099205 A1 | 5/2006 | Adams et al. | |
| 2006/0104971 A1 | 5/2006 | Garber et al. | |
| 2006/0153837 A1 | 7/2006 | Black et al. | 424/133.1 |
| 2006/0210564 A1 | 9/2006 | Kumagai et al. | |
| 2006/0263367 A1 | 11/2006 | Fey et al. | |
| 2007/0041967 A1 | 2/2007 | Jung et al. | |
| 2007/0059306 A1 | 3/2007 | Grosmaire et al. | 424/144.1 |
| 2007/0071675 A1 | 3/2007 | Wu et al. | |
| 2007/0237779 A1 | 10/2007 | Ledbetter et al. | 424/155.1 |
| 2008/0213273 A1 | 9/2008 | Burge | 424/141.1 |
| 2008/0214596 A1 | 9/2008 | Boulay et al. | |
| 2008/0279850 A1 | 11/2008 | Brady et al. | 424/133.1 |
| 2009/0041765 A1 | 2/2009 | Espling et al. | 424/133.1 |
| 2009/0053225 A1 | 2/2009 | Marzari et al. | |
| 2009/0088346 A1 | 4/2009 | Enzelberger et al. | 506/17 |
| 2009/0148447 A1 | 6/2009 | Ledbetter et al. | 424/134.1 |
| 2009/0162380 A1 | 6/2009 | Glaser et al. | |
| 2009/0175867 A1 | 7/2009 | Thompson et al. | 424/135.1 |
| 2009/0196870 A1 | 8/2009 | Ledbetter et al. | 424/133.1 |
| 2009/0204489 A1* | 8/2009 | Behrens et al. | 705/14 |
| 2009/0214539 A1 | 8/2009 | Grosmaire et al. | 424/135.1 |
| 2009/0252729 A1 | 10/2009 | Farrington et al. | |
| 2009/0274649 A1 | 11/2009 | Qu et al. | |
| 2009/0274692 A1 | 11/2009 | Tan et al. | 424/133.1 |
| 2010/0034820 A1 | 2/2010 | Ledbetter et al. | 424/134.1 |
| 2010/0135900 A1 | 6/2010 | Cerveny et al. | 424/1.11 |
| 2010/0203052 A1 | 8/2010 | Ledbetter et al. | 424/134.1 |
| 2010/0279932 A1 | 11/2010 | Ledbetter et al. | 514/7.3 |
| 2011/0033483 A1 | 2/2011 | Thompson et al. | 424/179.1 |
| 2011/0091461 A1 | 4/2011 | Ledbetter et al. | 424/134.1 |
| 2011/0105729 A1 | 5/2011 | Ledbetter et al. | 530/387.3 |
| 2011/0171208 A1 | 7/2011 | Tan et al. | 424/133.1 |
| 2011/0223164 A1 | 9/2011 | Ledbetter et al. | |
| 2012/0034245 A9 | 2/2012 | Thompson et al. | |
| 2012/0213773 A1 | 8/2012 | Ledbetter et al. | |

FOREIGN PATENT DOCUMENTS

| | | |
|---|---|---|
| EP | 0 274 394 A2 | 7/1988 |
| EP | 0 330 191 A2 | 8/1989 |
| EP | 0 332 865 A2 | 9/1989 |
| EP | 0 586 002 A2 | 3/1994 |
| EP | 0 682 039 A1 | 11/1995 |
| EP | 0 330 191 B1 | 10/1996 |
| EP | 0 757 099 A2 | 2/1997 |
| EP | 1 186 300 A1 | 3/2002 |
| EP | 0 555 880 A2 | 8/2004 |
| EP | 0 555 880 B1 | 8/2004 |
| EP | 1 444 268 B1 | 8/2004 |
| EP | 1 654 358 | 2/2005 |
| EP | 0 610 046 B1 | 12/2005 |
| EP | 1 666 500 A1 | 6/2006 |

(56) References Cited

FOREIGN PATENT DOCUMENTS

| | | | |
|---|---|---|---|
| EP | 1 746 162 A2 | 1/2007 |
| EP | 1 939 203 A2 | 7/2008 |
| EP | 1 654 358 B1 | 9/2011 |
| JP | 2000-516452 A | 12/2000 |
| WO | 88/04936 A1 | 7/1988 |
| WO | WO 89/01973 A2 | 3/1989 |
| WO | WO 89/01974 A1 | 3/1989 |
| WO | 89/07142 A1 | 8/1989 |
| WO | WO 90/07936 A1 | 7/1990 |
| WO | WO 91/00360 A1 | 1/1991 |
| WO | WO 91/02805 A2 | 3/1991 |
| WO | 91/04329 A1 | 4/1991 |
| WO | WO 91/09967 A1 | 7/1991 |
| WO | WO 91/11456 A1 | 8/1991 |
| WO | 91/13166 A1 | 9/1991 |
| WO | 92/00092 A1 | 1/1992 |
| WO | WO 92/08802 A1 | 5/1992 |
| WO | 92/21755 A1 | 12/1992 |
| WO | 93/00431 A1 | 1/1993 |
| WO | WO 93/03709 A1 | 3/1993 |
| WO | WO 93/25234 A1 | 12/1993 |
| WO | WO 93/25698 A1 | 12/1993 |
| WO | WO 94/03622 A1 | 2/1994 |
| WO | 94/04678 A1 | 3/1994 |
| WO | 94/05690 A1 | 3/1994 |
| WO | WO 94/09010 A1 | 4/1994 |
| WO | WO 94/09034 A1 | 4/1994 |
| WO | WO 94/11026 A2 | 5/1994 |
| WO | WO 94/13804 A1 | 6/1994 |
| WO | 94/25591 A1 | 11/1994 |
| WO | 95/03770 A1 | 2/1995 |
| WO | WO 95/08577 A1 | 3/1995 |
| WO | 95/09917 A1 | 4/1995 |
| WO | WO 95/16691 A1 | 6/1995 |
| WO | WO 95/24220 A1 | 9/1995 |
| WO | WO 95/30014 A1 | 11/1995 |
| WO | 96/34103 A1 | 10/1996 |
| WO | WO 96/40789 A1 | 12/1996 |
| WO | WO 96/41807 A1 | 12/1996 |
| WO | WO 97/09433 A1 | 3/1997 |
| WO | 98/02462 A1 | 1/1998 |
| WO | WO 98/02441 A2 | 1/1998 |
| WO | WO 98/02463 A1 | 1/1998 |
| WO | WO 98/23646 A2 | 6/1998 |
| WO | 98/56418 A1 | 12/1998 |
| WO | 98/58964 A1 | 12/1998 |
| WO | WO 99/02711 A2 | 1/1999 |
| WO | WO 99/10494 A2 | 3/1999 |
| WO | WO 99/15530 A1 | 4/1999 |
| WO | 99/22764 A1 | 5/1999 |
| WO | WO 99/37791 A1 | 7/1999 |
| WO | 99/42077 A2 | 8/1999 |
| WO | 99/43713 A1 | 9/1999 |
| WO | 99/51642 A1 | 10/1999 |
| WO | 99/57266 A2 | 11/1999 |
| WO | WO 99/57150 A2 | 11/1999 |
| WO | 00/09160 A1 | 2/2000 |
| WO | WO 00/06605 A2 | 2/2000 |
| WO | 00/20864 A1 | 4/2000 |
| WO | 00/27428 A1 | 5/2000 |
| WO | 00/27433 A1 | 5/2000 |
| WO | 00/27885 A1 | 5/2000 |
| WO | 00/42072 A1 | 7/2000 |
| WO | 00/44777 A1 | 8/2000 |
| WO | 00/44788 A1 | 8/2000 |
| WO | 00/67795 A1 | 11/2000 |
| WO | 00/67796 A1 | 11/2000 |
| WO | 00/69913 A1 | 11/2000 |
| WO | 00/74718 A1 | 12/2000 |
| WO | 00/76542 A1 | 12/2000 |
| WO | 01/03734 A1 | 1/2001 |
| WO | 01/10460 A1 | 2/2001 |
| WO | 01/10461 A1 | 2/2001 |
| WO | 01/10462 A1 | 2/2001 |
| WO | WO 01/09186 A2 | 2/2001 |
| WO | WO 01/09187 A2 | 2/2001 |
| WO | WO 01/09192 A1 | 2/2001 |
| WO | 01/13945 A1 | 3/2001 |
| WO | WO 01/14387 A1 | 3/2001 |
| WO | WO 01/34194 A1 | 5/2001 |
| WO | 01/72333 A1 | 10/2001 |
| WO | 01/74388 A1 | 10/2001 |
| WO | 01/77342 A1 | 10/2001 |
| WO | 01/80884 A1 | 11/2001 |
| WO | WO 01/85798 A2 | 11/2001 |
| WO | 01/97858 A2 | 12/2001 |
| WO | 02/04021 A1 | 1/2002 |
| WO | WO 02/02773 A2 | 1/2002 |
| WO | WO 02/08773 A2 | 1/2002 |
| WO | 02/34790 A1 | 5/2002 |
| WO | 02/056910 A1 | 7/2002 |
| WO | 02/060955 A2 | 8/2002 |
| WO | WO 02/064634 A2 | 8/2002 |
| WO | 02/072605 A2 | 9/2002 |
| WO | WO 02/072141 A2 | 9/2002 |
| WO | 02/079255 A1 | 10/2002 |
| WO | 02/096948 A2 | 12/2002 |
| WO | 02/102312 A2 | 12/2002 |
| WO | WO 02/100348 A2 | 12/2002 |
| WO | WO 03/020906 A2 | 3/2003 |
| WO | WO 03/025018 A2 | 3/2003 |
| WO | WO 03/026490 A2 | 4/2003 |
| WO | WO 03/030835 A2 | 4/2003 |
| WO | WO 03/048209 A1 | 6/2003 |
| WO | WO 03/057829 A2 | 7/2003 |
| WO | WO 03/074569 A2 | 9/2003 |
| WO | 03/083069 A2 | 10/2003 |
| WO | 03/106622 A2 | 12/2003 |
| WO | 2004/003019 A2 | 1/2004 |
| WO | WO 2004/016750 A2 | 2/2004 |
| WO | WO 2004/032857 A2 | 4/2004 |
| WO | WO 2004/032961 A1 | 4/2004 |
| WO | WO 2004/035537 A2 | 4/2004 |
| WO | WO 2004/035607 A2 | 4/2004 |
| WO | WO 2004/056312 A2 | 7/2004 |
| WO | WO 2004/058171 A2 | 7/2004 |
| WO | WO 2004/058191 A2 | 7/2004 |
| WO | WO 2004/076489 A1 | 9/2004 |
| WO | WO 2004/103404 A1 | 12/2004 |
| WO | WO 2005/000899 A2 | 1/2005 |
| WO | WO 2005/004809 A2 | 1/2005 |
| WO | 2005/017148 A1 | 2/2005 |
| WO | WO 2005/021710 A2 | 3/2005 |
| WO | 2005/037989 A2 | 4/2005 |
| WO | WO 2005/040220 A1 | 5/2005 |
| WO | WO 2005/061547 A2 | 7/2005 |
| WO | WO 2005/063816 A2 | 7/2005 |
| WO | WO 2005/070966 A2 | 8/2005 |
| WO | WO 2005/077981 A2 | 8/2005 |
| WO | WO 2005/077982 A1 | 8/2005 |
| WO | WO 2005/095460 A2 | 10/2005 |
| WO | WO 2005/103081 A2 | 11/2005 |
| WO | WO 2005/117978 A2 | 12/2005 |
| WO | WO 2005/120437 A2 | 12/2005 |
| WO | WO 2006/002438 A2 | 1/2006 |
| WO | WO 2006/008548 A2 | 1/2006 |
| WO | WO 2006/020258 A2 | 2/2006 |
| WO | WO 2006/028936 A2 | 3/2006 |
| WO | WO 2006/041680 A2 | 4/2006 |
| WO | WO 2006/063150 A2 | 6/2006 |
| WO | WO 2006/064121 A2 | 6/2006 |
| WO | WO 2006/074399 A2 | 7/2006 |
| WO | WO 2006/084264 A2 | 8/2006 |
| WO | WO 2006/113308 A1 | 10/2006 |
| WO | WO 2006/117782 A2 | 11/2006 |
| WO | WO 2006/106905 A1 | 12/2006 |
| WO | WO 2006/130458 A2 | 12/2006 |
| WO | WO 2007/011363 A2 | 1/2007 |
| WO | 2007/014238 A2 | 2/2007 |
| WO | 2007/014278 A2 | 2/2007 |
| WO | WO 2007/011363 A3 | 7/2007 |
| WO | WO 2007/095338 A2 | 8/2007 |
| WO | 2007/146968 A2 | 12/2007 |
| WO | 2008/052030 A2 | 5/2008 |

(56) References Cited

FOREIGN PATENT DOCUMENTS

| | | |
|---|---|---|
| WO | 2008/138834 A1 | 11/2008 |
| WO | 2008/152387 A1 | 12/2008 |
| WO | 2008/152390 A1 | 12/2008 |
| WO | 2008/152394 A1 | 12/2008 |
| WO | 2008/153636 A1 | 12/2008 |
| WO | 2009/019312 A2 | 2/2009 |
| WO | 2009/023386 A2 | 2/2009 |
| WO | 2009/036082 A2 | 3/2009 |
| WO | 2009/039140 A1 | 3/2009 |
| WO | 2009/040552 A2 | 4/2009 |
| WO | 2009/042607 A1 | 4/2009 |
| WO | 2009/045174 A1 | 4/2009 |
| WO | 2009/045175 A1 | 4/2009 |
| WO | 2009/046448 A1 | 4/2009 |
| WO | 2009/052145 A1 | 4/2009 |
| WO | 2009/053715 A1 | 4/2009 |
| WO | 2009/053716 A1 | 4/2009 |
| WO | 2009/055418 A1 | 4/2009 |
| WO | 2009/058361 A1 | 5/2009 |
| WO | 2009/059030 A1 | 5/2009 |
| WO | 2009/064802 A2 | 5/2009 |
| WO | 2009/066084 A1 | 5/2009 |
| WO | 2009/068482 A1 | 6/2009 |
| WO | 2009/070524 A1 | 6/2009 |
| WO | WO 2009/106356 A1 | 9/2009 |
| WO | 2009/126944 A1 | 10/2009 |
| WO | 2010/057047 A1 | 5/2010 |

OTHER PUBLICATIONS

Bernstein, I. et al., "High Dose Radiolabeled Antibody Therapy of Lymphoma," *Cancer Research (Suppl.)*, 50:1017S-1021s, Feb. 1, 1990.

Best, W. et al., "Development of Chron's Disease Activity Index," *Gastroenterology*, 70(3):439-444, 1976.

Braslawsky, G. et al., "Adriamycin(hydrazone)-antibody conjugates require internalization and intracelluclar acid hydrolysis for antitumor activity," *Cancer Immunol Immunother*, 33:367-374, 1991.

Brown, R. et al., "Intraumoral Microdistribuion of [$^{131}$]MB-1 in Patients with B-Cell Lymphoma Following Radioimmunotherapy," *Nuclear Medicine & Biology*, 24:657-663, 1997.

Buchsbaum, D. et al., "Therapy with unlabeled and $^{131}$I-labeled Pan-B-Cell Monoclonal Antibodies in Nude Mice Bearing Raji Burkitt's Lymphoma Xenografts," *Cancer Research*, 52:6476-6481, Dec. 1, 1992.

Cambridge, G. et al., "Serologic Changes Following B Lymphocyte Depletion Thearpy for Rheumatoid Arthritis," *Arthritis and Rheumatism*, 48(8):2146-2154, Aug. 2003.

Chan, O. et al., "A Novel Mouse with B Cells but Lacking Serum Antibody Reveals an Antibody-independent Role for B Cells in Murine Lupus," *J. Exp. Med.*, 189(10):1639-1647, May 17, 1999.

Chaudhary, V. et al., "A recombinant immunotoxin consisting of two antibody variable domains fused to *Pseudomonas* exotoxin," Nature, 339:394-397, Jun. 1, 1989.

Cheson, B., "CLL Response Criteria," *Clinical Advances in Hematology & Oncology*, 4(5)(Supplement 12):4-5, May 2006.

Cheson, B. et al., "Report of an internal working group to standardize response criteria for myelodysplastic syndromes," *Blood*, 96(12):3671-3674, Dec. 2000.

Cheson, B. et al. "Report of an International Workshop to Standardize Response Criteria for Non-Hodgkin's Lymphomas," *Journal of Clinical Oncology*, 17(4):1244-1252, Apr. 1999.

Cheson, B. et al., "Revised Recommendation of the International Working Group for Diagnosis, Standardization of Response Criteria, Treatment Outcomes, and Reporting Standards for Therapeutic Trials in Acute Myeloid Leukemia," *Journal of Clinical Oncology*, 21(24):4642-4649, Dec. 2003.

Cragg, M. et al., "Antibody specificity controls in vivo effector mechanisms of anti-CD20 reagents," *Blood*, 103(7):2738-2743, Apr. 1, 2004.

De Vita, S. et al., "Efficacy of Selective B Cell Blockade in the Treatment of Rheumatoid Arthritis," *Arthritis and Rheumatism*, 46(8):2029-2033, Aug. 2002.

Dong, H. et al., "B7-H1, a third member of the B7 family, co-stimulates T-cell proliferation and interleukin-10 secretion," *Nature Medicine*, 5(12):1365-1369, Dec. 1999.

Edwards, J.C.W. et al., "B-lymphocyte depletion therapy in rheumatoid arthritis and other autoimmune disorders," *Biochemical Society Transactions*, 30(4):824-828, 2002.

Edwards, J.C.W. et al., "Efficacy of B-Cell-Targeted Therapy with Rituximab in Patients with Rheumatoid Arthritis," *The New England Journal of Medicine*, 350(25):2572-2581, Jun. 17, 2004.

Edwards, J.C.W. et al., "Importance of T cells in rheumatoid synovitis: comment on the review by Firestein and Zvaifler," *Arthritis and Rheumatism*, 46(11):3102-3114, Nov. 2002.

Edwards, J.C.W. et al., "Sustained improvement in rheumatoid arthritis following a protocol designed to deplete B lymphocytes," *Rheumatology*, 40:205-211, 2001.

Einfeld, D.A. et al., "Molecular cloning of the human B cell CD20 receptor predicts a hydrophobic protein with multiple transmembrane domains," *The EMBO Journal*, 7(3):711-717, 1988.

Faure, P. et al, "Immunohistochemical. Profile of Cutaneous B-Cell Lymphoma on Cryostat and Paraffin Sections," *The American Journal of Dermatopathy*, 12(3):122-133, 1990.

Felson, D. et al., "American College of Rheumatology Preliminary Definition of Improvement in Rheumatoid Arthritis," *Arthritis and Rheumatism*, 38(6):727-735, Jun. 1995.

Fix, J., "Strategies for Delivery of Peptides Utilizing Absorption-Enhancing Agents," *Journal of Pharmaceutical Sciences*, 85(12):1282-1285, Dec. 1996.

Gladman, D. et al., "Sensitivity to Change of 3 Systemic Lupus Erythematosus Disease Activity Indices: International Validation," *The Journal of Rheumatology*, 21(8):1468-1471, 1994.

Gottdiener, J. et al., "Cardiac Manifestations in Polymyositis," *The American Journal of Cardiology*, 41:1141-1149, Jun. 1978.

Grillo-Lopez, A.J. et al., "Response Criteria for NHL: Improtance of "normal" lymph node size and correlations with response rates," *Annals of Oncology*, 11:399-408, 2000.

Hemler, M., "Targeting of tetraspanin proteins—potential benefits and strageties," *Nature Reviews*, 7:747-758, Sep. 2008.

Hinek, A. et al., "The Elastin Receptor: A Galactoside-Binding Protein," *Science*, 539:1539-1541, Mar. 25, 1988.

Huston, J. et al., "Protein engineering of antibody binding sites: Recovery of specific activity in an anti-digoxin single-chain Fv analogue produced in *Escherichia coli*," *Proc. Natl. Acad. Sci.*, 85:5879-5883, Aug. 1988.

International Search report dated Jul. 16, 2007, relating to International Application No. PCT/US2006/029038 filed Jul. 25, 2006, 14 pages.

Jones, P. et al., "Replacing the complementarity-determining regions in a human antibody with those from a mouse," *Nature*, 321:522-525, May 1986.

Jost, C. et al., "Mammalian Expression and Secretion of Functional Single-Chain Fv Molecules," *The Journal of Biological Chemistry*, 269(42):26267-26273, 1994.

Kamisnki, M. et al., "Imaging, Dosimetry and Radioimmunotherapy With Iodine 131—Labeled Anti-CD37 Antibody in B-Cell Lymphoma," *Journal of Clinical Oncology*, 10(11):1696-1711, Nov. 1992.

Knobleoch, K-P. et al., "Targeted Inactivation of the Tetraspanin CD37 Impairs T-Cell-Dependent B-Cell Response under Suboptimal Costimulatory Conditions," *Molecular and Cellular Biology*, 20(15):5363-5369, Aug. 2000.

Kurtzke, J., "Rating neurologic impairment in multiple sclerosis: An expanded disability status scale (EDSS)," *Neurology*, 33:1444-1452, Nov. 1983.

Leandro, M. et al., "B Lymphocyte Depletion in Rheumatoid Arthritis Early Evidence for Safety, Efficacy and Dose Response," *Arthritis and Rheumatism*, 44:S370, Abstract #1905, 2001.

Leandro, M. et al., "Clinical outcome in 22 patients with rheumatoid arthritis treated with B lymphocyte depletion," *Ann Rheum Dis*, 61:883-888, 2002.

(56) References Cited

OTHER PUBLICATIONS

Leandro, M. et al., "An Open Study of B Lymphocyte Depletion in Systemic Lupus Erythematosus," *Arthritis and Rheumatism*, 46(10):2673-2677, Oct. 2002.
Leget, G. et al., "Use of rituximab, the new FDA-approved antibody," *Curr. Opin. Oncol.*, 10:548-551, 1998.
Levine T. et al., "IgM antibody-related polyneuropathies: B-cell depletion chemotherapy using Rituximab," *Neurology*, 52:1701-1704, May 1999.
Lin, T. et al., "Rituximab in B-Cell Chronic Lymphocyte Leukemia," *Seminars in Oncology*, 30(4):483-492, Aug. 2003.
Link, M. et al., "A Unique Antigen on Mature B Cells Defined by a Monoclonal Antibody," *The Journal of Immunology*, 137(9):3013-3018, Nov. 1, 1986.
Liu, A. et al., "Production of a Mouse-Human Chimeric Monoclonal Antibody to CD20 with Potent Fc-Dependent Biologic Activity," *The Journal of Immunology*, 139(10):3521-3526, Nov. 15, 1987.
Looney, R. et al., "B Cell Depletion as a Novel Treatment for Systemic Lupus Erythematosus," *Arthritis and Rheumatism*, 50(8):2580-2589, Aug. 2004.
Matthews, R., "Medical Heretics," *New Scientist*, 34-37, Apr. 7, 2001.
McLaughlin, P. et al., "Clinical Studies and Optimal Use of Rituximab for B-Cell Lymphomas," *Oncology*, 12(12):1763-1781, Dec. 1998.
Merson, A., "Phenotypic heterogeneity of B cell chronic lymphocytic leukaemia," *Immunology Letters*, 19:269-272, 1988.
Minsavage, G. et al., "Bifunctional Alkylating Agent-Induced p53 and Nonclassical Nuclear Factor κB Responses and Cell Death Are Altered by Caffeic Acid Phenethyl Ester: A Potential Role for Antioxidant/Electrophilic Reseponse-Element Signaling," *The Journal of Pharmacology and Experimental Therapeutics*, 321(1): 202-212, Jan. 2, 2007.
Moldenhauer, G., "CD37," *Journal of Biological Regulator and Homeostatic Agents*, 14:281-283, 2000.
Monson, N. et al., "Effect of Rituximab on the Peripheral Blood and Cerebrospinal Fluid B Cells in Patients with Primary Progressive Multiple Sclerosis," *Arch Neruol*, 62:258-264, Feb. 2005.
Moore K. et al., "Use of the Monoclonal Antibody WR17, Identifying the CD37, gp40-45 Kd Antigen Complex, in the Diagnosis of B-Lymphoid Malignancy," *Journal of Pathology*, 152:13-21, 1987.
Nguyen, DT. et al., "IDEC-C2B8 anti CD20 (Rituximab) immunotherapy in patients with low-grade non-Hodgkin's lymphoma and lymphoproliferative disorders: evaluation of response on 48 patients," *European Journal of Hematology*, 62:76-82, 1999.
Oliyai, R. et al., "Prodrugs of Peptides and Proteins for Improved Formulation and Delivery," *Annu Rev. Pharmacol. Toxicol*, 32:521-544, 1993.
Padlan, E., "Anatomy of the Antibody Molecule," *Molecular Immunology*, 31(3):169-217, 1994.
Padlan, E., "A Possible Procedure for Reducing the Immunogenicity of Antibody Variable Domains While Preserving Their Ligand-Binding Properties," *Molecular Immunology*, 28(4/5):489-498, 1991.
Petri, M. et al., "Effects of Prasterone on Disease Activity and Symptoms in Women with Active Systemic Lupus Erythematosus," *Arthritis and Rheumatism*, 50(9):2858-2868, Sep. 2004.
Press, O. et al., "High-Dose Radioimmunotherapy of B Cell Lymphomas," *The Present and Future Role of Monoclonal Antibodies in the Management of Cancer, Front Radat Ther Oncol*, Vaet and Meyer (Eds.), Basel, Karger, 24:204-213, 1990.
Press, O. et al, "Radiolabeled Antibody Therapy of Human B Cell Lymphomas," *Immunobiology of Proteins and Peptides VI*, Platinum Press, New York, 1991.
Press O. et al., "Radiolabeled-Antibody Therapy of B-Cell Lymphoma With Autologuous Bone Marrow Support," *New England Journal of Medicine*, 329(17):1219-1224, Oct. 21, 1993.
Press, O. et al., "Treatment of Refractory Non-Hodgkin's Lymphoma with Radiolabled MB-1 (Anti-CD37) Antibody," *Journal of Clinical Oncology.*, 7(8):1027-1038, 1989.

Queen, C. et al., "A humanized antibody that binds to the interleukin 2 receptor," *Proc Natl. Acad. Sci.*, 86:100029-10033, Dec. 1989.
Rai, K. et al., "Fludarabine Compared with Chlorambucil as Primary Therapy for Chronic Lymphocytic Leukemia," *The New England Journal of Medicine*, 343(24):1750-1757, Dec. 14, 2000.
Reff, M. et al., "Depletion of B Cells in vivo by a Chimeric Mouse Human Monoclonal Antibody to CD20," *Blood*, 83(2):435-445, Jan. 15, 1994.
Rider, L. et al., "International Consensus on Preliminary Definitions of Improvement in Adult and Juvenile Myositis," *Arthritis and Rheumatism*, 50(7):2281-2290, Jul. 2004.
Riechmann, L. et al., "Reshaping human antibodies for therapy," *Nature*, 332:323-327, Mar. 24, 1988.
Rudick, R.A. et al., "Impact of interferon beta-la on neurologic disability in relapsing multiple sclerosis," *Neurology*, pp. 358-363, Aug. 1997.
Schwartz-Albiez, R. et al., "The B-Cell Associated CD37 Antigen (gp40-52) Structure and Subcellular Expression of an Extensively Glycosylated Glycoprotein," *The Journal of Immunology*, 140(3): 905-914, Feb. 1, 1988.
Shlomchik, M. et al., "The Role of B Cells in *lpr/lpr*-induced Autoimmunity," *J. Exp. Med.*, 180:1295-1306, Oct. 1994.
Simonis, B. et al., "Evaluation and Validation of a Chron's Disease Inflammatory Activity Index Reflecting Pattern of Endoscopic Severity," *Scandanavian Journal of Gastroenterology*, 33(3):283-288, 1998.
Stasi, R. et al., "Rituximab chimeric anti-CD20 monoclonal antibody treatment for adults with chronic idiopathic thrombocytopenic purpura," *Blood*, 98(4):952-957, Aug. 15, 2001.
Tan, E. et al., "The 1982 Revised Criteria for the Classification of Systemic Lupus Erythematosus," *Arthritis and Rheumatism*, 25(11):1271-1277, Nov. 1982.
Targoff, I., "Dermatomyositis and Polymyositis," *Curr. Probl. Dermatol*, pp. 131-180, Sep./Oct. 1991.
Traunecker, A. et al., "Bispecific single chain molecules (Janusins) target cytotoxic lymphocytes on HIV infected cases," *The EMBO Journals*, 10(12):3655-3659, 1991.
"Treanda Prescribing Information," Cephalon Oncology, 6 pages, 2008.
Treon, S. et al., "CD20-Directed Antibody-Mediated Immunotherapy Induces Responses and Facilitates Hematologic Recovery in Patients with Walendstrom's Macroglobulinemia," *Journal of Immunotherapy*, 24(3):272-279, 2001.
Van Spriel, A. et al., "A Regulatory Role for CD37 in T Cell Proliferation," *The Journal of Immunology*, pp. 2953-2961, 2004.
Verhoeyen, M. et al., "Reshaping Human Antibodies: Grafting an Antilysozyme Activity," *Science*, 239:1534-1536, Sep. 29, 1987.
White, C. et al., "Anti-CD20 monoclonal antibodies as novel treatments for non-Hodgkin's lymphoma," *PSTT*, 2(3):95-101, 1999.
Yokota, T. et al., "Rapid Tumor Penetration of a Single-Chain Fv and Comparison with Other Immunoglobulin Forms," *Cancer Research*, 52:3402-3408, Jun. 15, 1992.
Adlersberg, J.B, "The immunoglobulin hinge (interdomain) region," Ric. Clin. Lab. 6:191-205, 1976.
Afanasieva, T.A., et al., "Single-chain antibody and its derivatives directed against vascular endothelial growth factor: application for antiangiogenic gene therapy," Gene Therapy 10:1850-1859, 2003.
Aicher, A., et al., "Characterization of human inducible costimulator ligand expression and function," J. Immunol. 164:4689-4696, 2000.
Anderson, D.R., et al., "Targeting Cytotoxic Immunotherapy. Targeted anti-cancer therapy using rituximab, a chimaeric anti-CD20 antibody (IDEC-C2B8) in the treatment of non-Hodgkin's B-cell lymphoma," Biochem. Soc. Transactions, pp. 705-708, 1997.
Andritsos, L., et al., "A phase I trial of TRU-016, an anti-CD37 small modular immunopharmaceutical (SMIP) in relapsed and refractory CLL," 2009 Annual Meeting, American Society of Clinical Oncology (ASCO), J. Clin. Oncol. 27(suppl.):15s (Abstract 3017), 2009.
Angal, S., et al., "A single amino acid substitution abolishes the heterogeneity of chimeric mouse/human (IgG4) antibody," Mol. Immunol 30(1):105-108, 1993.
Anthony, K., Ed., "Selective inhibitors gain traction," Nat. Rev. Cancer 10:160, 2010.

(56) References Cited

OTHER PUBLICATIONS

Barone, D., et al., "Efficacy of SMIP-016, a novel CD37-directed biologic therapy, in human NHL tumor xenograft models," J. Clin. Oncol. 24(18S)(Jun. 20 Suppl.):Abstract 2565, 2006.

Baum, P.R., et al., "Evaluation of the effect of TRU-016, an anti-CD37 directed SMIP™, in combination with other therapeutic drugs in models of Non-Hodgkin's Lymphoma," 2009 Annual Meeting, American Society of Clinical Oncology (ASCO), J. Clin. Oncol. 27(May 20 Suppl.):15S (Abstract 8571), 2009.

Beavil, A.J., et al., "α-Helical coiled-coil stalks in the low-affinity receptor for IgE (FcεRII/CD23) and related C-type lectins," Proc. Natl. Acad. Sci. USA 89:753-757, 1992.

Beiske, K., et al., "Triggering of neoplastic B cells via surface IgM and the cell surface antigens CD20 and CDw40. Responses differ from normal blood B cells and are restricted to certain morphologic subsets," Int. J. Cancer 42:521-528, 1988.

Benoist, C., and Mathis, D., "A revival of the B cell paradigm for rheumatoid arthritis pathogenesis?" Arthritis Res. 2(2):90-94, 2000.

Berzofsky, J.A., and Berkower, I.J., "Immunogenicity and Antigen Structure," in Fundamental Immunology, Third Edition, William E. Paul, Ed., Chap. 8, pp. 235-282, Raven Press, Ltd., New York, 1993.

Bloom, J.W., et al., "Intrachain disulfide bond in the core hinge region of human IgG4," Protein Sci. 6:407-415, 1997.

Boehm, M.K., et al., "The Fab and Fc fragments of IgA1 exhibit a different arrangement from that in IgG: a study by X-ray and neutron solution scattering and homology modelling," J. Mol. Biol. 286:1421-1447, 1999.

Brekke, O.H., et al., "The structural requirements for complement activation by IgG: does it hinge on the hinge?" Immunol. Today 16(2):85-90, 1995.

Brinkmann, U., et al., "Recombinant immunotoxins containing the VH or VL domain of monoclonal antibody B3 fused to *Pseudomonas* exotoxin," J. Immunol 150(7):2774-2782, 1993.

Brok, H.P.M., et al., "Prophylactic and therapeutic effects of a humanized monoclonal antibody against the IL-2 receptor (DACLIZUMAB) on collagen-induced arthritis (CIA) in rhesus monkeys," Clin. Exp. Immunol. 124:134-141, 2001.

Brorson, K., et al., "Mutational analysis of avidity and fine specificity of anti-levan antibodies," J. Immunol 163:6694-6701, 1999.

Brown, S.L., et al., "Treatment of B-Cell Lymphomas with Anti-idiotype Antibodies Alone and in Combination with Alpha Interferon," Blood 73(3):651-661, 1989.

Brummell, D.A., et al., "Probing the Combining Site of an Anti-Carbohydrate Antibody by Saturation-Mutagenesis: Role of the Heavy-Chain CDR3 Residues," Biochemistry 32:1180-1187, 1993.

Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111:2129-2138, 1990.

Burke, J.M., et al., "Radioimmunotherapy for acute leukemia," Cancer Control 9(2):106-113, 2002.

Burks, E.A., et al., "In vitro scanning saturation mutagenesis of an antibody binding pocket," Proc. Natl. Acad. Sci. USA 94:412-417, 1997.

Bussel, J.B., "Overview of Idiopathic Thrombocytopenic Purpura: New Approach to Refractory Patients," Semin Oncol. 27(6 Suppl 12):91-98, 2000.

Cai, X., and Garen, A., "Comparison of fusion phage libraries displaying VH or single-chain Fv antibody fragments derived from the antibody repertoire of a vaccinated melanoma patient as a source of melanoma-specific targeting molecules," Proc. Natl. Acad. Sci. USA 94:9261-9266, 1997.

Calistoga Pharmaceuticals, "Preliminary evidence of clinical activity in a phase 1 study of CA:-101, a potent selective inhibitor of the p110δ isoform of phosphatidylinositol 3-kinase, in patients with B-cell malignancies," European Hematology Association, Jun. 4-7, 2009, Poster Session, 17 pages.

Capon, D.J., et al., "Designing CD4 immunoadhesins for AIDS therapy," Nature 337:525-531, 1989.

Casset, F., et al., "A peptide mimetic of an anti-CD4 monoclonal antibody by rational design," Biochem. Biophys. Res. Commun. 307:198-205, 2003.

Chatterjee, M.B., et al., "Idiotypic antibody immunotherapy of cancer," Cancer Immunol Immunother. 38:75-82, 1994.

Chen, Y., et al., "Selection and Analysis of an Optimized Anti-VEGF Antibody: Crystal Structure of an Affinity-matured Fab in Complex with Antigen," J. Mol. Biol. 293:865-881, 1999.

Chothia, C., et al., "Domain association in immunoglobulin molecules. The packing of variable domains," J. Mol. Biol. 186(3):651-663, 1985.

Clackson, T., et al., "Making antibody fragments using phage display libraries," Nature 352:624-628, 1991.

Clark, E.A., et al., "Role of the Bp35 cell surface polypeptide in human B-cell activation," Proc. Natl. Acad. Sci. USA 82:1766-1770, 1985.

Clark, E.A., and Einfeld, D, "Human B Cell Surface Molecules Defined by an International Workshop Panel of Monoclonal Antibodies," in Leukocyte Typing II (1986), vol. 2, Reinherz, E.L., et al., Eds., pp. 155-167, Springer-Verlag, New York, 1986.

Clark, E.A., and Ledbetter, J.A., "Activation of human B cells mediated through two distinct cell surface differentiation antigens, Bp35 and Bp50," Proc. Natl. Acad. Sci. USA 83:4494-4498, 1986.

Clark, E.A., and Ledbetter, J.A., "Structure, function, and genetics of human B cell-associated surface molecules," Adv. Cancer Res. 52:81-149, 1989.

Co, M.S., et al., "Genetically Engineered Deglycosylation of the Variable Domain Increases the Affinity of an Anti-CD33 Monoclonal Antibody," Mol. Immunol 30(15):1361-1367, 1993.

Coiffier, B., et al., "Rituximab (Anti-CD20 Monoclonal Antibody) for the Treatment of Patients With Relapsing or Refractory Aggressive Lymphoma: A Multicenter Phase II Study," Blood 92(6):1927-1932, 1998.

Colman, P.M., "Effects of amino acid sequence changes on antibody-antigen interactions," Res. Immunol 145:33-36, 1994.

Coloma, M.J., et al., "The hinge as a spacer contributes to covalent assembly and is required for function of IgG," J. Immunol. 158:733-740, 1997.

Cooke, S.P., et al., "A strategy for antitumor vascular therapy by targeting the vascular endothelial growth factor: receptor complex," Cancer Res. 61:3653-3659, 2001.

Crunkhorn, S., "Designing selective PI3K inhibitors," Nat. Rev. Drug Discovery 9:105, 2010.

Cruse, J.M., and Lewis, R.E., Illustrated Dictionary of Immunology, p. 157, CRC Press, Inc., 1995.

Dall'Acqua, W.F., et al., "Modulation of the Effector Functions of a Human IgG1 through Engineering of its Hinge Region," J. Immunol. 177:1129-1138, 2006.

Damle, N.K., et al., "Direct helper T cell-induced B cell differentiation involves interaction between T cell antigen CD28 and B cell activation antigen B7," Eur. J. Immunol. 21:1277-1282, 1991.

Davies, J., and Riechmann, L., "'Camelising' human antibody fragments: NMR studies on VH domains," FEBS Lett. 339:285-290, 1994.

Davies J., and Riechmann, L., "Single antibody domains as small recognition units: design and in vitro antigen selection of camelized, human VH domains with improved protein stability," Protein Eng. 9(6):531-537, 1996.

Davies, J., "Hematologic malignancies," American Society of Hematology—45th Annual Meeting and Exposition, Dec. 5-9, 2003, San Diego, CA, USA; iDrugs 7(1):1-3, 2004.

Davis, S.J., et al., "High Level Expression in Chinese Hamster Ovary Cells of Soluble Forms of CD4 T Lymphocyte Glycoprotein Including Glycosylation Variants," J. Biol. Chem. 265(18):10410-10418, 1990.

De Pascalis, R., et al., "Grafting of 'abbreviated' complementarity-determining regions containing specificity-determining residues essential for ligand contact to engineer a less immunogenic humanized monoclonal antibody," J. Immunol. 169(6):3076-3084, 2002.

Deans, J.P., et al., "Association of tyrosine and serine kinases with the B cell surface antigen CD20. Induction via CD20 of tyrosine phosphorylation and activation of phospholipase C-γ1 and PLC phospholipase C-γ2," J. Immunol. 151(9):4494-4504, 1993.

(56) References Cited

OTHER PUBLICATIONS

Dechant, M., et al., "Chimeric IgA antibodies against HLA class II effectively trigger lymphoma cell killing," Blood 100(13):4574-4580, 2002.
Decker, T., et al., "A pilot trial of the mTOR (mammalian target of rapamycin) inhibitor RAD001 in patients with advanced B-CLL," Ann. Hematol. 88:221-227, 2009.
Dermer, G.B., "Another Anniversary for the War on Cancer," Bio/Technology 12:320, 1994.
Desmyter, A., et al., "Crystal structure of a camel single-domain VH antibody fragment in complex with lysozyme," Nat. Struct. Biol. 3(9):803-811, 1996.
Dietsch, M.T., et al., "Bispecific receptor globulins, novel tools for the study of cellular interactions. Preparation and characterization of an E-selectin/P-selectin bispecific receptor globulin," J. Immunol. Methods 162:123-132, 1993.
Dietsch, M.T., et al., "Coengagement of CD2 with LFA-1 or VLA-4 by bispecific ligand fusion proteins primes T cells to respond more effectively to T cell receptor-dependent signals," J. Leukoc. Biol. 56:444-452, 1994.
Dillman, R.O., et al., "Continuous infusion of T101 monoclonal antibody in chronic lymphocytic leukemia and cutaneous T-cell lymphoma," J. Biol. Response Mod. 5:394-410, 1986.
Dorai, H., et al., "Role of inter-heavy and light chain disulfide bonds in the effector functions of human immunoglobulin IgG1," Mol. Immunol. 29(12):1487-1491, 1992.
Dorrington, K.J., and Klein, M., "Aspects of immunoglobulin G structure relevant to its interaction with Fc receptors," Arch. Immunol. Ther. Exp. (Warsz.) 29:275-282, 1981.
Dufner, P., et al., "Harnessing phage and ribosome display for antibody optimisation," Trends Biotechnol. 24(11):523-529, 2006.
Duncan, A.R., and Winter, G., "The binding site for C1q on IgG," Nature 332:738-740, 1988.
Durie, F.H., et al., "Prevention of collagen-induced arthritis with an antibody to gp39, the ligand for CD40," Science 261:1328-1330, 1993.
Dyer, M.J., et al., "Effects of CAMPATH-1 antibodies in vivo in patients with lymphoid malignancies: influence of antibody isotype," Blood 73(6):1431-1439, 1989.
Edwards, J.C.W., and Cambridge, G., "Rheumatoid Arthritis: The Predictable Effect of Small Immune Complexes in which Antibody is Also Antigen," Br. J. Rheumatol. 37:126-130, 1998.
Edwards, J.C.W., et al., "Do self-perpetuating B lymphocytes drive human autoimmune disease?" Immunology 97:188-196, 1999.
Elsässer, D., et al., "HLA Class II as Potential Target Antigen on Malignant B Cells for Therapy with Bispecific Antibodies in Combination with Granulocyte Colony-Stimulating Factor," Blood 87(9):3803-3812, 1996.
Feldman, M.E., et al., "Active-Site Inhibitors of mTOR Target Rapamycin-Resistant Outputs of mTORC1 and mTORC2," PLoS Biol. 7(2):0371-0383, 2009.
Fell, H.P., et al., "Genetic construction and characterization of a fusion protein consisting of a chimeric F(ab') with specificity for carcinomas and human IL-2," J. Immunol. 146(7):2446-2452, 1991.
Fell, H.P., et al., "Chimeric L6 Anti-tumor Antibody. Genomic construction, expression, and characterization of the antigen binding site," J. Biol. Chem. 267(22):15552-15558, 1992.
Filpula, et al., "Single-chain Fv designs for protein, cell and gene therapeutics," Exp. Opin. Ther. Patents 9(3):231-245, 1999.
Fonseca, R., et al., "Myeloma and the t(11;14)(q13;q32); evidence for a biologically defined unique subset of patients," Blood 99(10):3735-3741, 2002.
Foster, F.M., et al., "The phosphoinositide (PI) 3-kinase family," J. Cell Sci. 116(15):3037-3040, 2003.
Funakoshi, S., et al, "Inhibition of Human B-Cell Lymphoma Growth by CD40 Stimulation," Blood 83(10):2787-2794, 1994.
Funakoshi, S., et al., "Differential in Vitro and in Vivo Antitumor Effects Mediated by Anti-CD40 and Anti-CD20 Monoclonal Antibodies Against Human B-Cell Lymphomas," J. Immunother. 19(2):93-101, 1996.
Gillies, S.D., and Wesolowski, J.S., "Antigen binding and biological activities of engineered mutant chimeric antibodies with human tumor specificities," Hum. Antibod. Hybridomas 1(1):47-54, 1990.
Gillies, S.D., et al., "Improving the efficacy of antibody-interleukin 2 fusion proteins by reducing their interaction with Fc receptors," Cancer Res. 59:2159-2166, 1999.
Gilliland, L.K., et al., "Rapid and reliable cloning of antibody variable regions and generation of recombinant single chain antibody fragments," Tissue Antigens 47:1-20, 1996.
Grossbard, M.L., et al., "Monoclonal Antibody-Based Therapies of Leukemia and Lymphoma," Blood 80(4):863-878, 1992.
Gura, T., "Cancer Models. Systems for Identifying New Drugs Are Often Faulty," Science 278(5340):1041-1042, 1997.
Halin, C., et al., "Tumor-targeting properties of antibody-vascular endothelial growth factor fusion proteins," Int. J. Cancer 102:109-116, 2002.
Hamers-Casterman, C., et al., "Naturally occurring antibodies devoid of light chains," Nature 363:446-448, 1993.
Haritunians, T., et al., "Antiproliferative activity of RAD001 (everolimus) as a single agent and combined with other agents in mantle cell lymphoma," Leukemia 21:333-339, 2007.
Hayden, M.S., et al., "Single-chain mono- and bispecific antibody derivatives with novel biological properties and antitumour activity from a COS cell transient expression system," Ther. Immunol. 1:3-15, 1994.
Hayden, M.S., et al., "Costimulation by CD28 sFv expressed on the tumor cell surface or as a soluble bispecific molecule targeted to the L6 carcinoma antigen," Tissue Antigens 48:242-254, 1996.
Hayden, M.S., et al., "Antibody engineering," Curr. Opin. Immunol 9.201-212, 1997.
Hekman, A., et al., "Initial experience with treatment of human B cell lymphoma with anti-CD19 monoclonal antibody," Cancer Immunol Immunother. 32:364-372, 1991.
Hellström, I., et al., "Monoclonal Mouse Antibodies Raised against Human Lung Carcinoma," Canc. Res. 46:3917-3923, 1986.
Hinek, A., et al., "The Elastin Receptor: A Galactoside-Binding Protein," Science 239:1539-1541, 1988.
Hollenbaugh, D., et al., "The human T cell antigen gp39, a member of the TNF gene family, is a ligand for the CD40 receptor: expression of a soluble form of gp39 with B cell co-stimulatory activity," EMBO J. 11:4313-4321, 1992.
Holliger, P., and Hudson, P.J., "Engineered antibody fragments and the rise of single domains," Nat. Biotechnol. 23(9):1126-1136, 2005.
Holm, P., et al., "Functional mapping and single chain construction of the anti-cytokeratin 8 monoclonal antibody TS1," Mol. Immunol. 44:1075-1084, 2007.
Hu, S., et al., "Minibody: a novel engineered anti-carcinoembryonic antigen antibody fragment (single-chain Fv-CH3) which exhibits rapid, high-level targeting of xenografts," Cancer Res. 56:3055-3061, 1996.
Hudson, P.J., "Recombinant antibody fragments," Curr. Opin. Biotechnol. 9:395-402, 1998.
Hudson, P.J., "Recombinant antibodies: a novel approach to cancer diagnosis and therapy," Expert Opin. Investig. Drugs 9(6):1231-1242, 2000.
Huls, G., et al., "Antitumor Immune Effector Mechanisms Recruited by Phage Display-derived Fully Human IgG1 and IgA1 Monoclonal Antibodies," Cancer Res. 59:5778-5784, 1999.
Huston, J.S., et al., "Medical applications of single-chain antibodies," Int. Rev. Immunol. 10:195-217, 1993.
The International Non-Hodgkin's Lymphoma Prognostic Factors Project, "A Predictive Model for Aggressive Non-Hodgkin's Lymphoma," New Engl. J. Med. 329:987-994, 1993.
Isaacs, J.D., et al., "Therapy with monoclonal antibodies. II. The contribution of Fcγ receptor binding and the influence of $C_H1$ and $C_H3$ domains on in vivo effector function," J. Immunol. 161:3862-3869, 1998.
Isenman, D.E., et al., "Correlation between the exposure of aromatic chromophores at the surface of the Fc domains of immunoglobulin G and their ability to bind complement," Biochemistry 16(2):233-240, 1977.

(56) References Cited

OTHER PUBLICATIONS

"IUPAC-IUB commission on biochemical nomenclature rules for naming synthetic modifications of natural peptides tentative rules," J. Biol. Chem. 242:555-557, 1967.

Jacquemin, M., et al., "Variable region heavy chain glycosylation determines the anticoagulant activity of a factor VIII antibody," J. Thromb. Haemost. 4:1047-1055, 2006.

Jain, R.K., "Physiological barriers to delivery of monoclonal antibodies and other macromolecules in tumors," Cancer Res. 50 (Suppl.):814s-819s, 1990.

Janeway, C.A., et al., Eds., *Immunobiology: The Immune System in Health and Disease*, 4th ed., Chap. 3, p. 92, Elsevier Science Ltd., London, and Garland Publishing, New York, 1999.

Jang, Y.-J., et al., "The structural basis for DNA binding by an anti-DNA autoantibody," Mol. Immunol. 35:1207-1217, 1998.

Joosten, L.A.B., et al., "Protection against cartilage and bone destruction by systemic interleukin-4 treatment in established murine type II collagen-induced arthritis," Arthritis Res. 1:81-91, 1999.

Kaminski, M.S., et al., "Radioimmunotherapy of B-Cell Lymphoma with [$^{131}$I]Anti-B1 (Anti-CD20) Antibody," N. Engl. J. Med. 329(7):459-465, 1993.

Kato, K., et al., "A conformational change in the Fc precludes the binding of two Fcγ receptor molecules to one IgG," Immunol. Today 21:310-312, 2000.

Keystone, E., "B cell targeted therapies," Arthritis Res. Ther. 7(Suppl. 3):S13-S18, 2005.

Kiesel, S., et al., "Removal of Cells from a Malignant B-Cell Line from Bone Marrow with Immunomagnetic Beads and with Complement and Immunoglobulin Switch Variant Mediated Cytolysis," Leukemia Res. 11:1119-1125, 1987.

Klein, M., et al., "Expression of biological effector functions by immunoglobulin G molecules lacking the hinge region," Proc. Natl. Acad. Sci. USA 78(1):524-528, 1981.

Knobeloch, K.-P., et al., "Targeted Inactivation of the Tetraspanin CD37 Impairs T-Cell-Dependent B-Cell Response under Suboptimal Costimulatory Conditions," Mol. Cell. Biol. 20(15):5363-5369, 2000.

Kobayashi, H., et al., "Tryptophan H33 plays an important role in pyrimidine (6-4) pyrimidone photoproduct binding by a high-affinity antibody," Protein Eng. 12(10):879-884, 1999.

Koolwijk, P., et al., "Interaction between hybrid mouse monoclonal antibodies and the human high-affinity IgG FcR, huFcγ RI, on U937. Involvement of only one of the mIgG heavy chains in receptor binding," J. Immunol. 143(5):1656-1662, 1989.

Kortt, A.A., et al., "Recombinant anti-sialidase single-chain variable fragment antibody. Characterization, formation of dimer and higher-molecular-mass multimers and the solution of the crystal structure of the single-chain variable fragment/sialidase complex," Eur. J. Biochem. 221:151-157, 1994.

Kortt, A.A., et al., "Dimeric and trimeric antibodies: high avidity scFvs for cancer targeting," Biomol. Eng. 18:95-108, 2001.

Kumar, S., et al., "Molecular Cloning and Expression of the Fabs of Human Autoantibodies in *Escherichia coli*," J. Biol. Chem. 275(45):35129-35136, 2000.

Ladetto, M., et al., "Rituximab anti-CD20 monoclonal antibody induces marked but transient reductions of peripheral blood lymphocytes in chronic lymphocytic leukaemia patients," Med. Oncol. 17:203-210, 2000.

Lamminmäki, U., and Kankare, J.A., "Crystal Structure of a Recombinant Anti-estradiol Fab Fragment in Complex with 17β-Estradiol," J. Biol. Chem. 276(39):36687-36694, 2001.

Law, C.-L., et al., "Expression and characterization of recombinant soluble human CD3 molecules: presentation of antigenic epitopes defined on the native TCR-CD3 complex," Int. Immunol. 14(4):389-400, 2002.

Layios, N., et al., "Remission of severe cold agglutinin disease after Rituximab therapy," Leukemia, pp. 187-188, 2000.

Lazar, E., et al., "Transforming growth factor α: mutation of aspartic acid 47 and leucine 48 results in different biological activities," Mol. Cell. Biol. 8(3):1247-1252, 1988.

Ledbetter, J.A., et al., "Antibodies to Tp67 and Tp44 Augment and Sustain Proliferative Responses of Activated T Cells," J. Immunol. 135(4):2331-2336, 1985.

Ledbetter, J.A., et al., "Monoclonal antibodies to a new gp40-45 (CD37) B-cell-associated cluster group modulate B-cell proliferation," in Leucocyte Typing III: White Cell Differentiation Antigens, A.J. McMichael, Ed., pp. 339-340, Oxford University Press, Oxford (1987).

Ledbetter, J.A., et al., "Augmentation of normal and malignant B cell proliferation by monoclonal antibody to the B cell-specific antigen BP50 (CDW40)," J. Immunol. 138(3):788-794, 1987.

Lee, E.J., and Kueck, B., "Rituxan in the Treatment of Cold Agglutinin Disease," Blood 92(9):3490-3491, 1998.

Lee, H.-S., et al., "Generation and characterization of a novel single-gene-encoded single-chain immunoglobulin molecule with antigen binding activity and effector functions," Mol. Immunol. 36:61-71, 1999.

Lehninger, A.L., et al., Principles of Biochemistry, 2nd Ed., Figure 5-6, Worth Publishers, New York (1993).

Leigh, B.R., et al., "Preclinical evaluation of chimeric L6 antibody for the treatment of Kaposi's sarcoma with radioimmunotherapy," Cancer Biother. Radiopharm. 14(2):113-119, 1999.

Li, J.-Y., et al., "Detection of Translocation t(11;14)(q13;q32) in Mantle Cell Lymphoma by Fluorescence in Situ Hybridization," Amer. J. Pathol. 154(5):1449-1452, 1999.

Li, S.L., et al., "Single-chain antibodies against human insulin-like growth factor I receptor: expression, purification, and effect on tumor growth," Cancer Immunol Immunother. 49:243-252, 2000.

Lin, M.C, et al., "Structure-Function Relationships in Glucagon: Properties of Highly Purified Des-His-, Monoiodo-, and [Des-Asn$^{28}$, Thr$^{29}$](homoserine lactone$^{27}$)-glucagon," Biochemistry 14(8):1559-1563, 1975.

Linsley, P.S., et al., "T-cell antigen CD28 mediates adhesion with B cells by interacting with activation antigen B7/BB-1," Proc. Natl. Acad. Sci. USA 87:5031-5035, 1990.

MacCallum, R.M., et al., "Antibody-antigen interactions: contact analysis and binding site topography," J. Mol. Biol. 262:732-745, 1996.

Maloney, D.G., et al., "Phase I Clinical Trial Using Escalating Single-Dose Infusion of Chimeric Anti-CD20 Monoclonal Antibody (IDEC-C2B8) in Patients With Recurrent B-Cell Lymphoma," Blood 84(8):2457-2466, 1994.

Maloney, D.G., et al., "IDEC-C2B8: results of a phase I multiple-dose trial in patients with relapsed non-Hodgkin's lymphoma," J. Clin. Oncol. 15(10):3266-3274, 1997.

Maloney, D.G., et al., "IDEC-C2B8 (Rituximab) Anti-CD20 Monoclonal Antibody Therapy in Patients with Relapsed Low-Grade Non-Hodgkin's Lymphoma," Blood 90(6):2188-2195, 1997.

Martens, C.L., et al., "Heavy chain genes of rabbit IgG: Isolation of a cDNA encoding γ heavy chain and identification of two genomic Cγ genes," Proc. Natl. Acad. Sci. USA 79:6018-6022, 1982.

Martin, S., et al., "Efficient Neutralization and Disruption of Rhinovirus by Chimeric ICAM-1/Immunoglobulin Molecules," J. Virol. 67(6):3561-3568, 1993.

Mattu, T.S., et al., "The Glycosylation and Structure of Human Serum IgA1, Fab, and Fc Regions and the Role of N-Glycosylation on Fcα Receptor Interactions," J. Biol. Chem. 273(4):2260-2272, 1998.

McLaughlin, P., et al., "IDEC-C2B8 Anti-CD20 Antibody: Final Report on a Phase III Pivotal Trial in Patients (PTS) with Relapsed Low-Grade or Follicular Lymphoma (LG/F NHL)," Blood 88(10)(Suppl. 1):90a (Abstract 349), 1996.

McLaughlin, P., et al., "Clinical Status and Optimal Use of Rituximab for B-Cell Lymphomas," Oncology 12(12):1763-1769, 1998; review by Grossbard, M.L., and Multani, P.S., pp. 1769-1770; review by Raubitschek, A., pp. 1775-1776; review by Molina, A., pp. 1776-1777, 1781.

Michaelsen, T.E., et al., "Enhancement of complement activation and cytolysis of human IgG3 by deletion of hinge exons," Scand. J. Immunol. 32:517-528, 1990.

(56) References Cited

OTHER PUBLICATIONS

Michaelsen, T.E., et al., "Antibody dependent cell-mediated cytotoxicity induced by chimeric mouse-human IgG subclasses and IgG3 antibodies with altered hinge region," Mol. Immunol. 29(3):319-326, 1992.

Michaelsen, T.E., et al., "One disulfide bond in front of the second heavy chain constant region is necessary and sufficient for effector functions of human IgG3 without a genetic hinge," Proc. Natl. Acad. Sci. USA 91:9243-9247, 1994.

Miller, F.W., "Classification and Prognosis of Inflammatory Muscle Disease," Rheum. Dis. Clin. North Amer. 20(4):811-826, 1994.

Multani, P.S., and Grossbard, M.L., "Monoclonal antibody-based therapies for hematologic malignancies," J. Clin. Oncol. 16(11):3691-3710, 1998.

Muñoz, E., et al., "The $C_H1$ domain of IgG is not essential for C3 covalent binding: importance of the other constant domains as targets for C3," Int. Immunol. 10(2):97-106, 1998.

Muyldermans, S., et al., "Sequence and structure of VH domain from naturally occurring camel heavy chain immunoglobulins lacking light chains," Protein Eng. 7(9):1129-1135, 1994.

Muyldermans, S., "Single domain camel antibodies: current status," Rev. Mol. Biotechnol. 74:277-302, 2001.

Nadler, L.M., "B Cell/Leukemia Panel Workshop. Summary and Comments," in Leukocyte Typing II, vol. 2, Reinherz, E.L., et al., Eds., pp. 3-14, 20, 21, Springer Verlag, New York, 1986.

NCBI Reference Sequence NP_001765.1 for Leukocyte Surface Antigen CD37, Oct. 31, 2000.

Neve, R.M., et al., "Biological effects of anti-ErbB2 single chain antibodies selected for internalizing function," Biochem. Biophys. Res. Commun 280:274-279, 2001.

Nguyen, V.K., et al., "The specific variable domain of camel heavy-chain antibodies is encoded in the germline," J. Mol. Biol. 275:413-418, 1998.

Nguyen, V.K., et al., "Heavy-chain antibodies in *Camelidae*; a case of evolutionary innovation," Immunogenetics 54:39-47, 2002.

Nieba, L., et al., "Disrupting the hydrophobic patches at the antibody variable/constant domain interface: improved in vivo folding and physical characterization of an engineered scFv fragment," Protein Eng. 10(4):435-444, 1997.

Nikula, T.K., et al., "Impact of the high tyrosine fraction in complementarity determining regions: measured and predicted effects of radioiodination on IgG immunoreactivity," Mol. Immunol. 32(12):865-872, 1995.

Novak, H., et al., "Selective antibody-mediated targeting of class I MHC to EGFR-expressing tumor cells induces potent antitumor CTL activity in vitro and in vivo," Int. J. Cancer 120:329-336, 2006.

Nuttall, S.D., et al., "Immunoglobulin VH domains and beyond: design and selection of single-domain binding and targeting reagents," Curr. Pharm. Biotechnol. 1:253-263, 2000.

Okazaki, T., et al., "PD-1 immunoreceptor inhibits B cell receptor-mediated signaling by recruiting src homology 2-domain-containing tyrosine phosphatase 2 to phosphotyrosine," Proc. Natl. Acad. Sci. USA 98(24):13866-13871, 2001.

Oki, S., et al., "Augmentation of CTLA-4 expression by wortmannin: involvement of lysosomal sorting properties of CTLA-4," Int. Immunol. 11(9):1563-1571, 1999.

Pallesen, G., and Hager, H., "The expression of the 40-45 kDa pan-B cluster (CD37) in normal human tissues and in haematopoietic neoplasms as defined by immunohistology," in Leucocyte Typing III: White Cell Differentiation Antigens, A.J. McMichael, Ed., pp. 337-339, Oxford University Press, Oxford (1987).

Park, S.S., et al., "Generation and characterization of a novel tetravalent bispecific antibody that binds to hepatitis B virus surface antigens," Mol. Immunol. 37:1123-1130, 2000.

Pawson, R., et al., "Treatment of T-cell prolymphocytic leukemia with human CD52 antibody," J. Clin. Oncol. 15(7):2667-2672, 1997.

Peter, K. et al., "Construction and functional evaluation of a single-chain antibody fusion protein with fibrin targeting and thrombin inhibition after activation by factor Xa," Circulation 101:1158-1164, 2000.

Pezzutto, A., et al., "CD19 Monoclonal Antibody HD37 Inhibits Anti-Immunoglobulin-Induced B Cell Activation and Proliferation," J. Immunol. 138(9):2793-2799, 1987.

Portolano, S., et al., "Lack of promiscuity in autoantigen-specific H and L chain combinations as revealed by human H and L chain 'roulette'," J. Immunol. 150(3):880-887, 1993.

Press, O.W., et al., "Monoclonal Antibody 1F5 (Anti-CD20) Serotherapy of Human B Cell Lymphomas," Blood 69(2):584-591, 1987.

Protheroe, A., et al., "Remission of inflammatory arthropathy in association with anti-CD20 therapy for non-Hodgkin's lymphoma," Rheumatology 38:1150-1152, 1999.

PubMed (NCBI) search for "des-leucine," Publication Date to Jul. 26, 2003.

Radaev, S., et al., "The Structure of a Human Type III FcγReceptor in Complex with Fc," J. Biol. Chem. 276(19):16469-16477, 2001.

Radaev, S., and Sun, P.D., "Recognition of IgG by Fcγ receptor. The role of Fc glycosylation and the binding of peptide inhibitors," J. Biol. Chem. 276(19):16478-16483, 2001.

Rader, C., et al., "A phage display approach for rapid antibody humanization: Designed combinatorial V gene libraries," Proc. Nat. Acad. Sci. USA 95:8910-8915, 1998.

Ratanatharathorn, V., et al., "Anti-CD20 Chimeric Monoclonal Antibody Treatment of Refractory Immune-Mediated Thrombocytopenia in a Patient with Chronic Graft-versus-Host Disease," Ann Intern. Med. 133(4):275-279, 2000.

Redpath, S., et al., "The influence of the hinge region length in binding of human IgG to human Fcγ receptors," Hum. Immunol. 59:720-727, 1998.

Riechmann, L., "Rearrangement of the former VL interface in the solution structure of a camelised, single antibody VH domain," J. Mol. Biol. 259:957-969, 1996.

Rothe, C., et al., "The human combinatorial antibody library HuCAL GOLD combines diversification of all six CDRs according to the natural immune system with a novel display method for efficient selection of high-affinity antibodies," J. Mol. Biol. 376:1182-1200, 2008. PubMed Abstract only, PMID: 18191144.

Roux, K.H., et al., "Comparisons of the ability of human IgG3 hinge mutants, IgM, IgE, and IgA2, to form small immune complexes: a role for flexibility and geometry," J. Immunol 161:4083-4090, 1998.

Roux, K.H., et al., "Structural analysis of the nurse shark (new) antigen receptor (NAR): Molecular convergence of NAR and unusual mammalian immunoglobulins," Proc. Natl. Acad. Sci. USA 95:11804-11809, 1998.

Rudick, R.A., et al., "Impact of interferon beta-la on neurologic disability in relapsing multiple sclerosis," Neurology 49:358-363, 1997.

Rudikoff, S., et al., "Single amino acid substitution altering antigen-binding specificity," Proc. Natl. Acad. Sci. USA 79:1979-1983, 1982.

Saleh, M.N., et al., A Pilot Study of the Anti-CD20 Monoclonal Antibody Rituximab in Patients With Refractory Immune Thrombocytopenia, Semin. Oncol. 27(6)(Suppl 12):99-103, 2000.

Santos, L., et al., "Role of macrophage migration inhibitory factor (MIF) in murine antigen-induced arthritis: interaction with glucocorticoids," Clin. Exp. Immunol. 123:309-314, 2001.

Scheinberg, D.A., et al., "A phase I toxicity, pharmacology, and dosimetry trial of monoclonal antibody OKB7 in patients with non-Hodgkin's lymphoma: effects of tumor burden and antigen expression," J. Clin. Oncol. 8(5):792-803, 1990.

Schmidt, M., et al., "Suppression of metastasis formation by a recombinant single chain antibody-toxin targeted to full-length and oncogenic variant EGF receptors," Oncogene 18:1711-1721, 1999.

Schuster, M., et al., "Improved Effector Functions of a Therapeutic Monoclonal Lewis Y-Specific Antibody by Glycoform Engineering," Cancer Res. 65(17):7934-7941, 2005.

Schwartz, G.P., et al., "A superactive insulin: [B10-aspartic acid]insulin(human)," Proc. Natl. Acad. Sci. USA 84:6408-6411, 1987.

Search Output from ATCC Website for Hybridomas: 2H7 (pp. 1-2), 1D8 (p. 1), HD37 (p. 1), G28-1 (p. 1), 4.4.220 (p. 1), Fc2-2 (p. 1), UCHL-1 (p. 1), 5B9 (p. 1), L6 (p. 1), 10A8 (p. 1), 2e12 (p. 1). 40.2.36 (p. 1) and G19-4 (p. 1). (cited in Office Action dated Dec. 8, 2006 in U.S. Appl. No. 10/627,556, now U.S. Patent No. 7,829,084).

(56) References Cited

OTHER PUBLICATIONS

Seaver, S.S., "Monoclonal Antibodies in Industry: More Difficult Than Originally Thought," Genet. Eng. News 14(14):10, 21, 1994.
Segal, D.M., et al., "Introduction: bispecific antibodies," J. Immunol. Methods 248:1-6, 2001.
Sensel, M.G., et al., "Engineering novel antibody molecules," Chem. Immunol. 65:129-158, 1997.
Shan, D., et al., "Apoptosis of Malignant Human B Cells by Ligation of CD20 with Monoclonal Antibodies," Blood 91(5):1644-1652, 1998.
Shan, D., et al., "Characterization of scFv-Ig Constructs Generated from the Anti-CD20 mAb 1F5 Using Linker Peptides of Varying Lengths," J. Immunol. 162:6589-6595, 1999.
Shankar, S., et al., "Antiepidermal growth factor variant III scFv fragment: effect of radioiodination method on tumor targeting and normal tissue clearance," Nucl. Med. Biol. 33:101-110, 2006.
Shegogue, D., and Trojanowska, M., "Mammalian Target of Rapamycin Positively Regulates Collagen Type I Production via a Phosphatidylinositol 3-Kinase-independent Pathway," J. Biol. Chem. 279(22):23166-23175, 2004.
Shimoni, A., et al., "Autologous T Cells Control B-Chronic Lymphocytic Leukemia Tumor Progression in Human → Mouse Radiation Chimera," Cancer Res. 59:5968-5974, 1999.
Shin, S.-U., et al., "Genetically-Engineered Antibodies: Tools for the Study of Diverse Properties of the Antibody Molecule," Immunol. Rev. 130:87-107, 1992.
Shin, S.-U., et al., "Hybrid antibodies," Int. Rev. Immunol. 10:177-186, 1993.
Shu, L., et al., "Secretion of a single-gene-encoded immunoglobulin from myeloma cells," Proc. Natl. Acad. Sci. USA 90:7995-7999, 1993.
Simonds, H.M., and Miles, D., "Adjuvant treatment of breast cancer: impact of monoclonal antibody therapy directed against the HER2 receptor," Expert Opin. Biol. Ther. 7(4):487-491, 2007.
Simonis, B., et al., "Evaluation and Validation of a Crohn's Disease Inflammatory Activity Index Reflecting Pattern of Endoscopic Severity," Scand. J. Gastroenterol. 33(3):283-288, 1998.
Smellie, W.J.B., et al., "Radioimmunotherapy of breast cancer xenografts with monoclonal antibody ICR12 against c-erbB2 p185: comparison of iodogen and N-succinimidyl 4-methyl-3-(tri-n-butylstannyl)benzoate radioiodination methods," Cancer Res. 55(Suppl):5842s-5846s, 1995.
Smith, K.A., et al., "Isolation and characterisation of vascular endothelial growth factor-165 specific scFv fragments by phage display," Int. J. Oncol. 22:333-338, 2003.
Smith-Gill, S.J., et al., "Contributions of immunoglobulin heavy and light chains to antibody specificity for lysozyme and two haptens," J. Immunol. 139:4135-4144, 1987.
Sondermann, P., et al., "The 3.2-Å crystal structure of the human IgG1 Fc fragment-FcγRIII complex," Nature 406:267-273, 2000.
Song, M.-K., et al., "Light chain of natural antibody plays a dominant role in protein antigen binding," Biochem. Biophys. Res. Commun. 268:390-394, 2000.
Souriau, C., and Hudson, P.J., "Recombinant antibodies for cancer diagnosis and therapy," Expert Opin. Biol. Ther. 3(2):305-318, 2003.
Spiro, R.G., "Protein glycosylation: nature, distribution, enzymatic formation, and disease implications of glycopeptide bonds," Glycobiology 12(4):43R-56R, 2002.
Sporici, R.A., et al., "ICOS ligand costimulation is required for T-cell encephalitogenicity," Clin. Immunol. 100(3):277-288, 2001.
Stamenkovic, I., and Seed, B., "Analysis of Two cDNA Clones Encoding the B Lymphocyte Antigen CD20 (B1, Bp35), A Type III Integral Membrane Protein," J. Exp. Med. 167:1975-1980, 1988.
Stevenson, G.T., et al., "Mechanisms in Removal of Tumor by Antibody," Cell Biophys. 24/25:45-50, 1994.
Stevenson, G.T., et al., "Conjugation of Human Fcγ in Closed-Hinge or Open-Hinge Configuration to Fab'γ and Analogous Ligands," J. Immunol. 158:2242-2250, 1997.
Tamburini, J., et al., "Mammalian target of rapamycin (mTOR) inhibition activates phosphatidylinositol 3-kinase/Akt by up-regulating insulin-like growth factor-1 receptor signaling in acute myeloid leukemia: rationale for therapeutic inhibition of both pathways," Blood 111:379-382, 2008.
Tamura, H., et al., "B7-H1 costimulation preferentially enhances CD28-independent T-helper cell function," Blood 97(6):1809-1816, 2001.
Tan, L.K., et al., "Influence of the hinge region on complement activation, C1q binding, and segmental flexibility in chimeric human immunoglobulins," Proc. Natl. Acad. Sci. USA 87:162-166, 1990.
Tao, M.H., and Morrison, S.L., "Studies of aglycosylated chimeric mouse-human IgG. Role of carbohydrate in the structure and effector functions mediated by the human IgG constant region," J. Immunol. 143(8):2595-2601, 1989.
Tedder, T.F., et al., "Cloning of a Complementary DNA Encoding a New Mouse B Lymphocyte Differentiation Antigen, Homologous to the Human B1 (CD20) Antigen, and Localization of the Gene to Chromosome 19," J. Immunol. 141(12):4388-4394, 1988.
Terry, L.A., et al., "The monoclonal antibody, UCHL1, recognizes a 180,000 MW component of the human leucocyte-common antigen, CD45," Immunol. 64:331-336, 1988.
Thommesen, J.E., et al., "Lysine 322 in the human IgG3 C(H)2 domain is crucial for antibody dependent complement activation," Mol. Immunol. 37:995-1004, 2000.
Traunecker, A., et al., "Bispecific single chain molecules (Janusins) target cytotoxic lymphocytes on HIV infected cells," EMBO J. 10(12):3655-3659, 1991.
Treon, S.P., and Anderson, K.C., "The Use of Rituximab in the Treatment of Malignant and Nonmalignant Plasma Cell Disorders," Semin. Oncol. 27(Suppl 12):79-85, 2000.
Vajdos, F.F., et al., "Comprehensive Functional Maps of the Antigen-binding Site of an Anti-ErbB2 Antibody Obtained with Shotgun Scanning Mutagenesis," J. Mol. Biol. 320:415-428, 2002.
van den Abbeele, A.D., et al., "Antigen-binding site protection during radiolabeling leads to a higher immunoreactive fraction," J. Nucl. Med. 32(1):116-122, 1991.
van den Beucken, T., et al., "Building novel binding ligands of B7.1 and B7.2 based on human antibody single variable light chain domains," J. Mol. Biol. 310:591-601, 2001.
Vitaliti, A., et al , "Inhibition of tumor angiogenesis by a single-chain antibody directed against vascular endothelial growth factor," Cancer Res. 60:4311-4314, 2000.
Vlasveld, L.T., et al., "Treatment of low-grade non-Hodgkin's lymphoma with continuous infusion of low-dose recombinant interleukin-2 in combination with the B-cell-specific monoclonal antibody CLB-CD19," Cancer Immunol. Immunother. 40:37-47, 1995.
Walker, M.R., et al., "Aglycosylation of human IgG1 and IgG3 monoclonal antibodies can eliminate recognition by human cells expressing Fcγ RI and/or Fcγ RII receptors," Biochem. J. 259:347-353, 1989.
Wang, B., et al., "Human single-chain Fat immunoconjugates targeted to a melanoma-associated chondroitin sulfate proteoglycan mediate specific lysis of human melanoma cells by natural killer cells and complement," Proc. Natl. Acad. Sci. USA 96:1627-1632, 1999.
Ward, E.S., et al., "Binding activities of a repertoire of single immunoglobulin variable domains secreted from *Escherichia coli*," Nature 341:544-546, 1989.
Ward, E.S., and Ghetie, V., "The effector functions of immunoglobulins: implications for therapy," Ther. Immunol. 2:77-94, 1995.
Warnock, D., et al., "In Vitro Galactosylation of Human IgG at 1 kg Scale Using Recombinant Galactosyltransferase," Biotechnol. Bioeng. 92(7):831-842, 2005.
Welschof, M., et al., "The Antigen Binding Domain of Non-idiotypic Human Anti-F(ab')2 Autoantibodies: Study of their Interaction with IgG Hinge Region Epitopes," Hum. Immunol. 60:282-290, 1999.
Weston, K.M., et al., "In vivo binding of mouse IgG via polyreactive surface IgM abrogates progressive lymphocytosis in prolymphocytic leukemia," Leuk. Lymphoma 29:361-373, 1998.
White, M.W., et al., "Activation of Dense Human Tonsilar B Cells. Induction of *c-myc* Gene Exptession via Two Distinct Signal Transduction Pathways," J. Immunol. 146(3):846-853, 1991.

(56) References Cited

OTHER PUBLICATIONS

Wilson, I.A., and Stanfield, R.L., "A Trojan horse with a sweet tooth," Nat. Struct. Biol. 2:433-436, 1995. Abstract only.
Winberg, G., et al., "Surface Expression of CD28 Single Chain Fv for Costimulation by Tumor Cells," Immunol Rev. 153:209-223, 1996.
Wu, H., et al., "Humanization of a murine monoclonal antibody by simultaneous optimization of framework and CDR residues," J. Mol. Biol. 294:151-162, 1999.
Wu, A.M., et al., "Multimerization of a chimeric anti-CD20 single-chain Fv-Fc fusion protein is mediated through variable domain exchange," Protein Eng. 14(12):1025-1033, 2001.
Wörn, A., and Plückthun, A., "Stability engineering of antibody single-chain Fv fragments," J. Mol. Biol. 305(5):989-1010, 2001.
Ye, Z., et al., "Gene therapy for cancer using single-chain Fv fragments specific for 4-1BB," Nat. Med. 8(4):343-348, 2002.
Yoshinaga, S.K., et al., "Characterization of a new human B7-related protein: B7RP-1 is the ligand to the co-stimulatory protein ICOS," Int. Immunol. 12(10):1439-1447, 2000.
Zaja, F., et al., "Rituximab for myasthenia gravis developing after bone marrow transplant," Neurology 55:1062-1063, 2000.
Zarling, J.M., et al., "Lysis of Cells Infected with HIV-1 by Human Lymphocytes Targeted with Monoclonal Antibody Heteroconjugates," J. Immunol. 140(8):2609-2613, 1988.
Zhao, X.B., et al., "Novel Anti-CD37 Small Modular Immunopharmaceutical (SMIP) Induces B-Cell-Specific, Caspase-Independent Apoptosis in Human CLL Cells," Blood (ASH Annual Meeting Abstracts) 104:Abstract #2515, 2004, 1 page.
Albrecht, Huguette et al., "Monospecific bivalent scFv-SH: Effects of linker length and location of an engineered cysteine on production, antigen binding activity and free SH accessibility," *Journal of Immunological Methods 310*:100-116, 2006.
Fischer, Kirsten et al., "Bendamustine in Combination with Rituximab (BR) for Patients with Relapsed Chronic Lymphocytic Leukemia (CLL): A Multicentre Phase II Trial of the German CLL Study Group (GCLLSG)," *Blood* (ASH Annual Meeting Abstracts) 112:Abstract 330, 2008.
Francisco, Joseph A., et al., "Activity of a Single-Chain Immunotoxin That Selectively Kills Lymphoma and Other B-Lineage Cells Expressing the CD40 Antigen," *Cancer Research 55*:3099-3104, Jul. 15, 1995.
Mukai, Y., et al., "Optimization of anti-tumor necrosis factor-alpha single chain Fv displayed on phages for creation of functional antibodies," *Pharmazie 61*:889-890, 2006.
Rummel, Mathias J., et al., "Bendamustine Plus Rituximab Versus CHOP Plus Rituximab in the First-Line Treatment of Patients with Indolent and Mantle Cell Lymphomas—First Interim Results of a Randomized Phase III Study of the StiL (Study Group Indolent Lymphomas, Germany)," *Blood, American Society of Hematology 110*(11):120A, Nov. 16, 2007.
Rummel, Mathias J., "German Experience With Bendamustine Treating Relapsed/Refractory Indolent B-Cell and Mantle Cell Lymphomas," *Seminars in Hematology 44*(3) Suppl. 4:S22-S26, Jul. 1, 2007.
Zhao, Xiaobin, et al., "Targeting CD37-positive lymphoid malignancies with a novel engineered small modular immunopharmaceutical," *Blood 110*(7):2569-2577, Oct. 1, 2007.
Hwang, William Ying Khee et al., "Use of human germline genes in a CDR homology-based approach to antibody humanization," *Methods 36*:35-42, 2005.
Pelat, Thibaut et al., "Germline Humanization of a Non-human Primate Antibody that Neutralizes the Anthrax Toxin, by in Vitro and in Silico Engineering," *J. Mol. Biol. 384*:1400-1407, 2008.
Tan, Philip et al., "'Superhumanized' Antibodies: Reduction of Immunogenic Potential by Complementarity-Determining Region Grafting with Human Germline Sequences: Application to an Anti-CD28," *The Journal of Immunology 169*:1119-1125, 2002.
Barone, D., et al., "TRU-015, a novel CD20-directed biologic therapy, demonstrates significant anti-tumor activity in human tumor xenograft models," J. Clin. Oncol. 23(16S):178s (Abstract #2549) Jun. 1, 2005.

Bènistant, C., et al., "A specific function for phosphatidylinositol 3-kinase α (p85α-p110α) in cell survival and for phosphatidylinositol 3-kinase β (p85α-p110β) in de novo Dna synthesis of human colon carcinoma cells," Oncogene 19:5083-5090, 2000.
Better, M., et al., "*Escherichia coli* Secretion of an Active Chimeric Antibody Fragment," Science 240:1041-1043, 1988.
Bongini, L., et al., "Freezing immunoglobulins to see them move," Proc. Natl. Acad. Sci. USA 101(17):6466-6471, 2004.
Bonnema et al., "Fc Receptor Stimulation of Phosphatidylinositol 3-Kinase in Natural Killer Cells is Associated with Protein Kinase C-independent Granule Release and Cell-mediated Cytotoxicity," J. Exp. Med. 180:1427-1435 (1994).
Boussif, O., et al., "A versatile vector for gene and oligonucleotide transfer into cells in culture and in vivo: Polyethylenimine," Proc. Natl. Acad. Sci. USA 92:7297-7301, 1995.
Brandt et al., "Bispecific antibody fragments with CD20 X CD28 specificity allow effective autologous and allogeneic T-cell activation against malignant cells in peripheral blood and bone marrow cultures from patients with B-cell lineage leukemia and lymphoma," Exp. Hematol. 27:1264-1270 (1999).
Capaldi, R.A., et al., "Changes in Order of Migration of Polypeptides in Complex III and Cytochrome c Oxidase under Different Condtions of SDS Polyacrylamide Gel Electrophoresis," Biochem. Biophys. Res. Commun. 74(2):425-433, 1977.
Catley et al., "Monoclonal antibodies for the treatment of asthma," Pharmacol. Ther. 132:333-351 (2011).
Chakraborti, T., et al., "Complement activation in heart disease: Role of oxidants," Cell. Signal. 12:607-617, 2000.
Chan H.T.C et al., "CD20-induced lymphoma cell death is independent of both caspases and its redistribution into Triton X-100 insoluble membrane rafts." Cancer Research 63: 5480-5489, 2003.
Chothia, C., and Lesk, A.M., "Canonical Structures for the Hypervariable Regions of Immunoglobulins," J. Mol. Biol. 196:901-917, 1987.
Chothia, C., et al., "Conformations of immunoglobulin hypervariable regions," Nature 342:877-883, 1989.
Chowdhury, P.S., and Pastan, I., "Improving antibody affinity by mimicking somatic hypermutation in vitro," Nat. Biotechnol. 17:568-572, 1999.
Classon et al., "The hinge region of the CD8α chain: structure, antigenicity, and utility in expression of immunoglobulin superfamily domains," Int. Immunol. 4(2):215-225 (1992).
Co, M.S., et al., "Chimeric and Humanized Antibodies with Specificity for the CD33 Antigen," J. Immunol. 148(4):1149-1154, 1992.
Co, M.S., et al., "Humanized antibodies for antiviral therapy," Proc. Natl. Acad. Sci. USA 88:2869-2873, 1991.
Coloma, M.J., and Morrison, S.L., "Design and production of novel tetravalent bispecific antibodies," Nat. Biotechnol. 15:159-163, 1997.
Cote, R.J., et al., "Generation of human monoclonal antibodies reactive with cellular antigens," Proc. Natl. Acad. Sci. USA 80:2026-2030, 1983.
Cotten, M., et al., "High-efficiency receptor-mediated delivery of small and large (48 kilobase gene constructs using the endosome-disruption activity of defective or chemically inactivated adenovirus particles," Proc. Natl. Acad. Sci. USA 89:6094-6098, 1992.
Cree, B., et al., "Tolerability and Effects of Rituximab (Anti-CD20 Antibody) in Neuromyelitis Optica (NMO) and Tapidly Worsening Multiple Sclerosis (MS)," Neurology 62(Suppl 5):A492 (Abstract P06.090), Apr. 2004.
Cruczman, M.S., et al., "Treatment of Patients With Low-Grade B-Cell Lymphoma With the Combination of Chimeric Anti-CD20 Monoclonal Antibody and CHOP Chemotherapy," J. Clin. Oncol. 17(1):268-276, 1999.
Edwards, et al., Arthritis Rheum. 46:S197 (Abstract 446), 2002.
Engelhard, E.K., et al., "The insect tracheal system: A conduit for the systemic spread of Autographa californica M nuclear polyhedrosis virus," Proc. Natl. Acad. Sci. USA 91:3224-3227, 1994.
Feigner, P.L., et al., "Lipofection: A highly efficient, lipid-mediated DNA-transfection procedure," Proc. Natl. Acad. Sci. USA 84:7413-7417, 1987.

(56) References Cited

OTHER PUBLICATIONS

Gazzano-Santoro, H., et al., "A non-radioactive complement-dependent cytotoxicity assay for anti-CD20 monoclonal antibody," J. Immunol. Meth. 202:163-171, 1997.
Genbank Accession No. M17953, Mouse Ig rearranged H-chain V-region mRNA VJ1, Apr. 27, 1993.
Genbank Accession No. M17954, Mouse Ig rearranged kappa-chain mRNA VJ5, Apr. 27, 1993.
Gilliland, L.K., et al., "Elimination of the Immunogenicity of Therapeutic Antibodies," J. Immunol. 162:3663-3671, 1999.
Gluzman, Y., "SV40-Transformed Simian Cells Support the Replication of Early SV40 Mutants," Cell 23:175-182, 1981.
Gordan, L.N., et al., "Phase II Trial of Individualized Rituximab Dosing for Patients With CD20-Positive Lymphoproliferative Disorders," J. Clin. Oncol. 23(6):1096-1102, 2005.
Graff, C.P., et al., "Directed evolution of an anti-carcinoembryonic antigen scFv with a 4-day monovalent dissociation half-time at 37° C.," Prot. Eng. Des. Sel. 17(4):293-304, 2004.
Griffiths, A.D., et al., "Isolation of high affinity human antibodies directly from large synthetic repertoires," EMBO J. 13(14):3245-3260, 1994.
Grünwald, V., et al., "Inhibitors of mTOR Reverse Doxorubicin Resistance Conferred by PTEN Status in Prostate Cancer Cells," Cancer Res. 62:6141-6145, 2002.
Harris, C.L. et al., "Tumor cell killing using chemically engineered antibody constructs specific for tumor cells and the complement inhibitor CD59." Clin Exp Immunol 107; 364-371, 1997.
Harrison, "Phosphoinositide 3-kinase inhibitors," Nat. Rev. Drug Discovery 8:607, 2009.
Hay, N., and Sonenberg, N., "Upstream and downstream of mTOR," Genes Dev. 18:1926-1945, 2004.
Hillmen, P., "MRD in DLL," Clin. Adv. Hematol. Oncol. 4(5)(Suppl. 12):6-7, 2006.
Hoogenboom, H.R., and Winter, G., "By-passing Immunisation. Human Antibodies from Synthetic Repertoires of Germline VH Gene Segments Rearranged in Vitro," J. Mol. Biol. 227:381-388, 1992.
Humphreys et al., "F(ab')2 molecules made from *Escherichia coli* produced Fab' with hinge sequences conferring increased serum survival in an animal model," J. Immunol. Methods 217:1-10 (1998).
Ihle, N.T., et al., "Molecular pharmacology and antitumor activity of PX-866, a novel inhibitor of phosphoinositide-3-kinase signaling," Mol. Cancer Ther. 3(7):763-772, 2004.
Jendreyko, N., et al., "Intradiabodies, Bispecific, Tetravalent Antibodies for the Simultaneous Functional Knockout of Two Cell Surface Receptors," J. Biol. Chem. 278(48):47812-47819, 2003.
Jendreyko, N., et al., "Phenotypic knockout of VEGF-R2 and Tie-2 with an intradiabody reduces tumor growth and angiogenesis in vivo," Proc. Natl. Acad. Sci. USA 102(23):8293-8298, 2005.
Jermutus, L., et al., "Tailoring in vitro evolution for protein affinity of stability," Proc. Natl. Acad. Sci. USA 98(1):75-80, 2001.
Johnson, G., and Wu, T.T., "Kabat Database and its applications: 30 years after the first variability plot," Nucl. Acids Res. 28(1):214-218, 2000.
Kalergis, A.M., et al., "Efficient T cell activation requires an optimal dwell-time of interaction between the TCR and the pMHC complex," Nat. Immunol. 2(3):229-234, 2001.
Kersh, E.N., et al., "Fidelity of T Cell Activation Through Multistep T Cell Receptor ζ Phosphorylation," Science 281:572-575, 1998.
Kiel, C., et al., "Electrostatically optimized Ras-binding Ral guanine dissociation stimulator mutants increase the rate of association by stabilizing the encounter complex," Proc. Natl. Acad. Sci. USA 101(25):9223-9228, 2004.
Kienberger, F., et al., "Following single antibody binding to purple membranes in real time," EMBO Rep. 5(6):579-583, 2004.
Kirschfink, M., "Targeting complement in therapy," Immunol. Rev. 180:177-189, 2001.
Köhl, J., and Gessner, J.E., "On the role of complement and Fc γ-receptors in the Arthus reaction," Mol. Immunol. 36:893-903, 1999.

Kolls, J., et al., "Prolonged and effective blockade of tumor necrosis factor activity through adenovirus-mediated gene transfer," Proc. Natl. Acad. Sci. USA 91:215-219, 1994.
Kost et al., "Production of a urokinase plasminogen activator-IgG fusion protein (uPA-IgG) in the baculovirus expression system," Gene 190:139-144 (1997).
Kozbor, D., and Roder, J.C., "The production of monoclonal antibodies from human lymphocytes," Immunol. Today 4(3):72-79, 1983. (misspelled in 406C1 spec).
Kunkel, T.A., "Rapid and efficient site-specific mutagenesis without phenotypic selection," Proc. Natl. Acad. Sci. USA 82:488-492, 1985.
Kusumi, A., et al., "Confined Lateral Diffusion of Membrane Receptors as Studied by Single Particle Tracking (Nanovid Microscopy). Effects of Calcium-Induced Differentiation in Cultured Epithelial Cells," Biophys. J. 65:2021-2040, 1993.
Lazar, G.A., et al., "Engineered antibody Fc variants with enhanced effector function," Proc. Natl. Acad. Sci. USA 103(11):4005-4010, 2006.
Leatherbarrow, R.J., et al., "Effector Functions of a Monoclonal Aglycosylated Mouse IgG2a: Binding and Activation of Complement Component C 1 and Interaction with Human Monocyte Fc Receptor," Mol. Immunol. 22(4):407-415, 1985.
Leonard, P., et al., "High throughput ranking of recombinant avian scFv antibody fragments from crude lysates using the Biacore A100," J. Immunol. Meth. 323:172-179, 2007.
Leseux, L., et al., "Syk-dependent mTOR activation in follicular lymphoma cells," Blood 108(13):4156-4162, 2006.
Levine, T.D., "Rituximab in the Treatment of Dermatomyositis," Arthritis Rheum. 52(2):601-607, 2005.
Li, Q., et al., "Assessment of Recombinant Adenoviral Vectors for Hepatic Gene Therapy," Hum. Gene Ther. 4:403-409, 1993.
Lu, D., et al., "A Fully Human Recombinant IgG-like Bispecific Antibody to Both the Epidermal Growth Factor Receptor and the Insulin-like Growth Factor Receptor for Enhanced Antitumor Activity," J. Biol. Chem. 280(20):19665-19672, 2005.
Lu, D., et al., "Di-diabody: a novel tetravalent bispecific antibody molecule by design," J. Immunol. Meth. 279:219-232, 2003.
Lyons, D.S., et al., "A TCR Binds to Antagonist Ligands with Lower Affinities and Faster Dissociation Rates Than to Agonists," Immunity 5:53-61, 1996.
Marks, J.D., et al., "By-passing Immunization. Human Antibodies from V-gene Libraries Displayed on Phage," J. Mol. Biol. 222:581-597, 1991.
Marques et al., "Phosphoinositide 3-Kinases p110α and p110β Regulate Cell Cycle Entry, Exhibiting Distinct Activation Kinetics in $G_1$ Phase," Mol. Cell. Biol. 28(8):2803-2814 (2008).
Marsh, J.E., et al., "Targeting the complement system," Curr. Opin. Nephrol. Hypertens. 8:557-562, 1999.
Martin, A.C.R., et al., "Modeling antibody hypervariable loops: A combined algorithm," Proc. Natl. Acad. Sci. USA 86:9268-9272, 1989.
Matsui, K., et al., "Kinetics of T-cell receptor binding to peptide/I-Ek complexes: Correlation of the dissociation rate with T-cell responsiveness," Proc. Natl. Acad. Sci. USA 91:12862-12866, 1994.
May et al., "CAL-101, a Selective Inhibito of the p110 delta Isoform of Phosphatidylinositol 3-Kinase, Effectively Induces Apoptosis in Primary Chronic Lymphocytic Leukemia Cells Providing a Novel Therapeutic Strategy for the Treatment of This Disease," Blood 112(11):1085-1086 (2008).
McFarland et al., "Symmetry Recognizing Asymmetry: Analysis of the Interactions between the C-Type Lectin-like Immunoreceptor NKG2D and MHC Class 1=like Ligands," Structure 11:411-422 (2003).
McLaughlin, P., et al., "Pharmacokinetics (PK) and Pharmacodynamics (PD) of the Anti-CD20 Antibody (Mab) IDEC-C2B8 in Patients (Pts) with Relapsed Low-Grade or Follicular Lymphoma (LG/F NHL)," Blood 88(10)(Suppl. 1):90a (Abstract 350), 1996.
Mealy et al., "Annual Update 2004/2005—Treatment of Musculoskeletal Disorders," Drugs of the Future 30(2):181-232 (2005).
Miller, A.D., "Retrovirus Packaging Cells," Hum. Gene Ther. 1:5-14, 1990.

(56) References Cited

OTHER PUBLICATIONS

Mullinax, R.L., et al., "Identification of human antibody fragment clones specific for tetanus toxoid in a bacteriophage λ immunoexpression library," Proc. Natl. Acad. Sci. USA 87:8095-8099, 1990.
Muraoka, S., and Shulman, M.J., "Structural Requirements for IgM Assembly and Cytolytic Activity. Effects of Mutations in the Oligosaccharide Acceptor Site at Asn 402," J. Immunol. 142(2):695-701, 1989.
Nielsen, U.B., et al., "Targeting of Bivalent Anti-ErbB2 Diabody Antibody Fragments to Tumor Cells is Independent of the Intrinsic Antibody Affinity," Cancer Res. 60:6434-6440, 2000.
O'Brien, S., "Practical Applications of Measuring and Monitoring MRD in Patients With CLL," Clin. Adv. Hematol. Oncol. 4(5)(Suppl. 12):8-9, 2006.
Ogoshi, M., et al., "In Situ Hybridization Analysis of the Expression of Human Telomerase RNA in Normal and Pathologic Conditions of the Skin," J. Invest. Dermatol. 110:818-823, 1998.
Paar, J.M., et al., "Bivalent Ligands with Rigid Double-Stranded DNA Spacers Reveal Structural Constraints on Signaling by FcεRI," J. Immunol. 169:856-864, 2002.
Papadakis, K., et al., "Anti-CD20 Chimeric Monoclonal Antibody (Rituximab) Treatment of Immune-Mediated Thrombocytopenia Associated With Crohn's Disease," Gastroenterology 124(2):583, Feb. 2003.
Poljak, R.J., et al., "Three-Dimensional Structure of the Fab' Fragment of a Human Immunoglobulin at 2.8-Å Resolution," Proc. Natl. Acad. Sci. USA 70(12):3305-3310, 1973.
Pollard, H., et al., "Polyethylenimine but Not Cationic Lipids Promotes Transgene Delivery to the Nucleus in Mammalian Cells," J. Biol. Chem. 273(13):7507-7511, 1998.
Presta, L.G., et al., "Engineering therapeutic antibodies for improved function," Biochem. Soc. Trans. 30(4):487-490, 2002.
Prous, J.R., Ed., "Annual Update 2004/2005—Treatment of Musculoskeletal Disorders," Drugs Fut. 30(2):181-232, 2005.
Rastetter, W., et al., "Rituximab: Expanding Role in Therapy for Lymphomas and Autoimmune Diseases," Annu. Rev. Med. 55:477-503, 2004.
Roguska, M.A., et al., "A comparison of two murine monoclonal antibodies humanized by CDR-grafting and variable domain resurfacing," Protein Eng. 9(10):895-904, 1996.
Roux, K.H., et al., "Flexibility of Human IgG Subclasses," J. Immunol. 159:3372-3382, 1997.
Saldanha, J.W., et al., "A single backmutation in the human kIV framework of a previously unsuccessfully humanized antibody restores the binding activity and increases the secretion in cos cells," Mol. Immunol. 36:709-719, 1999.
Selzer, T., et al., "Rational design of faster associating and tighter binding protein complexes," Nat. Struct. Biol. 7(7):537-541, 2000.
Shahied, L.S., et al., "Bispecific Minibodies Targeting HER2/neu and CD16 Exhibit Improved Tumor Lysis When Placed in a Divalent Tumor Antigen Binding Format," J. Biol. Chem. 279(52):53907-53914, 2004.
Shipp, M.A., et al., "A Predictive Model for Aggressive Non-Hodgkin's Lymphoma," New Engl. J. Med. 329:987-994, 1993.
Smith, G.E., et al., "Molecular Engineering of the Autographa californica Nuclear Polyhedrosis Virus Genome: Deletion Mutations Within the Polyhedrin Gene," J. Virol. 46(2):584-593, 1983.
Speth, C., et al., "The complement system: Pathophysiology and clinical relevance," Wien. Klin. Wochenschr. 111(10):378-391, 1999.
Steukers, M., et al., "Rapid kinetic-based screening of human Fab fragments," J. Immunol. Meth. 310:126-135, 2006.
Stolovich, M., et al., "Transduction of Growth or Mitogenic Signals into Translational Activation of TOP mRNAs is Fully Reliant on the Phosphatidylinositol 3-Kinase-Mediated Pathway but Requires neither S6K1 nor rpS6 Phosphorylation," Mol. Cell Biol. 22(23):8101-8113, 2002.
Su, B., et al., "Automated high-throughput purification of antibody fragments to facilitate evaluation in functional and kinetic based assays," J. Immunol. Meth. 322:94-103, 2007.
Takemura, S., et al., "Lymphoid Neogenesis in Rheumatoid Synovitis," J. Immunol. 167:1072-1080, 2001.
Tannock, "Experimental Chemotherapy," Chapter 19. in the Basic Science of Oncology, Tannock and Hill, eds., New York, pp. 338, and 352-359 (1992).
Taylor, A.K., and Wall, R., "Selective Removal of a Heavy-Chain Glycosylation Sites Causes Immunoglobulin A Degradation and Reduced Secretion," Mol. Cell. Biol. 8(10):4197-4203, 1988.
Tempest, P.R., et al., "Reshaping a Human Monoclonal Antibody to Inhibit Human Respiratory Syncytial Virus Infection in Vivo," Bio/Technology 9:266-271, 1991.
Thompson et al., "Single-Chain Multivalent Binding Proteins With Effector Function," Office Action dated Dec. 16, 2011, for U.S. Appl. No. 12/304,562, 23 pages.
Thoreen, C.C., et al., "An ATP-competitive Mammalian Target of Rapamycin Inhibitor Reveals Rapamycin-resistant Functions of mTORC1," J. Biol. Chem. 284(12):8023-8032, 2009.
van der Kolk, et al., "Complement activation plays a key role in the side-effects of rituximab treatment," Brit. J. Haematol. 115:807-811, 2001.
Vanhove et al., "Selective blockade of CD28 and not CTLA-4 with a single-chain Fv-α1-antitrypsin fusion antibody,"Blood 102:564-570 (2003).
Vaswani, S.K., and Hamilton, R.G., "Humanized antibodies as potential therapeutic drugs," Ann. Allergy Asthma Immunol. 81:105-119, 1998.
Vincent, N., et al., "Long-term correction of mouse dystrophic degeneration by adenovirus-mediated transfer of a minidystrophin gene," Nat. Genet. 5:130-134, 1993.
Wang, C.-Y., and Huang, L., "pH-sensitive immunoliposomes mediate target-cell-specific delivery and controlled expression of a foreign gene in mouse," Proc. Natl. Acad. Sci. USA 84:7851-7855, 1987.
Wang, J., et al., "Generation and Characterization of CD20-Specific CD8+ Cytotoxic T Lymphocytes (CTL) Genetically Modified by Introduction of an scFvFc:zeta Chimeric T Cell Receptor Gene: Preclinical Studies Prior to a Phase I Trial of Cellular Immunotherapy of Follicular Lymphoma," 44th Annual Meeting of the American Society of Hematology, Blood 100(11), Abstract No. 755, Nov. 16, 2002, 1 page.
Willems et al., "CD3 x CD28cross-interacting bispecific antibodies improve tumor cell dependent T-cell activation," Cancer Immunol. Immunother. 54:1059-1071 (2005).
Wu, C.H., et al., "Targeting Genes: Delivery and Persistent Expression of a Foreign Gene Driven by Mammalian Regulatory Elements in Vivo," J. Biol. Chem. 264(29):16985-16987, 1989.
Xavier, K.A., and Willson, R.C., "Association and Dissociation Kinetics of Anti-Hen Egg Lysozyme Monoclonal Antibodies HyHEL-5 and HyHEL-10," Biophys. J. 74:2036-2045, 1998.
Yang, D., et al., "Human neutrophil defensins selectively chemoattract naïve T and immature dendritic cells," J. Leukoc. Biol. 68:9-14, 2000.
Yokoyama et al., "Immune Functions Encoded by the Natural Killer Gene Complex," Nature Reviews Immunology 3:304-316 (2003).
Robak et al., "Phase 2 Study of Otlertuzumab (TRU-016), an Anti-CD37 Adaptir™ Protein, in Combination with Bendamustine vs Bendamustine Alone in Patients with Relapsed Chronic Lymphocytic Leukemia (CLL)," Abstract #61690, American Society of Hematology Annual Meeting (Dec. 7-10, 2013).

\* cited by examiner

HEAVY CHAIN

```
                ......FR1..........          CDR1    .....FR2......          CDR2
G28-1       AVQLQQSGPESERKPGASVKISCKASGYSFT  GYNMN  WVKQNNGKSLEWIG   NIDPYYGGTTYNRKFKG
CAS-024     EVQLVQSGAEVKKPGESLKISCKGSGYSFT   GYNMN  WVRQMPGKGLEWMG   NIDPYYGGTTYNRKFKG
Consensus   -VQL-QSG-E--KPG-S-KISCK-SGYSFT   GYNMN  WV-Q--GK-LEW-G   NIDPYYGGTTYNRKFKG ......FR3..................          CDR3       ....FR4....
G28-1       KATLTVDKSSSTAYMQLKSLTSEDSAVYYCAR  SVGPMDY   WGQGTSVTVSS
CAS-024     QVTISADKSISTAYLQWSSLKASDTAMYYCAR  SVGPFDS   WGQGTLVTVSS
Consensus   --T---DKS-STAY-Q--SL---D-A-YYCAR  SVGP-D-   WGQGT-VTVSS
```

LIGHT CHAIN

```
                ......FR1..............           CDR1      .....FR2......     CDR2
G28-1       DIQMTQSPASLSASVGETVTITC          RTSENVYSYLA    WYQQKQGKSPQLLVS    FAKTLAE
CAS-024     EIVLTQSPATLSLSPGERATLSC          RASENVYSYLA    WYQQKPGQAPRLLIY    FAKTLAE
Consensus   -I--TQSPATLS-S-GE--T--C          R-SENVYSYLA    WYQQK-G--P-LL--    FAKTLAE ......FR3..............               CDR3       ....FR4....
G28-1       GVPSRFSGSGSGTQFSLKISSLQPEDSGSYFC  QHHSDNPWT   FGQGTKVEIK FGGGTELEIK
CAS-024     GIPARFSGSGSGTDFTLTISSLEPEDFAVYYC  QHHSDNPWT   FGQGTKVEIK
Consensus   G-P-RFSGSGSGT-F-L-ISSL-PED---Y-C  QHHSDNPWT   FGQGTKVEIK FG-GT--EIK
```

*Fig. 1*

CD37 IMMUNOTHERAPEUTIC AND COMBINATION WITH BIFUNCTIONAL CHEMOTHERAPEUTIC THEREOF

CROSS-REFERENCE TO RELATED APPLICATION

This application claims the benefit under 35 U.S.C. §119 (e) of U.S. Provisional Patent Application No. 61/190,067 filed Apr. 11, 2008, where this provisional application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING.txt. The text file is 295 KB, was created on Feb. 1, 2012, and is submitted electronically via EFS-Web.

BACKGROUND

1. Technical Field

The present disclosure generally provides compositions and methods for treating B-cell disorders and, more specifically, a humanized anti-CD37 small modular immunopharmaceutical (SMIP) molecule, as well as synergistic combination therapies of CD37-specific binding molecules with bifunctional chemotherapeutics for use in treating or preventing B-cell related autoimmune, inflammatory, or hyperproliferative diseases.

2. Description of the Related Art

The human immune system generally protects the body from invading foreign substances and pathogens. One component of the immune system is B lymphocytes, also referred to as B-cells, which produce antibodies that protect the body by binding to, and in some cases mediating destruction of, a foreign substance or pathogen. In some instances, however, the immune system functions can go awry and disease results. For example, there are numerous cancers, autoimmune diseases, and inflammatory diseases that involve uncontrolled proliferation of B-cells.

B-cells can be identified by molecules on their cell surface, such as CD37. CD37 is a heavily glycosylated 40-52 kDa protein that belongs to the tetraspanin transmembrane family of cell surface antigens, which is highly expressed on normal antibody-producing B-cells but not on pre-B-cells or plasma cells. In addition to normal B-cells, almost all malignancies of B-cell origin are positive for CD37 expression, including chronic lymphocytic leukemia (CLL), non-Hodgkins lymphoma (NHL), and hairy cell leukemia (Moore et al., J. Pathol. 152:13 (1987); Merson and Brochier, Immunol. Lett. 19:269 (1988); and Faure et al., Am. J. Dermatopathol. 12:122 (1990)).

A few CD37 specific immunotherapies have been developed. An IgG1 murine monoclonal antibody specific for CD37, MB-1, was labeled with $^{131}$I and tested in a clinical trial in the treatment of NHL (see Press et al., J. Clin. Oncol. 7:1027 (1989); Bernstein et al., Cancer Res. (Suppl.) 50:1017 (1990); Press et al., Front. Radiat. Ther. Oncol. 24:204 (1990); Press et al., Adv. Exp. Med. Biol. 303:91 (1991) and Brown et al., Nucl. Med. Biol. 24:657 (1997)). The MB-1 antibody lacks Fc effector functions, such as antibody-dependent cellular cytotoxicity (ADCC), and the naked MB-1 antibody did not inhibit tumor growth in an in vivo xenograft model (Buchsbaum et al., Cancer Res. 52:6476 (1992)). In addition, an immunoconjugate having adriamycin linked to G28-1, another murine monoclonal anti-CD37, was administered to mice and shown to be internalized with adriamycin being released intracellularly (see, Braslawsky et al., Cancer Immunol. Immunother. 33:367 (1991)). An engineered fusion protein, termed a small modular immunopharmaceutical (SMIP™) product, directed to CD37 is currently being tested in humans (see, e.g., US Patent Application Publications 2003/0133939 and 2007/0059306).

Although there has been extensive research carried out on antibody-based therapies, there remains a need in the art for alternative or improved compositions and methods for treating B-cell associated disorders or diseases.

BRIEF SUMMARY

In one aspect, the present disclosure provides humanized CD37-specific binding molecules and a method for reducing B-cells or treating a disease associated with aberrant B-cell activity comprising administering to a subject in need thereof an effective amount of a humanized CD37-specific binding molecule provided herein.

In certain embodiments, the present disclosure provides a humanized CD37-specific binding molecule, comprising from amino terminus to carboxyl terminus: (i) a humanized heavy chain variable region, (ii) a linker as set forth in SEQ ID NO:229, (iii) a humanized light chain variable region, (iv) an IgG1 hinge, (v) human IgG1 CH2 region, and (vi) human IgG1 CH3 region, wherein (a) the humanized heavy chain variable region comprises from amino terminus to carboxyl terminus: a humanized heavy chain FR1, a heavy chain CDR1 as set forth in SEQ ID NO:63, a humanized heavy chain FR2, a heavy chain CDR2 as set forth in SEQ ID NO:65, a humanized heavy chain FR3, a heavy chain CDR3 as set forth in SEQ ID NO:67, 68 or 69, and a humanized heavy chain FR4, and (b) the humanized light chain variable region comprises from amino terminus to carboxyl terminus: a humanized light chain FR1, a light chain CDR1 as set forth in SEQ ID NO:61 or 62, a humanized light chain FR2, a light chain CDR2 as set forth in SEQ ID NO:64, a humanized light chain FR3, and a light chain CDR3 as set forth in SEQ ID NO:66, and a humanized light chain FR4.

In certain embodiments of the above humanized CD37-specific binding molecules, the humanized heavy chain FR1 comprises SEQ ID NO:144, the humanized heavy chain FR2 comprises SEQ ID NO:151, the heavy chain FR3 comprises SEQ ID NO:158, and the heavy chain FR4 comprises SEQ ID NO:161 or 162.

In certain embodiments of any one of the above humanized CD37-specific binding molecules, the humanized light chain FR1 comprises SEQ ID NO:171, the light chain FR2 comprises SEQ ID NO:182, the light chain FR3 comprises SEQ ID NO:195, and the light chain FR4 comprises SEQ ID NO:206.

In a related aspect, the present disclosure provides a CD37-specific binding molecule that comprises the amino acid sequence as set forth in SEQ ID NO:253.

In certain embodiments, the CD37-specific binding molecule consists essentially of the amino acid sequence as set forth in SEQ ID NO:253.

In certain embodiments, the CD37-specific binding molecule consists of the amino acid sequence as set forth in SEQ ID NO:253.

In a related aspect, the present disclosure also provides an isolated nucleic acid molecule that comprises a nucleotide sequence encoding a humanized CD37-specific binding molecule provided herein.

In another related aspect, the present disclosure provides a vector that comprises an isolated nucleic acid molecule that encodes a humanized CD37-specific binding molecule provided herein.

In another related aspect, the present disclosure provides a host cell that comprises the above-described vector.

The present disclosure also provides a composition that comprises a humanized CD37-specific binding molecule provided herein and a pharmaceutically acceptable carrier.

In another aspect, the present disclosure provides a method for reducing B-cells or treating a disease associated with aberrant B-cell activity, comprising administering to a subject in need thereof an effective amount of a humanized CD37-specific binding molecule provided herein.

In certain embodiments, the disease associated with aberrant B-cell activity is a B-cell lymphoma, a B-cell leukemia, a B-cell myeloma, a disease characterized by autoantibody production, or a disease characterized by inappropriate T-cell stimulation associated with a B-cell pathway.

In certain embodiments, the disease characterized by autoantibody production is idiopathic inflammatory myopathy, rheumatoid arthritis, myasthenia gravis, Grave's disease, type I diabetes mellitus, multiple sclerosis, an autoimmune disease, dermatomyositis, polymyositis, or Waldenstrom's macroglobinemia.

In certain embodiments, the disease associated with aberrant B-cell activity is chronic lymphocytic leukemia (CLL).

In another aspect, the present disclosure provides compositions and methods for the combined use of CD37-specific binding molecules and bifunctional chemotherapeutics to reduce B-cells or treat a disease associated with aberrant B-cell activity. A surprising result of this combination is that these compounds act synergistically, which results in an increased B-cell reduction.

For example, the present disclosure provides a composition that comprises a CD37-specific binding molecule and bendamustine.

In certain embodiments, the CD37-specific binding molecule is a CD37-specific antibody or SMIP, such as a humanized antibody or a humanized SMIP.

In certain embodiments, the CD37-specific binding molecule competes with G28-1 mAb in CD37-specific binding.

In certain embodiments, the CD37-specific binding molecule is a humanized CD37-specific binding molecule provided herein, such as a humanized CD37-specific binding molecule that comprises, consists essentially of, or consists of, the amino acid sequence as set forth in SEQ ID NO:253.

In a related aspect, the present disclosure provides a method for reducing B-cells or treating a disease associated with aberrant B-cell activity, comprising administering to a subject in need thereof an effective amount of a CD37-specific binding molecule and bendamustine.

In certain embodiments, the disease associated with aberrant B-cell activity is a B-cell lymphoma, a B-cell leukemia, a B-cell myeloma, a disease characterized by autoantibody production, or a disease characterized by inappropriate T-cell stimulation associated with a B-cell pathway.

In certain further embodiments, the disease characterized by autoantibody production is idiopathic inflammatory myopathy, rheumatoid arthritis, myasthenia gravis, Grave's disease, type I diabetes mellitus, multiple sclerosis, an autoimmune disease, dermatomyositis, polymyositis, or Waldenstrom's macroglobinemia.

In certain other embodiments, the disease associated with aberrant B-cell activity is chronic lymphocytic leukemia (CLL).

In certain embodiments, the CD37-specific binding molecule and bendamustine are administered concurrently.

In certain other embodiments, the CD37-specific binding molecule and bendamustine are administered sequentially.

In certain embodiments, the CD37-specific binding molecule and bendamustine are formulated together.

In certain embodiments, the CD37-specific binding molecule is a CD37-specific antibody or SMIP, such as a humanized antibody or a humanized SMIP.

In certain embodiments, the CD37-specific binding molecule competes with G28-1 mAb in CD37-specific binding.

In certain embodiments, the CD37-specific binding molecule is a humanized CD37-specific binding molecule provided herein, such as a humanized CD37-specific binding molecule that comprises, consists essentially of, or consists of, the amino acid sequence as set forth in SEQ ID NO:253.

BRIEF DESCRIPTION OF THE DRAWINGS

FIG. 1 shows heavy and light chain variable region amino acid sequence alignments of mouse G28.1 (variable heavy chain: SEQ ID NO:241, variable light chain: SEQ ID NO:236) and CAS-024 (variable heavy chain: SEQ ID NO:245, variable light chain: SEQ ID NO:238) sequences, along with a consensus identity sequence for the variable heavy chain and variable light chain (SEQ ID NOs: 270 and 271).

DETAILED DESCRIPTION

Figure 2A:
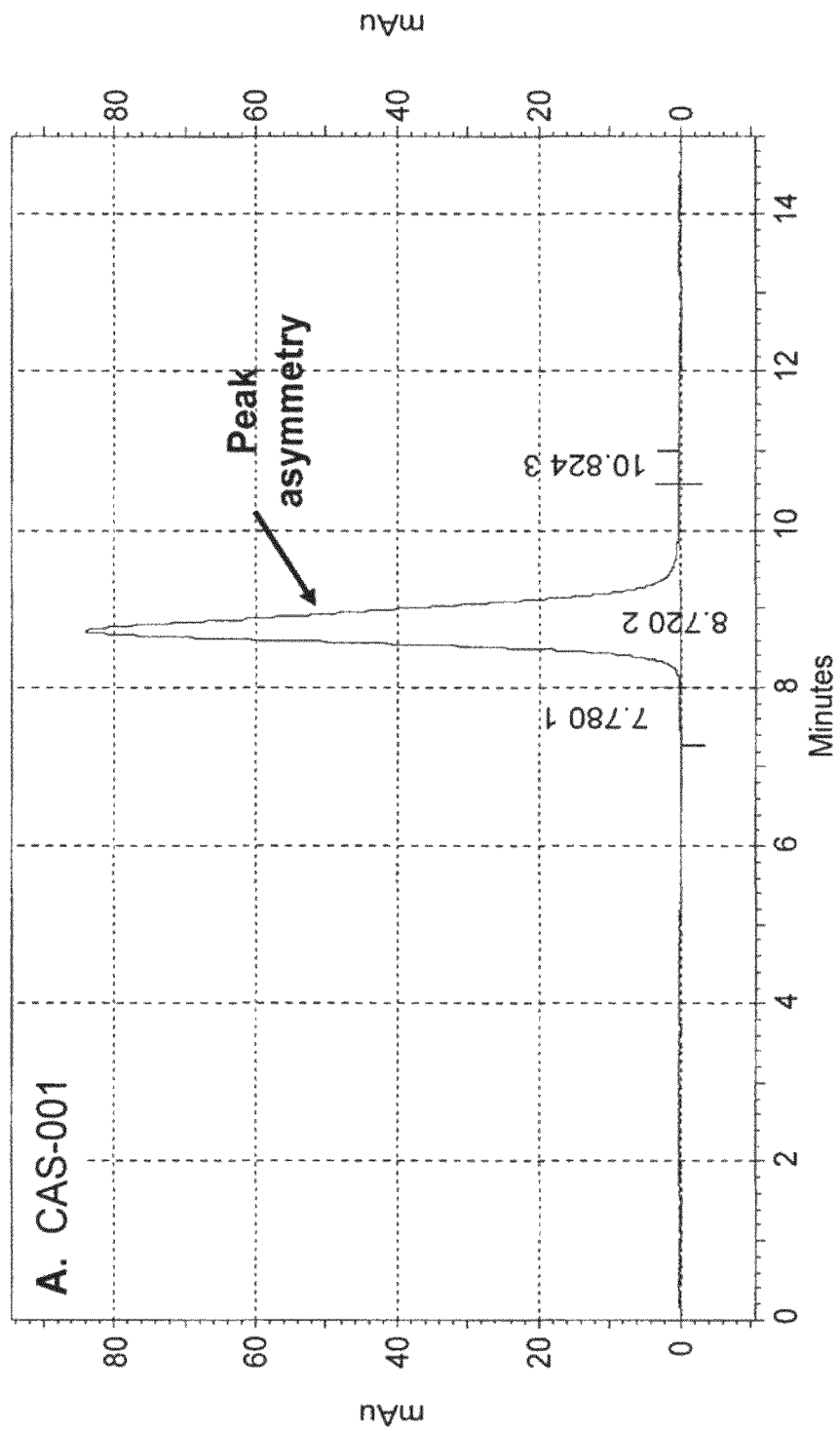
FIGS. 2A-2D show the size exclusion chromatography (SEC) chromatograms of CAS-001, CAS-002, CAS-003, and CAS-024. The peaks of interest (POI) have 98-99% of the SMIP molecules being purified. CAS-024 has a very sharp and symmetrical peak (indicating homogeneity), whereas CAS-001, CAS-002, and CAS-003 peaks have a slight shoulder (where upon integration, the shoulder accounts for about 35% of the POI), which indicates a heterogenous population of molecules.
Figure 2B:
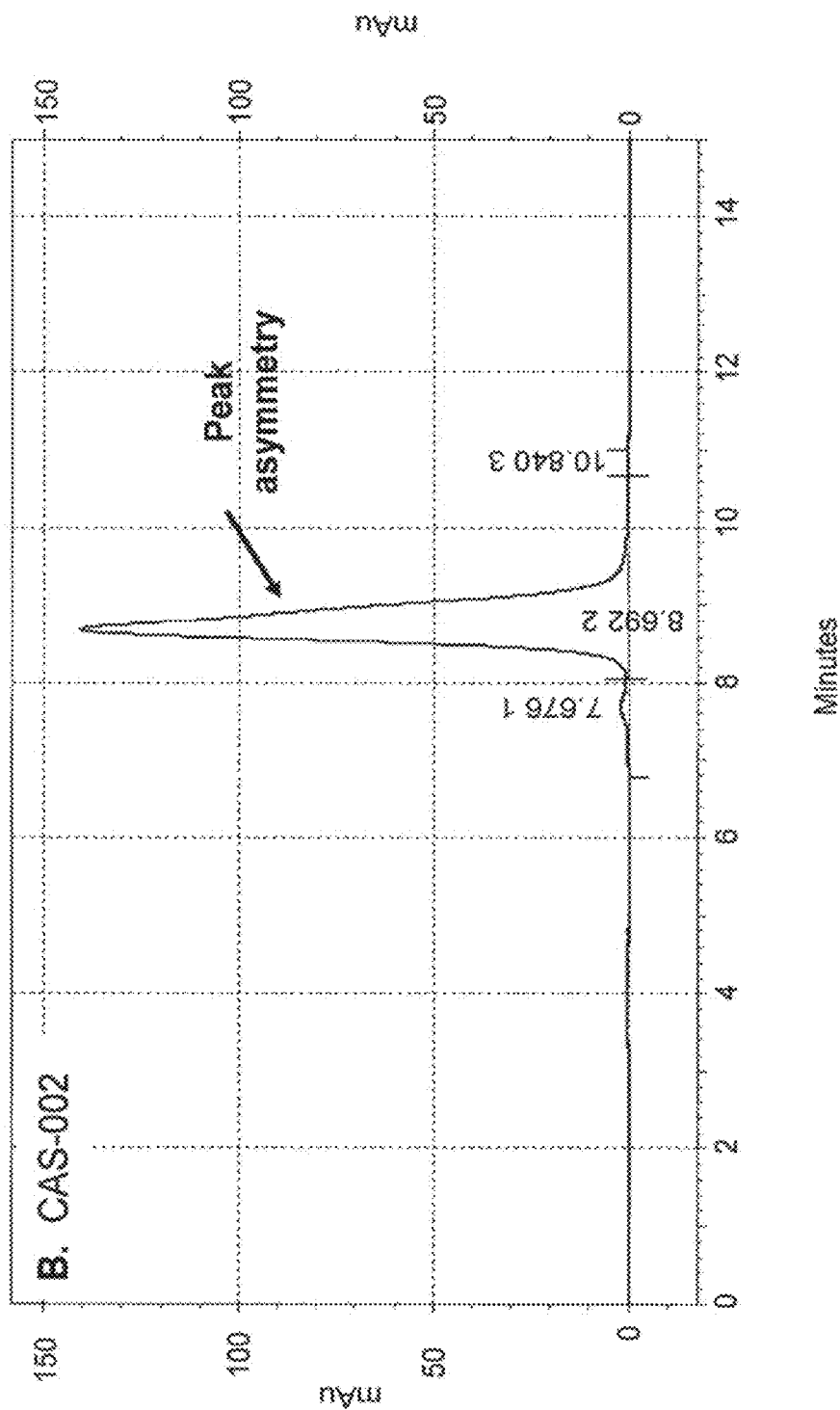
Figure 2C:
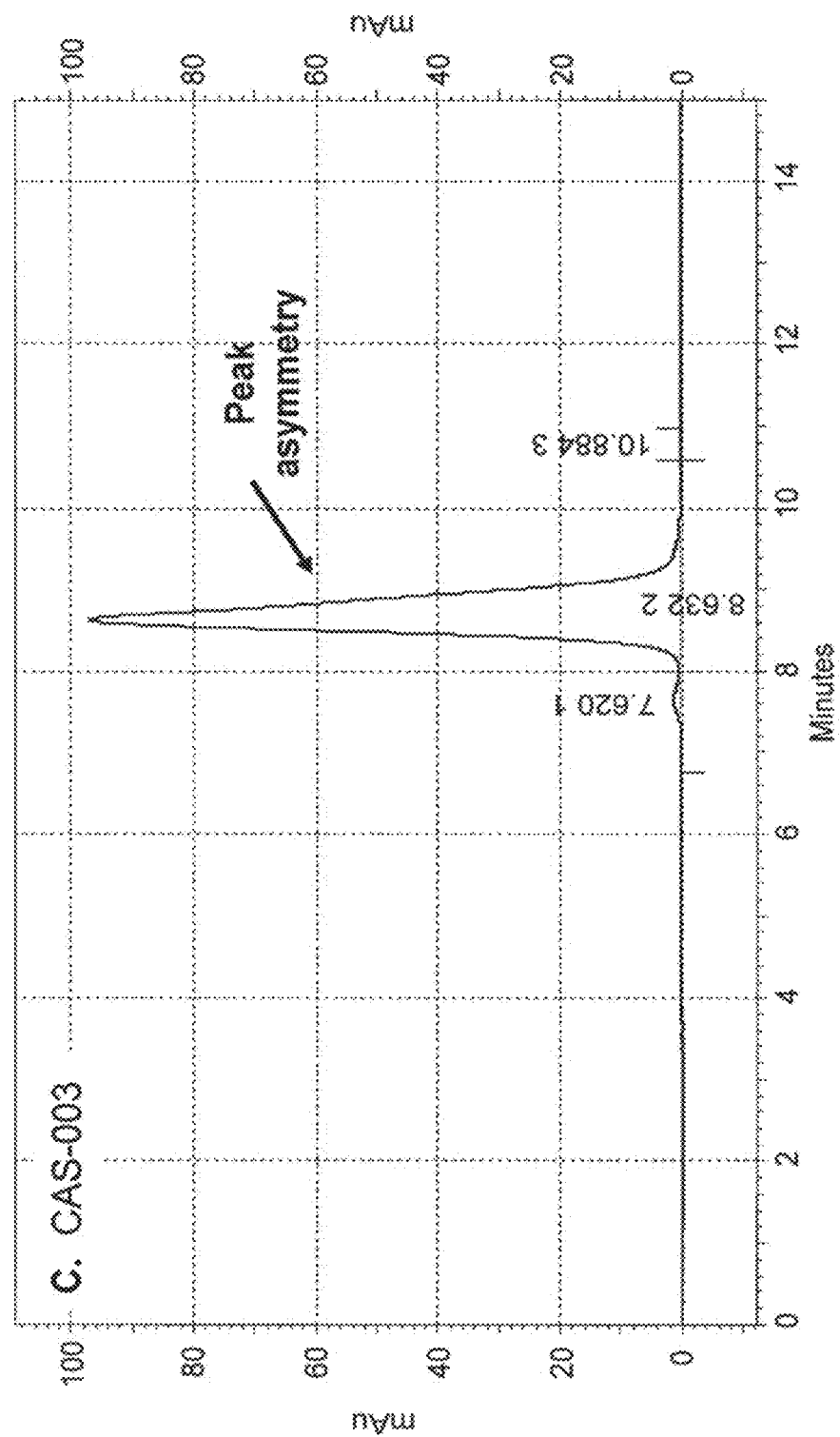
Figure 2D:
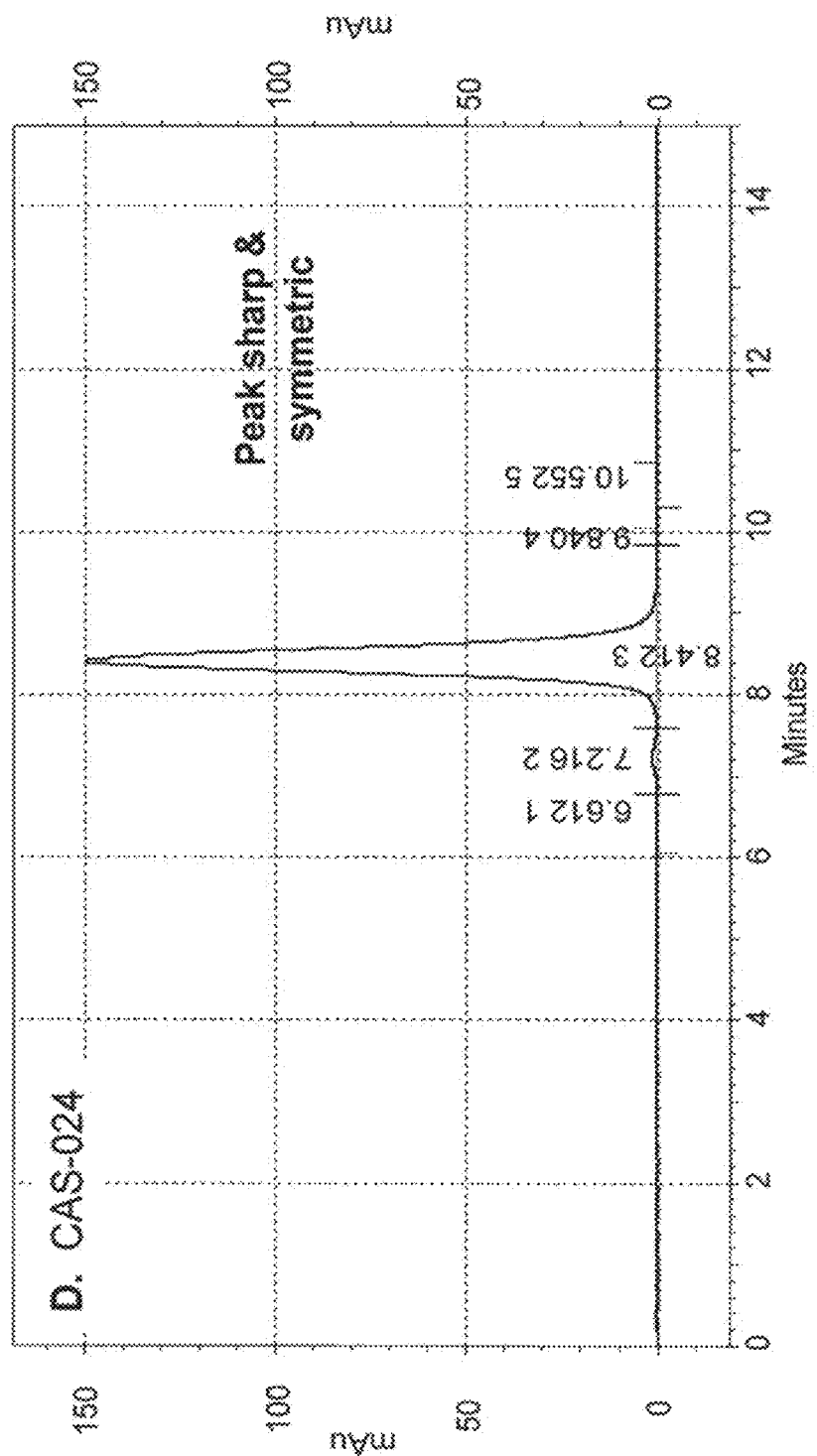

In one aspect, the present disclosure provides the CD37-specific binding molecule CAS-024 (SEQ ID NO:253), which is a humanized version of CAS-006 (a small modular immunopharmaceutical (SMIP) protein having the immunoglobulin variable regions from mouse anti-human CD37 monoclonal antibody G28-1). The CAS-024 SMIP protein is unexpectedly (1) expressed at up to about 25-fold higher levels than other humanized versions of CAS-006 (such as CAS-002, CAS-003; see Examples 2 and 5), (2) capable of binding CD37 as well as CAS-006 while other humanized versions do not (see Examples 4 and 5), and (3) produced as a homogenous population of molecules as compared the heterogenous nature of other humanized versions (see Example 3). Additionally, the instant disclosure provides the CD37-specific binding molecule CAS-024 (SEQ ID NO:253) for use in methods for reducing B-cells or treating disease associated with aberrant B-cell activity comprising administering to a subject in need thereof an effective amount of CAS-024 provided herein.

In another aspect, the present disclosure provides compositions and methods for the combined use of any CD37-specific binding molecule and bifunctional chemotherapeutics (such as bendamustine) to reduce B-cells or treat a disease associated with aberrant B-cell activity. A surprising result of this combination is that this combination of compounds acts synergistically and results in a substantially more effective therapeutic regimen.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include" and "comprise" are used synonymously. In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

A "binding domain" or "binding region" according to the present disclosure may be, for example, any protein, polypeptide, oligopeptide, or peptide that possesses the ability to specifically recognize and bind to a biological molecule (e.g., CD37) or complex of more than one of the same or different molecule or assembly or aggregate, whether stable or transient. A binding region includes any naturally occurring, synthetic, semi-synthetic, or recombinantly produced binding partner for a biological molecule or other target of interest. A variety of assays are known for identifying binding domains of the present disclosure that specifically bind a particular target, including Western blot, ELISA, or Biacore analysis.

Binding domains and fusion proteins thereof of this disclosure can be capable of binding to a desired degree, including "specifically or selectively binding" a target while not significantly binding other components present in a test sample, if they bind a target molecule with an affinity or $K_a$ (i.e., an equilibrium association constant of a particular binding interaction with units of 1/M) of, for example, greater than or equal to about $10^5 M^{-1}$, $10^6 M^{-1}$, $10^7 M^{-1}$, $10^8 M^{-1}$, $10^9 M^{-1}$, $10^{10} M^{-1}$, $10^{11} M^{-1}$, $10^{12} M^{-1}$, or $10^{13} M^{-1}$. "High affinity" binding domains refers to those binding domains with a $K_a$ of at least $10^7 M^{-1}$, at least $10^8 M^{-1}$, at least $10^9 M^{-1}$, at least $10^{10} M^{-1}$, at least $10^{11} M^{-1}$, at least $10^{12} M^{-1}$, at least $10^{13} M^{-1}$, or greater. "Low affinity" binding domains refers to those binding domains with a $K_a$ of up to $5\times10^7 M^{-1}$, up to $10^7 M^{-1}$, up to $10^6 M^{-1}$, up to $10^5 M^{-1}$, or less. Alternatively, affinity may be defined as an equilibrium dissociation constant ($K_d$) of a particular binding interaction with units of M (e.g., $10^{-5}$ M to $10^{-13}$ M). Affinities of binding domain polypeptides and fusion proteins according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

The term "CD37-specific binding molecules" refer to a protein, polypeptide, oligopeptide or peptide that specifically binds to CD37 with a $K_a$ of at least about $10^6$ $M^{-1}$ (e.g., at least about $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$).

The term "CD37-specific binding domain" refers to a portion or a domain of a CD37-specific binding molecule responsible for the specific CD37 binding of the molecule. A CD37-specific binding domain itself (i.e., without any other portion of the CD37-specific binding molecule) binds to CD37 with a $K_a$ of at least about $10^6$ $M^{-1}$ (e.g., at least about $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$). A CD37-specific binding domain itself may be sufficient as a CD37-specific binding molecule. Exemplary CD37-specific binding domains include CD37-specific scFv and Fab fragments, which can be derived from anti-CD37 antibodies, such as monoclonal antibody G28-1.

Terms understood by those in the art as referring to antibody technology are each given the meaning acquired in the art, unless expressly defined herein. For example, the terms "$V_L$" and "$V_H$" refer to the variable binding region derived from an antibody light and heavy chain, respectively. The variable binding regions are made up of discrete, well-defined sub-regions known as "complementarity determining regions" (CDRs) and "framework regions" (FRs). The terms "$C_L$" and "$C_H$" refer to an "immunoglobulin constant region," i.e., a constant region derived from an antibody light or heavy chain, respectively, with the latter region understood to be further divisible into $C_{H1}$, $C_{H2}$, $C_{H3}$ and $C_{H4}$ constant region domains, depending on the antibody isotype (IgA, IgD, IgE, IgG, IgM) from which the region was derived. A portion of the constant region domains makes up the Fc region (the "fragment crystallizable" region), which contains domains responsible for the effector functions of an immunoglobulin, such as ADCC (antibody-dependent cell-mediated cytotoxicity), CDC (complement-dependent cytotoxicity) and complement fixation, binding to Fc receptors, greater half-life in vivo relative to a polypeptide lacking an Fc region, protein A binding, and perhaps even placental transfer (see Capon et al., Nature, 337:525 (1989)). Further, a polypeptide containing an Fc region allows for dimerization or multimerization of the polypeptide.

A "hinge region" is an amino acid sequence interposed between and connecting a CD37-specific binding domain and another region (e.g., a CH2 region) in a fusion protein so that the fusion protein is still capable of specific binding to CD37 (i.e., with a $K_a$ of at least about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$). In certain embodiments, a hinge region is an immunoglobulin hinge region.

An "immunoglobulin hinge region" refers to a wild type immunoglobulin hinge region or an altered wild type immunoglobulin hinge region.

According to crystallographic studies, the immunoglobulin hinge region can be further subdivided functionally into three regions: the upper hinge region, the core region, and the lower hinge region. The upper hinge region includes amino acids from the carboxy end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the CH2 domain and includes residues in CH2. Id. The core hinge region of human IgG1 contains the sequence Cys-Pro-Pro-Cys (SEQ ID NO:264) which, when dimerized by disulfide bond formation, results in a cyclic octapeptide believed to act as a pivot, thus conferring flexibility.

A "wild type immunoglobulin hinge region," as used herein refers to a naturally occurring amino acid sequence interposed between and connecting CH1 and CH2 regions of a single chain of an antibody. It contains the upper hinge region, the core hinge region, and the portion of the lower hinge region that is not part of CH2 region. An exemplary wild type immunoglobulin hinge region is human IgG1 hinge region as set forth in SEQ ID NO:90, in which from its amino terminus to its carboxyl terminus, the first ten amino acids (EPKSCDKTHT, SEQ ID NO:263) form the upper hinge region, the next four amino acids (CPPC, SEQ ID NO:264) form the core hinge region, and the last amino acid (i.e., proline) is the first amino acid in the lower hinge region and is not part of CH2.

An "altered wild type immunoglobulin hinge region" or "altered immunoglobulin hinge region" refers to (a) a wild type immunoglobulin hinge region with up to 30% amino acid changes (e.g., up to 25%, 20%, 15%, 10%, or 5% amino acid substitutions or deletions), (b) a portion of a wild type immunoglobulin hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or (c) a portion of a wild type immunoglobulin hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length). When an altered wild type immunoglobulin hinge region is interposed between and connecting a CD37-specific binding domain and another region (e.g., a CH2 region) in a fusion protein, it allows the fusion protein to specifically bind to CD37 (i.e., with a $K_a$ of at least about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$). In certain embodiments, one or more cysteine residues in a wild type immunoglobulin hinge region may be substituted by one or more other amino acid residues (e.g., one or more serine residues). An altered immunoglobulin hinge region may alternatively or additionally have a proline residue of a wild type immunoglobulin hinge region substituted by another amino acid residue (e.g., a serine residue).

A "linker" refers to an amino acid sequence that connects a heavy chain variable region and a light chain variable region together and provides a spacer function compatible with interaction of the two sub-binding domains so that the resulting polypeptide is capable of CD37-specific binding.

"Derivative" as used herein refers to a chemically or biologically modified version of a compound that is structurally similar to a parent compound and (actually or theoretically) derivable from that parent compound. Generally, a "derivative" differs from an "analogue" in that a parent compound may be the starting material to generate a "derivative," whereas the parent compound may not necessarily be used as the starting material to generate an "analogue." A derivative may have different chemical or physical properties from the parent compound. For example, a derivative may be more hydrophilic or it may be a mutated sequence having altered reactivity (e.g., a CDR having an amino acid change that alters its affinity for a target) as compared to the parent compound or sequence.

"B-cell associated disorder or disease" refers to aberrant B-cell activity or activity that deviates from the normal, proper, or expected course. For example, a B-cell associated disorder or disease may include inappropriate proliferation of cells that have damaged or defective DNA or other cellular components. Aberrant B-cell activity may include cell proliferation characterized by inappropriately high levels of cell division, inappropriately low levels of apoptosis, or both. Such diseases may have, for example, single or multiple local abnormal proliferations of cells, groups of cells or tissue(s), whether cancerous or non-cancerous, benign or malignant. A B-cell associated disorder or disease may also include aberrant antibody production, such as production of autoantibodies, or overproduction of antibodies more desirable when produced at normal levels. It is also contemplated herein that aberrant B-cell activity may occur in certain subpopulations of B-cells and not in other subpopulations, or may include inappropriate stimulation of T-cells, such as by inappropriate antigen presentation to T-cells or by other B-cells pathway.

"Treatment" or "treating" refers to either a therapeutic treatment or prophylactic/preventative treatment. A therapeutic treatment may improve at least one symptom of disease in an individual receiving treatment or may delay worsening of a progressive disease in an individual, or prevent onset of additional associated diseases.

A "therapeutically effective amount (or dose)" or "effective amount (or dose)" of a specific binding molecule or compound refers to that amount of the compound sufficient to result in amelioration of one or more symptoms of the disease being treated. When applied to an individual active ingredient, administered alone, a therapeutically effective dose refers to that ingredient alone. When applied to a combination, a therapeutically effective dose refers to combined amounts of the active ingredients that result in the therapeutic effect, whether administered serially or simultaneously. The invention specifically contemplates that one or more specific binding molecules may be administered according to methods of the invention, each in an effective dose.

"An individual having, or suspected of having, a disease associated with aberrant B-cell activity" is an individual in whom a disease or a symptom of a disorder may be caused by aberrant B-cell activity or B-cell proliferation, may be exacerbated by aberrant B-cell activity, or may be relieved by regulation of B-cell activity. Examples of such diseases are a B-cell malignancy or B-cell cancer (for example, B-cell lymphoma, a B-cell leukemia or a B-cell myeloma), a disease characterized by autoantibody production or a disease characterized by inappropriate T-cell stimulation caused by inappropriate B-cell antigen presentation to T-cells or caused by other pathways involving B-cells.

Additional definitions are provided in the following detailed description of the present disclosure.

Humanized CD37-Specific Binding Molecules

In one aspect, the present disclosure provides humanized CD37-specific binding molecules. These molecules may be in any form that contains a humanized CD37-specific binding domain, including a humanized anti-CD37 antibody, an Fab fragment of a humanized anti-CD37 antibody, a humanized CD37-specific single chain Fv (scFv), a humanized CD37-specific SMIP protein, a humanized CD37-specific PIMS protein (a fusion protein comprising the components of SMIP in the reverse orientation), a humanized CD37-specific SCORPION protein, and other bi- or multi-specific binding proteins that comprise at least one humanized CD37-specific binding domain. Detailed description of SMIP proteins and methods for making the same may be found, for example, in U.S. Patent Publication Nos. 2003/0133939, 2003/0118592, and 2005/0136049 and WO 2005017148. Constructs and methods for making PIMS proteins are described in U.S. application Ser. No. 12/168,875. Methods for making SCORPION proteins may be found, for example, in PCT Application Publication No. WO 2007/146968. Other exemplary multi-functional fusion proteins may be found, for example, in U.S. Patent Application Publication No. 2006/0051844 and U.S. Pat. No. 7,166,707. Certain bi- or multi-specific binding proteins may comprise a CD37-specific scFv and one or more other binding domains that are not derived from an immunoglobulin.

Humanized CD37-Specific Binding Domains

An exemplary "humanized CD37-specific binding domain" is an immunoglobulin variable region specific for CD37 that comprises at least one human framework region.

A "human framework region" refers to a wild type (i.e., naturally occurring) framework region of a human immunoglobulin variable region, an altered framework region of a human immunoglobulin variable region with less than about 50% (e.g., preferably less than about 45%, 40%, 30%, 25%, 20%, 15%, 10%, 5%, or 1%) of the amino acids in the region are deleted or substituted (e.g., with one or more amino acid residues of a nonhuman immunoglobulin framework region at corresponding positions), or an altered framework region of a nonhuman immunoglobulin variable region with less than about 50% (e.g., less than 45%, 40%, 30%, 25%, 20%, 15%, 10%, or 5%) of the amino acids in the region deleted or substituted (e.g., at positions of exposed residues and/or with one or more amino acid residues of a human immunoglobulin framework region at corresponding positions) so that, in one aspect, immunogenicity is reduced.

In certain embodiments, a human framework region is a wild type framework region of a human immunoglobulin variable region. In certain other embodiments, a human framework region is an altered framework region of a human immunoglobulin variable region with amino acid deletions or substitutions at one, two, three, four or five positions. In yet certain other embodiments, a human framework region is an altered framework region of a non-human immunoglobulin variable region with amino acid deletions or substitutions at one, two, three, four or five positions.

In certain embodiments, a humanized CD37-specific binding domain comprises at least one, two, three, four, five, six, seven or eight human framework regions (FR) selected from human light chain FR1, human heavy chain FR1, human light chain FR2, human heavy chain FR2, human light chain FR3, human heavy chain FR3, human light chain FR4, and human heavy chain FR4.

Exemplary human FRs are set forth in SEQ ID NOS:140-146 (human heavy chain FR1), SEQ ID NOS:147, 150 and 151 (human heavy chain FR2), SEQ ID NO:154-160 (human heavy chain FR3), SEQ ID NOS: 161-163, 168 and 169 (human heavy chain FR4), SEQ ID NOS:170-172, 175, and 177-181 (human light chain FR1), SEQ ID NOS:182, 184-188 and 191 (human light chain FR2), SEQ ID NOS:194-198, 203 and 205 (human light chain FR3), and SEQ ID NOS:206-210 (human light chain FR4). Additional exemplary human FR regions may be found in FR regions of the CD37-specific SMIP proteins provided herein, such as CAS-001, CAS-002, CAS-003, or CAS-024.

Human FRs that may be present in CD37-specific binding domains also include variants of the exemplary FRs provided herein in which one or two amino acids of the exemplary FRs have been substituted or deleted.

In certain embodiments, a humanized CD37-specific binding domain comprises (a) a humanized light chain variable region that comprises a human light chain FR1, a human light chain FR2, a human light chain FR3, and a human light chain FR4, and (b) a humanized heavy chain variable region that comprises a human heavy chain FR1, a human heavy chain FR2, a human heavy chain FR3, and a human heavy chain FR4.

CD37-specific binding domains provided herein also comprise one, two, three, four, five, or six CDRs. Such CDRs may be nonhuman CDRs or altered nonhuman CDRs selected from CDR1, CDR2 and CDR3 of the light chain and CDR1, CDR2 and CDR3 of the heavy chain. In certain embodiments, a CD37-specific binding domain comprises (a) a light chain variable region that comprises a light chain CDR1, a light chain CDR2, and a light chain CDR3, and (b) a heavy chain variable region that comprises a heavy chain CDR1, a heavy chain CDR2, and a heavy chain CDR3.

Exemplary CDRs include CDR1 of the light chain as set forth in SEQ ID NO:61 (RASENVYSYLA) or SEQ ID NO:62 (RTSENVYSYLA), CDR1 of the heavy chain as set forth in SEQ ID NO:63 (GYNMN), CDR2 of the light chain as set forth in SEQ ID NO:64 (FAKTLAE), CDR2 of the heavy chain as set forth in SEQ ID NO:65 (NIDPYYGGT-TYNRKFKG), CDR3 of the light chain as set forth in SEQ ID NO:66 (QHHSDNPWT), CDR3 of the heavy chain as set forth in SEQ ID NO:67 (SVGPFDY), CDR3 of the heavy chain as set forth in SEQ ID NO:68 (SVGPFDS), and CDR3 of the heavy chain as set forth in SEQ ID NO:69 (SVGP-MDY). Preferred light chain CDR1 is SEQ ID NO:61 (RA-SENVYSYLA) and preferred heavy chain CDR3 include SEQ ID NO:68 (SVGPFDS) or SEQ ID NO:69 (SVGP-MDY).

Additional exemplary CDRs include CDR1 of the light chain as set forth in SEQ ID NO:128 (RTSQNVYSYLA), 129 (RTSESVYSYLA), 130 (RASQSVYSYLA), 131 (RASQSVSSYLA) and 132 (RASQSVSYYLA), CDR1 of the heavy chain as set forth in SEQ ID NOS:133 (SYMNM) and 134 (SYWIG), CDR2 of the light chain as set forth in SEQ ID NOS:135 (AASSLQS), 136 (GASTRAT) and 137 (DASNRAT), CDR2 of the heavy chain as set forth in SEQ ID NOS:138 (IIYPGDSDTRYSPSFQG) and 139 (RIDPSD-SYTNYSPSFQG), CDR3 of the light chain as set forth in SEQ ID NO:220 (QHHSDNPWT), and CDR3 of the heavy chain as set forth in SEQ ID NOS:211 (SVGPMDY), 212 (SVGPFDY), 213 (SVGPMDV), 214 (SVGPFDS), 215 (SVGPFDP), 216 (SVGPFQH), 217 (SVGPFDV), 218 (SVGPFDI) and 219 (SVGPFDL). Further exemplary CDRs include the CDRs in the CD37-specific SMIP proteins provided herein.

In certain embodiments, CD37-specific binding domains comprise a humanized light chain variable region that comprises from its amino terminus to carboxyl terminus: human light chain FR1, light chain CDR1, human light chain FR2, light chain CDR2, human light chain FR3, light chain CDR3, and human light chain FR4.

In certain embodiments, CD37-specific binding domains comprise a humanized light chain variable region that comprises from its amino terminus to carboxyl terminus: human light chain FR1, light chain CDR1 as set forth in SEQ ID NO:61 or 62, human light chain FR2, light chain CDR2 as set forth in SEQ ID NO:64, human light chain FR3, light chain CDR3 as set forth in SEQ ID NO:66, and human light chain FR4. In further embodiments, CD37-specific binding domains comprise, consist essentially of, or consist of a humanized light chain variable region that comprises from its amino terminus to carboxyl terminus: human light chain FR1 as set forth in SEQ ID NO:171, light chain CDR1 as set forth in SEQ ID NO:61, human light chain FR2 as set forth in SEQ ID NO:182, light chain CDR2 as set forth in SEQ ID NO:64, human light chain FR3 as set forth in SEQ ID NO:195, light chain CDR3 as set forth in SEQ ID NO:66, and human light chain FR4 as set forth in SEQ ID NO:206. Additional exemplary humanized light chains are set forth in SEQ ID NOS: 237-240 and include the light chains in humanized CD37-specific SMIP proteins provided herein.

In certain embodiments, CD37-specific binding domains comprise a humanized heavy chain variable region that comprises from its amino terminus to carboxyl terminus: human heavy chain FR1, heavy chain CDR1, human heavy chain FR2, heavy chain CDR2, human heavy chain FR3, heavy chain CDR3, and human heavy chain FR4.

In certain embodiments, CD37-specific binding domains comprise a humanized heavy chain variable region that comprises from its amino terminus to carboxyl terminus: human heavy chain FR1, heavy chain CDR1 as set forth in SEQ ID NO:63, human heavy chain FR2, heavy chain CDR2 as set forth in SEQ ID NO:65, human heavy chain FR3, heavy chain CDR3 as set forth in SEQ ID NO:67, 68 or 69, and human heavy chain FR4. In further embodiments, CD37-specific binding domains comprise consist essentially of, or consist of a humanized heavy chain variable region that comprises from its amino terminus to carboxyl terminus: human heavy chain FR1 as set forth in SEQ ID NO:144, heavy chain CDR1 as set forth in SEQ ID NO:63, human heavy chain FR2 as set forth in SEQ ID NO:151, heavy chain CDR2 as set forth in SEQ ID NO:65, human heavy chain FR3 as set forth in SEQ ID NO:158, heavy chain CDR3 as set forth in SEQ ID NO:67, 68 or 69, and human heavy chain FR4 as set forth in SEQ ID NO:161. Additional exemplary humanized light chains are set forth in SEQ ID NOS:242-245 and include the light chains in humanized CD37-specific SMIP proteins provided herein.

In certain embodiments, CD37-specific binding domains may be in the form of a Fab or scFv fragment. In a preferred embodiment, the CD37-specific binding domain is a humanized CD37-specific scFv that comprises a light chain variable region and a heavy chain variable region joined together via a linker. In further embodiments, both the light and heavy chain variable regions are humanized, and may comprise both a humanized light chain variable region as set forth in SEQ ID NO:238 and a humanized heavy chain variable region as set forth in SEQ ID NO:245.

In still further embodiments, only the light or heavy chain variable region is humanized. For example, CD37-specific binding domains may comprise a humanized light chain variable region (i.e., a light chain variable region that comprises at least one human FR) and a nonhuman heavy chain variable chain region (e.g., mouse or rat). Alternatively, CD37-specific binding domains may comprise a nonhuman light chain variable region (e.g., mouse or rat) and a humanized heavy chain variable chain region (i.e., a heavy chain variable region that comprises at least one human FR). Both types of CD37-specific binding domains may be referred to as a "hybrid human-nonhuman CD37-specific binding domain" or as a "chimeric CD37-specific binding domains."

In certain embodiments, the carboxyl terminus of the light chain variable region in a humanized CD37-specific scFv is linked to the amino terminus of the heavy chain variable region via a linker. Thus, the resulting scFv has from its amino terminus to its carboxyl terminus: the light chain variable region, the linker, and the heavy chain variable region. In certain other embodiments, the carboxyl terminus of the heavy chain variable region in a humanized CD37-specific scFv is linked to the amino terminus of the light chain variable region via a linker. Thus, the resulting scFv has from its amino terminus to its carboxyl terminus: the heavy chain variable region, the linker, and the heavy chain variable region.

In certain embodiments, the linkers have 5-30 amino acids, such as 15-25 amino acids. In certain embodiments, the linkers comprises $(Gly_nSer)_m$, wherein n and m may be an integer independently selected from 1 to 5 (SEQ ID NOs: 229, 272-293). For example, in certain embodiments, n is 4, and m is 1, 2, 3, 4 or 5 (SEQ ID NOs: 229, 272-275). In certain embodiments, one or two amino acids other than Gly or Ser may be present at the amino terminus, carboxyl terminus or both termini. In certain other embodiments, one or two amino acids other than Gly or Ser may be used to substitute a Gly or Ser in a linker that comprises $(Gly_nSer)_m$ with m and n as defined above. An exemplary linker has the sequence $(Gly_4S)_5$ as set forth in SEQ ID NO:229. Additional exemplary linker sequences are set forth in SEQ ID NOS:225-228.

In certain embodiments, humanized CD37-specific binding domains or CD37-specific binding molecules competes with G28-1 mAb for binding to CD37. In other words, in such embodiments, CD37 binding of G28-1 mAb is reduced in the presence of other CD37-specific binding domains (such as anti-CD37 monoclonal antibodies) or CD37-specific binding molecules compared to CD37 binding of G28-1 mAb in the absence of CD37-specific binding domains or CD37-specific binding molecules. Competitive binding assays are known in the art, such as those described in the Examples 4-6, and may be used to determine whether a given CD37-specific binding domain or CD37-specific binding molecule is capable of competing with G28-1 mAb for binding to CD37.

Humanized CD37-Specific SMIP Polypeptides

In certain embodiments, CD37-specific binding molecules are CD37-specific small modular immunopharmaceutical (SMIP) polypeptides. SMIP proteins are binding domain-immunoglobulin fusion proteins that typically comprise from their amino termini to carboxyl termini: a binding domain derived from an immunoglobulin (e.g., a scFv), a hinge region, and an effector domain (e.g., IgG CH2 and CH3 regions). In preferred embodiments, the CD37-specific binding SMIP polypeptides are humanized.

The hinge region of a humanized CD37-specific binding SMIP polypeptide may be an immunoglobulin hinge region. In certain embodiments, the hinge region is a wild type immunoglobulin hinge region, such as an IgG hinge, IgA hinge, IgD hinge, IgE hinge or a fragment thereof (e.g., 4 to 20 or 5 to 15 amino acids in length) that comprises a core hinge region. In certain preferred embodiments, a hinge region may be an antibody hinge region selected from human IgG1, human IgG2, human IgG3, human IgG4, or fragments or variants thereof. In some embodiments, the hinge region is a wild type immunoglobulin hinge region or portion thereof, such as a human immunoglobulin hinge region. Exemplary hinges for such embodiments are wild type human IgG1 hinge region as set forth in SEQ ID NO:90, wild type human IgA1 hinge as set forth in SEQ ID NO:115, wild type human IgA2 hinge as set forth in SEQ ID NO:116, wild type human IgG3 hinge as set forth in SEQ ID NO:118, a portion of human IgG3 hinge as set forth in SEQ ID NO:258, and human IgD hinge as set forth in SEQ ID NO:127. In certain embodiments, one or more amino acid residues may be added at the amino- or carboxy-terminus of a wild type immunoglobulin hinge region as part of fusion protein construct design. Such amino acid residues are referred to as "junction amino acids" (see Table 4).

In certain embodiments, the hinge region is an altered (mutated) wild type immunoglobulin hinge region, such as an altered wild type IgG immunoglobulin hinge region, or an altered portion of a wild type immunoglobulin hinge region. For example, the wild type human IgG1 hinge region contains three cysteine residues—the most N-terminal cysteine is referred to the first cysteine, whereas the most C-terminal cysteine in the hinge region is the third cysteine. In certain embodiments, the mutated human IgG1 hinge region has only two cysteine residues, such as a human IgG1 hinge region with the first cysteine substituted by a serine. In certain other embodiments, the mutated human IgG1 hinge region has only one cysteine residue. In certain embodiments, the proline C-terminal to the third cysteine in the human IgG1 hinge region is substituted, for example, by a serine. Exemplary mutated human IgG1 hinge regions are as set forth in SEQ ID NOS:92, 94, 102, 104, 255, 256, 106, 108, 257, 96, 110, 112, 98, and 100. Exemplary mutated portions of human IgG3 hinge regions are as set forth in SEQ ID NOS:120, 126, 259-261, 122, and 124. In certain embodiments, one or more amino acid residues may be added at the amino- or carboxy-terminus of a mutated immunoglobulin hinge region as part of fusion protein construct design. Examples of such modified hinge regions are indicated in italics in SEQ ID NOS:231-235.

In certain embodiments, a hinge region comprises or has a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical to a wild type immunoglobulin hinge region, such as a wild type human IgG1, IgG2, IgG3, IgG4, IgA1, IgA2, IgD and IgE hinges.

In further embodiments, altered hinge regions can be based on a wild type immunoglobulin hinge region (e.g., an IgG1 hinge region) and contain one or more (e.g., 1, 2, 3, or 4) insertions, one or more (e.g., 1, 2, 3, or 4) deletions, one or more (e.g., 1, 2, 3, or 4) amino acid substitutions (e.g., conservative amino acid substitutions or non-conservative amino acid substitutions), or a combination of the above-noted mutations, when compared with the wild type immunoglobulin hinge region, but provided that the modified hinge retains the flexibility or rigidity suitable for properly orienting the binding domain of a fusion binding protein to interact with its target. The insertion(s), deletion(s) or substitution(s) may be anywhere in the wild type immunoglobulin hinge region, including at the amino- or carboxy-terminus or both.

As described herein, CD37-specific SMIP polypeptides may comprise an immunoglobulin $C_{H2}$ region. In certain embodiments, the immunoglobulin $C_{H2}$ region is a wild type immunoglobulin $C_{H2}$ region, such as a wild type human immunoglobulin $C_{H2}$ region, including wild type human IgA1, IgA2, IgD, IgE, IgG1, IgG2, IgG3, IgG4 and IgM $C_{H2}$ regions. In certain embodiments, the immunoglobulin $C_{H2}$ region is a human IgG1 $C_{H2}$ region.

In certain other embodiments, the immunoglobulin $C_{H2}$ region is an altered wild type immunoglobulin $C_{H2}$ region. For example, the altered wild type immunoglobulin $C_{H2}$ region may be a human IgG1 $C_{H2}$ region but with one, two, three, four or five mutations at positions 234 to 238, 253, 279, 310, 318, 320, 322, and 331 (EU numbering, Ward et al., 1995 *Therap. Immunol.* 2:77-94). The mutations in such positions reduce or eliminate the antibody-dependent cell-mediated cytotoxicity (ADCC) activity, Fc receptor-binding capability, and/or complement fixation.

As described herein, a humanized CD37-specific SMIP polypeptides may comprise an immunoglobulin $C_{H3}$ region. In certain embodiments, an immunoglobulin $C_{H3}$ region polypeptide is a wild type immunoglobulin $C_{H3}$ region polypeptide, including a wild type $C_{H3}$ region of any one of the various immunoglobulin isotypes (e.g., IgA, IgD, IgG1, IgG2, IgG3, IgG4, IgE, or IgM) from various species (i.e., human, mouse, rat or other mammals). In other embodiments, an immunoglobulin $C_{H3}$ region polypeptide is a mutated immunoglobulin $C_{H3}$ region polypeptide. The mutations in the immunoglobulin $C_{H3}$ region may be at one or more positions that are involved in complement fixation, such as at H433 or N434.

In certain embodiments, a humanized CD37-specific SMIP polypeptides may contain one or more additional regions. Such additional regions may be a leader sequence at the amino-terminus for secretion of an expressed SMIP polypeptide, an additional Fc sub-region (e.g., a wild type or mutated $C_{H4}$ region of IgM or IgE), a tail sequence at its carboxy-terminus for identification or purification purposes (e.g., epitope tags for detection or purification, including a 6-Histidine tag or a FLAG epitope), or additional amino acid residues that arise from use of specific expression systems. Exemplary leader peptides of this disclosure include natural leader sequences or others, such as those as set forth in SEQ ID NOS:223 and 224.

This disclosure includes CD37-specific SMIP polypeptides that exhibit at least 80 percent identity (e.g., 82%, 84%, 85%, 86%, 88%, 90%, 92%, 94%, 95%, 96%, 97%, 98% or 99%) to the polypeptide set forth in SEQ ID NO:2, wherein the CD37-specific SMIP polypeptide binds CD37. In further embodiments, such polypeptides having at least 80% identity with SEQ ID NO:2 may be further humanized. Exemplary humanized CD37-specific SMIP polypeptides comprise, consist essential of, or consist of any amino acid sequence selected from the group consisting of SEQ ID NOS:6, 8, 10, 12, 14, 16, 18, 20, 22, 24, 26, 28, 30, 32, 34, 36, 38, 40, 42, 44, 46, 48, 52, 80, 82, 84, 86, 88, and 222 in which the leader sequences are deleted, as well as SEQ ID NOS:247-254 and 266-269.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values are generated by the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

In a preferred embodiment, the present disclosure provides a humanized CD37-specific SMIP polypeptide that comprises from amino terminus to carboxyl terminus: a humanized heavy chain variable region ($V_H$), a $(G_4S)_5$ linker (SEQ ID NO:229), a humanized light chain variable region ($V_L$), an altered IgG1 hinge, a human IgG1 CH2 region, and a human IgG1 CH3 region. The humanized heavy chain variable region comprises from its amino terminus to its carboxyl terminus: a human heavy chain FR1, a heavy chain CDR1 as set forth in SEQ ID NO:63, a human heavy chain FR2, a CDR2 as set forth in SEQ ID NO:65, a human heavy chain FR3, CDR3 as set forth in SEQ ID NO:67, 68 or 69, and a human heavy chain FR4. The humanized light chain variable region comprises from its amino terminus to its carboxyl terminus: a human light chain FR1, a light chain CDR1 as set forth in SEQ ID NO:61 or 62, a human light chain FR2, a light chain CDR2 as set forth in SEQ ID NO:64, a human light chain FR3, and a light chain CDR3 as set forth in SEQ ID NO:66, and a human light chain FR4.

In some of the above preferred embodiments, the human heavy chain FR1, FR2, and FR3 comprise SEQ ID NOS:144, 151, and 158, respectively, and the heavy chain FR4 comprises SEQ ID NO:161 or 162. In further preferred embodiments, the human light chain FR1, FR2, FR3, and FR4 comprise SEQ ID NOS:171, 182, 195, and 206, respectively. Alternatively, both the heavy and light chains contain these sequences.

The CAS-024 SMIP protein is unexpectedly (1) expressed at up to about 25-fold higher levels than other humanized versions of CAS-006 (such as CAS-002, CAS-003; see Examples 2 and 5), (2) capable of binding CD37 as well as CAS-006 while other humanized versions do not (see Examples 4 and 5), and (3) produced as a homogenous population of molecules as compared the heterogenous nature of other humanized versions (see Example 3) In a preferred embodiment, the instant disclosure provides a CD37-specific binding protein that comprises or consists of CAS-024 (SEQ ID NO:253). In particular, this humanized CD37-specific binding molecule has substantially the same CD37 binding affinity as its parent chimeric molecule (CAS-006, SMIP protein having the immunoglobulin variable regions from mouse anti-human CD37 monoclonal antibody G28-1) in contrast to other humanized molecules, is expressed at high levels compared to other humanized molecules, and/or shows a high degree of homogeneity when purified, for example, via size exclusion chromatography (SEC) in contrast to other humanized molecules. In addition, this CAS-024 CD37-specific binding molecule has been shown to be effective in inhibiting tumor growth and causing long term tumor regression.

The disclosure also includes an isolated nucleic acid molecule comprising a nucleotide sequence encoding humanized CD37-specific binding molecules and the components thereof, including human or humanized FRs, CDRs, humanized light chain variable regions, humanized heavy chain variable regions, humanized scFv, and humanized SMIP polypeptides. Exemplary isolated nucleic acid molecules that encode humanized CD37-specific SMIP polypeptides include those that comprise SEQ ID NOS:5, 7, 9, 11, 13, 15, 17, 19, 21, 23, 25, 27, 29, 31, 33, 35, 37, 39, 41, 43, 45, 47, 51, 79, 81, 83, 85, 87, and 221. In one embodiment, the disclosure includes vectors that comprise these nucleic acid molecules and host cells that comprise the vectors.

The disclosure also includes processes of producing the polypeptides described herein, comprising culturing the host cells under suitable conditions to express the polypeptides, and optionally isolating the polypeptides from the culture.

Compounds Useful for Combination Therapy

The present disclosure also provides a combination therapy using any of the CD37-specific binding molecules known in the art or disclosed herein and bifunctional chemotherapeutics (e.g., bendamustine).

The CD37-specific binding molecules useful for the combination therapy may be in any forms that contain a CD37-specific binding domain, including an anti-CD37 antibody, an Fab fragment of anti-CD37 antibody, a CD37-specific single chain Fv (scFv), a CD37-specific SMIP, a CD37-specific PIMS, a CD37-specific SCORPION, and other bi- or multi-specific binding proteins that comprise at least one CD37-specific binding protein.

In certain embodiments, the CD37-specific binding molecules useful for combination therapy with a bifunctional chemotherapeutic are CD37-specific antibodies. Such antibodies include those used for characterizing the CD37 antigen in the Third HLDA Workshop, i.e., HD28, G28-1, HH1, Bl14, WR17 and F93G6 (see, Ling and MacLennan, pp.

302-335 in Leucocyte Typing III. White Cell Differentiation Antigens, Oxford University Press (1987)). Other CD37-specific antibodies useful for the combination therapy include RFB-7, Y29/55, MB-1, M-B371, M-B372 and IPO-24 (see, Moldenhaurer, J. Biol., Regul. Homeost. Agents, 14: 281-283 (2000), stating that all these antibodies recognize only one CD37 epitope, and Schwartz-Albiez et al., 14: 905-914 (1988), indicating that the epitope is situated in the carbohydrate moiety of CD37). Another CD37-specific antibody that may be used in combination therapy is S-B3 (Biosys).

In certain embodiments, the CD37-specific binding molecules useful for combination therapy with a bifunctional chemotherapeutic are CD37-specific SMIP polypeptides. An exemplary SMIP polypeptide comprises SEQ ID NO:2. Additional exemplary SMIP polypeptides include those described in WO 2005017148, such as (1) G28-1 scFv (SSS-S) H WCH2 WCH3 comprising a G28-1 scFv, an altered human IgG1 hinge in which all three cysteine residues and a proline carboxyl terminus to the third cysteine in a human IgG1 hinge region are mutated to serine residues, and wild type human IgG1 CH2 and CH3 domains; (2) G28-1 scFv IgAH WCH2 WCH3 comprising a G28-1 scFv, a portion of human IgA hinge, and human IgG1 CH2 and CH3 domains; (3) G28-1 scFv VHL11S (SSS-S) H WCH2 CH3 comprising a G28-1 scFv, an altered human IgG1 hinge in which all three cysteine residues and a proline carboxyl terminus to the third cysteine in the hinge region are mutated to serine residues, and human IgG1 CH2 and CH3 domains, wherein the leucine at position 11 of the heavy chain variable region is substituted with a serine; (4) G28-1 scFv VH L11S (CSS-S) H WCH2 CH3 comprising a G28-1 scFv, an altered human IgG1 hinge in which the cysteine residues at the second and third positions and a proline carboxyl terminus to the third cysteine are substituted with serine residues, and human IgG1 CH2 and CH3 domains, wherein the leucine at position 11 of the heavy chain variable region is substituted with a serine; (5) G28-1 scFv VHL11S (CSC-S) H WCH2 CH3 comprising a G28-1 scFv, an altered human IgG1 hinge in which the cysteine residue at the second position and a proline carboxyl terminus to the cysteine at the third position were substituted with serine residues, and human IgG1 CH2 and CH3 domains, wherein the leucine at position 11 of the heavy chain variable region is substituted with a serine; (6) G28-1 scFv VH11S (SSC-P) H WCH2 WCH3 comprising a G28-1 scFv, an altered human IgG1 hinge in which the first and second cysteine residues in the hinge region are mutated to serine residues, and human IgG1 CH2 and CH3 domains, wherein the leucine at position 11 of the heavy chain variable region is substituted with a serine; (7) G28-1 scFv VH11S (SCS-S) H WCH2 WCH3 comprising a G28-1 scFv, an altered human IgG1 hinge in which the first and third cysteine residues and a proline carboxyl terminus to the third cysteine in the hinge regions are mutated to serine residues, and human IgG1 CH2 and CH3 domains, wherein the leucine at position 11 of the heavy chain variable region is substituted with a serine; (8) G28-1 scFv VHL11S (CCS-P) H WCH2 WCH3 comprising a G28-1 scFv, an altered human IgG1 hinge in which the third cysteine residue in the hinge region is substituted with a serine, and human IgG1 CH2 and CH3 domains, wherein the leucine at position 11 of the heavy chain variable region is substituted with a serine (9) G28-1 scFv VHL11S (SCC-P) H WCH2 WCH3 comprising a G28-1 scFv, an altered human IgG1 hinge in which the first cysteine is substituted with a serine, and human CH2 and CH3 domains, wherein the leucine at position 11 of the heavy chain variable region is substituted with a serine; (10) G28-1 scFv VH L11S mIgE CH2 CH3 CH4, comprising a G28-1 scFv and mouse IgE CH2, CH3 and CH4 regions, wherein the leucine at position 11 of the heavy chain variable region is substituted with a serine; (11) G28-1 scFv VH L11S mIgA WIgACH2 T4-CH3, comprising a G28-1 scFv, a mouse IgA hinge, and a wild type IgA CH2 and a truncated IgA CH3 domain lacking the 4 carboxy amino acids GTCY (SEQ ID NO:265); (12) G28-1 scFv VHL11S hIgE CH2 CH3 CH4, comprising a G28-1 scFv and human IgE CH2, CH3 and CH4 regions, wherein the leucine at position 11 of the heavy chain variable region is substituted with a serine; and (13) G28-1 scFv VHL11S hIgAH WIgACH2 TCH3 comprising a G28-1 scFv, a portion of human IgA hinge, a wild type IgA CH2 and a truncated IgA CH3 domain lacking the 4 carboxy amino acids GTCY (SEQ ID NO:265), wherein the leucine at position 11 of the heavy chain variable region is substituted with a serine.

In certain embodiments, CD37-specific binding molecules useful for combination therapy with a bifunctional chemotherapeutic are humanized CD37-specific binding molecules described herein, including humanized anti-CD37 antibodies, Fab fragments of humanized anti-CD37 antibody, humanized CD37-specific PIMS protein, humanized CD37-specific SCORPION protein, and other bi- or multi-specific binding proteins that comprise at least one humanized CD37-specific binding protein, especially humanized CD37-specific single chain Fv (scFv) and humanized CD37-specific SMIP polypeptides.

Certain CD37-specific binding molecules contemplated in this disclosure have affinities for CD37 of about 0.5 to about 10 nM. Another characteristic of certain CD37-binding molecules contemplated in this disclosure is that they exhibit a half life in circulation of about 5 to about 30 days.

In certain embodiments, CD37-specific binding molecules are capable of competing with G28-1 mAb in CD37-specific binding.

Bendamustine (4-[5-[Bis(2-chloroethyl)amino]-1-methylbenzimidazol-2-yl]butanoic acid) is a nitrogen mustard with alkylator and antimetabolite activities. Bendamustine has both an alkylating group and a benzimidazole ring. The alkylating group allows bendamustine metabolites to alkylate and crosslink macromolecules, resulting in DNA, RNA and protein synthesis inhibition, and subsequently apoptosis. The benzimidazole ring may allow bendamustine to act as a purine analogue. Bendamustine hydrochloride has trade names TREANDA® and RIBOMUSTIN®.

Although bendamustine or its salts are preferred therapeutic agents that may be used in combination with CD37-specific binding molecules, other therapeutic agents that both comprise one or more alkylating groups and are capable of functioning as a purine analogue may also be used in combination with CD37-specific binding molecules according to the present disclosure.

The term "alkylating group," as used herein, refers to a group that enables the compound comprising this group to attach an alkyl group to DNA. The compound that comprises an alkylating group may be referred to as an "alkylating agent." In certain embodiments, alkylating agents are nitrogen mustards.

The term "purine analogue" refers to an antimetabolite that mimics the structure of metabolic purines (e.g., adenine and guanine) and has one, two, three or four substituents at the purine ring that differ from metabolic purines. Exemplary purine analogues include azathioprine, mercaptopurine, thioguanine, fludarabine, pentostatin and cladribine.

A therapeutic agent is "capable of functioning as a purine analogue" if it possesses at least one function of a purine analogue. Exemplary functions of purine analogues include interference with or inhibition of purine nucleotide synthesis, purine nucleotide metabolism, nucleic acid synthesis, nucleic acid processing, or nucleic acid function, such as inhibiting ribonucleotide reductase, DNA polymerase, adenosine deaminase, and being incorporated into DNA or RNA.

Compositions and Methods

In one aspect, the present disclosure provides a method for reducing B cells or treating a disease associated with aberrant B cell activity comprising administering to a subject in need thereof (i.e., an individual having or suspected of having a disease associated with aberrant B-cell activity) an effective amount of a humanized CD37-specific binding molecule provided herein (e.g., CAS-024).

In another aspect, the present disclosure provides a method for reducing B cells or treating a disease associated with aberrant B cell activity comprising administering to a subject in need thereof an effective amount of a CD37-specific binding molecule (e.g., CAS-024) and a bifunctional chemotherapeutic (e.g., bendamustine). As described above, CD37-specific binding molecules useful for combination therapy with a bifunctional chemotherapeutic are not limited to humanized CD37-specific binding molecules, but include other CD37-specific binding molecules that have not been humanized.

In one embodiment, a composition comprising a CD37 therapeutic and a bifunctional chemotherapeutic act synergistically in reducing B cells or treating a disease associated with aberrant B cell activity. Two or more compounds that act synergistically interact such that the combined effect of the compounds is greater than the sum of the individual effects of each compound when administered alone (see, e.g., Berenbaum, Pharmacol. Rev. 41:93, 1989). For example, an interaction between small modular immunopharmaceutical that targets CD37 and another agent or compound may be analyzed by a variety of mechanistic and empirical models (see, e.g., Ouzounov et al., Antivir. Res. 55:425, 2002). A commonly used approach for analyzing the interaction between a combination of agents employs the construction of isoboles (iso-effect curves, also referred to as isobolograms), in which the combination of agents ($d_a$, $d_b$) is represented by a point on a graph, the axes of which are the dose-axes of the individual agents (see, e.g., Ouzounov et al., supra; see also Tallarida, J. Pharmacol. Exp. Therap. 298:865, 2001).

Another method for analyzing drug-drug interactions (antagonism, additivity, synergism) known in the art includes determination of combination indices (CI) according to the median effect principle to provide estimates of $IC_{50}$ values of compounds administered alone and in combination (see, e.g., Chou. In Synergism and Antagonism Chemotherapy. Eds. Chou and Rideout. Academic Press, San Diego Calif., pages 61-102, 1991; CalcuSyn™ software). A CI value of less than one represents synergistic activity, equal to one represents additive activity, and greater than one represents antagonism.

Still another exemplary method is the independent effect method (Pritchard and Shipman, Antiviral Res. 14:181, 1990; Pritchard and Shipman, Antiviral Therapy 1:9, 1996; MACSYNERGY™ II software, University of Michigan, Ann Arbor, Mich.). MACSYNERGY™ II software allows a three-dimensional (3-D) examination of compound interactions by comparing a calculated additive surface to observed data to generate differential plots that reveal regions (in the form of a volume) of statistically greater than expected (synergy) or less than expected (antagonism) compound interactions. For example, a composition comprising a CD37-specific binding molecule and a bifunctional chemotherapeutic alters viral replication will be considered to have synergistic activity or have a synergistic effect when the volume of synergy produced as calculated by the volume of the synergy peaks is preferably about 15% greater than the additive effect (that is, the effect of each agent alone added together), or preferably about a 2-fold to 10-fold greater than the additive effect, or preferably about a 3-fold to 5-fold or more greater than the additive effect.

In further embodiments, a CD37-specific binding molecule and a bifunctional chemotherapeutic can be administered to act synergistically in the treatment of B-cell malignancies or B-cell cancers. B-cell malignancies or B-cell cancers include B-cell lymphomas [such as various forms of Hodgkin's disease, non-Hodgkins lymphoma (NHL) or central nervous system lymphomas], leukemias [such as acute lymphoblastic leukemia (ALL), chronic lymphocytic leukemia (CLL), Hairy cell leukemia and chronic myoblastic leukemia] and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt lymphoma/leukemia, B-cell proliferations of uncertain malignant potential, lymphomatoid granulomatosis, and post-transplant lymphoproliferative disorder.

Burkitt's lymphoma (or "Burkitt's B cell malignancy", or "Burkitt's tumor", or "Malignant lymphoma, Burkitt's type") is a cancer of the lymphatic system (in particular, B lymphocytes). It can be divided into three main clinical variants: the endemic, the sporadic and the immunodeficiency-associated variants.

Non-Burkitt's B cell malignancies include, but are not limited to, B-cell chronic lymphocytic leukemia (CLL)/small lymphocytic lymphoma, B-cell prolymphocytic leukemia, an acute lymphoblastic leukemia (ALL), lymphoplasmacytic lymphoma (including, but not limited to, Waldenstrom's macroglobulinemia), marginal zone lymphomas (including, but not limited to, splenic marginal zone B-cell lymphoma, nodal marginal zone lymphoma, and extranodal marginal zone B-cell lymphoma of mucosa-associated lymphoid tissue (MALT) type), hairy cell leukemia, plasma cell myeloma/plasmacytoma, follicular lymphoma, mantle cell lymphoma (MCL), diffuse large cell B-cell lymphoma, transforming large B cell lymphoma, mediastinal large B-cell lymphoma, intravascular large B-cell lymphoma, primary effusion lymphoma, and non-Burkitt's non-Hodgkins lymphoma (NHL).

Disorders characterized by autoantibody production are often considered autoimmune diseases. Autoimmune diseases include, but are not limited to: arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic thrombocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans, autoimmune thyroid disease (such as Graves' disease and Hashimoto's thyroiditis), Sjogren's syndrome, and idiopathic inflammatory myopathy (IIM), including dermatomyositis (DM) and polymyositis (PM). The above autoimmune diseases may also be treated with humanized CD37-specific binding molecules or with the combination of CD37-specific binding molecules and a bifunctional chemotherapeutic.

In one aspect of the disclosure, a humanized CD37-specific binding molecule or a combination of a CD37-specific binding molecule with a bifunctional chemotherapeutic is administered in a pharmaceutical composition. To administer a humanized CD37-specific binding molecule or a combination of a CD37-specific binding molecule with a bifunctional chemotherapeutic to human or test animals, it is preferable to formulate the binding molecule or the combination in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below.

"Pharmaceutically acceptable carriers" include any and all clinically useful solvents, dispersion media, coatings, antibacterial and antifungal agents, isotonic and absorption delaying agents and the like. In addition, compounds may form solvates with water or common organic solvents. Such solvates are contemplated as well.

Pharmaceutical compositions of the present disclosure containing a humanized CD37-specific binding molecule or a combination of a CD37-specific binding molecule with a bifunctional chemotherapeutic used in a method of the disclosure may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present disclosure.

Formulation of the pharmaceutical composition will vary according to the route of administration selected (e.g., solution, emulsion). An appropriate composition comprising the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

A CD37-specific binding molecule, a combination of a CD37-specific binding molecule with a bifunctional chemotherapeutic, or a composition comprising the binding molecule or the combination can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of CD37-specific binding molecule or bifunctional chemotherapeutic in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 mL sterile buffered water, and 50 mg of antibody. A typical composition for intravenous infusion could be made up to contain 250 mL of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of CD37-specific binding molecules (including humanized CD37-specific binding molecules) is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial or antifungal agents, for example, parabens, chlorobutanol, phenol, sorbic acid, thimerosal, or the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (J. Pharm. Sci., 85:1282-1285, 1996) and Oliyai and Stella (Ann. Rev. Pharmacol. Toxicol., 32:521-544, 1993).

In addition, the properties of hydrophilicity and hydrophobicity of the compositions contemplated for use in the disclosure are well balanced, thereby enhancing their utility for both in vitro and especially in vivo uses, while other compositions lacking such balance are of substantially less utility. Specifically, compositions contemplated for use in the disclosure have an appropriate degree of solubility in aqueous media which permits absorption and bioavailability in the body, while also having a degree of solubility in lipids which permits the compounds to traverse the cell membrane to a putative site of action. Thus, antibody compositions contemplated are maximally effective when they can be delivered to the site of target antigen activity.

In one aspect, methods of the disclosure include a step of administration of a CD37-specific binding molecule composition. In certain embodiments, the combinations of compounds may be administered concurrently, together in the same pharmaceutically acceptable carrier, or separately (but concurrently). In other embodiments, the CD37 immunotherapeutic (i.e., the CD37-specific binding molecule) and a bifunctional chemotherapeutic can be administered sequentially, in any order and in any combination.

The binding molecule, bifunctional chemotherapeutic, or combination compositions may be administered orally, topically, transdermally, parenterally, by inhalation spray, vaginally, rectally, or by intracranial injection, or any combination thereof. In one embodiment, both the CD37-specific binding molecule and the bifunctional chemotherapeutic are administered parenterally, either concurrently or sequentially. The term parenteral, as used herein, includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient. Injection, especially intravenous, is preferred.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly or monthly.

Binding molecule, bifunctional chemotherapeutic, or combination compositions of this disclosure may comprise one or more than one binding molecule, bifunctional chemotherapeutic, or any combination thereof. Also contemplated by the present disclosure is the administration of binding molecule, bifunctional chemotherapeutic, or combination compositions in conjunction with a further therapeutic agent. Further therapeutic contemplated by the disclosure are listed in paragraphs below.

A further therapeutic agent may be a B-cell-associated molecule. Other B-cell-associated molecules contemplated by the disclosure include binding molecules which bind to B-cell surface molecules that are not CD37. B-cell-associated molecules, include CD19 (B-lymphocyte antigen CD19, also referred to as B-lymphocyte surface antigen B4, or Leu-12), CD20, CD21, CD22 (B-cell receptor CD22, also referred to as Leu-14, B-lymphocyte cell adhesion molecule, or BL-CAM), CD23, CD40 (B-cell surface antigen CD40, also referred to as Tumor Necrosis Factor receptor superfamily member 5, CD40L receptor, or Bp50), CD80 (T lymphocyte activation antigen CD80, also referred to as Activation B7-1 antigen, B7, B7-1, or BB1), CD86 (T lymphocyte activation antigen CD86, also referred to as Activation B7-2 antigen, B70, FUN-1, or BU63), CD137 (also referred to as Tumor Necrosis Factor receptor superfamily member 9), CD152 (also referred to as cytotoxic T-lymphocyte protein 4 or CTLA-4), L6 (Tumor-associated antigen L6, also referred to as Transmembrane 4 superfamily member 1, Membrane component surface marker 1, or M3S1), CD30 (lymphocyte activation antigen CD30, also referred to as Tumor Necrosis Factor receptor superfamily member 8, CD30L receptor, or Ki-1), CD50 (also referred to as Intercellular adhesion molecule-3 (ICAM3), or ICAM-R), CD54 (also referred to as Intercellular adhesion molecule-1 (ICAM1), or Major group rhinovirus receptor), B7-H1 (ligand for an immunoinhibitory receptor expressed by activated T cells, B-cells, and myeloid cells, also referred to as PD-L1; see Dong, et al., "B7-H1, a third member of the B7 family, co-stimulates T-cell proliferation and interleukin-10 secretion," Nat. Med., 5:1365-1369 (1999), CD134 (also referred to as Tumor Necrosis Factor receptor superfamily member 4, OX40, OX40L receptor, ACT35 antigen, or TAX-transcriptionally activated glycoprotein 1 receptor), 41 BB (4-1 BB ligand receptor, T-cell antigen 4-1 BB, or T-cell antigen ILA), CD153 (also referred to as Tumor Necrosis Factor ligand superfamily member 8, CD30 ligand, or CD30-L), CD154 (also referred to as Tumor Necrosis Factor ligand superfamily member 5, TNF-related activation protein, TRAP, or T cell antigen Gp39), Toll receptors, or the like.

Examples of chemotherapeutic agents contemplated as further therapeutic agents include alkylating agents, such as nitrogen mustards (e.g., mechlorethamine, cyclophosphamide, ifosfamide, melphalan, and chlorambucil); nitrosoureas (e.g., carmustine (BCNU), lomustine (CCNU), and semustine (methyl-CCNU)); ethyleneimines and methylmelamines (e.g., triethylenemelamine (TEM), triethylene thiophosphoramide (thiotepa), and hexamethylmelamine (HMM, altretamine)); alkyl sulfonates (e.g., buslfan); and triazines (e.g., dacabazine (DTIC)); antimetabolites, such as folic acid analogues (e.g., methotrexate, trimetrexate, and pemetrexed (multi-targeted antifolate)); pyrimidine analogues (such as 5-fluorouracil (5-FU), fluorodeoxyuridine, gemcitabine, cytosine arabinoside (AraC, cytarabine), 5-azacytidine, and 2,2'-difluorodeoxycytidine); and purine analogues (e.g, 6-mercaptopurine, 6-thioguanine, azathioprine, 2'-deoxycoformycin (pentostatin), erythrohydroxynonyladenine (EHNA), fludarabine phosphate, 2-chlorodeoxyadenosine (cladribine, 2-CdA)); Type I topoisomerase inhibitors such as camptothecin (CPT), topotecan, and irinotecan; natural products, such as epipodophylotoxins (e.g., etoposide and teniposide); and vinca alkaloids (e.g., vinblastine, vincristine, and vinorelbine); anti-tumor antibiotics such as actinomycin D, doxorubicin, and bleomycin; radiosensitizers such as 5-bromodeozyuridine, 5-iododeoxyuridine, and bromodeoxycytidine; platinum coordination complexes such as cisplatin, carboplatin, and oxaliplatin; substituted ureas, such as hydroxyurea; and methylhydrazine derivatives such as N-methylhydrazine (MIH) and procarbazine.

Further therapeutic agents contemplated by this disclosure for treatment of autoimmune diseases are referred to as immunosuppressive agents, which act to suppress or mask the immune system of the individual being treated. Immunosuppressive agents include, for example, non-steroidal anti-inflammatory drugs (NSAIDs), analgesics, glucocorticoids, disease-modifying antirheumatic drugs (DMARDs) for the treatment of arthritis, or biologic response modifiers. Compositions in the DMARD description are also useful in the treatment of many other autoimmune diseases aside from RA.

Exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g. etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

It is contemplated the binding molecule composition and the further therapeutic agent may be given simultaneously in the same formulation. Alternatively, the agents are administered in a separate formulation but concurrently, with concurrently referring to agents given, for example, within minutes, hours or days of each other.

In another aspect, the further therapeutic agent is administered prior to administration of the binding molecule, bifunctional chemotherapeutic, or combination composition. Prior administration refers to administration of the further therapeutic agent within the range of minutes, hours, or one week prior to treatment with the binding molecule, bifunctional chemotherapeutic, or combination composition. It is further contemplated that the further therapeutic agent is administered subsequent to administration of the binding molecule composition. Subsequent administration is meant to describe administration more than minutes, hours, or weeks after binding molecule, bifunctional chemotherapeutic, or combination composition treatment or administration.

It is further contemplated that when the binding molecule is administered in combination with a further therapeutic agent, wherein the further therapeutic agent is a cytokine or growth factor, or a chemotherapeutic agent, the administration may also include use of a radiotherapeutic agent or radiation therapy. The radiation therapy administered in combination with an antibody composition is administered as determined by the treating physician, and at doses typically given to patients being treated for cancer.

These compositions may be administered in a single dose or in multiple doses. Standard dose-response studies, first in animal models and then in clinical testing, reveal optimal dosages for particular disease states and patient populations.

The administration of the binding molecule, bifunctional chemotherapeutic or combination composition decreases the B-cell population by at least 20% after a single dose of treatment. In one embodiment, the B-cell population is decreased by at least about 20, about 30, about 40, about 50, about 60, about 70, about 80, about 90, or about 100%. B-cell reduction is defined as a decrease in absolute B-cell count below the lower limit of the normal range. B-cell recovery is defined as a return of absolute B-cell count to, for example, 70%, 80%, 90% of a subject's baseline value or normal range. Further, the administration of binding molecule, bifunctional chemotherapeutic, or combination composition of this disclosure results in desired clinical effects in the disease or disorder being treated.

In some embodiments, patients suffering from a disease associated with aberrant B cell activity who receive treatment according to the disclosure may demonstrate an overall beneficial response to the treatment, based on clinical criteria well known and commonly used in the art and as described below.

For example, in patients affected by rheumatoid arthritis, the administration may improve the patient's condition by a clinically significant amount [e.g., achieves the American College of Rheumatology Preliminary Detection of Improvement (ACR20)], and/or an improvement of 20% in tender and swollen joint and 20% improvement in 3/5 remaining ACR measures (Felson et al., *Arthritis Rheum.* 1995, 38:727-35). Biological measures for improvement in an RA patient after administration of CD37-specific and CD20-specific binding molecules include measurement of changes in cytokine levels, measured via protein or RNA levels. Cytokines of interest include, but are not limited to, TNF-α, IL-1, interferons, Blys, and APRIL. Cytokine changes may be due to reduced B cell numbers or decreased activated T cells. In RA patients, markers relevant to bone turnover (bone resorption or erosion) are measured before and after administration of CD20-specific binding molecules. Relevant markers include, but are not limited to, alkaline phosphatase, osteocalcin, collagen breakdown fragments, hydroxyproline, tartrate-resistant acid phosphatase, and RANK ligand (RANKL). Other readouts relevant to the improvement of RA include measurement of C reactive protein (CRP) levels, erythrocyte sedimentation rate (ESR), rheumatoid factor, CCP (cyclic citrullinated peptide) antibodies and assessment of systemic B cell levels and lymphocyte count via flow cytometry. Specific factors can also be measured from the synovium of RA patients, including assessment of B cell levels in synovium from synovium biopsy, levels of RANKL and other bone factors and cytokines set out above.

In a related aspect, the effects of combination administration on other diseases may be measured according to standards known in the art. For example, it is contemplated that Crohn's disease patients treated according to the invention achieve an improvement in Crohn's Disease Activity Index (CDAI) in the range of about 50 to about 70 units, wherein remission is at 150 units (Simonis et al, *Scand. J. Gastroent.* 1998, 33:283-8). A score of 150 or 200 is considered normal, while a score of 450 is considered a severe disease score. It is further desired that administration of the CD37-specific and CD20-specific binding molecules results in a reduction in perinuclear anti-neutrophil antibody (pANCA) and anti-*Saccharomyces cerevisiae* antibody (ASCA) in individuals affected by inflammatory bowel disease.

It is further contemplated that adult and juvenile myositis patients treated according to the disclosure may achieve an improvement in core set of evaluations, such as 3 out of 6 of the core set measured improved by approximately 20%, with not more than 2 of the core measurements worse by approximately 25% (see Rider et al., *Arthritis Rheum.* 2004, 50:2281-90).

It is further contemplated that SLE patients treated according to the disclosure may achieve an improvement in Systemic Lupus Activity Measure (SLAM) or SLE Disease Activity Index (SLEDAI) score of at least 1 point (Gladman et al, *J Rheumatol* 1994, 21:1468-71) (Tan et al., Arthritis Rheum. 1982, 25:1271-7). A SLAM score of >5, or SLEDAI score>2, is considered clinically active disease. A response to treatment may be defined as improvement or stabilization over the in 2 disease activity measures (the SLE Disease Activity Index [SLEDAI] and the Systemic Lupus Activity Measure) and 2 quality of life measures (patient's global assessment and the Krupp Fatigue Severity Scale) (Petri et al., *Arthritis Rheum.* 2004, 50:2858-68.) It is further contemplated that administration of the binding molecule to SLE patients results in a reduction in anti-double-stranded DNA antibodies. Alternatively, improvement may be gauged using the British Isles Lupus Assessment Group Criteria (BILAG).

It is further contemplated that multiple sclerosis patients treated according to the disclosure may achieve an improvement in clinical score on the Kurtzke Expanded Disability status scale (EDSS) (Kurtzke, F., *Neurology* 1983, 33:1444-52) of at least 0.5, or a delay in worsening of clinical disease of at least 1.0 on the Kurtzke scale (Rudick et al., Neurology 1997, 49:358-63).

It is further contemplated that patients suffering from IIM treated according to the disclosure may achieve a reduction in at least one of five criteria set out in the Idiopathic Inflammatory Myopathy Criteria (IIMC) assessment (Miller, F., supra). It is further contemplated that administration to IIM patients may result in a reduction in IIM associated factors selected from the group consisting of creatine kinase (CK), lactate dehydrogenase, aldolase, C-reactive protein, aspartate aminotransferase (AST), alanine aminotransferase (ALT), and antinuclear autoantibody (ANA), myositis-specific antibodies (MSA), and antibody to extractable nuclear antigens. Alternatively, patients meet 3 out of 6 of the criteria set out in Rider et al., Arthritis Rheum., 50(7):2281-2290 (2004), with worsening in no more than 2 criteria.

In some embodiments, patients suffering from a B cell cancer that receive treatment according to the disclose may demonstrate an overall beneficial response to the treatment, based on clinical criteria well-known and commonly used in the art, and as described below, such as a decrease in tumor size, decrease in tumor number and/or an improvement in disease symptoms.

Exemplary clinical criteria are provided by the U.S. National Cancer Institute (NCI), which has divided some of the classes of cancers into the clinical categories of "indolent" and "aggressive" lymphomas. Indolent lymphomas include follicular cell lymphomas, separated into cytology "grades," diffuse small lymphocytic lymphoma/chronic lymphocytic leukemia (CLL), lymphoplasmacytoid/Waldenstrom's Macroglobulinemia, Marginal zone lymphoma and Hairy cell leukemia. Aggressive lymphomas include diffuse mixed and large cell lymphoma, Burkitt's lymphoma/diffuse small noncleaved cell lymphoma, Lymphoblastic lymphoma, Mantle cell lymphoma and AIDS-related lymphoma. In some cases, the International Prognostic Index (IPI) is used in cases of aggressive and follicular lymphoma. Factors to consider in the IPI include age (<60 years of age versus>60 years of age), serum lactate dehydrogenase (levels normal versus elevated), performance status (0 or 1 versus 2-4) (see definition below), disease stage (I or II versus III or IV), and extranodal site involvement (0 or 1 versus 2-4). Patients with 2 or more risk factors have less than a 50% chance of relapse-free and overall survival at 5 years.

Performance status in the aggressive IPI is defined as follows: Grade Description: 0 Fully active, able to carry on all pre-disease performance without restriction; 1 Restricted in physically strenuous activity but ambulatory and able to carry out work of a light or sedentary nature, e.g., light house work, office work; 2 Ambulatory and capable of all selfcare but unable to carry out any work activities, up to and about more than 50% of waking hours; 3 Capable of only limited selfcare, confined to bed or chair more than 50% of waking hours; 4 Completely disabled, unable to carry on any selfcare, totally confined to bed or chair; and, 5 Dead. (See, The International Non-Hodgkin's Lymphoma Prognostic Factors Project. A predictive model for aggressive non-Hodgkin's lymphoma. *N. Engl. J. Med.* 329:987-94, 1993.)

Typically, the grade of lymphoma is clinically assessed using the criterion that low-grade lymphoma usually presents as a nodal disease and is often indolent or slow-growing. Intermediate- and high-grade disease usually presents as a much more aggressive disease with large extranodal bulky tumors.

The Ann Arbor classification system is also used to measure progression of tumors, especially non-Hodgkin's lymphomas. In this system, stages I, II, III, and IV of adult NHL can be classified into A and B categories depending on whether the patient has well-defined generalized symptoms (B) or not (A). The B designation is given to patients with the following symptoms: unexplained loss of more than 10% body weight in the 6 months prior to diagnosis, unexplained fever with temperatures above 38° C. and drenching night sweats. Definitions of the stages are as follows: Stage I-involvement of a single lymph node region or localized involvement of a single extralymphatic organ or site. Stage II-involvement of two or more lymph node regions on the same side of the diaphragm or localized involvement of a single associated extralymphatic organ or site and its regional lymph nodes with or without other lymph node regions on the same side of the diaphragm. Stage III-involvement of lymph node regions on both sides of the diaphragm, possibly accompanying localized involvement of an extralymphatic organ or site, involvement of the spleen, or both. Stage IV-disseminated (multifocal) involvement of one or more extralymphatic sites with or without associated lymph node involvement or isolated extralymphatic organ involvement with distant (non-regional) nodal involvement. For further details, see The International Non-Hodgkin's Lymphoma Prognostic Factors Project: A predictive model for aggressive non-Hodgkin's lymphoma, New England J. Med. (1993) 329:987-994.

In one aspect, a therapeutic effect of the methods according to the disclosure is determined by the level of response, for example, a partial response is defined as tumor reduction to less than one-half of its original size. A complete response is defined as total elimination of disease confirmed by clinical or radiological evaluation. In one embodiment, the individual receiving treatment according to the invention demonstrates at least a partial response to treatment.

According to the Cheson criteria for assessing NHL developed in collaboration with the National Cancer Institute (Cheson et al., *J Clin Oncol.* 1999, 17:1244; Grillo-Lopez et al., *Ann Oncol.* 2000, 11:399-408), a complete response is obtained when there is a complete disappearance of all detectable clinical and radiographic evidence of disease and disease-related symptoms, all lymph nodes have returned to normal size, the spleen has regressed in size, and the bone marrow is cleared of lymphoma.

An unconfirmed complete response is obtained when a patient shows complete disappearance of the disease and the spleen regresses in size, but lymph nodes have regressed by more than 75% and the bone marrow is indeterminate. An unconfirmed complete response meets and exceeds the criteria for partial response. An overall response is defined as a reduction of at least 50 percent in overall tumor burden.

Similar criteria have been developed for various other forms of cancers or hyperproliferative diseases and are readily available to a person of skill in the art. See, e.g., Cheson et al., *Clin Adv Hematol Oncol* 2006, 4:4-5, which describes criteria for assessing CLL; Cheson et al., *J Clin Oncol.* 2003, 21:4642-9, which describes criteria for AML; Cheson et al., *Blood* 2000, 96:3671-4, which describes criteria for myelodysplastic syndromes.

In another aspect, a therapeutic response in patients having a B cell cancer is manifest as a slowing of disease progression compared to patients not receiving therapy. Measurement of slowed disease progression or any of the above factors may be carried out using techniques well-known in the art, including bone scan, CT scan, gallium scan, lymphangiogram, MRI, PET scans, ultrasound, and the like.

As an additional aspect, the disclosure includes kits which comprise one or more compounds or compositions useful in the methods of this disclosure packaged in a manner which facilitates their use to practice methods of the disclosure. In a simplest embodiment, such a kit includes a compound or composition described herein as useful for practice of a method of the disclosure packaged in a container such as a sealed bottle or vessel, with a label affixed to the container or included in the package that describes use of the compound or composition to practice the method of the disclosure. Preferably, the compound or composition is packaged in a unit dosage form. The kit may further include a device suitable for administering the composition according to a preferred route of administration or for practicing a screening assay. The kit may include a label that describes use of the binding molecule composition(s) in a method of the disclosure.

EXAMPLES

Example 1

CD37-Specific Binding Molecules

Various CD37-specific binding proteins can be made with exemplary components provided in Tables 2-4. For example, antibodies or SMIP molecules can be made, and these molecules can be chimeric, humanized, or human. More specifically, preferred light chain variable region CDRs are found in SEQ ID NOS:236-240 and 247-254 and preferred heaving chain variable domain CDRs include SEQ ID NOS:241-245 and 247-254. Also, preferred light and heavy chain variable regions are provided in SEQ ID NOS:236-240 and SEQ ID NOS:241-245, respectively. Preferred light and heavy chain variable regions may also be found in SEQ ID NOS:247-254. Preferred variable domain linkers include SEQ ID NOS:225-229, while preferred hinges include SEQ ID NOS:230-235.

A particularly preferred embodiment is CAS-024 [G28-1 VH (M99F, Y102S)—VL (T25A) scFv (SSC-P) H WCH2 WCH3], which is a recombinant, 483 amino acid single-chain fusion protein that binds to human CD37. The binding domain comprises a humanized scFv based on the G28-1 antibody variable region CDRs, including mutations in the heavy chain CDR3 and in the light chain CDR1. The variable domains are linked by a $(G_4S)_5$ (25 amino acid) sequence (SEQ ID NO:229), which is connected via a three amino acid junction (GDQ) to the amino terminus of a modified upper and core IgG1 hinge region (wherein the first two of three cysteines found in these hinge regions are each substituted with a serine). The carboxy-terminus of the hinge is fused to an effector domain comprising CH2 and CH3 domains of $IgG_1$. The amino acid sequence of CAS-024 is set out in SEQ ID NO:253. FIG. 1 shows heavy and light chain variable region amino acid sequence alignments of mouse G28.1 and CAS-024 sequences, along with a consensus identity sequence.

TABLE 1

Exemplary CD-37 Specific SMIP Constructs

| Construct | Description† | Linker | Hinge* | AA SEQ ID NO. |
|---|---|---|---|---|
| CAS-001 | Vk3: VH5-51 | 16aa $(G_4S)_2(G_4T)G$ | SSC-P | 6 |
| CAS-002 | Vk3: VH5 JH4 CDRL1 (T25A); CDRH3 (M99F) | 16aa $(G_4S)_2(G_4T)G$ | SSC-P | 48 |
| CAS-003 | Vk3: VH5 JH5a CDRL1 (T25A); CDRH3 (M99F; Y102S) | 16aa $(G_4S)_2(G_4T)G$ | SSC-P | 52 |
| CAS-007 | Vk3: VH5-51 (Linker TG→SS) | 16aa $(G_4S)_3S$ | SSC-P | 8 |
| CAS-008 | Vk3: VH5-51 VH V11S | 16aa $(G_4S)_2(G_4T)G$ | SSC-P | 10 |
| CAS-009 | Vk3: VH5-51 CDRL1 (E27Q) | 16aa $(G_4S)_2(G_4T)G$ | SSC-P | 12 |
| CAS-010 | Vk3: VH5-51 CDRL1 (N28S) | 16aa $(G_4S)_2(G_4T)G$ | SSC-P | 14 |
| CAS-011 | Vk3: VH5-51 CDRL1 (T25A) | 16aa $(G_4S)_2(G_4T)G$ | SSC-P | 16 |
| CAS-012 | mVk: VH5-5a | 16aa $(G_4S)_2(G_4A)S$ | SSC-P | 18 |
| CAS-013 | Vk3: VH5 VH3 FW1 | 16aa $(G_4S)_2(G_4A)S$ | SSC-P | 22 |
| CAS-014 | mVH: Vk3 | 22aa $(G_4S)_4AS$ | SSC-P | 24 |
| CAS-015 | Vk3: mVH (2H7 Leader) | 16aa $(G_4S)_2(G_4A)S$ | SSC-P | 26 |
| CAS-016 | mVH: Vk3 | 22aa $(G_4S)_4AS$ | SCC-P | 28 |
| CAS-017 | Vk3: mVH | 16aa $(G_4S)_2(G_4A)S$ | SSC-P | 30 |
| CAS-018 | Vk3: mVH | 16aa $(G_4S)_2(G_4A)S$ | SCC-P | 32 |
| CAS-019 | Vk3: VH5 VH3 FW1 | 16aa $(G_4S)_2(G_4A)S$ | SCC-P | 34 |
| CAS-020 | Vk3: VH5 VH3-13 FW1 | 16aa $(G_4S)_2(G_4A)S$ | SSC-P | 38 |
| CAS-021 | Vk3: VH5 VH3-13 FW1 | 16aa $(G_4S)_2(G_4A)S$ | SCC-P | 40 |
| CAS-022 | Vk3: VH5 VH3-13 V11S FW1 | 16aa $(G_4S)_2(G_4A)S$ | SSC-P | 42 |
| CAS-023 | Vk3: VH5 VH3-13 V11S FW1 | 16aa $(G_4S)_2(G_4A)S$ | SCC-P | 44 |
| CAS-024 | VHVL | 25aa $(G_4S)_5$ | SSC-P | 253 |
| CAS-060 | Vk3: VH5 VH3 FW1 | 16aa $(G_4S)_2(G_4A)S$ | SSC-P | 36 |
| CAS-061 | Vk3: VH5 CDRL1 (T25A, E27Q) | 16aa $(G_4S)_2(G_4T)G$ | SSC-P | 46 |
| CAS-062 | Vk3: CDR-H3 JH6 CDRL1 (T25A); CDRH3 (Y102V) | 16aa $(G_4S)_2(G_4T)G$ | SSC-P | 254 |
| CAS-063 | Vk3: VH5 JH5b CDRL1 (T25A); CDRH3 (M99F; Y102P) | 16aa $(G_4S)_2(G_4T)G$ | SSC-P | 266 |
| CAS-064 | Vk3: VH5 JH1 CDRL1 (T25A) CDRH3 (D101E; Y102H) | 16aa $(G_4S)_2(G_4T)G$ | SSC-P | 267 |
| CAS-065 | Vk3: CDR-H3 JH3a CDRL1 (T25A); CDRH3 (M99F; Y102V) | 16aa $(G_4S)_2(G_4T)G$ | SSC-P | 268 |
| CAS-066 | Vk3: CDR-H3 JH3b CDRL1 (T25A); CDRH3 (M99F; Y102I) | 16aa $(G_4S)_2(G_4T)G$ | SSC-P | 269 |
| CAS-067 | Vk3: CDR-H3 JH2 CDRL1 (T25A); CDRH3 (M99F; Y102L) | 16aa $(G_4S)_2(G_4T)G$ | SSC-P | 80 |
| CAS-068 | Vk3: VH5 JH2 CDRL1 (T25A) CDRH2 (T59N; N61A; R62Q; K65Q) | 16aa $(G_4S)_2(G_4A)S$ | SSC-P | 82 |
| CAS-069 | Vk3: VH5 JH2 CDRL1 (T25A) CDRH2 (T59G; N61A; R62Q; K65Q) | 16aa $(G_4S)_2(G_4A)S$ | SSC-P | 262 |
| CAS-070 | Vk3: VH5 JH5a CDRL1 (T25A); CDRH3 (M99F; Y102S) | 20aa $(G_4S)_3(G_3A)S$ | CPPCP | 84 |

*Entries represent abbreviations regarding IgG1 hinges having mutations in only the first or the first and second cysteines found within the upper and core regions. The only exception is SEQ ID NO: 84, which depicts the full-length hinge amino acid (CPPCP, SEQ ID NO: 230) sequence used (essentially, only the core IgG1 seqeunce with a proline at the end).
†CDR mutation numbering is based on the Kabat numbering scheme.

Additional hinge regions that may be used in CD-37 specific binding molecules, such as SMIP molecules or antibodies, are provided in the following table.

TABLE 2

Exemplary Hinge Regions for CD37-Specific Binding Proteins

| Hinge description | Amino Acid Sequence | SEQ ID NO: |
|---|---|---|
| ccc(p)-hIgG1 | EPKSCDKTHTCPPCP | 90 |
| scc(p)-hIgG1 | EPKSSDKTHTCPPCP | 92 |
| scc(s)-hIgG1 | EPKSSDKTHTCPPCS | 94 |
| csc(p)-hIgG1 | EPKSCDKTHTSPPCP | 102 |
| csc(s)-hIgG1 | EPKSCDKTHTSPPCS | 104 |
| ccs(p)-hIgG1 | EPKSCDKTHTCPPSP | 255 |
| ccs(s)-hIgG1 | EPKSCDKTHTCPPSS | 256 |
| ssc(p)-hIgG1 | EPKSSDKTHTSPPCP | 106 |
| ssc(s)-hIgG1 | EPKSSDKTHTSPPCS | 108 |
| scs(p)-hIgG1 | EPKSSDKTHTCPPSP | 257 |
| scs(s)-hIgG1 | EPKSSDKTHTCPPSS | 96 |
| css(p)-hIgG1 | EPKSCDKTHTSPPSP | 110 |
| css(s)-hIgG1 | EPKSCDKTHTSPPSS | 112 |
| sss(p)-hIgG1 | EPKSSDKTHTSPPSP | 98 |
| sss(s)-hIgG1 | EPKSSDKTHTSPPSS | 100 |
| hIgA1 | VPSTPPTPSPSTPPTPSPS | 115 |
| hIgA2 | VPPPPP | 116 |
| hIgG3 | ELKTPLGDTTHTCPRCPEPKSCDTPPPCPRCPEPKSCDTPPPCPRCPEPKSCDTPPPCPRCP | 118 |
| hIgG3(ccc) | EPKSCDTPPPCPRCP | 258 |
| hIgG3(scc) | EPKSSDTPPPCPRCP | 120 |
| hIgG3(csc) | EPKSCDTPPPSPRCP | 126 |
| hIgG3(ccs) | EPKSCDTPPPCPRSP | 259 |
| hIgG3(ssc) | EPKSCDTPPPSPRCP | 260 |
| hIgG3(scs) | EPKSCDTPPPCPRSP | 261 |
| hIgG3(css) | EPKSCDTPPPSPRSP | 122 |
| hIgG3(sss) | EPKSSDTPPPSPRSP | 124 |
| hIgD | ESPKAQASSVPTAQPQAEGSLAKATTAPATTRNTGRGGEEKKKEKEKEEQEERETKTP | 127 |

Additional framework regions that may be used in CD-37 specific binding molecules, such as SMIP molecules or antibodies, are provided in the following tables.

TABLE 3A

Human Heavy Chain Framework Regions for CD37-Specific Binding Proteins

| V-region | Human VH Framework Regions | SEQ ID NO. |
|---|---|---|
| FR1 | | |
| VH1 | QVQLVQSGAEVKKPGASVKVSCKASGYTFT | 140 |
| VH1 | QVQLVQSGAEVKKPGSSVKVSCKASGGTFS | 141 |
| VH1 | EVQLVQSGAEVKKPGATVKISCKVSGYTFT | 143 |
| VH5 | EVQLVQSGAEVKKPGESLKISCKGSGYSFT | 144 |
| VH5 | EVQLVQSGAEVKKPGESLRISCKGSGYSFT | 145 |
| VH7 | QVQLVQSGSELKKPGASVKVSCKASGYTFT | 146 |
| FR2 | | |
| VH1 | WVRQAPGQGLEWMG | 147 |
| VH1 | WVQQAPGKGLEWMG | 150 |
| VH5 | WVRQMPGKGLEWMG | 151 |
| FR3 | | |
| VH1 | RVTMTTDTSTSTAYMELRSLRSDDTAVYYCAR | 154 |
| VH1 | RVTITADESTSTAYMELSSLRSEDTAVYYCAR | 155 |
| VH1 | RVTITADKSTSTAYMELSSLRSEDTAVYYCAR | 156 |
| VH1 | RVTITADTSTDTAYMELSSLRSEDTAVYYCAT | 157 |
| VH5 | QVTISADKSISTAYLQWSSLKASDTAMYYCAR | 158 |
| VH5 | HVTISADKSISTAYLQWSSLKASDTAMYYCAR | 159 |
| VH7 | RFVFSLDTSVSTAYLQISSLKAEDTAVYYCAR | 160 |
| FR4 | | |
| JH1, JH4, JH5a, JH5b | WGQGTLVTVSS | 161 |
| JH2 | WGRGTLVTVSS | 162 |
| JH3a, JH3b | WGQGTMVTVSS | 163 |
| JH6 | WGQGTTVTVSS | 168 |
| | WGKGTTVTVSS | 169 |

TABLE 3B

Human Light Chain Framework Regions for CD37-Specific Binding Proteins

| V-region | Human VK Framework Regions | SEQ ID NO. |
|---|---|---|
| FR1 | | |
| VK3 | EIVMTQSPATLSVSPGERATLSC | 170 |
| VK3 | EIVLTQSPATLSLSPGERATLSC | 171 |
| VK1 | DIQMTQSPSSLSASVGDRVTITC | 172 |
| VK1 | NIQMTQSPSAMSASVGDRVTITC | 175 |
| VK1 | AIQLTQSPSSLSASVGDRVTITC | 177 |
| VK1 | DIQLTQSPSFLSASVGDRVTITC | 178 |
| VK1 | AIRMTQSPFSLSASVGDRVTITC | 179 |
| VK1 | AIQMTQSPSSLSASVGDRVTITC | 180 |
| VK1 | DIQMTQSPSTLSASVGDRVTITC | 181 |
| FR2 | | |
| VK3 | WYQQKPGQAPRLLIY | 182 |
| VK1 | WYQQKPGKAPKLLIY | 184 |
| VK1 | WYQQKPGKVPKLLIY | 185 |
| VK1 | WYQQKPGKAPKRLIY | 186 |
| VK1 | WFQQKPGKVPKHLIY | 187 |
| VK1 | WFQQKPGKAPKSLIY | 188 |
| VK1 | WYQQKPAKAPKLFIY | 191 |
| FR3 | | |
| VK3 | GIPARFSGSGSGTEFTLTISSLQSEDFAVYYC | 194 |
| VK3 | GIPARFSGSGSGTDFTLTISSLEPEDFAVYYC | 195 |
| VK1 | GVPSRFSGSGSGTDFTLTISSLQPEDFATYYC | 196 |

TABLE 3B-continued

Human Light Chain Framework Regions for CD37-Specific Binding Proteins

| V-region | Human VK Framework Regions | SEQ ID NO. |
|---|---|---|
| VK1 | GVPSRFSGSGSGTDFTLTISSLQPEDVATYYC | 197 |
| VK1 | GVPSRFSGSGSGTEFTLTISSLQPEDFATYYC | 198 |
| VK1 | GVPSRFSGSGSGTDYTLTISSLQPEDFATYYC | 203 |
| VK1 | GVPSRFSGSGSGTEFTLTISSLQPDDFATYYC | 205 |
| FR4 | | |
| JK1 | FGQGTKVEIK | 206 |
| | FGQGTKLEIK | 207 |
| | FGPGTKVDIK | 208 |
| | FGGGTKVEIK | 209 |
| | FGQGTRLEIK | 210 |

Preferred exemplary component parts of CD-37 specific SMIP molecules (including leader sequences used for expression and export, but which are removed from the mature fusion protein when exported from a cell; linker sequences used to join light and heavy chain variable domains to form scFv binding domains; hinges used to join scFv binding domains to effector domains; and effector domains), as well as certain CD-37 specific SMIP molecules, including the preferred CAS-024 fusion protein, are provided in Table 4.

TABLE 4

SMIP Component Parts and Select CD37-Specific SMIP Polypeptides

| Construct No. | SEQ ID NO. | Amino Acid Sequence |
|---|---|---|
| Leader Sequence | 223 | MDFQVQIFSFLLISASVIIARGV |
| Leader Sequence | 224 | MEAPAQLLFLLLLWLPDTTG |
| Variable Domain Linker | 225 | GGGGSGGGGSGGGGSS |
| Variable Domain Linker | 226 | GGGGSGGGGSGGGGAS |
| Variable Domain Linker | 227 | GGGGSGGSGSGGGGAS |
| Variable Domain Linker | 228 | GGGGSGGGGSGGGGTG |
| Variable Domain Linker | 229 | GGGGSGGGGSGGGGSGGGGSGGGGS |
| Hinge | 230 | CPPCP |
| Hinge (junction amino acid italicized) | 231 | *S*EPKSSDKTHTSPPCP |
| Hinge (junction amino acids italicized) | 232 | *DL*EPKSSDKTHTSPPCP |
| Hinge (junction amino acids italicized) | 233 | *DQ*EPKSSDKTHTSPPCP |
| Hinge (junction amino acids italicized) | 234 | *GDQ*EPKSSDKTHTSPPCP |
| Hinge (junction amino acids italicized) | 235 | *GSS*EPKSSDKTHTSPPCP |

TABLE 4-continued

SMIP Component Parts and Select CD37-Specific SMIP Polypeptides

| Construct No. | SEQ ID NO. | Amino Acid Sequence |
|---|---|---|
| Mouse CD37 VL (CDRs highlighted) | 236 | DIQMTQSPASLSASVGETVTITC*RTSENVYSYLA*WYQQKQGKSPQLLVS*FAKTLAE*GVPSRFSGSGSGTQFSLKISSLQPEDSGSYFC*QHHSDNPWT*FGGGTELEIK |
| Humanized CD37 VL (CDRs highlighted) a | 237 | EIVLTQSPATLSLSPGERATLSC*RTSENVYSYLA*WYQQKPGQAPRLLIY*FAKTLAE*GIPARFSGSGSGTDFTLTISSLEPEDFAVYYC*QHHSDNPWT*FGQGTKVEIK |
| Humanized CD37 VL (CDRs highlighted) b | 238 | EIVLTQSPATLSLSPGERATLSC*RASENVYSYLA*WYQQKPGQAPRLLIY*FAKTLAE*GIPARFSGSGSGTDFTLTISSLEPEDFAVYYC*QHHSDNPWT*FGQGTKVEIK |
| Humanized CD37 VL (CDRs highlighted) c | 239 | EIVLTQSPATLSLSPGERATLSC*RTSQNVYSYLA*WYQQKPGQAPRLLIY*FAKTLAE*GIPARFSGSGSGTDFTLTISSLEPEDFAVYYC*QHHSDNPWT*FGQGTKVEIK |
| Humanized CD37 VL (CDRs highlighted) d | 240 | EIVLTQSPATLSLSPGERATLSC*RTSESVYSYLA*WYQQKPGQAPRLLIY*FAKTLAE*GIPARFSGSGSGTDFTLTISSLEPEDFAVYYC*QHHSDNPWT*FGQGTKVEIK |
| Mouse CD37 VH (CDRs highlighted) | 241 | AVQLQQSGPESEKPGASVKISCKASGYSFT*GYNMN*WVKQNNGKSLEWIG*NIDPYYGGTTYNRKFKG*KATLTVDKSSSTAYMQLKSLTSEDSAVYYCAR*SVGPMDY*WGQGTSVTVSS |
| Humanized CD37 VH (CDRs highlighted) a | 242 | EVQLVQSGAEVKKPGESLKISCKGSGYSFT*GYNMN*WVRQMPGKGLEWMG*NIDPYYGGTTYNRKFKG*QVTISADKSISTAYLQWSSLKASDTAMYYCAR*SVGPMDY*WGQGTLVTVSS |
| Humanized CD37 VH (CDRs highlighted) a | 243 | EVQLVQSGAEVKKPGESLKISCKGSGYSFT*GYNMN*WVRQMPGKGLEWMG*NIDPYYGGTTYNRKFKG*QVTISADKSISTAYLQWSSLKASDTAMYYCAR*SVGPMDV*WGQGTLVTVSS |
| Humanized CD37 VH (CDRs highlighted) b | 244 | EVQLVQSGAEVKKPGESLKISCKGSGYSFT*GYNMN*WVRQMPGKGLEWMG*NIDPYYGGTTYNRKFKG*QVTISADKSISTAYLQWSSLKASDTAMYYCAR*SVGPFDY*WGQGTLVTVSS |
| Humanized CD37 VH (CDRs highlighted) c | 245 | EVQLVQSGAEVKKPGESLKISCKGSGYSFT*GYNMN*WVRQMPGKGLEWMG*NIDPYYGGTTYNRKFKG*QVTISADKSISTAYLQWSSLKASDTAMYYCAR*SVGPFDS*WGQGTLVTVSS |
| IgG1 CH2CH3 | 246 | APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| CAS-006 (chimeric anti-CD37 SMIP) | 247 | DIQMTQSPASLSASVGETVTITC*RTSENVYSYLA*WYQQKQGKSPQLLVS*FAKTLAE*GVPSRFSGSGSGTQFSLKISSLQPEDSGSYFC*QHHSDNPWT*FGGGTELEIKGGGGSGGGGSGGGGSSAVQLQQSGPESEKPGASVKISCKASGYSFT*GYNMN*WVKQNNGKSLEWIG*NIDPYYGGTTYNRKFKG*KATLTVDKSSSTAYMQLKSLTSEDSAVYYCAR*SVGPMDY*WGQGTSVTVS*SDLEPKSSDKTHTSPPCP*APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| CAS-001 | 248 | EIVLTQSPATLSLSPGERATLSC*RTSENVYSYLA*WYQQKPGQAPRLLIY*FAKTLAE*GIPARFSGSGSGTDFTLTISSLEPEDFAVYYC*QHHSDNPWT*FGQGTKVEIKGGGGSGGGGSGGGGTGEVQLVQSGAEVKKPGESLKISCKGSGYSFT*GYNMN*WV |

TABLE 4-continued

SMIP Component Parts and Select CD37-Specific SMIP Polypeptides

| Construct No. | SEQ ID NO. | Amino Acid Sequence |
|---|---|---|
| | | RQMPGKGLEWMG*NIDPYYGGTTYNRKFKG*QVTISADKSI STAYLQWSSLKASDTAMYYCAR*SVGPMDY*WGRGTLVTV *SSDQEPKSSDKTHTSPPC*PAPELLGGPSVFLFPPKPKDTLMI SRTPEVTCVVVDVSHEDPEVKFNWYVDGVEVHNAKTKP REEQYNSTYRVVSVLTVLHQDWLNGKEYKCKVSNKALP APIEKTISKAKGQPREPQVYTLPPSRDELTKNQVSLTCLVK GFYPSDIAVEWESNGQPENNYKTTPPVLDSDGSFFLYSKL TVDKSRWQQGNVFSCSVMHEALHNHYTQKSLSLSPGK |
| CAS-002 | 249 | EIVLTQSPATLSLSPGERATLSC*RASENVYSYLA*WYQQKPG QAPRLLIY*FAKTLAE*GIPARFSGSGSGTDFTLTISSLEPEDF AVYYC*QHHSDNPWT*FGQGTKVEIK*GGGGSGGGGSGGGG TGEVQLVQSGAEVKKPGESLKISCKGSGYSFTGYNMNWV RQMPGKGLEWMG*NIDPYYGGTTYNRKFKG*QVTISADKSI STAYLQWSSLKASDTAMYYCAR*SVGPFDY*WGQGTLVTV *SSDQEPKSSDKTHTSPPC*PAPELLGGPSVFLFPPKPKDTLMI SRTPEVTCVVVDVSHEDPEVKFNWYVDGVEVHNAKTKP REEQYNSTYRVVSVLTVLHQDWLNGKEYKCKVSNKALP APIEKTISKAKGQPREPQVYTLPPSRDELTKNQVSLTCLVK GFYPSDIAVEWESNGQPENNYKTTPPVLDSDGSFFLYSKL TVDKSRWQQGNVFSCSVMHEALHNHYTQKSLSLSPGK |
| CAS-003 | 250 | EIVLTQSPATLSLSPGERATLSC*RASENVYSYLA*WYQQKPG QAPRLLIY*FAKTLAE*GIPARFSGSGSGTDFTLTISSLEPEDF AVYYC*QHHSDNPWT*FGQGTKVEIK*GGGGSGGGGSGGGG TGEVQLVQSGAEVKKPGESLKISCKGSGYSFT*GYNMN*WV RQMPGKGLEWMG*NIDPYYGGTTYNRKFKG*QVTISADKSI STAYLQWSSLKASDTAMYYCAR*SVGPFDS*WGQGTLVTV *SSDQEPKSSDKTHTSPPC*PAPELLGGPSVFLFPPKPKDTLMI SRTPEVTCVVVDVSHEDPEVKFNWYVDGVEVHNAKTKP REEQYNSTYRVVSVLTVLHQDWLNGKEYKCKVSNKALP APIEKTISKAKGQPREPQVYTLPPSRDELTKNQVSLTCLVK GFYPSDIAVEWESNGQPENNYKTTPPVLDSDGSFFLYSKL TVDKSRWQQGNVFSCSVMHEALHNHYTQKSLSLSPGK |
| CAS-014 (mouse-human hybrid) | 251 | AVQLQQSGPESEKPGASVKISCKASGYSFT*GYNMN*WVKQ NNGKSLEWIG*NIDPYYGGTTYNRKFKG*KATLTVDKSSTA YMQLKSLTSEDSAVYYCAR*SVGPMDY*WGQGTSVTVSSG *GGGGSGGGGSGGGGSGGGGS*ASEIVLTQSPATLSLSPGERAT LSC*RTSENVYSYLA*WYQQKPGQAPRLLIY*FAKTLAE*GIPA RFSGSGSGTDFTLTISSLEPEDFAVYYC*QHHSDNPWT*FGQ GTKVEIK*GSSEPKSSDKTHTSPPC*PAPELLGGPSVFLFPPKP KDTLMISRTPEVTCVVVDVSHEDPEVKFNWYVDGVEVHN AKTKPREEQYNSTYRVVSVLTVLHQDWLNGKEYKCKVS NKALPAPIEKTISKAKGQPREPQVYTLPPSRDELTKNQVSL TCLVKGFYPSDIAVEWESNGQPENNYKTTPPVLDSDGSFF LYSKLTVDKSRWQQGNVFSCSVMHEALHNHYTQKSLSLS PGK |
| CAS-017 (human-mouse hybrid) | 252 | EIVLTQSPATLSLSPGERATLSC*RTSENVYSYLA*WYQQKPG QAPRLLIY*FAKTLAE*GIPARFSGSGSGTDFTLTISSLEPEDF AVYYC*QHHSDNPWT*GQGTKVEIK*GGGGSGGGGSGGGG* ASAVQLQQSGPESEKPGASVKISCKASGYSFT*GYNMN*WV KQNNGKSLEWIG*NIDPYYGGTTYNRKFKG*KATLTVDKSSS TAYMQLKSLTSEDSAVYYCAR*SVGPMDY*WGQGTSVTVS *SSEPKSSDKTHTSPPC*PAPELLGGPSVFLFPPKPKDTLMISR TPEVTCVVVDVSHEDPEVKFNWYVDGVEVHNAKTKPRE EQYNSTYRVVSVLTVLHQDWLNGKEYKCKVSNKALPAPI EKTISKAKGQPREPQVYTLPPSRDELTKNQVSLTCLVKGF YPSDIAVEWESNGQPENNYKTTPPVLDSDGSFFLYSKLTV DKSRWQQGNVFSCSVMHEALHNHYTQKSLSLSPGK |
| CAS-024 | 253 | EVQLVQSGAEVKKPGESLKISCKGSGYSFT*GYNMN*WVRQ MPGKGLEWMG*NIDPYYGGTTYNRKFKG*QVTISADKSISTA YLQWSSLKASDTAMYYCAR*SVGPFDS*WGQGTLVTVSS*G GGGSGGGGSGGGGSGGGGSGGGGS*EIVLTQSPATLSLSPG ERATLSC*RASENVYSYLA*WYQQKPGQAPRLLIY*FAKTLAE* GIPARFSGSGSGTDFTLTISSLEPEDFAVYYC*QHHSDNPWT* FGQGTKVEIK*GDQEPKSSDKTHTSPPC*PAPELLGGPSVFLF PPKPKDTLMISRTPEVTCVVVDVSHEDPEVKFNWYVDGV EVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSD |

TABLE 4-continued

SMIP Component Parts and Select CD37-Specific SMIP Polypeptides

| Construct No. | SEQ ID NO. | Amino Acid Sequence |
|---|---|---|
| | | GSFFLYSKLTVDKSRWQQGNVFSCSVMHEALHNHYTQKS LSLSPGK |

Example 2

Expression of CAS-024 and Other CD37-Specific Binding Proteins

CAS-024 and other CD37-specific binding SMIP molecules were cloned into a Chinese Hamster Ovary (CHO) mammalian cell expression system. Transfected CHO cells that produced the SMIP molecules were cultured in shake flasks and harvested cell culture supernatants were titered using Octec Q Protein A sensor.

Table 5 shows that the CAS-024 construct (VHVL format with 25 amino acid variable domain linker) had an unexpectedly superior expression level, up to about 10-fold better, than the other humanized anti-CD37 SMIP molecules (mostly VLVH format with 15 amino acid variable domain linker). Indeed, all fully humanized VLVH constructs expressed poorly (data not shown), as did mouse-human hybrid molecules in either orientation (see Example 5).

TABLE 5

SMIP Expression

| SMIP Protein | Clones Screened | Protein Titer Range (µg/ml) |
|---|---|---|
| CAS-001 | 492 | 65-80 |
| CAS-002 | 425 | 200-280 |
| CAS-003 | 611 | 300-360 |
| CAS-024 | 203 | 500-650 |

Example 3

Purification and Size Exclusion Chromatography of CAS-024 and Other CD37-Specific Binding Proteins To produce more protein, nucleic acid encoding CAS-024 and several other CD37-specific binding SMIP molecules were cloned into a Chinese Hamster Ovary (CHO) mammalian cell expression system. Transfected CHO cells that produced the SMIP molecules were cultured in shake flasks.

All of the CD37-specific binding SMIP molecules were purified from CHO culture supernatants by Protein A affinity chromatography. A 50 mL rProtein A FF sepharose column (GE Healthcare) was equilibrated at 5.0 mls/min (150 cm/hr) for 1.5 column volumes (CV) with dPBS. The culture supernatant was loaded onto the rProtein A Sepharose FF column at a flow rate of 1.7 mls/min using the AKTA Explorer 100 Air (GE healthcare), capturing the recombinant SMIP molecules. The column was washed with dPBS for 5 Column Volumes (CV), then 1.0 M NaCl, 20 mM Sodium Phosphate, pH 6.0, and then with 25 mM NaCl, 25 mM NaOAc, pH 5.0. The recombinant CD37-specific binding molecules were eluted from the column with 100 mM glycine, pH 3.5. Fractions (10 mL) of the eluted product were recovered and then brought to pH 5.0 with 20% of the eluted volume of 0.5 M 2-(N-morpholino)ethanesulfonic acid (MES), pH6.0. This eluted product was concentrated to approximately 25 mg/mL protein and filter sterilized.

This concentrated and sterilized protein was further purified by GPC size exclusion chromatography (SEC) to achieve separate SMIP (dimer) molecule from higher molecular weight aggregates. An XK 50/100 column (GE healthcare) containing 1 L of Superdex 200 FF sepharose was equilibrated at 12.6 ml/min (38 cm/hr) for 1.5 column volumes (CV) with dPBS. A maximum volume of 54 mls (3% CV) of sample was applied to the column. The column continued to run at 12.6 ml/min and the eluted protein was fractionated in 40 mL fractions. Each fraction was analyzed for product quality using an analytic HPLC, and the eluted fractions were pooled to greater than about 95% protein of interest (non-aggregated). The resultant pool was filter sterilized at 0.22 µm, concentrated, and then formulated with 20 mM sodium phosphate, 240 mM sucrose, pH 6.0.

The SEC traces showing the peaks containing the protein of interest (POI) for CAS-001 (SEQ ID NO:6), CAS-002 (SEQ ID NO:48), CAS-003 (SEQ ID NO:52), and CAS-024 (SEQ ID NO:253) are shown in FIGS. 2A-2D, respectively. The CAS-024 peak is narrower and more symmetric than the CAS-001, CAS-002, and CAS-003 samples (broader and asymmetric). The CAS-006 (chimeric) molecule produces a sharp peak similar to CAS-024. The CAS-001, CAS-002, and CAS-003 samples all had a slight tailing shoulder, which if integrated, accounts for about 35% of the POI area. This 'shoulder' would be difficult to separate from the POI and probably represents either misfolded conformers or a heterogenous population of molecules (e.g., have different levels of glycosylation). This indicates that CAS-024 was not only expressed better, but this construct also produces a more homogenous population of molecules.

Example 4

Cell Binding by CAS-024 is Unexpectedly Superior to Other CD37-Specific Binding Proteins A competition assay was used to compare the binding affinity of different anti-CD37 specific small modular immunopharmaceutical (SMIP) molecules to CD-37 found on Ramos cells (a B-lymphoblastoid cell line derived from a Burkitt lymphoma). An SEC purified chimeric anti-CD37 SMIP molecule (CAS-006, SEQ ID NO:247) was labeled with the FMAT Blue® fluorescence dye (Applied Biosystems) and used as the standard to compete with purified unlabeled chimeric anti-CD37 SMIP molecule (positive control) and purified unlabeled humanized anti-CD37 SMIP test molecules. Higher affinity showed up as a weaker fluorescence signal and an FL1 fluorescence value was used to generate the competition curve. Briefly, the reagent FMAT Blue® labeled chimeric anti-CD37 SMIP molecule was diluted to 2 µg/ml in FACS blocking buffer and the purified protein samples (CAS-001 (SEQ ID NO:6), CAS-002 (SEQ ID NO:48), CAS-003 (SEQ ID NO:52), and CAS-024 (SEQ ID NO:253)) were serially diluted 1:2 to concentrations ranging from 50 µg/ml to 0.02 µg/ml. Ramos cells were harvested at 1,000 rpm for 5 minutes and resuspend in FACS blocking buffer at $4 \times 10^6$ cells/10 ml buffer. To each well of a black 96-well plate the following was added: 50 µl sample, 50 µl FMAT Blue® labeled chimeric anti-CD37 SMIP molecule, and 50 µl Ramos cells ($4 \times 10^4$/well). The plates were incubated at room temperature for 30 min and read on an 8200 Cellular Detection System (Applied Biosystems) gated for middle cell size and low signal.

Figure 3:
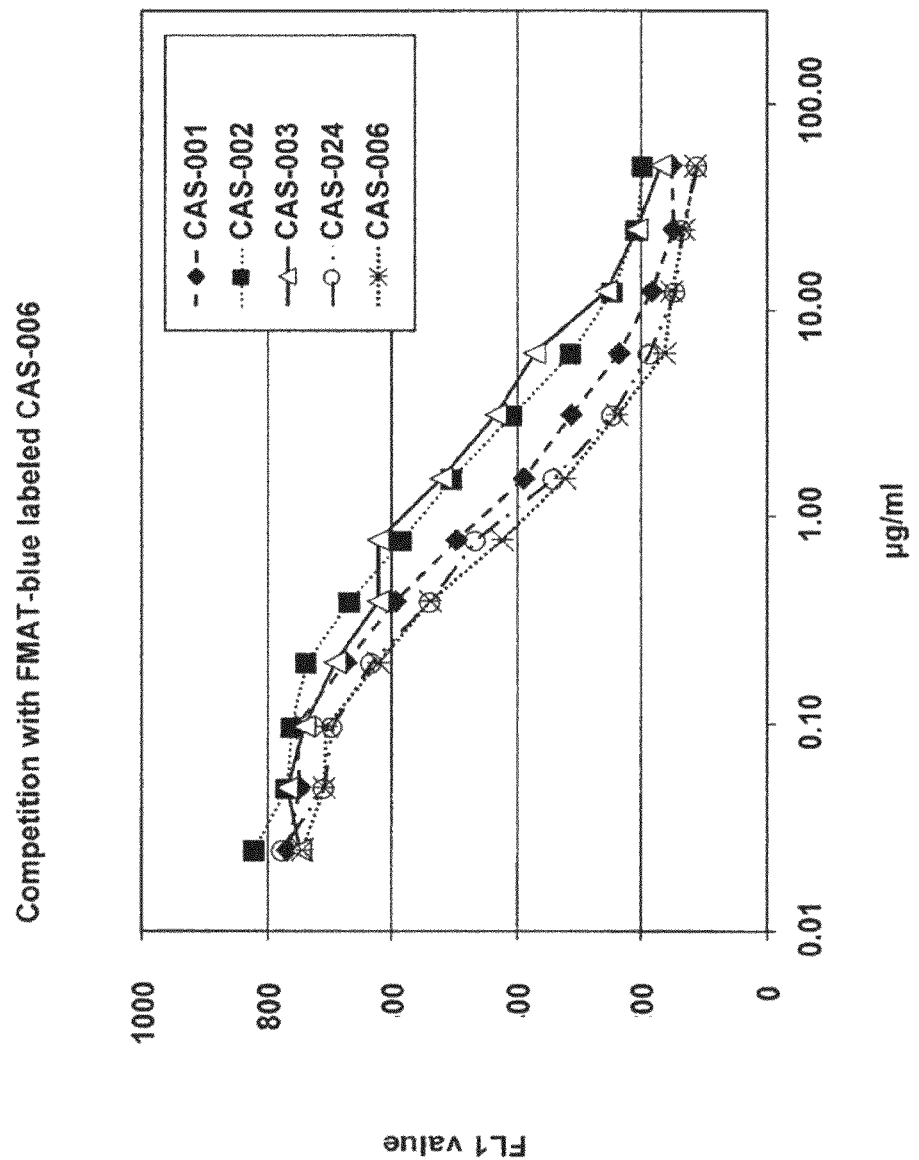
FIG. 3 is graph showing how various anti-CD37 specific SMIP proteins compete with the parent CAS-006 molecule (chimeric anti-CD37 SMIP protein, mVLmVH) for binding to CD37 on Ramos cells, which provides an indication on the affinity of binding as compared to the parent molecule. CAS-024 (hVHhVL) has substantially the same affinity for CD37 as does CAS-006, whereas the other molecules (CAS-001, CAS-002, and CAS-003, all hVLhVH) have a 2- to 4-fold decrease in affinity.

This FMAT competition assay showed that CAS-024 (humanized anti-CD37 SMIP molecule having a VHVL scFv with a 25 amino acid variable domain linker) has the same affinity for CD37 as the parent chimeric anti-CD37 SMIP molecule and, in contrast, has an unexpectedly up to a 4-fold greater affinity for CD37 than the humanized anti-CD37 SMIP molecules having the reverse VLVH structure and a shorter 16 amino acid variable domain linker (see FIG. 3). The best binding, although still significantly less than CAS-006 or CAS-024, was found in a VLVH construct that does not have any CDR mutations (CAS-001). However, CAS-001 was consistently the worst expressing construct and produced a non-homogenous population of purified molecules—even for this construct, CAS-024 bound from 1.5- to 2-fold better than CAS-001.

This result was also surprising because M99 and Y102 in the heavy chain CDR3 of CAS-024 are mutated—the Y102 position is generally conserved and it would be expected that a change at this position alone would diminish or even abolish binding (e.g., CAS-062, mutated at position Y102, has detectable but severely decreased binding compared to CAS-001 or CAS-024, while CAS-063 to CAS-067 each have barely detectable to no binding activity in this assay when a mutation at position M99 or D101 is added, data not shown). Thus, the structure of CAS-024 provided a molecule that surprisingly bound as well as the chimeric molecule, CAS-006.

Example 5

Expression and Cell Binding of CAS-024 Compared to Mouse-Human Hybrid CD37-Specific Binding Proteins CAS-024 and other CD37-specific binding SMIP molecules were produced by recombinant DNA technology and transfected into HEK293 cells for 7 days. Cell culture supernatants were harvested on day 7 and titered using Octec Q Protein A sensor.

Similar to the results found in Example 2, here Table 6 shows that CAS-024 (VHVL format with 25 amino acid variable domain linker) expressed from about 5-fold to about 27-fold better than the other humanized or mouse-human hybrid anti-CD37 SMIP molecules. The mouse-human hybrid molecules did not express well regardless of the VHVL or VLVH orientation.

TABLE 6

| SMIP Expression | |
|---|---|
| SMIP Protein | Protein Titer (µg/ml) |
| CAS-002 (hVLhVH) | 0.47 |
| CAS-003 (hVLhVH) | 2.39 |
| CAS-014 (mVHhVL) | 2.16 |

TABLE 6-continued

| SMIP Expression | |
|---|---|
| SMIP Protein | Protein Titer (µg/ml) |
| CAS-017 (hVLmVH) | 0.70 |
| CAS-006 (mVLmVH) | 9.3 |
| CAS-024 (hVHhVL) | 12.7 |

A competition assay as described in Example 4 was used to compare the binding affinity of different mouse-human hybrid anti-CD37 SMIP molecules compared to CAS-024 binding to Ramos cells. An SEC purified chimeric anti-CD37 SMIP molecule (CAS-006, SEQ ID NO:247) was labeled with the FMAT Blue® fluorescence dye (Applied Biosystems) and used as the standard to compete with purified unlabeled chimeric anti-CD37 SMIP molecule (CAS-006, positive control) and purified unlabeled humanized anti-CD37 SMIP test molecules—CAS-002 (SEQ ID NO:48), CAS-003 (SEQ ID NO:52), CAS-014 (SEQ ID NO:251), CAS-017 (SEQ ID NO:252), and CAS-024 (SEQ ID NO:253).

Figure 4A:
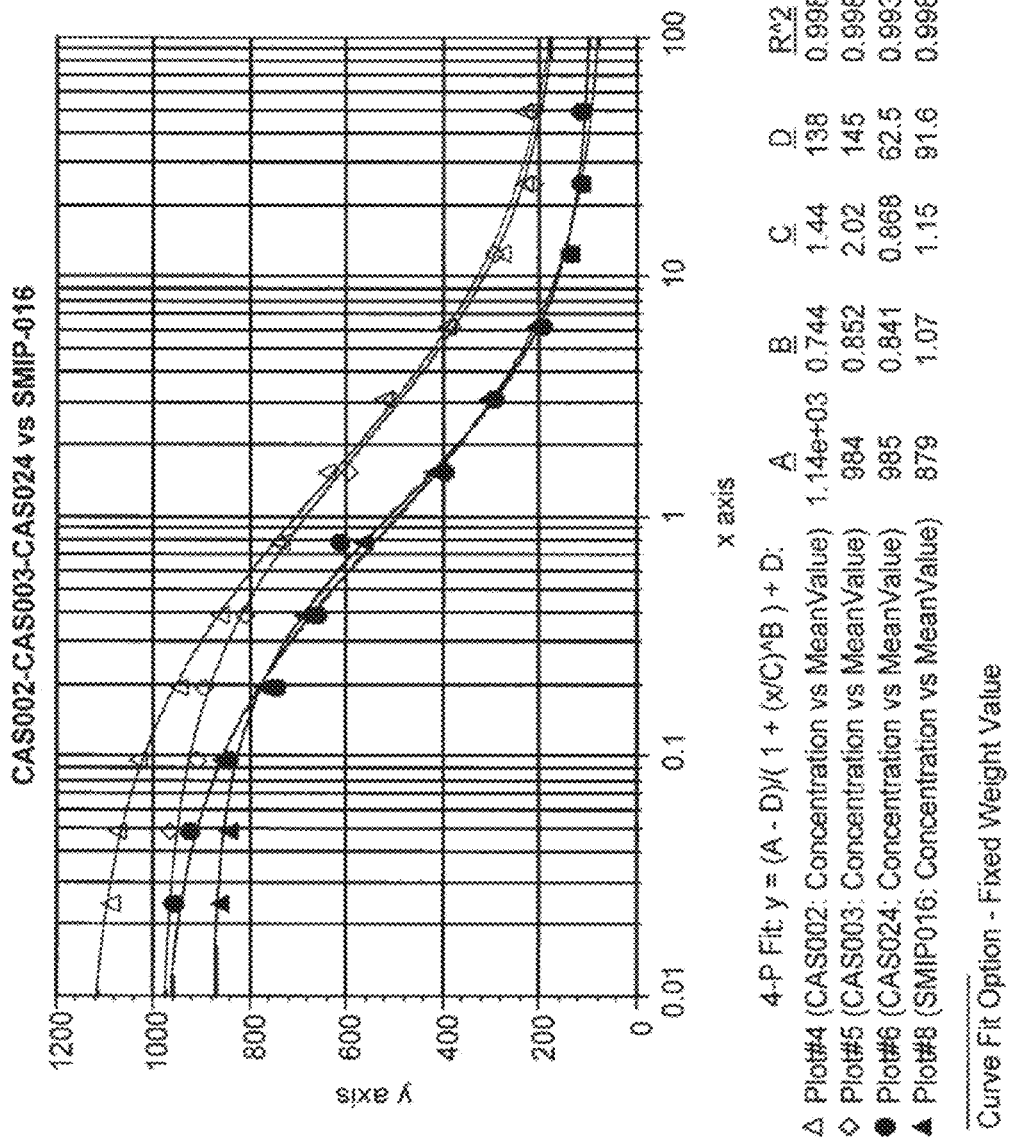
FIGS. 4A and 4B are graphs of additional binding competition assays against CAS-006 (labeled as SMIP-016 in these graphs). Here, mouse-human hybrid SMIP molecules (CAS-014 mVHhVL and CAS-017 hVLmVH) have an affinity that is higher than CAS-006, whereas CAS-024 shows the same binding affinity as CAS-006 and CAS-003 (hVLhVH) has a lower binding affinity.

This FMAT competition assay again showed that CAS-024 (VHVL humanized molecule with a 25 amino acid linker) has the same affinity for CD37 as the parent chimeric anti-CD37 SMIP molecule (CAS-006), whereas CAS-002 and CAS-003 (VLVH humanized molecules with a 16 amino acid linker) did not bind as well (showing a 2- to 3-fold reduction) (see FIG. 4A). The mouse-human hybrid molecules, regardless of variable domain orientation (mouseVH-humanizedVL with a 22 amino acid linker or humanizedVL-mouseVH with a 16 amino acid linker), bound as well as or even better than (1.5- to 2-fold) CAS-006 and CAS-024 (see FIG. 4B). These data show that a mouse-human hybrid molecule without mutations binds as well as or better than CAS-006, regardless of orientation, and that a fully humanized VLVH construct with no CDR mutations binds better than other humanized molecules but still has diminished binding compared to CAS-006 or CAS-024. Together, these data suggest that no mutations in CDRs for this molecule would be better binders. Also, the particular order (VLVH or VHVL) did not seem to solve the expression problem, even when a longer variable domain linker is used (see CAS-014). Thus, it was unpredictable to select a molecule with the CAS-024 structure and properties similar to the parent molecule CAS-006.

Example 6

CAS-006 and Various CD37-Specific Antibodies Bind Same or an Overlapping Epitope on CD37

Experiments were performed to identify the CD37 epitope bound by CAS-006 and other previously described CD37-specific antibodies. Unconjugated MB371 (#555457) and FITC-conjugated MB371 (#555456) were obtained from BD Pharmingen (San Jose, Calif.), FITC-conjugated BL14 (#0457) from Immunotech/Beckman Coulter (Fullerton, Calif.), FITC-conjugated NMN46 (#RDI-CBL 136FT) and unconjugated NMN46 (#RDI-CBL 136) from RDI (Flanders, N.J.), FITC-conjugated IPO24 (#186-040) and unconjugated IPO-24 (#186-020) from Ancell Corporation (Bayport, Minn.), FITC-conjugated HH1 (#3081) and unconjugated HH1 (#3080) from DiaTec.Com (Oslo, Norway) and FITC-conjugated WR17 (YSRTMCA483F) and unconjugated WR17 (YSRTMCA483S) from Accurate Chemical & Scientific (Westbury, N.Y.). CAS-006 SMIP protein was produced as described in Example 2.

CAS-006 was conjugated to FITC using a Molecular Probes Fluororeporter FITC Labeling Kit (F6434) according to manufacturer's instructions as follows: CAS-006 protein peak of interest (POI) at 13.5 mg/mL was adjusted to 5 mg/mL with PBS. One mg (200 ul) was added to kit tubes with a stirbar, and 1M $NaHCO_3$ (adjusted to pH 8.5 with 6N NaOH), was added to a final concentration of 0.1M. 50 ul DMSO was added to 370 ug of FITC and was added to the tubes at molar ratios of 15, 20, 30 and 40 FITC: protein using the following formula to determine the ul of FITC to add: [μl of FITC solution to add=5 mg/mL protein×0.2 mL×389× 100× desired molar ratio/Molecular weight of CAS-006 (110,000)].

Reactions were shielded from light and stirred continuously for 75 minutes at room temperature. Reactions were added to spin columns prepared as described in the kit and spun at 1100 g for 5 minutes to buffer exchange into PBS with azide and remove unconjugated FITC. The OD at 280 nM and 494 nM was determined with 2 ul drops on the Nanodrop; the extinction coefficient for CAS-016 was experimentally determined for this instrument by reading dilutions of the starting unconjugated SMIP molecule, the concentration of each of the conjugates was 4.25 mg/ml and the following FITC:protein rations were determined: 2.7 FITC/CAS-016 at a ratio of 15; 3.7 FITC/CAS-016 at a ratio of 20; 4.4 FITC/CAS-016 at a ratio of 30; and 5.1 FITC/CAS-016 at a ratio of 40.

BSA was added to 3 mg/mL to help stabilize the protein. Binding of each fraction was assessed at dilutions ranging from 100-24,300× on Ramos and 3200-25,600 on human PBMC. All bound, but the MR30 ratio was chosen for further use since it gave a high MFI that was well maintained over the titration range used, indicating that binding avidity was least affected in this reaction.

FITC labeled antibody conjugates were titrated from 10 ng/mL to 10 μg/mL in an initial binding study to determine the optimal amount to use in the blocking studies. The level chosen was just below saturating amounts, and was kept constant in the subsequent assays, while levels of blocking antibody were increased over a 10-fold range. Data were plotted as percent of maximal binding versus concentration of blocking antibody, so that higher levels indicate less efficient blocking, while lower levels indicate more efficient blocking activity. All of the antibodies tested showed blocking activity of the maximal binding observed without unlabeled reagents (FIGS. 5A-5E).

BJAB-cells, a lymphoblastoid B-cell line were then stained with a panel of various clones of anti-CD37 mAbs, including MB371, BL14, NMN46, IPO24, HH1, WR17, and chimeric CAS-006 SMIP.

For competitive binding assays, $2.5 \times 10^5$ BJAB cells were incubated in 96-well V-bottom plates in staining media (PBS with 2% mouse sera) with the FITC-conjugated anti-CD37 mAbs at 1.25 μg/mL in the presence of unconjugated anti-CD37 MAb at the indicated concentrations (2.5, 1.25, 0.6, or 0.3 μg/ml) or staining media for 45 minutes on ice in the dark. Blocking antibodies and FITC labeled antibody conjugates were added to reactions prior to addition of cells. The cells were then washed 2.5 times with PBS and fixed with 1% paraformaldehyde (USB, Cleveland, Ohio). The treated cells were analyzed by flow cytometry using a FACsCalibur instrument and CellQuest software (BD Biosciences, San Jose, Calif.).

For FACs cross blocking assays, $2.5 \times 10^5$ BJAB cells were incubated in 96-well V-bottom plates in staining media (PBS with 2% mouse sera) in the presence of unconjugated anti-CD37 MAb at 5 μg/mL staining media for 45 minutes at room temperature in the dark. FITC-conjugated anti-CD37 mAbs were added to a final concentration of 2 μg/ml, resulting in a dilution of the unlabelled reagents to 3.3 μg/ml. The reactions were further incubated for 45 minutes at room temperature in the dark, then washed 2.5 times with PBS, and finally fixed in 1% paraformaldehyde in PBS (USB, Cleveland, Ohio). Cells were analyzed by flow cytometry on a FACsCalibur instrument using Cell Quest software (BD Biosciences, San Jose, Calif.).

For cell binding assays, cells were suspended in PBS (Gibco/Invitrogen, Grand Island N.Y.) containing 2% FBS (Gibco/Invitrogen), (staining media) at a concentration of approximately $4 \times 10^6$ cells/mL. Cells were then plated and test samples, diluted in staining media, were then added 1:1 to the final designated concentrations. Reactions were incubated for 45 minutes on ice. Samples were centrifuged and washed 2 times with PBS. FITC goat anti-human IgG (Cal-Tag, Burlingame Calif.) was added at a final dilution of 1:50, and incubated 45 minutes on ice. Samples were centrifuged, washed in PBS, then fixed in 200 μl 1% paraformaldehyde in PBS (USB, Cleveland, Ohio). Cells were analyzed by flow cytometry on a FACsCalibur instrument using Cell Quest software (BD Biosciences, San Jose, Calif.).

Each antibody showed dose dependent inhibition of binding, indicating that all the molecules tested bind to an identical or closely related epitope. A different potency for inhibition of binding was observed for each antibody. CAS-006 SMIP had the highest level of blocking activity of all molecules tested, while HH1 gave an intermediate level of blocking activity, and WR17, IPO24 blocked better than MB371, but showed less effective blocking than the other two unlabeled molecules (FIGS. 5A-5E).

In addition to analysis of blocking activity, a similar series of experiments was performed in which various CD37 targeted antibodies were tested for their ability to compete with one another for binding to the CD37 receptor. The results from these experiments, like results obtained in the blocking studies for all the molecules tested, indicated that the various CD37 targeted antibodies and CAS-006 have the same or closely overlapping epitopes.

Example 7

Dose Response of CAS-024 in an Established Subcutaneous Human Tumor (DOHH2) Xenograft Model in SCID Mice The objective of this experiment was to examine the dose response to treatment with CAS-024 in a model of established subcutaneous human tumor (DOHH2) xenograft model in SCID mice. DOHH2 is a $CD20^+CD37^+$ human B-lymphoblastoid cell line derived from a patient with follicular lymphoma (Kluin-Nelemans et al., Leukemia 5:221, 1991). Thus, DOHH2 was derived from a patient with a non-Burkitt's NHL.

Five million DOHH2 cells were injected subcutaneously into the flank of female CB-17SCID mice (Harlan, Somerville, N.J.) at 6.5 weeks of age and at a mean weight of 18.0±0.1 g (ranging from 14.6 to 22.6 g). On day 8 post-tumor inoculation, palpable tumors were apparent in a majority of mice. The tumor-bearing mice were sorted into four groups with equivalent mean tumor volumes (n=14 per group; 2 cages of 5 mice and 1 cage of 4 mice for each group). The day of the sort was defined as day 0. Tumor diameters were determined with a pair of calipers and tumor volumes were calculated using the formula: $V=\frac{1}{2}[length \times (width)^2]$. The baseline mean tumor volume was 228 mm³, the median baseline tumor size was 224 mm³, and the range was 179 to 284 mm³.

TABLE 7

Reagents for In Vivo Use

| Reagent | % POI | Concentration and Endotoxin | Preparation for Injection |
|---|---|---|---|
| PBS | NA | 1X<br>Endotoxin <0.03 EU/mg | NA |
| Human IgG (huIgG) | Not tested | 10 mg/mL<br>Endotoxin = 10 EU/mg | Diluted to 1.0 mg/mL PBS |
| CAS-024 | 100 | 9.6 mg/mL<br>Endotoxin = 0.01 EU/mg | Diluted to 1.0 mg/mL PBS for 200 µg dose; then diluted 1:2 to prepare 100 µg dose, then serially diluted 1:3 to prepare the other dose solutions. |

Tumor-bearing groups of SCID mice were treated on days 0, 4, and 8 via IP injection of 0.2 mL of PBS containing 200 µg of huIgG (negative control) or 200, 100, 30, 10, or 3 µg of CAS-024. The two lowest dose solutions of CAS-024 were prepared on the day of injection to avoid the need to add a carrier protein to the most dilute solutions. Drug solutions were color-coded as described below (see Table 8 below).

TABLE 8

Experimental Design

| Group ID | No. Mice, Route of Injection, and Treatment Days | Dose per injection (µg) | mg/kg per Injection[a] | Cumulative Dose (µg) | Cumulative Dose (~mg/kg)[a] |
|---|---|---|---|---|---|
| huIgG | 14 per group | 200 | 11.1 | 600 | 33 |
| CAS-024 200 | IP injection<br>Days 0, 4, 8 | 200 | 11.1 | 600 | 33 |
| CAS-024 100 | | 100 | 5.6 | 300 | 16.7 |
| CAS-024 30 | | 30 | 1.7 | 90 | 5.0 |
| CAS-024 10 | | 10 | 0.6 | 30 | 1.7 |
| CAS-024 3 | | 3 | 0.2 | 9 | 0.5 |

[a]Note that huIgG and CAS-024 were delivered in µg per mouse, not in mg/kg. The approximate mg/kg is noted for convenience, and is based on the mean weight (18.0 ± 0.1 g) of mice on day 0. The weight range in this experiment was 14.6 to 22.6 g.

Dose solutions were prepared in similar volumes and the contents of the tubes were noted on removable labels. An investigator who was not treating or assessing the mice placed a color code on each tube and noted the code and identity of the tube contents in a laboratory notebook. Mice were monitored daily by visual inspection. Weights were determined weekly, and tumor diameters were determined at least 3 times per week (M, W, F) by an observer blinded (see above) to the treatment groups. Tumor volumes were calculated as described above. Mice were euthanized if their tumor volume reached more than 1500 mm³ (or 1200 mm³ on Fridays). Death was not an endpoint in the tumor protocols and, unless noted otherwise, "survival" of a mouse was determined by the time it was euthanized due to its tumor volume reaching the predetermined limits. (The protocol called for mice to be euthanized if (1) their tumor volume exceeded the parameters noted above, (2) ulceration of a tumor occurred, (3) the tumor inhibited the mobility of the mouse, and (4) weight loss exceeded 20% of body weight.)

One mouse in the CAS-024 100 µg treatment group was euthanized on day 35 due to weight loss>20%. This mouse had a tumor volume of 266 mm³ at that time, and was treated as censored data for the survival analysis (not euthanized as of day 35 due to tumor growth). For the calculation of tumor-free incidence at the end of the study, this mouse was classified as one that was euthanized during the study due to growth of its tumor (its tumor was growing back at the time of its death). No other mice were found dead and none were euthanized due to weight loss, tumor ulceration, or impaired mobility. No overt signs of toxicity or weight loss were observed in any of the treatment groups (data not shown).

All statistical analyses were performed using GraphPad Prism software. Significant differences in mean tumor volumes and mean relative tumor volumes were determined using a one-way ANOVA for nonparametric data (Kruskal-Wallis test) with Dunn's multiple comparison post test. To examine differences between each of the CAS-024 treated groups and the huIgG group, all groups were compared. For comparisons between the CAS-024 groups only, the huIgG group was excluded. In addition, the high and middle dose (200, 100, and 30 µg) groups were analyzed as a one data set, and the middle and low dose (30, 10, and 3 µg) groups were analyzed as another data set. Significant differences in survival of mice over time were determined using Kaplan-Meier survival analysis with a log-rank test for comparing survival curves. Significant differences in the incidence of tumor-free mice were determined using Fisher's exact test. p values<0.05 were considered significant.

CAS-024 had a dose-dependent inhibitory effect on the growth of DOHH2 tumors. With the exception of the low (3 µg) dose regimen group, the mean tumor volume of each CAS-024 treated group was significantly lower than that of the human IgG treated group as early as day 5, and remained lower through day 12. The huIgG treated mice were euthanized starting on day 12; therefore, comparisons of tumor volumes of the CAS-024 treated groups to the huIgG group were not performed for later time points. In terms of a dose response, there was no significant difference in the mean tumor volumes of the two highest dose groups at any point in the study. In contrast, the mean tumor volumes of these two groups differed significantly from those of each of the three lower dose groups from days 12 through 16 (day 16 was the last evaluable timepoint for the low dose group). Similarly, the mean tumor volumes in mice of the 30 µg and 10 µg dose groups differed from each other and from the low dose group over this same period.

The tumors in the mice treated with huIgG grew rapidly, and all of the mice in this group were euthanized by day 19. As summarized in Tables 9 and 10 below, the survival of mice treated with any of the CAS-024 dose regimens was prolonged relative to the huIgG treated group (p<0.0001 in all cases). In terms of a dose response, there was no significant difference in the survival curves of mice treated with the highest (200 and 100 µg) dose regimens (p=0.7091). With the exception of this group comparison, there was a significant difference between the survival curve of each dose group and the survival curve of each of the groups treated with a lower dose regimen (p values ranged from 0.0132 to <0.0001).

tumors in the groups of mice treated with 200 or 100 µg of CAS-024 regressed to the point that no palpable tumor was present. By the end of the study, 11/14 (79%) of the mice in each of the two highest dose groups and 5/14 (36%) of the mice in the 30 µg dose group remained tumor-free (p<0.0001 and 0.0407, respectively, vs. huIgG group).

Thus, CAS-024 exhibited dose-dependent inhibitory effects on the growth of established subcutaneous human tumor (DOHH2) xenografts in SCID mice. The two highest dose regimens (100 or 200 µg per IP injection; cumulative dose of 300 or 600 µg, which corresponds to about 16.7 or 33 mg/kg, respectively) had similar inhibitory effects and were the most efficacious of the regimens tested in terms of inhibiting tumor growth, prolonging survival, and inducing complete tumor regression.

TABLE 9

Median Survival Time and Incidence of Tumor-Free Mice

| Treatment Group[a] | Cumulative Dose | Median Survival Time (Days)[b] | Death (Not Due to Large Tumor Volume) | Tumor-Free Incidence at End of Study[c] | p Value for Fischer's Exact Test (comparison of tumor-free incidence)[d] |
|---|---|---|---|---|---|
| HuIgG 200 | 600 µg | 14 | 0/14 | 0/14 (0%) | NA |
| CAS-024 200 | 600 µg | Undefined[e,f] | 0/14 | 11/14 (79%)[g] | <0.0001 |
| CAS-024 100 | 300 µg | Undefined | 1/14[h] | 11/14 (79%) | <0.0001 |
| CAS-024 30 | 90 µg | 35 | 0/14 | 5/14 (36%) | 0.0407 |
| CAS-024 10 | 30 µg | 28 | 0/14 | 0/14 (0%) | NA |
| CAS-024 3 | 9 µg | 19 | 0/14 | 0/14 (0%) | NA |

[a]Mice were treated with the indicated protein via IP injection on days 0, 4, and 8. The numbers indicate the amount of protein (µg) injected per day.
[b]"Survival" of a mouse was determined by the day it was euthanized due to tumor growth. One mouse in the CAS-024 100 µg dose group was euthanized on day 35 due to >20% weight loss. The mouse had a tumor volume of 266 mm³ at that time, and was treated as censored data (tumor volume did not reach predetermined limit by day 35) for the Kaplan Meier analysis. No other mice were euthanized for reasons other than its tumor volume reaching the predetermined limit.
[c]"Tumor-free" mice had no palpable SC tumors. The absence of tumor cells was not confirmed by histology. The study ended on day 61.
[d]Each group was compared with the HuIgG treated control group.
[e]The median survival time is undefined when >50% of the mice are alive at the end of the observation period.
[f]Values in bold face indicate that the survival curves of the indicated group are significantly different from those of HuIgG control (p < 0.0001 in each case, log rank test).
[g]Values in bold face are significantly different from the huIgG treated control group.
[h]One mouse was euthanized on day 35 due to >20% weight loss. The mouse had a tumor volume of 266 mm³ at that time and was treated as censored data for the Kaplan Meier analysis.

TABLE 10 p-Values for Comparison of Survival Curves and Tumor-Free Incidence Between CAS-024 Treated Groups

| | p Values for Indicated Comparisons | |
|---|---|---|
| Group Comparison[a] | Log rank test (comparison of survival curves) | Fisher's exact test (comparison of tumor-free incidence) |
| 200 vs 100 | 0.7091 | 1.0000 |
| 200 vs 30 | 0.0132[b] | 0.0542 |
| 200 vs 10 | <0.0001 | <0.0001 |
| 200 vs 3 | <0.0001 | <0.0001 |
| 100 vs 30 | 0.0035 | 0.0542 |
| 100 vs 10 | <0.0001 | <0.0001 |
| 100 vs 3 | <0.0001 | <0.0001 |
| 30 vs 10 | 0.0002 | 0.0407 |
| 30 vs 3 | <0.0001 | 0.0407 |
| 10 vs 3 | <0.0001 | NA |

[a]See legend to Table 7 for information on the groups.
[b]p values <0.05 are in bold face for emphasis.

All of the mice in the huIgG treated group and in the two lowest (10 and 3 µg) CAS-024 dose groups were euthanized due to growth of their tumors. In contrast, the majority of Example 8

Efficacy of CAS-024 and Rituxan® as Single Agents in an Established Human Tumor (DOHH2) Xenograft Model in SCID Mice The objective of this study was to examine the efficacy of CAS-024 and RITUXAN® (rituximab) as single agents in a model of established human tumor (DOHH2) xenografts in SCID mice. As set out above, DOHH2 is a CD20+CD37+ human B lymphoblastoid cell line derived from a patient with follicular lymphoma. Five million DOHH2 cells were injected subcutaneously into the flank of female CB-17SCID mice (Harlan, Somerville, N.J.) at 6.5 weeks of age. On day 8 post-tumor inoculation, palpable tumors were apparent in a majority of the mice.

The tumor-bearing mice were sorted into four groups (n=15 per group; 3 cages of 5 mice for each group) with equivalent mean tumor volumes. The day of the sort was defined as day 0 of the study. Tumor diameters were determined with a pair of calipers and tumor volumes were calculated using the formula: $V=\frac{1}{2}[\text{length}\times(\text{width})^2]_3$. The baseline mean tumor volume was 228 mm$^3$; the median baseline tumor size was 227 mm; and the range was 181 to 272 mm$^3$. Mice (15 per treatment group) were treated on days 0, 4, and 8 via IP injection of 0.2 ml of PBS containing 200 μg human IgG, CAS-024, or RITUXAN® (rituximab) (for a total of 600μg after the three treatments). For the huIgG, CAS-024, and RITUXAN® (rituximab) IP treated groups, solutions were prepared in similar volumes and the contents of the tubes were noted on removable labels. An investigator who was not treating or assessing the mice placed a color code on each tube and noted the code and identity of the tube contents in a laboratory notebook.

Mice were monitored daily by visual inspection. Weights were determined weekly, and tumor diameters were determined at least 3 times per week (M, W, F) by an observer blinded (see above) to the treatment groups. Tumor volumes were calculated as described above. Tumor volumes on the last day that all mice were alive in each group were also expressed in terms of tumor volumes relative to day 0, using the formula:

$$\text{Relative tumor volume on day of interest} = \frac{(\text{volume on day of interest} - \text{volume on day 0})}{\text{volume on day 0}}$$

Mice were euthanized if their tumor volume reached more than 1500 mm3 (or 1200 mm3 on Fridays). Death is not an endpoint in our tumor protocols, and unless noted otherwise, "survival" of a mouse was determined by the time it was euthanized due to its tumor volume reaching the predetermined limits. (Our protocol calls for mice to be euthanized if their tumor volume exceeds the parameters noted above, ulceration of a tumor occurs, the tumor inhibits the mobility of the mouse, or if weight loss exceeds 20%.)

All statistical analyses were performed using GraphPad Prism software. Significant differences in mean tumor volumes and mean relative tumor volumes were determined using a one-way ANOVA for nonparametric data (Kruskal-Wallis test) with Dunn's multiple comparison post test. Significant differences in survival of mice over time were determined using Kaplan-Meier survival analysis with a log-rank test for comparing survival curves. Significant differences in the incidence of tumor-free mice were determined using Fisher's exact test (p values<0.05 were considered significant).

Mice were euthanized when their tumor volume reached the limits described above. One mouse in the CAS-024 treatment group was euthanized on day 45 due to weight loss>20%. This mouse had no apparent SC tumor at that time, and was treated as censored data for the survival analysis (not euthanized as of day 45 due to tumor growth) and was not included in the comparison of tumor-free incidence at the end of the study. No other mice were found dead and none were euthanized due to weight loss, tumor ulceration, or impaired mobility. No overt signs of toxicity or weight loss were observed in any of the treatment groups (data not shown).

The CAS-024 and RITUXAN® (rituximab) treated mice exhibited a rapid response to treatment. Mean tumor volumes of the CAS-024- and RITUXAN® (rituximab)-treated groups were significantly lower than that of the human IgG treated group as early as day 4 (after a single injection of drug) and remained lower through day 11. There were no significant differences in mean tumor volumes or mean relative tumor volumes between the CAS-024 and RITUXAN® (rituximab) treated groups through day 11. The huIgG treated mice were euthanized starting on day 11; therefore, comparisons of tumor volumes were not performed for later time points.

Figure 6A:
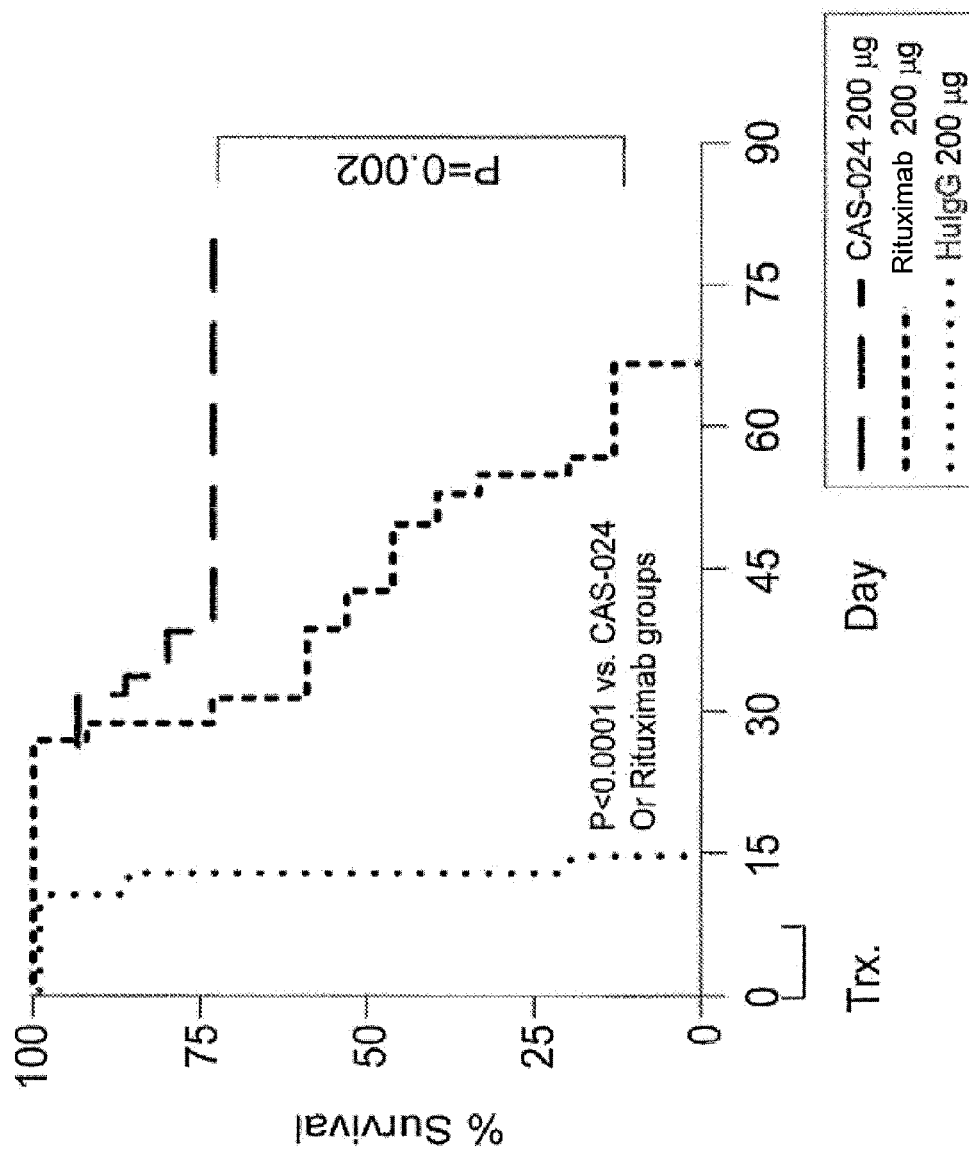
FIGS. 6A and 6B show that CAS-024 was statistically superior to RITUXAN® (rituximab) in the in vivo treatment of an animal model of follicular lymphoma as shown by (A) survival rate and (B) tumor-free percentage.
Figure 6B:
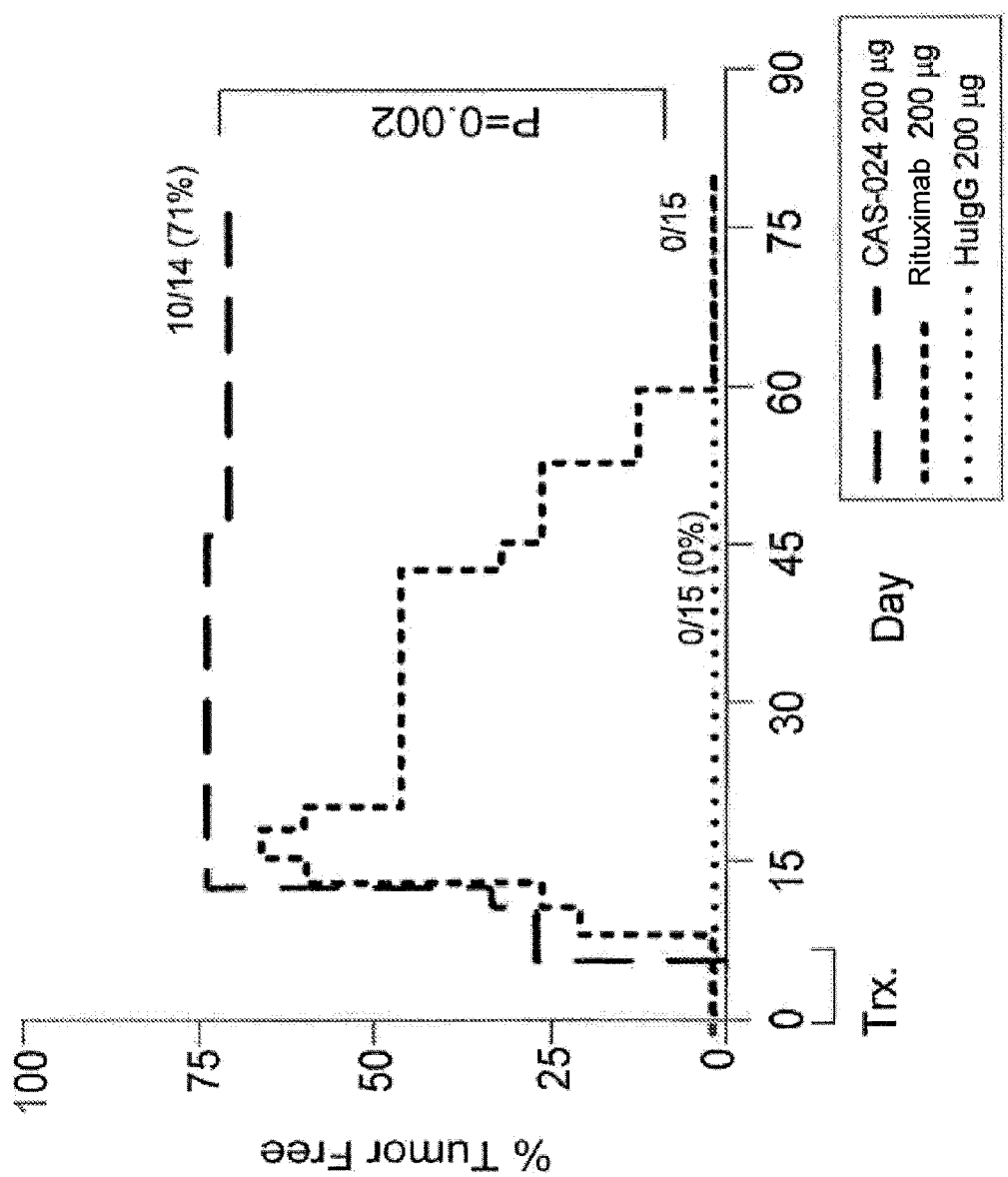

The tumors in the mice treated with huIgG grew rapidly and all mice in this group were euthanized by day 15. In contrast, by day 15, the majority of tumors in the CAS-024 and RITUXAN® (rituximab) treated groups had regressed to the point that no palpable tumor was present. Notably, the response to treatment was durable only in the CAS-024 treated group. By the end of the study, all of the RITUXAN® (rituximab)-treated mice were euthanized due to growth of their tumors, whereas 10/14 (71%) of the mice in the CAS-024 treated group remained tumor-free. See Table 9. Thus, at the end of the study, the survival curves and the incidence of tumor-free mice in the CAS-024 treated group differed significantly from the huIgG control group and the RITUXAN® (rituximab) treated group. FIG. 6 shows that CAS-024 was statistically superior to RITUXAN® (rituximab) in the in vivo treatment of this animal model of follicular lymphoma.

TABLE 11

Median Survival Time and Incidence of Tumor-Free Mice

| Treatment Group | Treatment Days and Cumulative Dose | Median Survival Time (Days)[a] | p Value from Log Rank Test[b] | Death (other than for Tumor Size Sacrifice) | Tumor-Free Mice at Day 81[c] | Fischer's Exact Test (Comparison of tumor-free incidence)[b] |
|---|---|---|---|---|---|---|
| HuIgG | Days 0, 4, 8 600 μg | 13 | — | 0/15 | 0/15 (0%) | NA |
| CAS-024 IP | Days 0, 4, 8 600 μg | Undefined[d,e] | <0.0001 | 1/15[f] | 10/14 (71%)[f] | <0.0001 |
| Rituxan ® IP | Days 0, 4, 8 600 μg | 43 | <0.0001 | 0/15 | 0/15 (0%) | NA |

[a]"Survival" was determined by the day a mouse was euthanized due to tumor growth. Other than one mouse in the CAS-024 dose group (see (f)), no mice were euthanized for reasons other than tumor volume reaching the predetermined limit.
[b]Each group was compared with the HuIgG treated control group.
[c]"Tumor-free" mice had no palpable SC tumors; confirmation of tumor cells absence was not confirmed by histology.
[d]The median survival time is undefined when >50% of the mice are alive at the end of the observation period.
[e]Bold-faced values are significantly different from those of HuIgG control.
[f]One mouse was euthanized on day 45 due to >20% weight loss. The mouse had no apparent SC tumor at that time and was excluded from the group for the comparison of tumor-free mice at day 81.

In conclusion, CAS-024 and RITUXAN® (rituximab) were efficacious as single agents in a human tumor (DOHH2) xenograft model in SCID mice. While both agents caused an initial tumor regression in the majority of mice, long-term tumor regression was observed only in the group of mice treated with CAS-024 as tumors relapsed after optimal anti-CD20 treatment. Consequently, CAS-024, a humanized anti-CD37 SMIP, shows significant efficacy in pre-clinical tumor xenograft models including models that show that RITUXAN® (rituximab) treatment fails over time. These results therefore suggest that CAS-024 treatment of B cell lymphoma and leukemia patients is beneficial and is a viable alternative treatment in patients who fail RITUXAN® (rituximab) treatment.

Example 9

In Vitro Evaluation of CAS-024 Combined with Chemotherapeutic Agents

It was previously demonstrated that CAS-006 acts synergistically in combination with the chemotherapeutic agent fludarabine to kill chronic lymphocytic leukemia (CLL) cells in vitro (see, e.g., US Patent Application Publication No. 2007/0059306). As CLL cells do not actively divide in cell culture in vitro, the data indicate that cell proliferation is not required for the pro-apoptotic effect of CAS-006 or CAS-024 for its synergy with chemotherapeutic agents. The purpose of this study, therefore, was to determine whether CAS-024 and various chemotherapeutic agents were effective on a mantle cell lymphoma (MCL) cell line, Rec-1, that actively grows and divides in cell culture in vitro and whether the combination of CAS-024 and a chemotherapeutic agent (drug) would desensitize or enhance the response of mantle cell lymphoma cells to various chemotherapeutic agents. The chemotherapeutic agents tested were doxorubicin, vincristine, and fludarabine, which are used to treat non-Hodgkin's lymphoma and other lymphoid malignancies.

Figure 7:
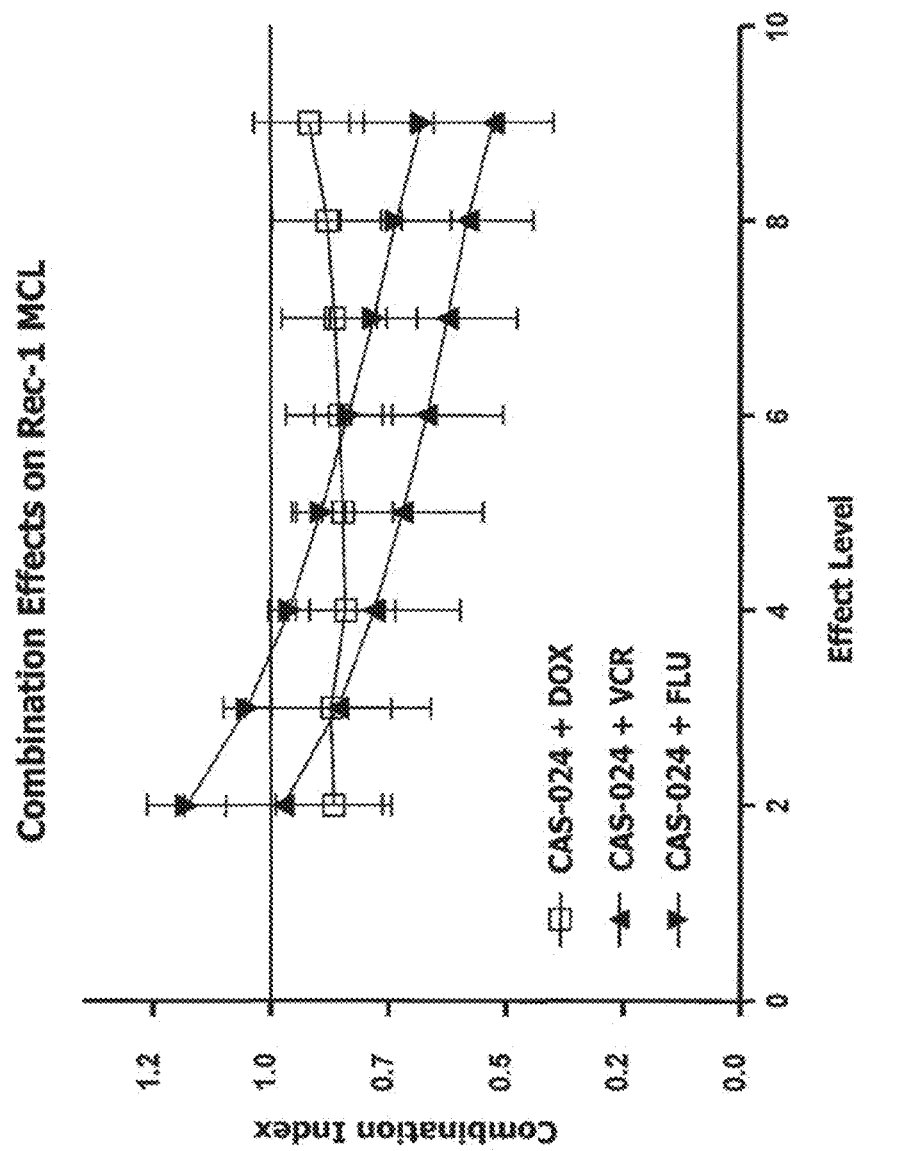
FIG. 7 shows that CAS-024 acts synergystically with chemotherapeutic agents fludarabine and vincristine to kill mantle cell lymphoma (MCL) cells, Rec-1 cells.

Rec-1 cells, a CD37+ human B cell line established from a patient with mantle cell lymphoma, were tested for growth inhibition in response to crosslinked CAS-024 in the presence or absence of doxorubicin, vincristine, or fludarabine (see FIG. 7). CAS-024 was preincubated with anti-human IgG F(ab)'$_2$ to crosslink the protein. Cells were cultured with medium alone or with medium containing various concentrations of the crosslinked CAS-024 protein, in the presence or absence of various concentrations of doxorubicin, vincristine, or fludarabine. Cultures were incubated for 96 hours and growth inhibition was assessed using an ATP viable cell detection system (i.e., viable cells quantified by ATP release).

The Median Effect/Combination Index (CI) method of Chou and Talalay (Adv. Enzyme Regul. 22:27, 1984) was used for data analysis. A numerical value, assigned to each drug combination at predefined dose levels, enabled quantitative drug/drug interaction comparisons between different drug combinations. Results were expressed as combination indices (CI) vs. effect level, in which effect level represented percent inhibition of cell growth. The mean CI±SEM for each effect level was averaged over three experiments. A CI<1.0 was considered synergy, CI=1.0 additivity, and CI>1.0 antagonism. Values presented are the mean±SEM for each effect level, averaging three independent assays.

The combination of CAS-024 with vincristine or fludarabine was synergistic (CI<1.0) and the combination of CAS-024 and doxorubicin was additive (CI not significantly different from 1.0). None of CAS-024 and chemotherapeutic agent combinations were antagonistic (CI>1.0) across all effect levels. Therefore, the combination of CAS-024 with each of the three chemotherapeutic agents tested did not desensitize target cells to drug-induced growth inhibition, but instead resulted in synergistic or additive inhibitory effects on target cell growth. A preferred embodiment would be the combination of CAS-024 (SEQ ID NO:253) with vincristine or fludarabine. These data indicate that the efficacy of established chemotherapeutics increase when used in combination with CAS-024.

Example 10

Preliminary Clinical Phase ½ Results

As provided herein, pre-clinical studies have demonstrated that CD37 SMIP molecules mediate significantly greater direct and natural killer (NK)-cell mediated killing of chronic lymphocytic leukemia (CLL) cells as compared to other therapeutic antibodies used in CLL. Hence, a Phase ½, open label, dose escalation study has been initiated in patients with relapsed chronic lymphocytic leukemia (CLL).

Patients with relapsed/refractory CLL or small lymphocytic lymphoma (SLL) who had adequate organ function, platelets>30,000/mm$^3$ were eligible. Six doses and two different schedules (cohorts 1-10) have/or will be studied. The planned doses range from 0.03 mg/kg to 10 mg/kg IV once a week for 4 doses (cohort 1-6 and 9). The second schedule (cohort 7, 8, and 10) will test 3.0, 6.0, or 10.0 mg/kg on days 1, 3 and 5 the first week followed by 3 weekly doses. Dose escalation and de-escalation is based on Common Toxicity Criteria Adverse Events (CTC AE) toxicity grades. Patients may receive 2 additional cycles, if positive biologic effect after first cycle.

Figure 8:
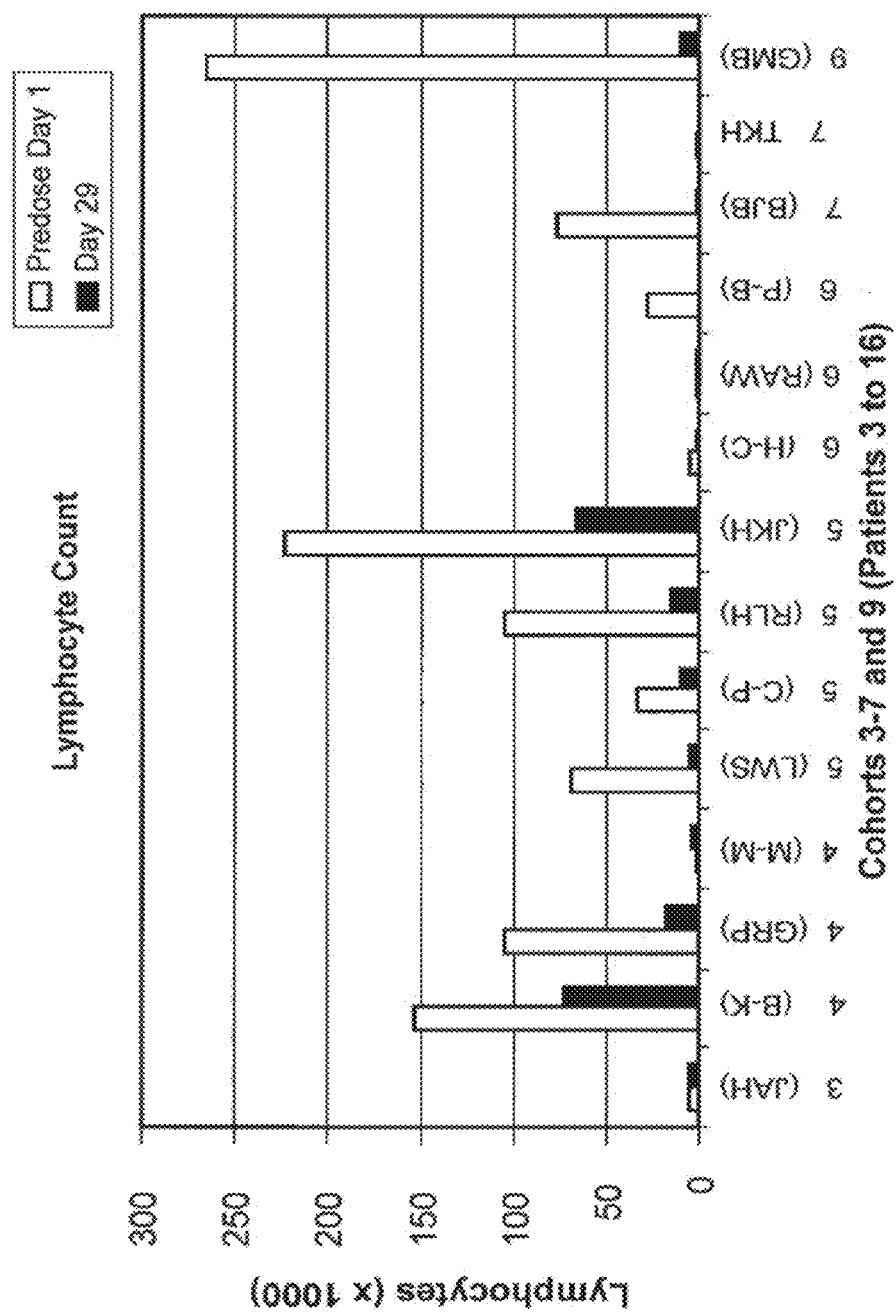
FIG. 8 is a bar graph showing the level of depletion of peripheral blood lymphocytes in human patients treated with an anti-CD37 SMIP molecule of this disclosure.
Figure 9:
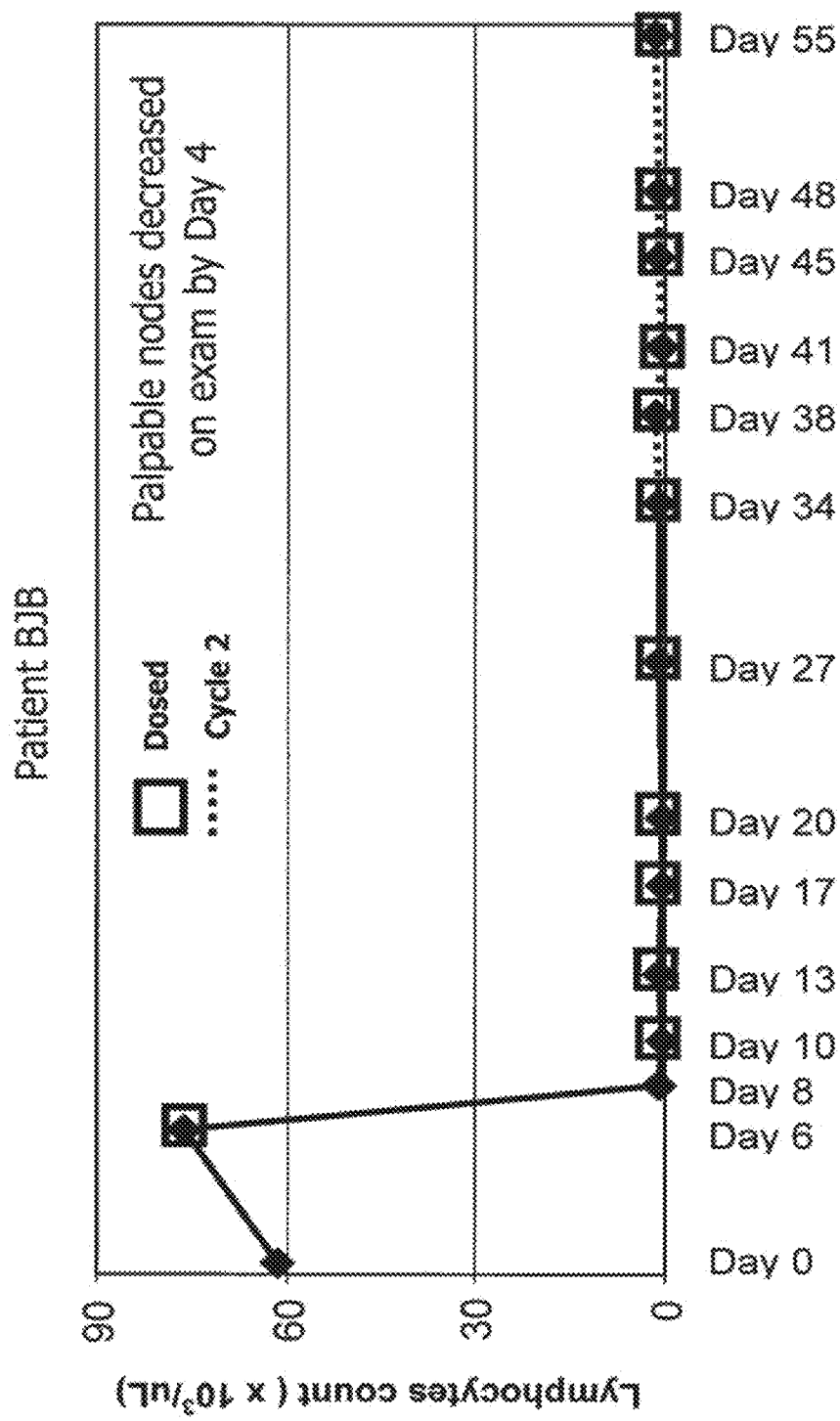
FIG. 9 shows the lymphocyte depletion and course of treatment for patient BJB. BJB (part of Cohort 7) was treated with 3.0 mg/kg on days 1, 3 and 5 the first week followed by 3 weekly doses in the first cycle, and this same treatment was administered in a second cycle. Patient BJB showed a dramatic drop in lymphocytes (within 48 hrs), showed a decrease in palpable lymph nodes by day 4, and continues to respond to treatment.
Figure 10:
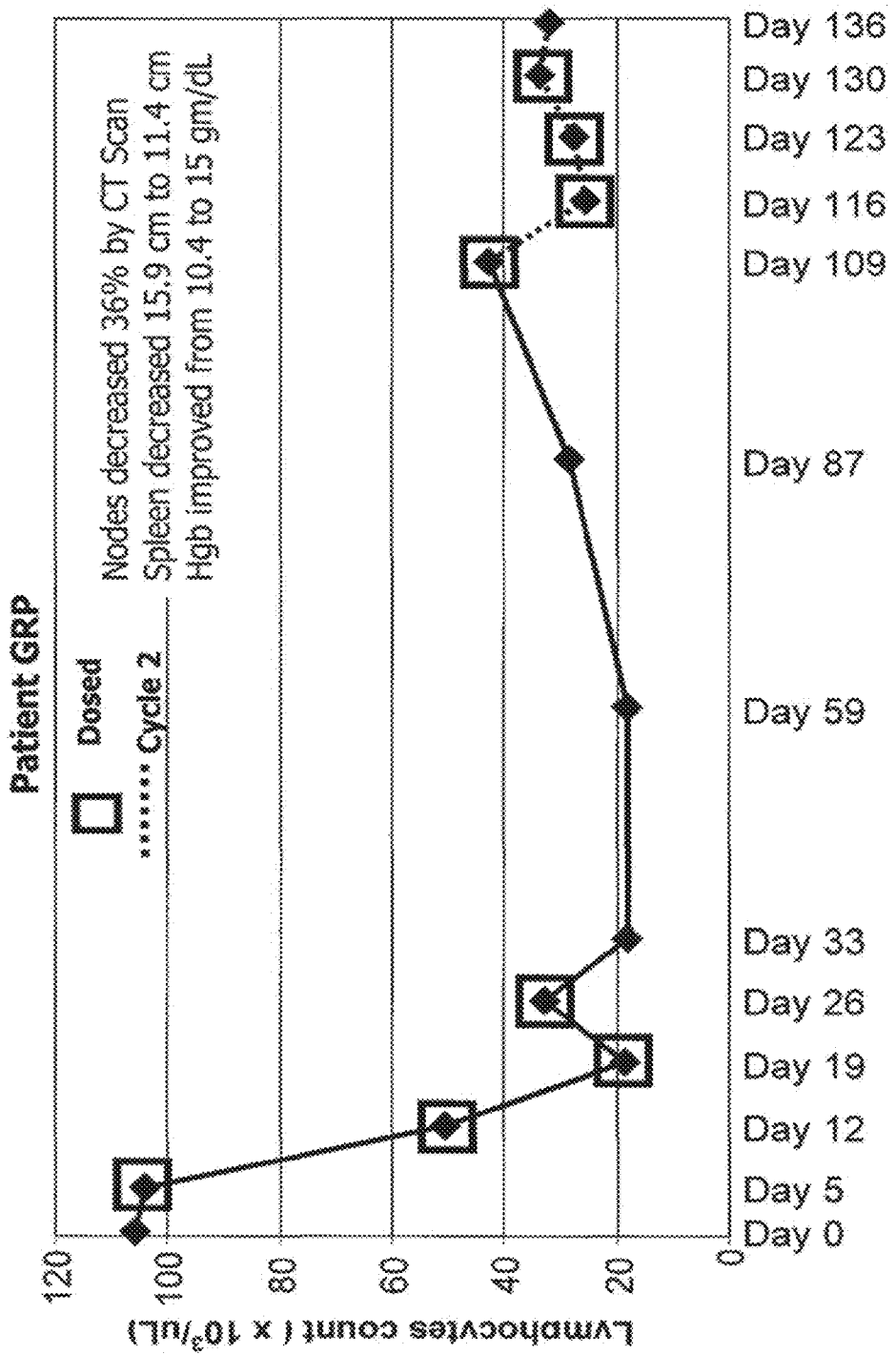
FIG. 10 shows the lymphocyte depletion and course of treatment for patient GRP. GRP (part of Cohort 4) was treated with 1.0 mg/kg once a week for four weeks as the first cycle, and then two months later was treated in the same way in a second cycle. Patient GRP showed a dramatic drop in lymphocytes (within 2 weeks), showed a 36% decrease in lymph node size by CT scan, a decrease in spleen size, improved hemoglobin level, and continues to respond to treatment.

Results: To date, 22 patients have been enrolled (cohort 1-7 and 9) and completed treatment (all have received prior fludarabine and rituximab treatment). Six patients have entered a second cycle and two patients have entered a third cycle. The patients being treated have gone through a number of prior regimens (e.g., Cohort 4 patients had from 6 to 10 (median 6) and Cohort 5 had 5 to 13 (median 9.5) prior regimens). Eight of the ten have high risk genomic features [del(17p13.1), n=5 and del(11q22.3), n=3]. No dose limiting toxicities or serious adverse events have occurred. Mild (grade 1-2) infusion toxicity has been observed in three patients. Beginning with the 0.3 mg/kg dose, all eight patients demonstrated evidence of biological activity including patients with del(17p13.1). Two patients had partial clearing of leukemia cutis, and the median reduction in peripheral lymphocyte count has been 64% (see FIG. 8). One patient had a 99% reduction in peripheral lymphocyte count with no serious adverse events and a continuing response after 3 months of treatment (see FIG. 9). One patient had an increase in hemoglobin of 40% and a reduction in lymph node size of 36% as determined by CT scan and continues to respond after 3 months of treatment (see FIG. 10). Two patients had a significant increase in platelet count.

Conclusion: To date, this CD37 SMIP molecule is a well tolerated treatment with minimal infusional toxicity and no observed dose limiting toxicity. There also seems to be any complement involvement since patients with severe drops in lymphocyte counts are not showing signs of tumor lysis syndrome. Encouraging reduction in tumor lymphocyte blood counts, reduction in lymph node/spleen size, clearing of leukemia cutis, and/or partial clearing of marrow disease, and/or improvement in normal hematopoeitic function in patients with high risk genomic CLL have already been observed at low, non-saturating doses of CD37 SMIP molecule.

Example 11

In Vitro Efficacy of CAS024 Combined with Bendamustine

This study was to determine the effects of CAS024, bendamustine, and the combination of CAS024 and bendamustine on Rec-1 (a mantle cell lymphoma cell line) and SU-DHL-6 (a diffuse large cell lymphoma line) cells.

The following human cell lines expressing CD37 were used: Rec-1 and SU-DHL-6 (both from DSMZ, Braunschweig, Germany). Bendamustine (TREANDA®) was purchased from the University of Washington Pharmacy (Seattle, Wash.) and was dissolved in PBS and stored at −20° C. until use.

Rec-1 and SU-DHL-6 cells were plated at $1 \times 10^4$ cells/well in 100 μL medium in 96 well black-sided, black-bottomed plates. Cells were treated with various concentrations of CAS024 that had been preincubated with anti-human IgG F(ab)'$_2$ and plates were incubated for 96 hr at 37° C., 5% $CO_2$ in the presence of serial dilutions of bendamustine. The final volume in each well was 150 μL. After incubation, plates were cooled to room temperature and labeled with 100 μL/well of ATPlite detection reagent (Perkin Elmer, Boston, Mass.). The assay measures cellular ATP as a marker for viable cells. Samples were analyzed by detection of luminescence using a Topcount NXT (Perkin Elmer, Waltham, Mass.) plate reader. Data were reduced using a 4-parameter curve fit in Prism (version 4.0, Graphpad Software, San Diego, Calif.) and the $IC_{50}$ defined as the concentration resulting in 50% inhibition compared to untreated cultures.

Figure 11:
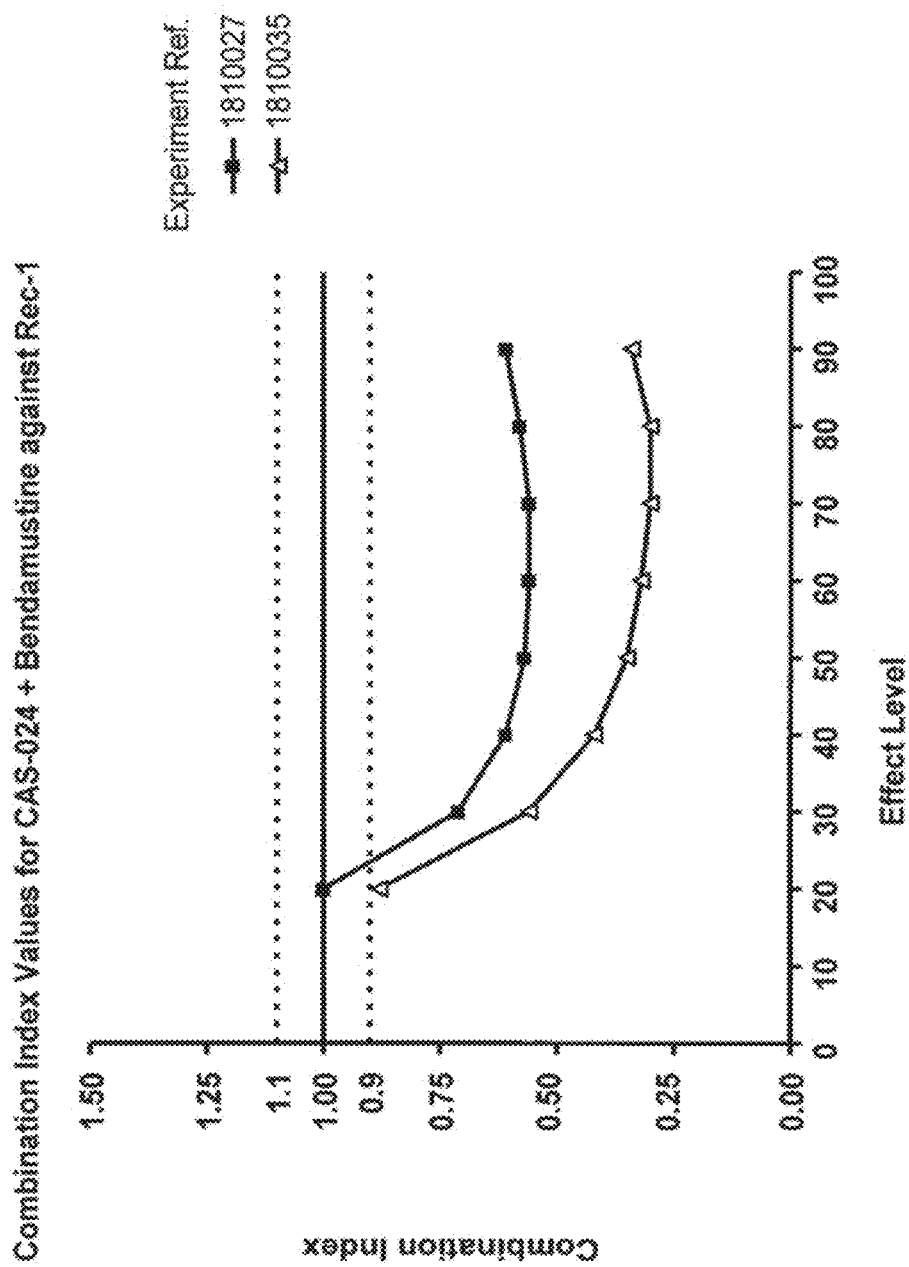
FIG. 11 shows a combination index (CI) plot for inhibitory effects of CAS-024 and bendamustine against Rec-1 cell growth.

For synergy determination the Median Effect/Combination Index (CI) method was used for data analysis (Chou and Talalay). A numerical value, assigned to each drug combination at predefined dose levels, enables quantitative drug/drug interaction comparisons between different drug combinations. The CI values assign interactions into three categories: synergism, additivity, and antagonism (CI<1.0, =1, or >1.0 respectively). After labeling and data reduction, Combination Index (CI) values were determined using the Calcusyn software package (Biosoft, Cambridge, UK). The results of two separate experiments show that the combination of CAS024 with bendamustine resulted in synergistic inhibitory effects on target cell growth (see, FIG. 11). Similar results were obtained showing that the combination of CAS024 with bendamustine also synergistically inhibited SU-DHL-6 cell growth.

Figure 12:
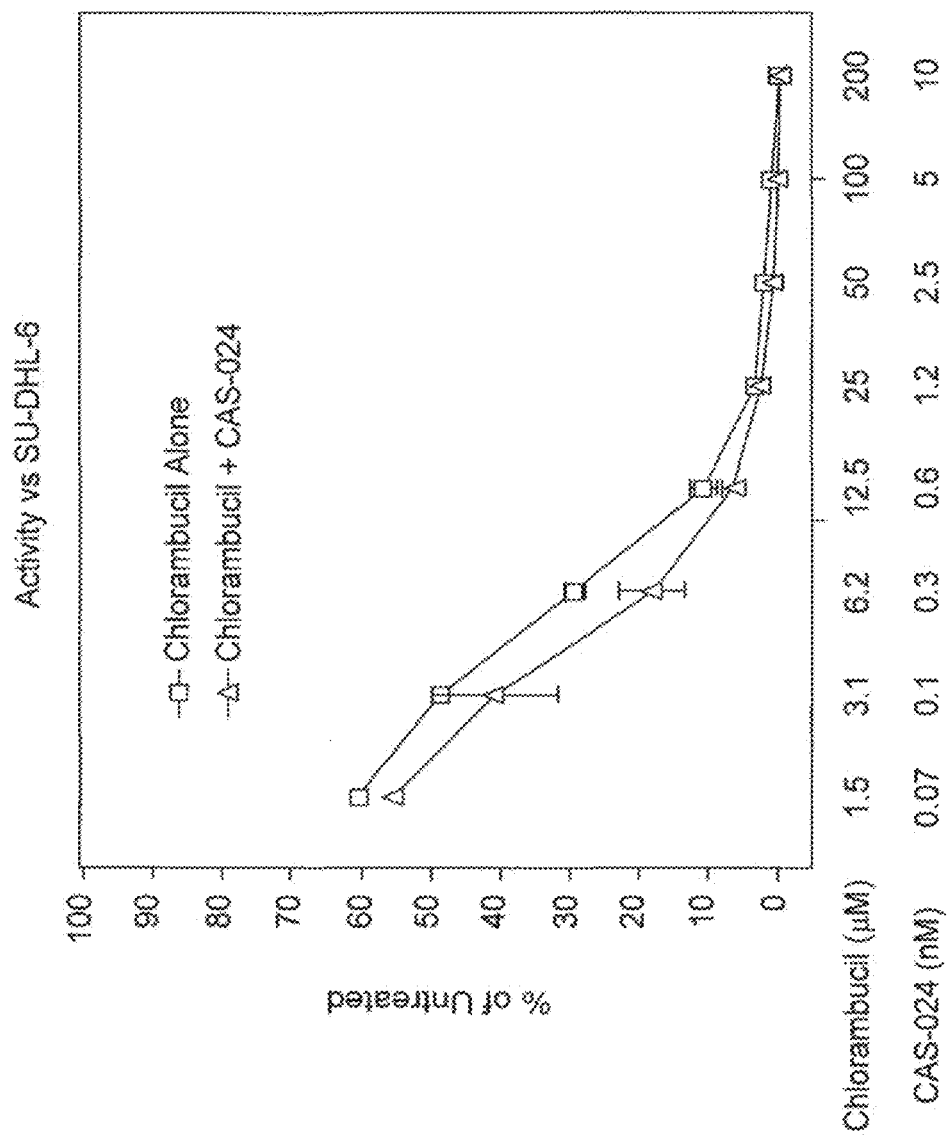
FIG. 12 shows inhibitory effects of chlorambucil alone and in combination with CAS-024 on SU-DHL-6 cell growth.
Figure 13:
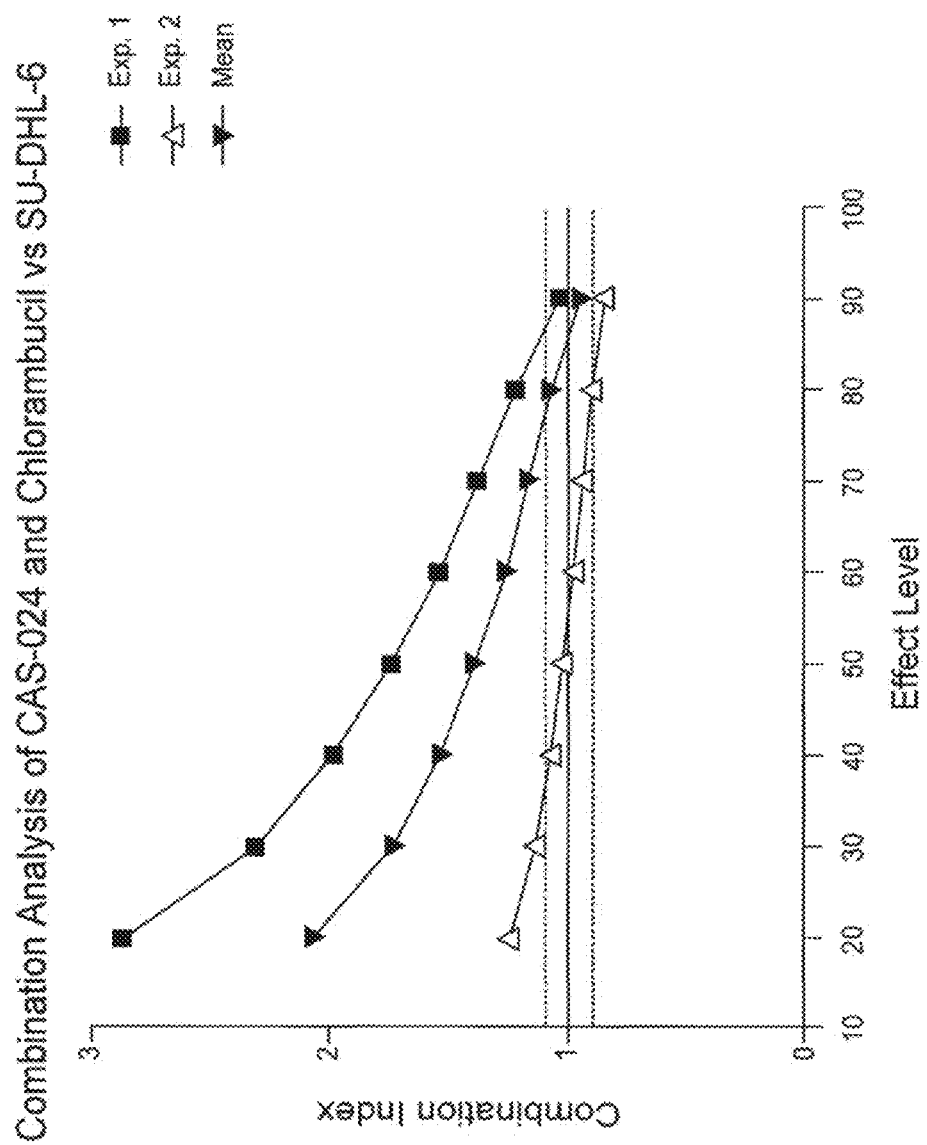
FIG. 13 shows a combination index plot for inhibitory effects of CAS-024 and chlorambucil on SU-DHL-6 cell growth.

Combination effects of CAS-024 with another alkylating agent, chlorambucil, were also determined using the method described above and the concentrations shown in FIG. 12. Unlike bendamustine, chlorambucil in combination with CAS-024 did not result in synergistic inhibitory effects on SU-DHL-6 cell growth (see, FIG. 13)

Example 12

Efficacy of CAS024 Combined with Bendamustine in Human Tumor Xenograft Model

This study was to compare the efficacy of CAS024 combined with bendamustine against each agent individually administered against subcutaneous DOHH2 human tumor xenografts in SCID mice.

Establishment of tumor xenografts and sorting into treatment groups. As described above, DOHH2 is a $CD20^+CD37^+$ human B-lymphoblastoid cell line derived from a patient with follicular lymphoma. Five million DOHH2 cells were injected subcutaneously into the flank of female CB-17 SCID mice. On day 8 post-tumor inoculation, palpable tumors were apparent in majority of mice. The tumor-bearing mice were sorted into five groups with equivalent mean tumor volumes (n=15 per group; 3 cages of 5 mice for each group). The day of the sort was defined as day 0. Tumor diameters were determined with a pair of calipers and tumor volumes were calculated using the formula: V=½[length×(width)$^2$]. The baseline mean tumor volume was 231 mm$^3$, the median baseline tumor size was 229 mm$^3$, and the range was 201 to 261 mm$^3$.

In vivo treatment. Groups of mice were treated with an injection of 0.2 mL of PBS containing 10 μg huIgG (days 0, 4, 8 IV), 10 μg CAS024 (days 0, 4, 8 IV), 10 mg/kg Bendamustine (0, 2, 4, 7, 9 IP), or 10 μg CAS024 (days 0, 4, 8 IV) AND 10 mg/kg Bendamustine (0, 2, 4, 7, 9 IP).

Monitoring and endpoints. Mice were monitored daily by visual inspection. Weights were determined weekly, and tumor diameters were determined at least 3 times per week (M, W, F) by an observer blinded (see above) to the treatment groups. Tumor volumes were calculated as described above.

Mice were euthanized if their tumor volume reached more than 1500 mm$^3$ (or 1200 mm$^3$ on Fridays). Death was not an endpoint in this study, and unless noted otherwise, "survival" of a mouse was determined by the time it was euthanized due to its tumor volume reaching the predetermined limits. Mice were euthanized if their tumor volume exceeded the parameters noted above, ulceration of a tumor occurs, the tumor inhibits the mobility of the mouse, or if weight loss exceeds 20%.

Statistical analyses. All statistical analyses were performed using GraphPad Prism software. Significant differences in mean tumor volumes and mean relative tumor volumes were determined using a one-way ANOVA for nonparametric data (Kruskal-Wallis test) with Dunn's multiple comparison post test. Significant differences in survival of mice over time were determined using Kaplan-Meier survival analysis with a log-rank test for comparing survival curves. Significant differences in the incidence of tumor-free mice were determined using Fisher's exact test. p values<0.05 were considered significant.

In the Bendamustine treated groups scruffy coats and diarrhea were seen starting around day 6. On day 10, one mouse in the CAS024+Bendamustine treatment group was euthanized due to ≥20% weight loss. This mouse was treated as censored data for the analysis of survival curves. No clinical signs of toxicity were seen in the CAS024 alone treatment group.

Figure 4B:
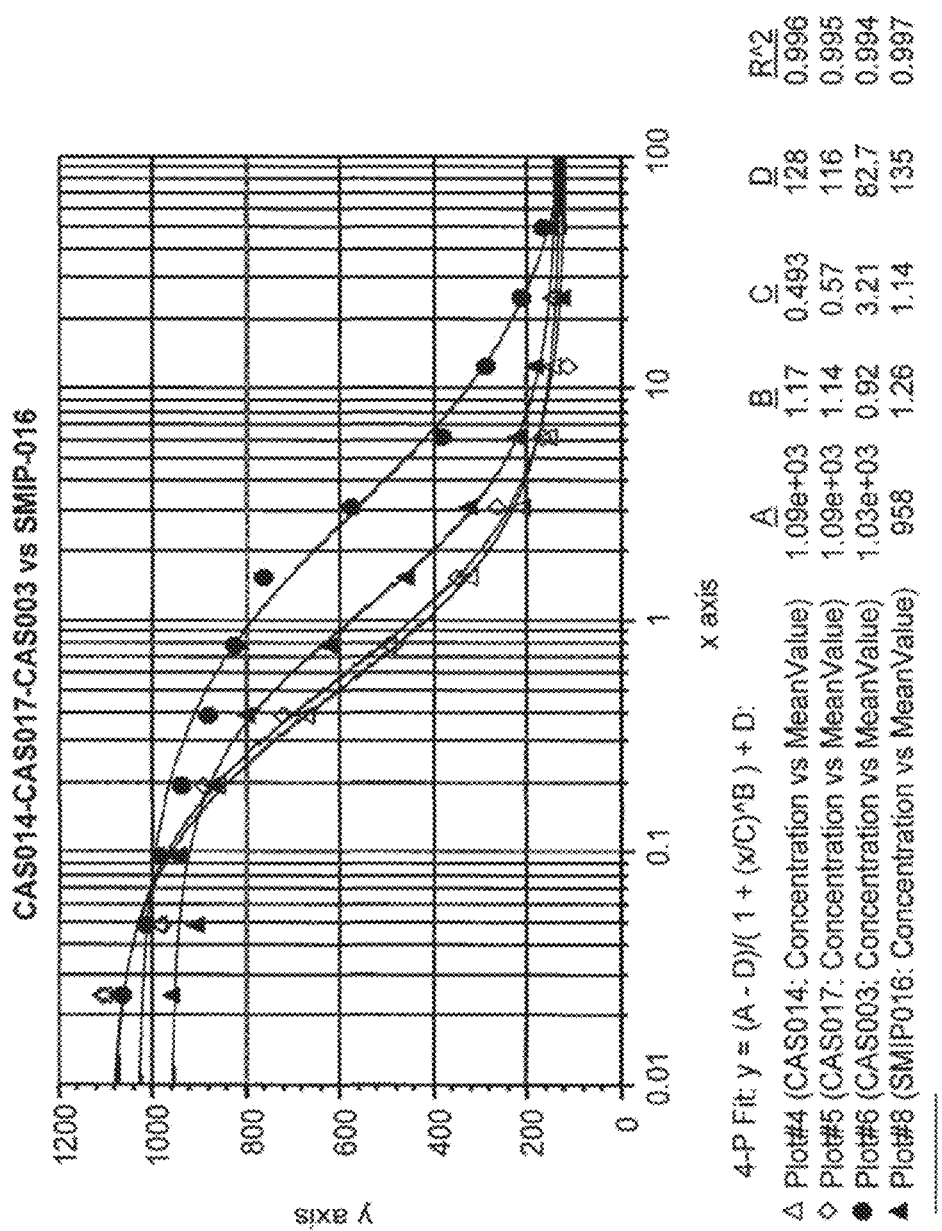
Figures 5A, 5B:
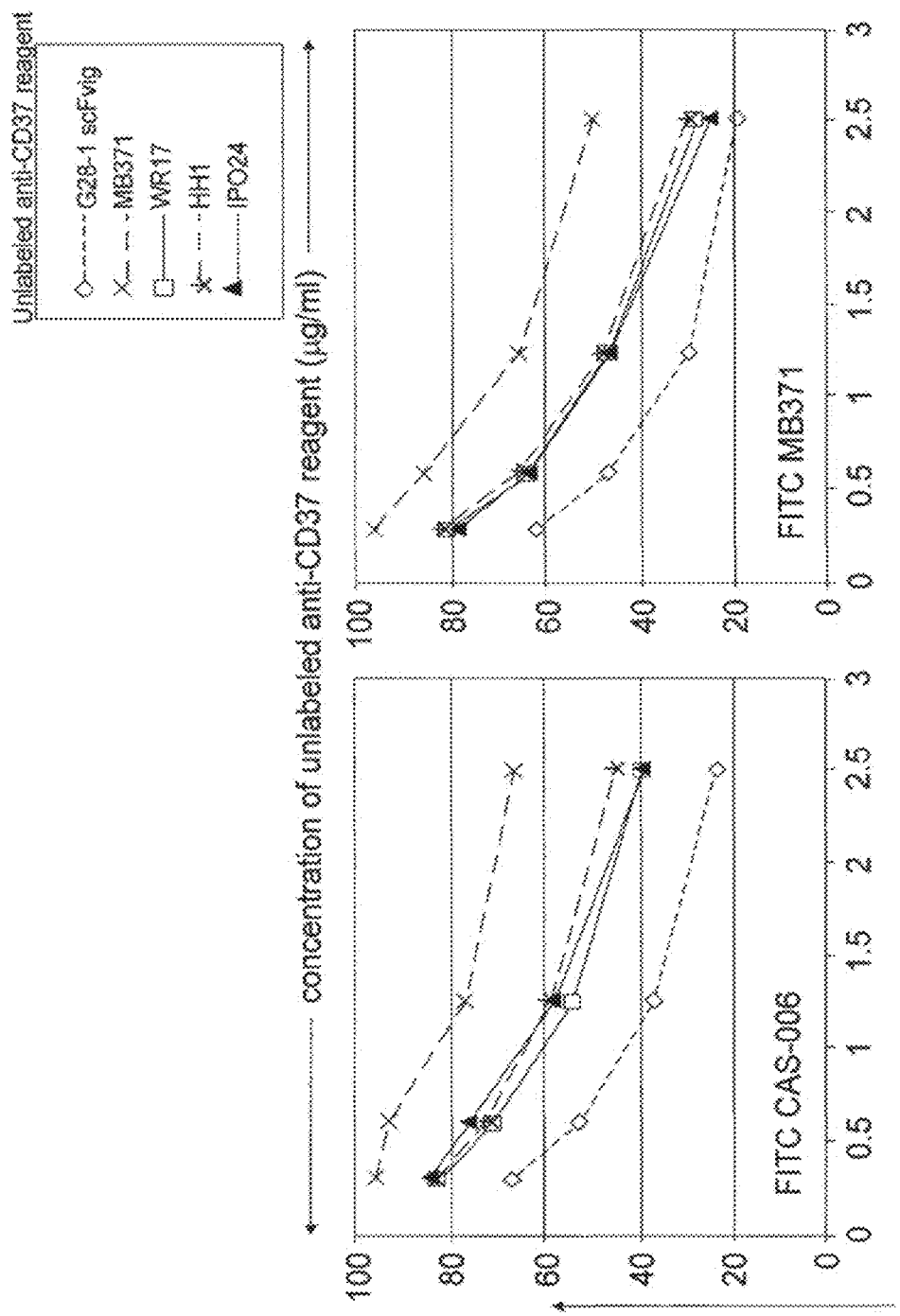
FIGS. 5A-5E show competitive binding between various different anti-CD37 antibodies and CAS-006 (a chimeric anti-CD37 SMIP molecule).
Figures 5C, 5D:
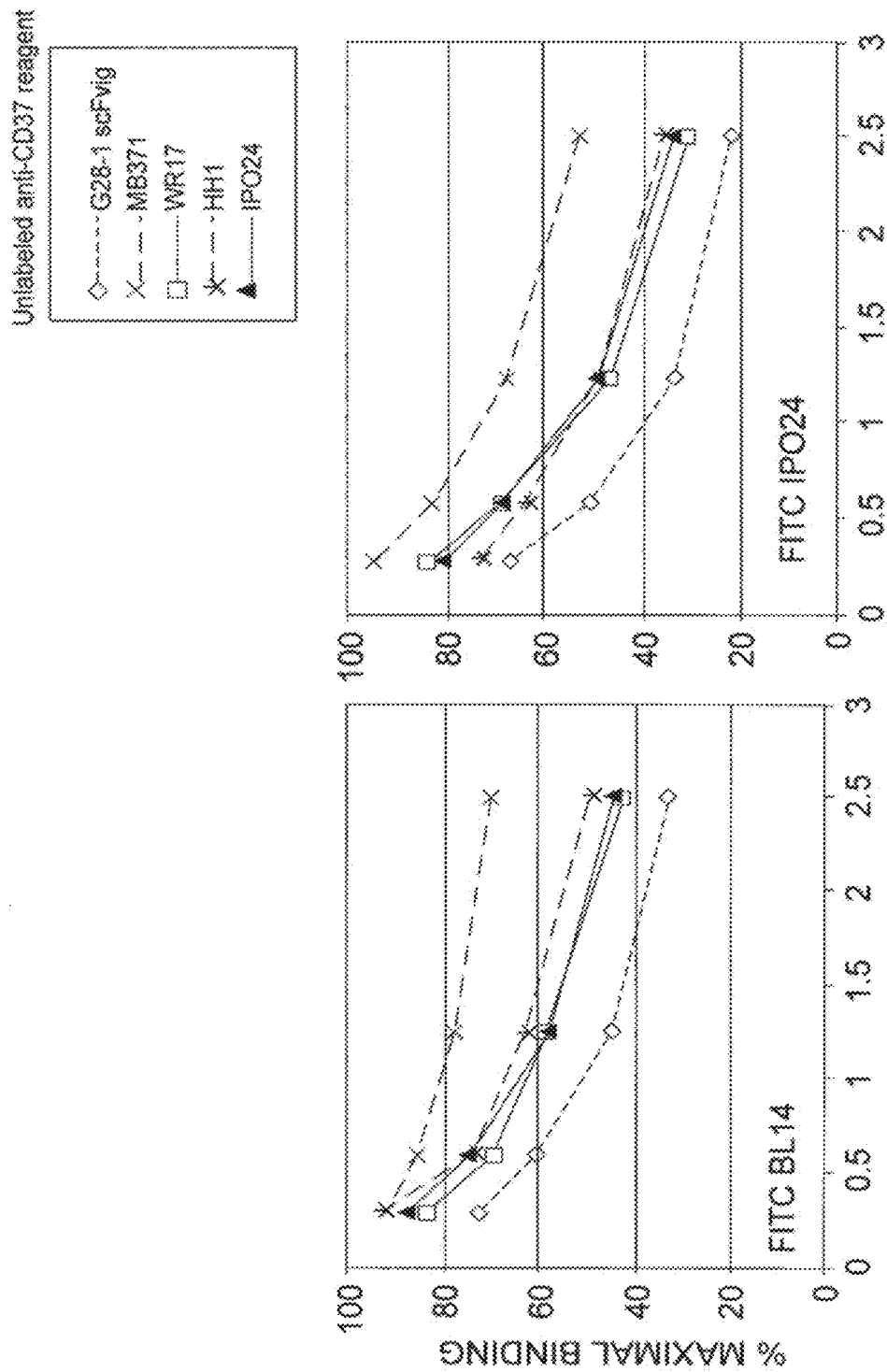
Figure 5E:
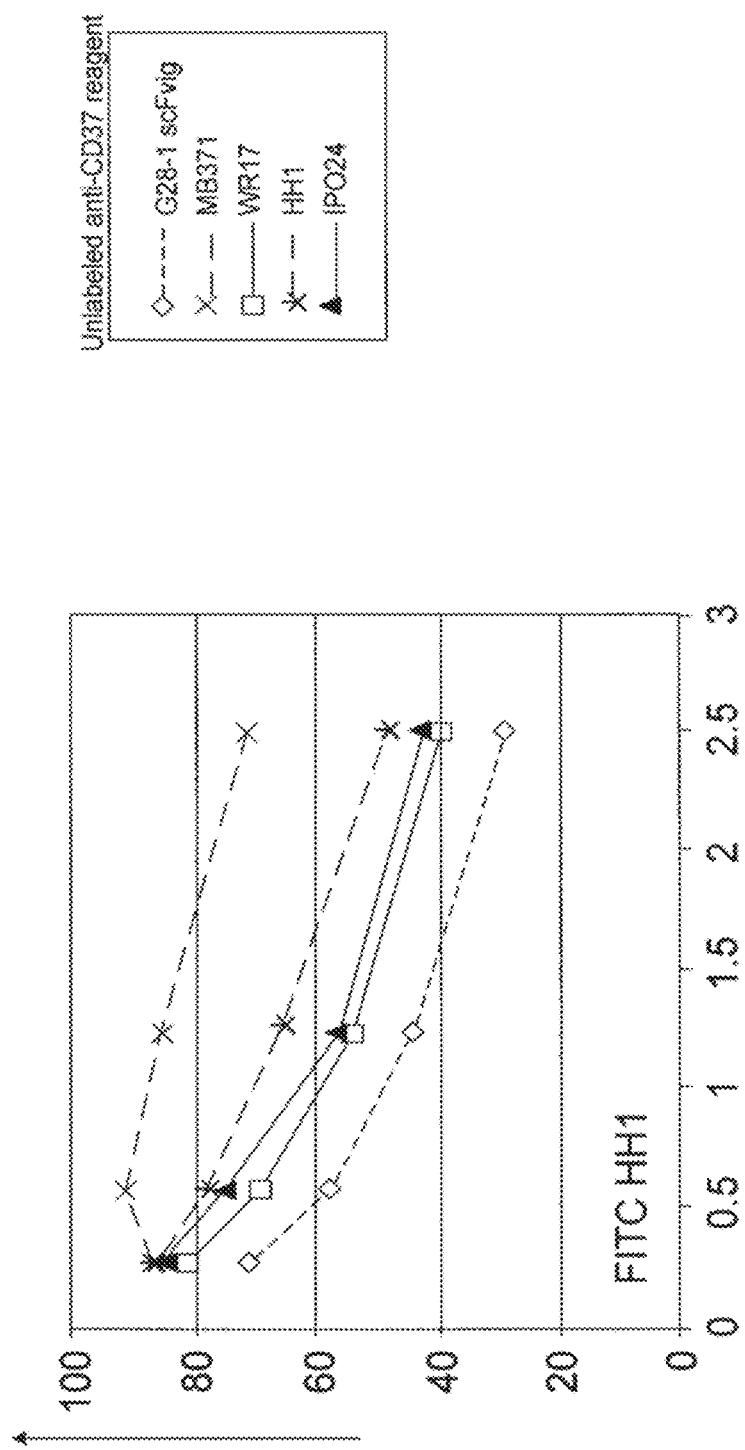
Figure 14A:
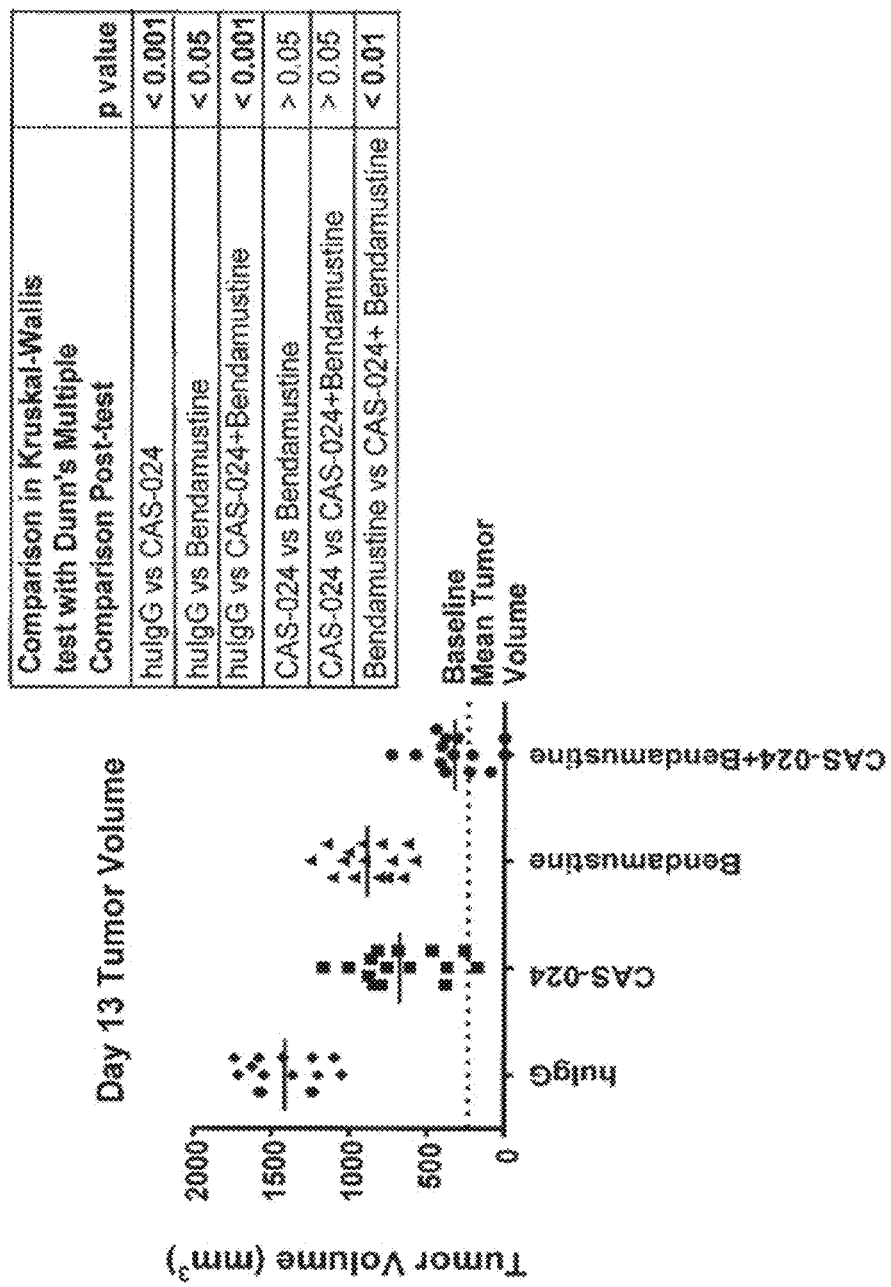
FIG. 14A shows tumor volume comparisons in tumor-bearing mice resulted from injections of DOHH2 cells and subsequently treated with huIgG (Human IgG, R&D Systems), CAS-024, bendamustine, and the combination of CAS-024 and bendamustine.
Figure 14B:
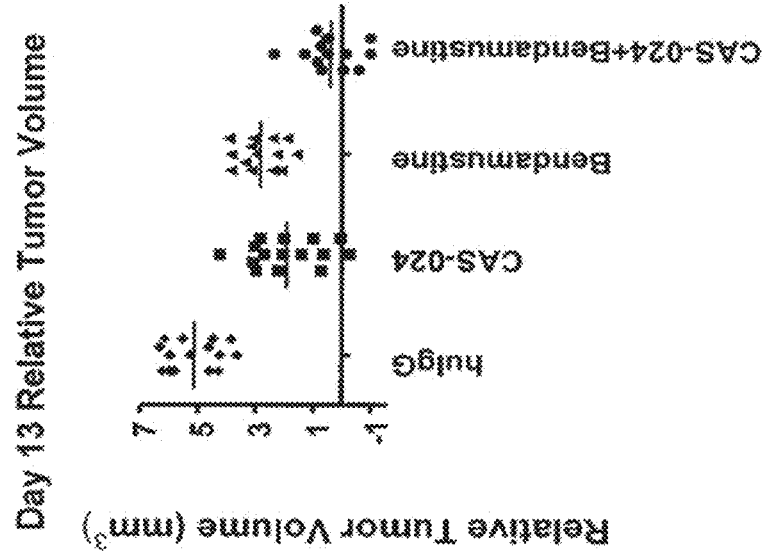
FIG. 14B shows tumor volume of individual mice on day 13 relative to day 0.
Figure 15:
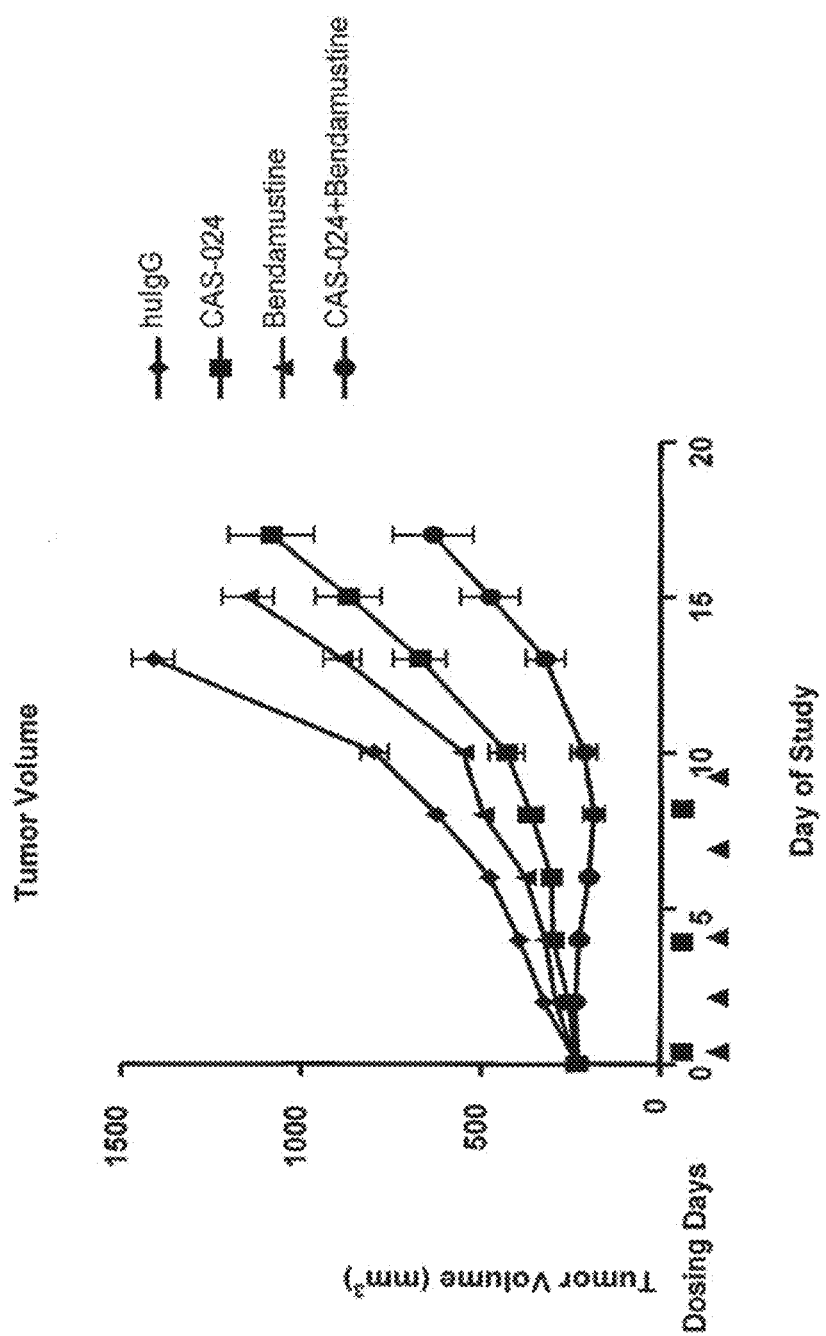
FIG. 15 shows mean tumor volumes over time in tumor-bearing mice resulted from injections of DOHH2 cells and subsequently treated with huIgG, CAS-024, bendamustine, and the combination of CAS-024 and bendamustine. Values are the mean±the standard error of the mean for each measurement day. Curves for each group end after one or more of the mice in the group were euthanized.

All treatments, demonstrated an inhibitory effect on the growth of DOHH2 compared to huIgG. On day 13 (which was the last day all mice were alive) the mean tumor volume and mean relative tumor volume of all the treatment groups were statistically different than the huIgG control group of mice (FIGS. 14A and 4B). A significant difference in mean tumor volumes and mean relative tumor volumes was also seen between Bendamustine and the CAS024+Bendamustine combination treatment group. There were no significant differences in mean tumor volumes or mean relative tumor volumes between any two other treatment groups. Mean tumor volumes over time of the four groups are shown in FIG. 15.

Figure 16:
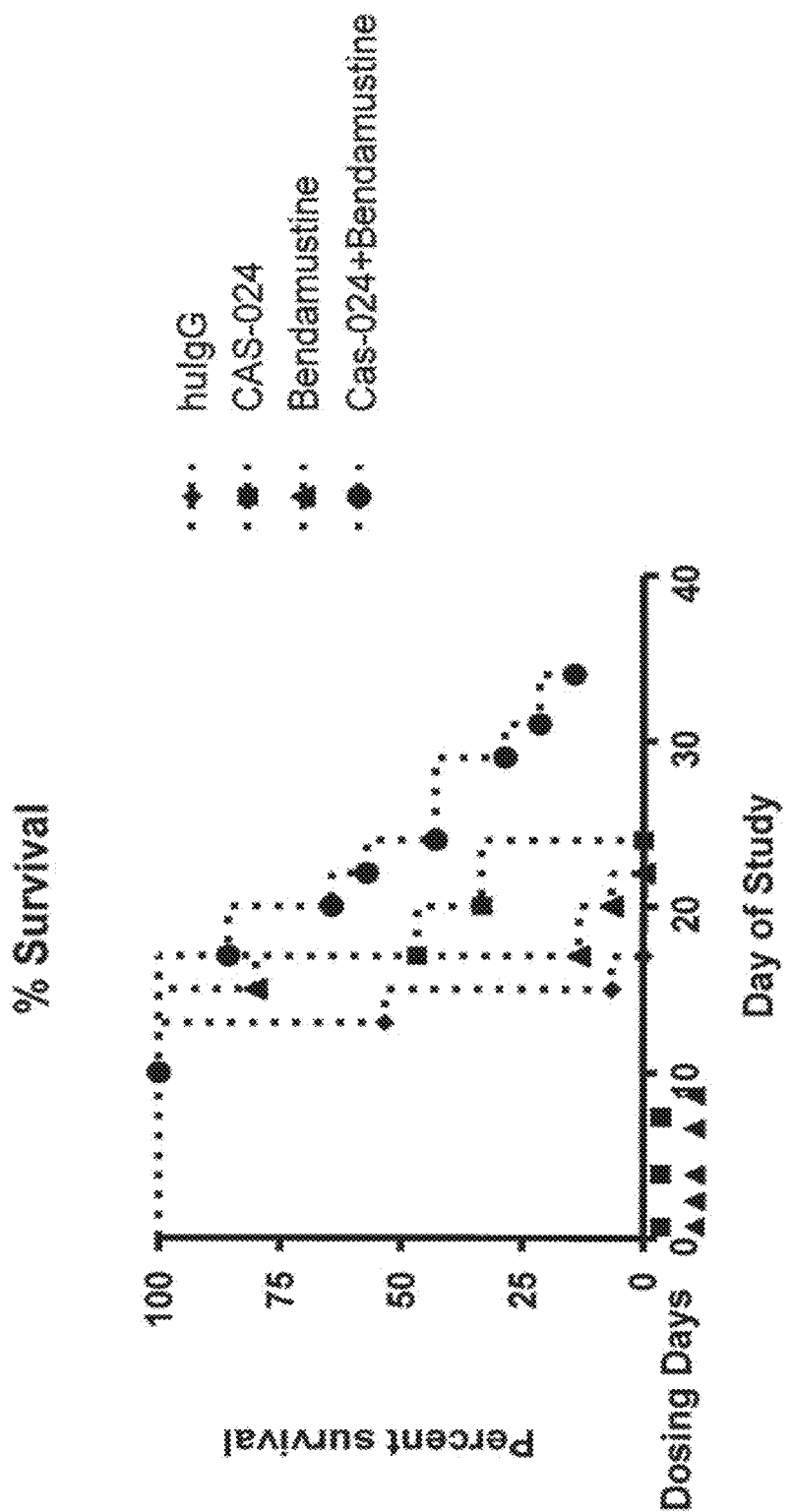
FIG. 16 shows survival percentages over time of tumor-bearing mice resulted from injections of DOHH2 cells and subsequently treated with huIgG, CAS-024, bendamustine, and the combination of CAS-024 and bendamustine.

The tumors in the mice treated with huIgG grew rapidly, and all of the mice in this group were euthanized by day 17. As shown in FIG. 16 and summarized in Tables 12 and 13, the survival of mice dosed with any of the treatment groups was prolonged compared to the huIgG treated group (p≤0.0001 for all groups). There was also a significant difference between the survival curves of all three treatment groups and each other with the CAS024/bendamustine combination being superior to either single agent.

Figure 17:
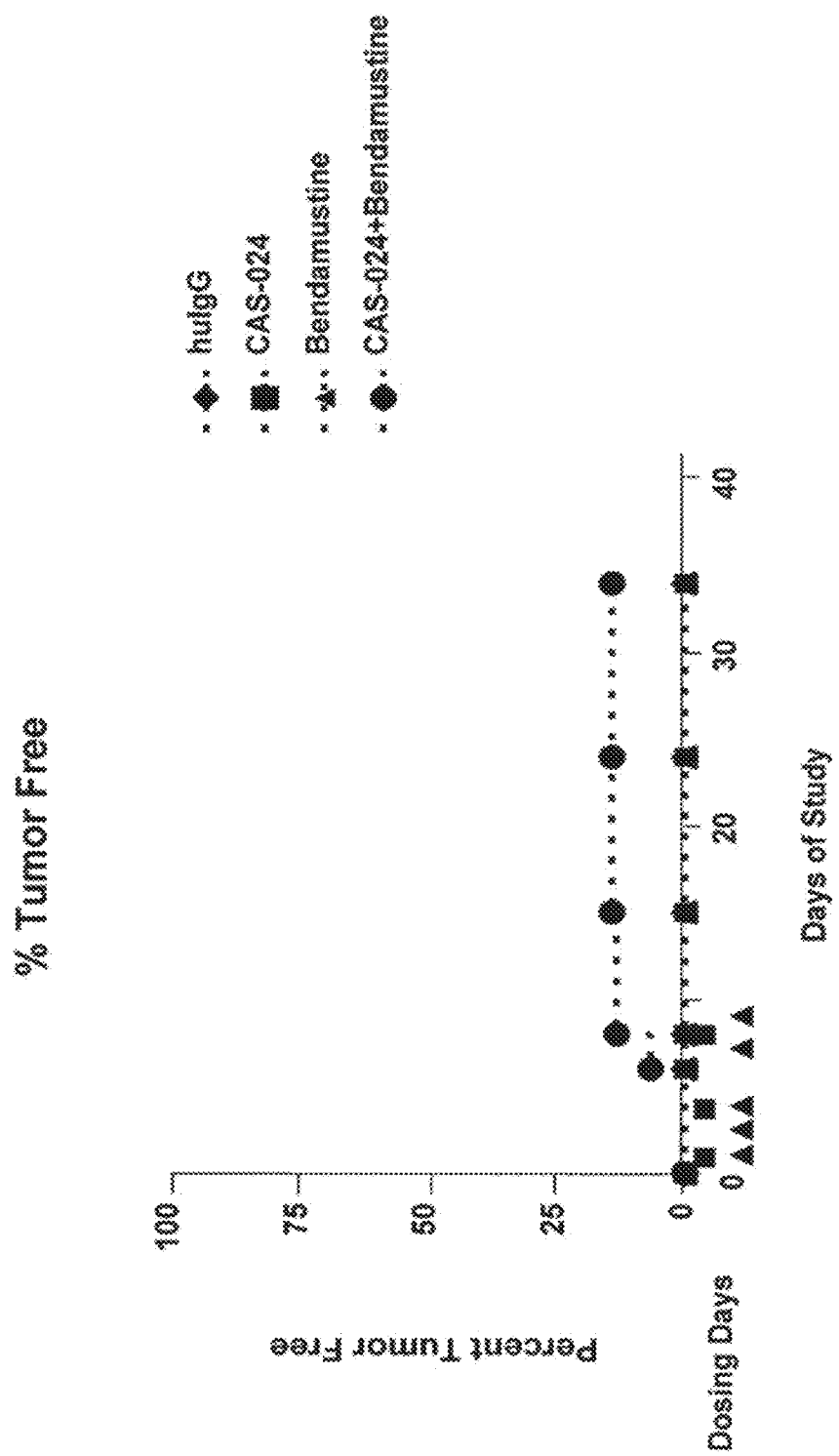
FIG. 17 shows incidence of tumor free mice over time after treatments with huIgG, CAS-024, bendamustine, and the combination of CAS-024 and bendamustine.

None of the huIgG-treated mice were alive (thus none were tumor-free) at the end of the study (day 34) (FIG. 17 and Table 12). The incidence of tumor-free mice in the other groups was 0/15 (0%) in the CAS024 and Bendamustine treatment groups and 2/14 (14%) in the CAS024+Bendamustine combination treatment group. There was no significant difference in the incidence of tumor-free mice between any of the treatment groups.

TABLE 12

Median Survival Time and Incidence of Tumor-Free Mice at the end of the Observation Period

| Treatment Group[a] | Treatment Days | Median Survival Time (Days)[a] | Tumor-Free Incidence at End of Study |
|---|---|---|---|
| huIgG | Days 0, 4, 8 | 15 | 0/15 (0%) |
| CAS024 10 µg | Days 0, 4, 8 | 17[b] | 0/15 (0%) |
| Bendamustine 10 mg/kg | Days 0, 2, 4, 7, 9 | 17 | 0/15 (0%) |
| CAS024 + Bendamustine | Days 0, 4, 8 0, 2, 4, 7, 9 | 24 | 2/14 (14%)[d] |

[a]"Survival" of a mouse was determined by the day it was euthanized due to tumor growth. One mouse in the CAS024 + Bendamustine combo group was euthanized on day 10 due to ≥20% weight loss. This mouse was treated as censored data when calculating survival curves. No other mice were euthanized for reasons other than its tumor volume reaching the predetermined limit.
[b]Values in bold face indicate that the survival curves of the indicated group are significantly different from those of huIgG control (p < 0.0001 for all treatment groups; log rank test).
[c]"Tumor-free" mice have no palpable SC tumors. The absence of tumor cells was not confirmed by histology. Study ended on day 34.
[d]In the CAS024 + Bendamustine combo group one mouse was euthanized on day 10 due to ≥20% weight loss. No other mice were euthanized for toxicity reasons.

TABLE 13 p Values for Comparison of Survival Curves Between Treated Groups
p Values for Comparison of survival curves (log- rank test)

| | huIgG | TRU-016 | Bendamustine | TRU-016 + Bendamustine |
|---|---|---|---|---|
| huIgG | NA | <0.0001 | <0.0001 | <0.0001 |
| TRU-016 | <0.0001[a] | NA | 0.0050 | 0.01 |
| Bendamustine | <0.0001 | 0.0050 | NA | <0.0001 |
| TRU-016 + Bendamustine | <0.0001 | 0.01 | <0.0001 | NA |

This study shows that CAS024 combined with Bendamustine exhibited inhibitory effects on the growth of DOHH2 tumors in SCID mice greater than that seen with either agent alone.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A humanized CD37-specific binding molecule, comprising from amino terminus to carboxyl terminus:
   (i) a humanized heavy chain variable region,
   (ii) a linker as set forth in SEQ ID NO:229,
   (iii) a humanized light chain variable region,
   (iv) an IgG1 hinge,
   (v) a human IgG1 CH2 region, and
   (vi) a human IgG1 CH3 region,
   wherein
   (a) the humanized heavy chain variable region comprises from amino terminus to carboxyl terminus: a human heavy chain FR1, a heavy chain CDR1 as set forth in SEQ ID NO:63, a human heavy chain FR2, a heavy chain CDR2 as set forth in SEQ ID NO:65, a human heavy chain FR3, a heavy chain CDR3 as set forth in SEQ ID NO:67, 68 or 69, and a human heavy chain FR4, and
   (b) the humanized light chain variable region comprises from amino terminus to carboxyl terminus: a human light chain FR1, a light chain CDR1 as set forth in SEQ ID NO:61 or 62, a human light chain FR2, a light chain CDR2 as set forth in SEQ ID NO:64, a human light chain FR3, and a light chain CDR3 as set forth in SEQ ID NO:66, and a human light chain FR4.

2. The humanized CD37-specific binding molecule of claim 1, wherein the human heavy chain FR1 comprises SEQ ID NO:144, the human heavy chain FR2 comprises SEQ ID NO:151, the human heavy chain FR3 comprises SEQ ID NO:158, and the human heavy chain FR4 comprises SEQ ID NO:161 or 162.

3. The humanized CD37-specific binding molecule of claim 1, wherein the human light chain FR1 comprises SEQ ID NO:171, the human light chain FR2 comprises SEQ ID NO:182, the human light chain FR3 comprises SEQ ID NO:195, and the human light chain FR4 comprises SEQ ID NO:206.

4. A composition comprising a humanized CD37-specific binding molecule according to claim 1 and a pharmaceutically acceptable carrier.

5. The humanized CD37-specific binding molecule of claim 1, wherein the human heavy chain FR1 comprises SEQ ID NO:144, the human heavy chain FR2 comprises SEQ ID NO:151, the human heavy chain FR3 comprises SEQ ID NO:158, and the human heavy chain FR4 comprises SEQ ID NO:161 or 162, the human light chain FR1 comprises SEQ ID NO:171, the human light chain FR2 comprises SEQ ID NO:182, the human light chain FR3 comprises SEQ ID NO:195, and the human light chain FR4 comprises SEQ ID NO:206.

* * * * *

SEQUENCE LISTING

<160> NUMBER OF SEQ ID NOS: 293

<210> SEQ ID NO 1
<211> LENGTH: 1510
<212> TYPE: DNA
<213> ORGANISM: Artificial sequence
<220> FEATURE:
<223> OTHER INFORMATION: CD37 specific binding protein -continued

<400> SEQUENCE: 1

```
aagcttgccg ccatggattt tcaagtgcag attttcagct tcctgctaat cagtgcttca      60
gtcataattg ccagaggagt cgacatccag atgactcagt ctccagcctc cctatctgca     120
tctgtgggag agactgtcac catcacatgt cgaacaagtg aaaatgttta cagttatttg     180
gcttggtatc agcagaaaca gggaaaatct cctcagctcc tggtctcttt tgcaaaaacc     240
ttagcagaag gtgtgccatc aaggttcagt ggcagtggat caggcacaca gttttctctg     300
aagatcagca gcctgcagcc tgaagattct ggaagttatt tctgtcaaca tcattccgat     360
aatccgtgga cgttcggtgg aggcaccgaa ctggagatca aggtggcgg tggctcgggc      420
ggtggtgggt cgggtggcgg cggatcgtca gcggtccagc tgcagcagtc tggacctgag     480
tcggaaaagc ctggcgcttc agtgaagatt tcctgcaagg cttctggtta ctcattcact     540
ggctacaata tgaactgggt gaagcagaat aatggaaaga gccttgagtg gattggaaat     600
attgatcctt attatggtgg tactacctac aaccggaagt tcaagggcaa ggccacattg     660
actgtagaca atcctccag cacagcctac atgcagctca agagtctgac atctgaggac      720
tctgcagtct attactgtgc aagatcggtc ggccctatgg actactgggg tcaaggaacc     780
tcagtcaccg tctcttcaga tctggagccc aaatcttctg acaaaactca cacatctcca     840
ccgtgcccag cacctgaact cttgggtgga ccgtcagtct tcctcttccc cccaaaaccc     900
aaggacaccc tcatgatctc ccggacccct gaggtcacat gcgtggtggt ggacgtgagc     960
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag gcagccccg agaaccacag     1200
gtgtacaccc tgcccccatc ccgggatgag ctgaccaaga accaggtcag cctgacctgc    1260
ctggtcaaag gcttctatcc aagcgacatc gccgtggagt gggagagcaa tgggcaaccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggtaaa    1500
tgagtctaga                                                            1510
```

<210> SEQ ID NO 2
<211> LENGTH: 496
<212> TYPE: PRT
<213> ORGANISM: Artificial sequence
<220> FEATURE:
<223> OTHER INFORMATION: CD37 specific binding protein

<400> SEQUENCE: 2

```
Met Asp Phe Gln Val Gln Ile Phe Ser Phe Leu Leu Ile Ser Ala Ser
  1               5                  10                  15

Val Ile Ile Ala Arg Gly Val Asp Ile Gln Met Thr Gln Ser Pro Ala
             20                  25                  30

Ser Leu Ser Ala Ser Val Gly Glu Thr Val Thr Ile Thr Cys Arg Thr
         35                  40                  45

Ser Glu Asn Val Tyr Ser Tyr Leu Ala Trp Tyr Gln Gln Lys Gln Gly
     50                  55                  60

Lys Ser Pro Gln Leu Leu Val Ser Phe Ala Lys Thr Leu Ala Glu Gly
 65                  70                  75                  80
```

-continued

```
Val Pro Ser Arg Phe Ser Gly Ser Gly Ser Gly Thr Gln Phe Ser Leu
                85                  90                  95

Lys Ile Ser Ser Leu Gln Pro Glu Asp Ser Gly Ser Tyr Phe Cys Gln
            100                 105                 110

His His Ser Asp Asn Pro Trp Thr Phe Gly Gly Gly Thr Glu Leu Glu
            115                 120                 125

Ile Lys Gly Gly Gly Gly Ser Gly Gly Gly Gly Ser Gly Gly Gly Gly
        130                 135                 140

Ser Ser Ala Val Gln Leu Gln Gln Ser Gly Pro Glu Ser Glu Lys Pro
145                 150                 155                 160

Gly Ala Ser Val Lys Ile Ser Cys Lys Ala Ser Gly Tyr Ser Phe Thr
                165                 170                 175

Gly Tyr Asn Met Asn Trp Val Lys Gln Asn Asn Gly Lys Ser Leu Glu
            180                 185                 190

Trp Ile Gly Asn Ile Asp Pro Tyr Tyr Gly Gly Thr Thr Tyr Asn Arg
            195                 200                 205

Lys Phe Lys Gly Lys Ala Thr Leu Thr Val Asp Lys Ser Ser Ser Thr
        210                 215                 220

Ala Tyr Met Gln Leu Lys Ser Leu Thr Ser Glu Asp Ser Ala Val Tyr
225                 230                 235                 240

Tyr Cys Ala Arg Ser Val Gly Pro Met Asp Tyr Trp Gly Gln Gly Thr
                245                 250                 255

Ser Val Thr Val Ser Ser Asp Leu Glu Pro Lys Ser Ser Asp Lys Thr
            260                 265                 270

His Thr Ser Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
        450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495
```

<210> SEQ ID NO 3

<400> SEQUENCE: 3

000

<210> SEQ ID NO 4

<400> SEQUENCE: 4

000

<210> SEQ ID NO 5
<211> LENGTH: 1482
<212> TYPE: DNA
<213> ORGANISM: Artificial sequence
<220> FEATURE:
<223> OTHER INFORMATION: CD37 specific binding protein

<400> SEQUENCE: 5

| | | |
|---|---|---|
| atggaagccc cagctcagct tctcttcctc ctgctactct ggctcccaga taccaccgga | 60 |
| gaaattgtgt tgacacagtc tccagccacc ctgtctttgt ctccaggcga agagccacc | 120 |
| ctctcctgcc gaacaagtga aaatgtttac agctacttag cctggtacca acagaaacct | 180 |
| ggccaggctc ctaggctcct catctatttt gcaaaaacct tagcagaagg aattccagcc | 240 |
| aggttcagtg gcagtggatc cgggacagac ttcactctca ccatcagcag cctagagcct | 300 |
| gaagattttg cagtttatta ctgtcaacat cattccgata tccgtggac attcggccaa | 360 |
| gggaccaagg tggaaatcaa aggtggcggt ggctcgggcg tggtggatc tggaggaggt | 420 |
| gggaccggtg aggtgcagct ggtgcagtct ggagcagagg tgaaaaagcc cggagagtct | 480 |
| ctgaagattt cctgtaaggg atccggttac tcattcactg gctacaatat gaactgggtg | 540 |
| cgccagatgc ccgggaaagg cctcgagtgg atgggcaata ttgatcctta ttatggtggt | 600 |
| actacctaca accggaagtt caagggccag gtcactatct ccgccgacaa gtccatcagc | 660 |
| accgcctacc tgcaatggag cagcctgaag gcctcggaca ccgccatgta ttactgtgca | 720 |
| cgctcagtcg gccctatgga ctactggggc gcggcaccc tggtcactgt ctcctctgat | 780 |
| caggagccca atcttctga caaaactcac acatctccac cgtgcccagc acctgaactc | 840 |
| ctgggtggac cgtcagtctt cctcttcccc ccaaaaccca aggacaccct catgatctcc | 900 |
| cggaccctg aggtcacatg cgtggtggtg gacgtgagcc acgaagaccc tgaggtcaag | 960 |
| ttcaactggt acgtggacgg cgtggaggtg cataatgcca agacaaagcc gcgggaggag | 1020 |
| cagtacaaca gcacgtaccg tgtggtcagc gtcctcaccg tcctgcacca ggactggctg | 1080 |
| aatggcaagg agtacaagtg caaggtctcc aacaaagccc tcccagcccc catcgagaaa | 1140 |
| accatctcca aagccaaagg gcagccccga gaaccacagg tgtacaccct gcccccatcc | 1200 |
| cgggatgagc tgaccaagaa ccaggtcagc ctgacctgcc tggtcaaagg cttctatcca | 1260 |
| agcgacatcg ccgtggagtg ggagagcaat gggcagccgg agaacaacta caagaccacg | 1320 |
| cctcccgtgc tggactccga cggctccttc ttcctctaca gcaagctcac cgtggacaag | 1380 |
| agcaggtggc agcaggggaa cgtcttctca tgctccgtga tgcatgaggc tctgcacaac | 1440 |
| cactacacgc agaagagcct ctccctgtct ccgggtaaat ga | 1482 |

<210> SEQ ID NO 6
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 6

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400
```

```
Arg Asp Glu Leu Thr Lys Asn Gln Val Ser Leu Thr Cys Leu Val Lys
                405                 410                 415
Gly Phe Tyr Pro Ser Asp Ile Ala Val Glu Trp Glu Ser Asn Gly Gln
            420                 425                 430
Pro Glu Asn Asn Tyr Lys Thr Thr Pro Pro Val Leu Asp Ser Asp Gly
        435                 440                 445
Ser Phe Phe Leu Tyr Ser Lys Leu Thr Val Asp Lys Ser Arg Trp Gln
    450                 455                 460
Gln Gly Asn Val Phe Ser Cys Ser Val Met His Glu Ala Leu His Asn
465                 470                 475                 480
His Tyr Thr Gln Lys Ser Leu Ser Leu Ser Pro Gly Lys
                485                 490
```

```
<210> SEQ ID NO 7
<211> LENGTH: 1482
<212> TYPE: DNA
<213> ORGANISM: Artificial sequence
<220> FEATURE:
<223> OTHER INFORMATION: CD37 specific binding protein

<400> SEQUENCE: 7
atggaagccc cagctcagct tctcttcctc ctgctactct ggctcccaga taccaccgga    60
gaaattgtgt tgacacagtc tccagccacc ctgtctttgt ctccaggcga aagagccacc   120
ctctcctgcc gaacaagtga aaatgtttac agctactag cctggtacca acagaaacct    180
ggccaggctc ctaggctcct catctatttt gcaaaaacct tagcagaagg aattccagcc   240
aggttcagtg gcagtggatc cgggacagac ttcactctca ccatcagcag cctagagcct   300
gaagattttg cagtttatta ctgtcaacat cattccgata tccgtggac attcggccaa    360 gggaccaagg tggaaatcaa aggtggcggt ggctcgggcg gtggtggatc tggaggaggt   420
gggagctctg aggtgcagct ggtgcagtct ggagcagagg tgaaaaagcc cggagagtct   480
ctgaagattt cctgtaaggg atccggttac tcattcactg ctacaatat gaactgggtg    540 cgccagatgc ccgggaaagg cctcgagtgg atgggcaata ttgatcctta ttatggtggt   600
actacctaca accggaagtt caagggccag gtcactatct ccgccgacaa gtccatcagc   660
accgcctacc tgcaatggag cagcctgaag gcctcggaca cgccatgta ttactgtgca    720 cgctcagtcg gccctatgga ctactgggc gcggcaccc tggtcactgt ctcctctgat    780
caggagccca atcttctga caaaactcac acatctccac cgtgcccagc acctgaactc   840
ctgggtggac cgtcagtctt cctcttcccc ccaaaaccca aggacaccct catgatctcc   900
cggacccctg aggtcacatg cgtggtggtg gacgtgagcc acgaagaccc tgaggtcaag   960
ttcaactggt acgtggacgg cgtggaggtg cataatgcca agacaaagcc gcgggaggag  1020
cagtacaaca gcacgtaccg tgtggtcagc gtcctcaccg tcctgcacca ggactggctg  1080
aatggcaagg agtacaagtg caaggtctcc aacaaagccc tcccagcccc catcgagaaa  1140
accatctcca aagccaaagg gcagccccga gaaccacagg tgtacaccct gcccccatcc  1200
cgggatgagc tgaccaagaa ccaggtcagc ctgacctgcc tggtcaaagg cttctatcca  1260
agcgacatcg ccgtggagtg ggagagcaat gggcagccgg agaacaacta caagaccacg  1320
cctcccgtgc tggactccga cggctccttc ttcctctaca gcaagctcac cgtggacaag  1380
agcaggtggc agcaggggaa cgtcttctca tgctccgtga tgcatgaggc tctgcacaac  1440
cactacacgc agaagagcct ctccctgtct ccgggtaaat ga                     1482
```

<210> SEQ ID NO 8
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 8

```
Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Ser Ser Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365
```

| | | | | | | | | | | | | |
|---|---|---|---|---|---|---|---|---|---|---|---|---|
|Val|Ser|Asn|Lys|Ala|Leu|Pro|Ala|Ile|Glu|Lys|Thr|Ile|Ser|Lys|
| |370| | | |375| | | |380| | | | | |

| Ala | Lys | Gly | Gln | Pro | Arg | Glu | Pro | Gln | Val | Tyr | Thr | Leu | Pro | Pro | Ser |
|---|---|---|---|---|---|---|---|---|---|---|---|---|---|---|---|
| 385 | | | | | 390 | | | | 395 | | | | | 400 | |

| Arg | Asp | Glu | Leu | Thr | Lys | Asn | Gln | Val | Ser | Leu | Thr | Cys | Leu | Val | Lys |
|---|---|---|---|---|---|---|---|---|---|---|---|---|---|---|---|
| | | | | 405 | | | | | 410 | | | | | 415 | |

| Gly | Phe | Tyr | Pro | Ser | Asp | Ile | Ala | Val | Glu | Trp | Glu | Ser | Asn | Gly | Gln |
|---|---|---|---|---|---|---|---|---|---|---|---|---|---|---|---|
| | | | 420 | | | | | 425 | | | | | 430 | | |

| Pro | Glu | Asn | Asn | Tyr | Lys | Thr | Thr | Pro | Pro | Val | Leu | Asp | Ser | Asp | Gly |
|---|---|---|---|---|---|---|---|---|---|---|---|---|---|---|---|
| | | | 435 | | | | 440 | | | | | 445 | | | |

| Ser | Phe | Phe | Leu | Tyr | Ser | Lys | Leu | Thr | Val | Asp | Lys | Ser | Arg | Trp | Gln |
|---|---|---|---|---|---|---|---|---|---|---|---|---|---|---|---|
| 450 | | | | | 455 | | | | | 460 | | | | | |

| Gln | Gly | Asn | Val | Phe | Ser | Cys | Ser | Val | Met | His | Glu | Ala | Leu | His | Asn |
|---|---|---|---|---|---|---|---|---|---|---|---|---|---|---|---|
| 465 | | | | | 470 | | | | | 475 | | | | | 480 |

| His | Tyr | Thr | Gln | Lys | Ser | Leu | Ser | Leu | Ser | Pro | Gly | Lys |
|---|---|---|---|---|---|---|---|---|---|---|---|---|
| | | | | 485 | | | | | 490 | | | |

<210> SEQ ID NO 9
<211> LENGTH: 1482
<212> TYPE: DNA
<213> ORGANISM: Artificial sequence
<220> FEATURE:
<223> OTHER INFORMATION: CD37 specific binding protein

<400> SEQUENCE: 9

```
atggaagccc cagctcagct tctcttcctc ctgctactct ggctcccaga taccaccgga    60
gaaattgtgt tgacacagtc tccagccacc ctgtctttgt ctccaggcga agagccacc   120
ctctcctgcc gaacaagtga aaatgtttac agctacttag cctggtacca acagaaacct   180
ggccaggctc ctaggctcct catctatttt gcaaaaacct tagcagaagg aattccagcc   240
aggttcagtg gcagtggatc cgggacagac ttcactctca ccatcagcag cctagagcct   300
gaagattttg cagtttatta ctgtcaacat cattccgata tccgtggac attcggccaa   360
gggaccaagg tggaaatcaa aggtggcggt ggctcgggcg gtggtggatc tggaggaggt   420
gggaccggtg aggtgcagct ggtgcagtct ggagcagagt cgaaaaagcc cggagagtct   480
ctgaagattt cctgtaaggg atccggttac tcattcactg gctacaatat gaactgggtg   540
cgccagatgc ccgggaaagg cctcgagtgg atgggcaata ttgatcctta ttatggtggt   600
actacctaca accggaagtt caagggccag gtcactatct ccgccgacaa gtccatcagc   660
accgcctacc tgcaatggag cagcctgaag gcctcggaca ccgccatgta ttactgtgca   720
cgctcagtcg gccctatgga ctactgggc cgcggcaccc tggtcactgt ctcctctgat   780
caggagccca atcttctga caaaactcac acatctccac cgtgcccagc acctgaactc   840
ctgggtggac cgtcagtctt cctcttcccc ccaaaaccca aggacaccct catgatctcc   900
cggacccctg aggtcacatg cgtggtggtg gacgtgagcc acgaagaccc tgaggtcaag   960
ttcaactggt acgtggacgg cgtggaggtg cataatgcca agacaaagcc gcggaggag   1020
cagtacaaca gcacgtaccg tgtggtcagc gtcctcaccg tcctgcacca ggactggctg   1080
aatggcaagg agtacaagtg caaggtctcc aacaaagccc tcccagcccc catcgagaaa   1140
accatctcca aagccaaagg gcagccccga gaaccacagg tgtacaccct gcccccatcc   1200
cgggatgagc tgaccaagaa ccaggtcagc ctgacctgcc tggtcaaagg cttctatcca   1260
agcgacatcg ccgtggagtg ggagagcaat gggcagccgg agaacaacta caagaccacg   1320
cctcccgtgc tggactccga cggctccttc ttcctctaca gcaagctcac cgtggacaag   1380
```

```
agcaggtggc agcaggggaa cgtcttctca tgctccgtga tgcatgaggc tctgcacaac    1440
cactacacgc agaagagcct ctccctgtct ccgggtaaat ga                       1482
```

<210> SEQ ID NO 10
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 10

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Thr Gly Glu
    130                 135                 140

Val Gln Leu Val Gln Ser Gly Ala Glu Ser Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
```

```
            340                 345                 350
Thr Val Leu His Gln Asp Trp Leu Asn Gly Lys Glu Tyr Lys Cys Lys
                355                 360                 365

Val Ser Asn Lys Ala Leu Pro Ala Pro Ile Glu Lys Thr Ile Ser Lys
        370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490
```

<210> SEQ ID NO 11
<211> LENGTH: 1482
<212> TYPE: DNA
<213> ORGANISM: Artificial sequence
<220> FEATURE:
<223> OTHER INFORMATION: CD37 specific binding protein

<400> SEQUENCE: 11

```
atggaagccc cagctcagct tctcttcctc ctgctactct ggctcccaga taccaccgga      60
gaaattgtgt tgacacagtc tccagccacc ctgtctttgt ctccaggcga agagccacc      120
ctctcctgcc gaacaagtca aatgtttac agctacttag cctggtacca acagaaacct      180
ggccaggctc ctaggctcct catctatttt gcaaaaacct agcagaagg aattccagcc      240
aggttcagtg gcagtggatc cgggacagac ttcactctca ccatcagcag cctagagcct      300
gaagattttg cagtttatta ctgtcaacat cattccgata tccgtggac attcggccaa      360
gggaccaagg tggaaatcaa aggtggcggt ggctcgggcg gtggtggatc tggaggaggt      420
gggaccggtg aggtgcagct ggtgcagtct ggagcagagt gaaaaagcc cggagagtct      480
ctgaagattt cctgtaaggg atccggttac tcattcactg gctacaatat gaactgggtg      540
cgccagatgc ccgggaaagg cctcgagtgg atgggcaata ttgatcctta ttatggtggt      600
actacctaca accggaagtt caagggccag gtcactatct ccgccgacaa gtccatcagc      660
accgcctacc tgcaatggag cagcctgaag gcctcggaca ccgccatgta ttactgtgca      720
cgctcagtcg gccctatgga ctactgggc gcgcggcaccc tggtcactgt ctcctctgat      780
caggagccca atcttctga caaaactcac acatctccac cgtgcccagc acctgaactc      840
ctgggtggac cgtcagtctt cctcttcccc ccaaaaccca aggacaccct catgatctcc      900
cggaccctg aggtcacatg cgtggtggtg gacgtgagcc acgaagaccc tgaggtcaag      960
ttcaactggt acgtggacgg cgtggaggtg cataatgcca agacaaagcc gcggaggag     1020
cagtacaaca gcacgtaccg tgtggtcagc gtcctcaccg tcctgcacca ggactggctg     1080
aatggcaagg agtacaagtg caaggtctcc aacaaagccc tcccagcccc catcgagaaa     1140
accatctcca aagccaaagg gcagcccga gaaccacagg tgtacaccct gcccccatcc     1200
```

```
cgggatgagc tgaccaagaa ccaggtcagc ctgacctgcc tggtcaaagg cttctatcca    1260
agcgacatcg ccgtggagtg ggagagcaat gggcagccgg agaacaacta caagaccacg    1320
cctcccgtgc tggactccga cggctccttc ttcctctaca gcaagctcac cgtggacaag    1380
agcaggtggc agcaggggaa cgtcttctca tgctccgtga tgcatgaggc tctgcacaac    1440
cactacacgc agaagagcct ctccctgtct ccgggtaaat ga                       1482
```

<210> SEQ ID NO 12
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 12

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Gln Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320
```

```
Phe Asn Trp Tyr Val Asp Gly Val Glu Val His Asn Ala Lys Thr Lys
                325                 330                 335
Pro Arg Glu Glu Gln Tyr Asn Ser Thr Tyr Arg Val Val Ser Val Leu
            340                 345                 350
Thr Val Leu His Gln Asp Trp Leu Asn Gly Lys Glu Tyr Lys Cys Lys
        355                 360                 365
Val Ser Asn Lys Ala Leu Pro Ala Pro Ile Glu Lys Thr Ile Ser Lys
    370                 375                 380
Ala Lys Gly Gln Pro Arg Glu Pro Gln Val Tyr Thr Leu Pro Pro Ser
385                 390                 395                 400
Arg Asp Glu Leu Thr Lys Asn Gln Val Ser Leu Thr Cys Leu Val Lys
                405                 410                 415
Gly Phe Tyr Pro Ser Asp Ile Ala Val Glu Trp Glu Ser Asn Gly Gln
            420                 425                 430
Pro Glu Asn Asn Tyr Lys Thr Thr Pro Pro Val Leu Asp Ser Asp Gly
        435                 440                 445
Ser Phe Phe Leu Tyr Ser Lys Leu Thr Val Asp Lys Ser Arg Trp Gln
    450                 455                 460
Gln Gly Asn Val Phe Ser Cys Ser Val Met His Glu Ala Leu His Asn
465                 470                 475                 480
His Tyr Thr Gln Lys Ser Leu Ser Leu Ser Pro Gly Lys
                485                 490

<210> SEQ ID NO 13
<211> LENGTH: 1482
<212> TYPE: DNA
<213> ORGANISM: Artificial sequence
<220> FEATURE:
<223> OTHER INFORMATION: CD37 specific binding protein

<400> SEQUENCE: 13
atggaagccc cagctcagct tctcttcctc ctgctactct ggctcccaga taccaccgga      60
gaaattgtgt tgacacagtc tccagccacc ctgtctttgt ctccaggcga agagccacc     120
ctctcctgcc gaacaagtga aagtgtttac agctacttag cctggtacca acagaaacct     180
ggccaggctc ctaggctcct catctatttt gcaaaaacct agcagaagg aattccagcc      240
aggttcagtg gcagtggatc cgggacagac ttcactctca ccatcagcag cctagagcct     300
gaagattttg cagtttatta ctgtcaacat cattccgata tccgtggac attcggccaa     360
gggaccaagg tggaaatcaa aggtggcggt ggctcgggcg tggtggatc tggaggaggt     420
gggaccggtg aggtgcagct ggtgcagtct ggagcagagg tgaaaaagcc cggagagtct     480
ctgaagattt cctgtaaggg atccggttac tcattcactg gctacaatat gaactgggtg     540
cgccagatgc ccgggaaagg cctcgagtgg atgggcaata ttgatcctta ttatggtggt     600
actacctaca accggaagtt caagggccag gtcactatct ccgccgacaa gtccatcagc     660
accgcctacc tgcaatggag cagcctgaag gcctcggaca ccgccatgta ttactgtgca     720
cgctcagtcg ccctatggga ctactggggc gcggcaccc tggtcactgt ctcctctgat     780
caggagccca atcttctga caaaactcac acatctccac cgtgcccagc acctgaactc     840
ctgggtggac cgtcagtctt cctcttcccc ccaaaaccca aggacaccct catgatctcc     900
cggaccctg aggtcacatg cgtggtggtg gacgtgagcc acgaagaccc tgaggtcaag     960
ttcaactggt acgtgacgg cgtggaggtg cataatgcca agacaaagcc gcggaggag    1020
cagtacaaca gcacgtaccg tgtggtcagc gtcctcaccg tcctgcacca ggactggctg    1080
```

-continued

```
aatggcaagg agtacaagtg caaggtctcc aacaaagccc tcccagcccc catcgagaaa    1140
accatctcca agccaaagg gcagccccga gaaccacagg tgtacaccct gcccccatcc    1200
cgggatgagc tgaccaagaa ccaggtcagc ctgacctgcc tggtcaaagg cttctatcca    1260
agcgacatcg ccgtggagtg ggagagcaat gggcagccgg agaacaacta caagaccacg    1320
cctcccgtgc tggactccga cggctccttc ttcctctaca gcaagctcac cgtggacaag    1380
agcaggtggc agcaggggaa cgtcttctca tgctccgtga tgcatgaggc tctgcacaac    1440
cactacacgc agaagagcct ctccctgtct ccgggtaaat ga                       1482
```

<210> SEQ ID NO 14
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 14

```
Met Glu Ala Pro Ala Gln Leu Leu Phe Leu Leu Leu Trp Leu Pro
1               5                  10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Ser
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285
```

```
Phe Pro Pro Lys Pro Lys Asp Thr Leu Met Ile Ser Arg Thr Pro Glu
        290                 295                 300
Val Thr Cys Val Val Val Asp Val Ser His Glu Asp Pro Glu Val Lys
305                 310                 315                 320
Phe Asn Trp Tyr Val Asp Gly Val Glu Val His Asn Ala Lys Thr Lys
                325                 330                 335
Pro Arg Glu Glu Gln Tyr Asn Ser Thr Tyr Arg Val Val Ser Val Leu
            340                 345                 350
Thr Val Leu His Gln Asp Trp Leu Asn Gly Lys Glu Tyr Lys Cys Lys
        355                 360                 365
Val Ser Asn Lys Ala Leu Pro Ala Pro Ile Glu Lys Thr Ile Ser Lys
370                 375                 380
Ala Lys Gly Gln Pro Arg Glu Pro Gln Val Tyr Thr Leu Pro Pro Ser
385                 390                 395                 400
Arg Asp Glu Leu Thr Lys Asn Gln Val Ser Leu Thr Cys Leu Val Lys
                405                 410                 415
Gly Phe Tyr Pro Ser Asp Ile Ala Val Glu Trp Glu Ser Asn Gly Gln
            420                 425                 430
Pro Glu Asn Asn Tyr Lys Thr Thr Pro Pro Val Leu Asp Ser Asp Gly
        435                 440                 445
Ser Phe Phe Leu Tyr Ser Lys Leu Thr Val Asp Lys Ser Arg Trp Gln
450                 455                 460
Gln Gly Asn Val Phe Ser Cys Ser Val Met His Glu Ala Leu His Asn
465                 470                 475                 480
His Tyr Thr Gln Lys Ser Leu Ser Leu Ser Pro Gly Lys
                485                 490
```

<210> SEQ ID NO 15
<211> LENGTH: 1482
<212> TYPE: DNA
<213> ORGANISM: Artificial sequence
<220> FEATURE:
<223> OTHER INFORMATION: CD37 specific binding protein

<400> SEQUENCE: 15

```
atggaagccc agctcagct tctcttcctc ctgctactct ggctcccaga taccaccgga    60
gaaattgtgt tgacacagtc tccagccacc ctgtctttgt ctccaggcga agagccacc   120
ctctcctgcc agcaagtga aaatgtttac agctacttag cctggtacca acagaaacct   180
ggccaggctc ctaggctcct catctatttt gcaaaaacct agcagaagg aattccagcc   240
aggttcagtg gcagtggatc cgggacagac ttcactctca ccatcagcag cctagagcct   300
gaagattttg cagtttatta ctgtcaacat cattccgata tccgtggac attcggccaa   360
gggaccaagg tggaaatcaa aggtggcggt ggctcgggcg tggtggatc tggaggaggt   420
gggaccggtg aggtgcagct ggtgcagtct ggagcagagg tgaaaaagcc cggagagtct   480
ctgaagattt cctgtaaggg atccggttac tcattcactg gctacaatat gaactgggtg   540
cgccagatgc ccgggaaagg cctcgagtgg atgggcaata ttgatcctta ttatggtggt   600
actacctaca accggaagtt caagggccag gtcactatct ccgccgacaa gtccatcagc   660
accgcctacc tgcaatggag cagcctgaag gcctcggaca ccgccatgta ttactgtgca   720
cgctcagtcg gcctatgga ctactggggc gcgggcaccc tggtcactgt ctcctctgat   780
caggagccca atcttctga caaaactcac acatctccac cgtgcccagc acctgaactc   840
ctgggtggac cgtcagtctt cctcttcccc ccaaaaccca aggacaccct catgatctcc   900
```

-continued

```
cggacccctg aggtcacatg cgtggtggtg acgtgagcc acgaagaccc tgaggtcaag    960
ttcaactggt acgtggacgg cgtggaggtg cataatgcca agacaaagcc gcgggaggag   1020
cagtacaaca gcacgtaccg tgtggtcagc gtcctcaccg tcctgcacca ggactggctg   1080
aatggcaagg agtacaagtg caaggtctcc aacaaagccc tcccagcccc catcgagaaa   1140
accatctcca aagccaaagg gcagccccga gaaccacagg tgtacaccct gcccccatcc   1200
cgggatgagc tgaccaagaa ccaggtcagc ctgacctgcc tggtcaaagg cttctatcca   1260
agcgacatcg ccgtggagtg ggagagcaat gggcagccgg agaacaacta caagaccacg   1320
cctcccgtgc tggactccga cggctccttc ttcctctaca gcaagctcac cgtggacaag   1380
agcaggtggc agcaggggaa cgtcttctca tgctccgtga tgcatgaggc tctgcacaac   1440
cactacacgc agaagagcct ctccctgtct ccgggtaaat ga                      1482
```

<210> SEQ ID NO 16
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 16

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
```

```
            260                 265                 270
Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
        290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
        370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 17
<211> LENGTH: 1479
<212> TYPE: DNA
<213> ORGANISM: Artificial sequence
<220> FEATURE:
<223> OTHER INFORMATION: CD37 specific binding protein

<400> SEQUENCE: 17
atggaagcac cagcgcagct tctcttcctc ctgctactct ggctcccaga taccaccggt    60
gacatccaga tgactcagtc tccagcctcc ctatctgcat ctgtgggaga gactgtcacc   120
atcacatgtc gaacaagtga aaatgtttac agttatttgg cttggtatca gcagaaacag   180
ggaaaatctc ctcagctcct ggtctctttt gcaaaaacct tagcagaagg tgtgccatca   240
aggttcagtg gcagtggatc aggcacacag ttttctctga gatcagcagc ctgcagcct   300 gaagattctg gaagttattt ctgtcaacat cattccgata tccgtggac gttcggtgga   360 ggcaccgaac tggagatcaa aggtggcggt ggctcgggcg gtggtgggtc gggtggcggc   420
ggagctagcg aggtgcagct ggtgcagtct ggagcagagg tgaaaaagcc cggagagtct   480
ctgaggattt cctgtaaggg atccggttac tcattcactg ctacaatat gaactgggtg   540 cgccagatgc ccgggaaagg cctggagtgg atgggcaata ttgatcctta ttatggtggt   600
actacctaca accggaagtt caagggccag gtcactatct ccgccgacaa gtccatcagc   660
accgcctacc tgcaatggag cagcctgaag gcctcggaca ccgccatgta ttactgtgca   720
cgctcagtcg gccctatgga ctactggggc cgcggcaccc tggtcactgt ctcctcgagc   780
```

-continued

```
gagcccaaat cttctgacaa aactcacaca tctccaccgt gcccagcacc tgaactcctg      840
ggtggaccgt cagtcttcct cttccccca aaacccaagg acaccctcat gatctcccgg       900
acccctgagg tcacatgcgt ggtggtggac gtgagccacg aagaccctga ggtcaagttc     960
aactggtacg tggacggcgt ggaggtgcat aatgccaaga caaagccgcg ggaggagcag    1020
tacaacagca cgtaccgtgt ggtcagcgtc ctcaccgtcc tgcaccagga ctggctgaat    1080
ggcaaggagt acaagtgcaa ggtctccaac aaagccctcc cagcccccat cgagaaaacc    1140
atctccaaag ccaaagggca gccccgagaa ccacaggtgt acaccctgcc cccatcccgg    1200
gatgagctga ccaagaacca ggtcagcctg acctgcctgg tcaaaggctt ctatccaagc    1260
gacatcgccg tggagtggga gagcaatggg cagccggaga acaactacaa gaccacgcct    1320
cccgtgctgg actccgacgg ctccttcttc ctctacagca agctcaccgt ggacaagagc    1380
aggtggcagc aggggaacgt cttctcatgc tccgtgatgc atgaggctct gcacaaccac    1440
tacacgcaga gagcctctc cctgtctccg ggtaaatga                              1479
```

<210> SEQ ID NO 18
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 18

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ala Ser Leu Ser
            20                  25                  30

Ala Ser Val Gly Glu Thr Val Thr Ile Thr Cys Arg Thr Ser Glu Asn
        35                  40                  45

Val Tyr Ser Tyr Leu Ala Trp Tyr Gln Gln Lys Gln Gly Lys Ser Pro
    50                  55                  60

Gln Leu Leu Val Ser Phe Ala Lys Thr Leu Ala Glu Gly Val Pro Ser
65                  70                  75                  80

Arg Phe Ser Gly Ser Gly Ser Gly Thr Gln Phe Ser Leu Lys Ile Ser
                85                  90                  95

Ser Leu Gln Pro Glu Asp Ser Gly Ser Tyr Phe Cys Gln His His Ser
            100                 105                 110

Asp Asn Pro Trp Thr Phe Gly Gly Gly Thr Glu Leu Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Gln Ser Gly Ala Glu Val Lys Lys Pro Gly Glu Ser
145                 150                 155                 160

Leu Arg Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240
```

```
Arg Ser Val Gly Pro Met Asp Tyr Trp Gly Arg Gly Thr Leu Val Thr
                245                 250                 255
Val Ser Ser Ser Glu Pro Lys Ser Ser Asp Lys Thr His Thr Ser Pro
            260                 265                 270
Pro Cys Pro Ala Pro Glu Leu Leu Gly Gly Pro Ser Val Phe Leu Phe
        275                 280                 285
Pro Pro Lys Pro Lys Asp Thr Leu Met Ile Ser Arg Thr Pro Glu Val
    290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
            340                 345                 350
Val Leu His Gln Asp Trp Leu Asn Gly Lys Glu Tyr Lys Cys Lys Val
        355                 360                 365
Ser Asn Lys Ala Leu Pro Ala Pro Ile Glu Lys Thr Ile Ser Lys Ala
    370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
        435                 440                 445
Phe Phe Leu Tyr Ser Lys Leu Thr Val Asp Lys Ser Arg Trp Gln Gln
    450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys
                485                 490

<210> SEQ ID NO 19
<211> LENGTH: 1479
<212> TYPE: DNA
<213> ORGANISM: Artificial sequence
<220> FEATURE:
<223> OTHER INFORMATION: CD37 specific binding protein

<400> SEQUENCE: 19
atggaagcac cagcgcagct tctcttcctc ctgctactct ggctcccaga taccaccggt    60
gaaattgtgt tgacacagtc tccagccacc ctgtctttgt ctccaggcga agagccacc    120 ctctcctgcc gaacaagtga aaatgtttac agctacttag cctggtacca acagaaacct    180
ggccaggctc ctaggctcct catctatttt gcaaaaacct agcagaagg aattccagcc    240 aggttcagtg gcagtggatc cgggacagac ttcactctca ccatcagcag cctagagcct    300
gaagattttg cagtttatta ctgtcaacat cattccgata tccgtggac attcggccaa    360 gggaccaagg tggaaatcaa aggtggcggt ggctcgggcg gtagtggatc tggaggaggt    420
ggagctagcg cggtccagct gcagcagtct ggacctgagt cggaaaagcc tggcgcttca    480
gtgaagattt cctgcaaggc ttctggttac tcattcactg gctacaatat gaactgggtg    540
aagcagaata tggaaagag ccttgagtgg attggaaata ttgatcctta ttatggtggt    600
```

```
actacctaca accggaagtt caagggcaag gccacattga ctgtagacaa atcctccagc    660
acagcctaca tgcagctcaa gagtctgaca tctgaggact ctgcagtcta ttactgtgca    720
agatcggtcg gccctatgga ctactggggt caaggaacct cagtcaccgt ctcctcgagc    780
gagcccaaat cttctgacaa aactcacaca tctccaccgt gcccagcacc tgaactcctg    840
ggtggaccgt cagtcttcct cttccccccca aaacccaagg acaccctcat gatctcccgg    900
accccctgagg tcacatgcgt ggtggtggac gtgagccacg aagaccctga ggtcaagttc    960
aactggtacg tggacggcgt ggaggtgcat aatgccaaga caaagccgcg ggaggagcag   1020
tacaacagca cgtaccgtgt ggtcagcgtc ctcaccgtcc tgcaccagga ctggctgaat   1080
ggcaaggagt acaagtgcaa ggtctccaac aaagccctcc cagcccccat cgagaaaacc   1140
atctccaaag ccaaagggca gccccgagaa ccacaggtgt acaccctgcc cccatcccgg   1200
gatgagctga ccaagaacca ggtcagcctg acctgcctgg tcaaaggctt ctatccaagc   1260
gacatcgccg tggagtggga gagcaatggg cagccggaga acaactacaa gaccacgcct   1320
cccgtgctgg actccgacgg ctccttcttc ctctacagca agctcaccgt ggacaagagc   1380
aggtggcagc aggggaacgt cttctcatgc tccgtgatgc atgaggctct gcacaaccac   1440
tacacgcaga agagcctctc cctgtctccg ggtaaatga                           1479
```

<210> SEQ ID NO 20
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 20

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Ser Gly Ser Gly Gly Gly Ala Ser Ala
    130                 135                 140

Val Gln Leu Gln Gln Ser Gly Pro Glu Ser Glu Lys Pro Gly Ala Ser
145                 150                 155                 160

Val Lys Ile Ser Cys Lys Ala Ser Gly Tyr Ser Phe Thr Gly Tyr Asn
                165                 170                 175

Met Asn Trp Val Lys Gln Asn Asn Gly Lys Ser Leu Glu Trp Ile Gly
            180                 185                 190

Asn Ile Asp Pro Tyr Tyr Gly Gly Thr Thr Tyr Asn Arg Lys Phe Lys
        195                 200                 205
```

```
Gly Lys Ala Thr Leu Thr Val Asp Lys Ser Ser Thr Ala Tyr Met
            210                 215                 220
Gln Leu Lys Ser Leu Thr Ser Glu Asp Ser Ala Val Tyr Tyr Cys Ala
225                 230                 235                 240
Arg Ser Val Gly Pro Met Asp Tyr Trp Gly Gln Gly Thr Ser Val Thr
                245                 250                 255
Val Ser Ser Ser Glu Pro Lys Ser Ser Asp Lys Thr His Thr Ser Pro
            260                 265                 270
Pro Cys Pro Ala Pro Glu Leu Leu Gly Gly Pro Ser Val Phe Leu Phe
        275                 280                 285
Pro Pro Lys Pro Lys Asp Thr Leu Met Ile Ser Arg Thr Pro Glu Val
290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
            340                 345                 350
Val Leu His Gln Asp Trp Leu Asn Gly Lys Glu Tyr Lys Cys Lys Val
        355                 360                 365
Ser Asn Lys Ala Leu Pro Ala Pro Ile Glu Lys Thr Ile Ser Lys Ala
370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
        435                 440                 445
Phe Phe Leu Tyr Ser Lys Leu Thr Val Asp Lys Ser Arg Trp Gln Gln
450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys
                485                 490

<210> SEQ ID NO 21
<211> LENGTH: 1479
<212> TYPE: DNA
<213> ORGANISM: Artificial sequence
<220> FEATURE:
<223> OTHER INFORMATION: CD37 specific binding protein

<400> SEQUENCE: 21
atggaagcac cagcgcagct tctcttcctc ctgctactct ggctcccaga taccaccggt      60
gaaattgtgt tgacacagtc tccagccacc ctgtctttgt ctccaggcga aagagccacc     120
ctctcctgcc gaacaagtga aaatgtttac agctacttag cctggtacca acagaaacct     180
ggccaggctc ctaggctcct catctatttt gcaaaaacct agcagaagg aattccagcc      240 aggttcagtg gcagtggatc cgggacagac ttcactctca ccatcagcag cctagagcct     300
gaagattttg cagtttatta ctgtcaacat cattccgata tccgtggac attcggccaa      360 gggaccaagg tggaaatcaa aggtggcggt ggctcgggcg tggtggatc tggaggaggt      420 ggagctagcc aggtgcagct ggtggagtct ggtggaggcg tggtccagcc tggaggtcc      480
```

```
ctgagactct cctgtgcagc ctctggattc accttcagtg gctacaatat gaactgggtc      540
cgccagatgc ccgggaaagg cctggagtgg atgggcaata ttgatcctta ttatggtggt      600
actacctaca accggaagtt caagggccag gtcactatct ccgccgacaa gtccatcagc      660
accgcctacc tgcaatggag cagcctgaag gcctcggaca ccgccatgta ttactgtgca      720
cgctcagtcg gccctatgga ctactggggc cgcggcaccc tggtcactgt ctcctcgagc      780
gagcccaaat cttctgacaa aactcacaca tctccaccgt gcccagcacc tgaactcctg      840
ggtggaccgt cagtcttcct cttcccccca aaacccaagg acaccctcat gatctcccgg      900
acccctgagg tcacatgcgt ggtggtggac gtgagccacg aagaccctga ggtcaagttc      960
aactggtacg tggacggcgt ggaggtgcat aatgccaaga caaagccgcg ggaggagcag     1020
tacaacagca cgtaccgtgt ggtcagcgtc ctcaccgtcc tgcaccagga ctggctgaat     1080
ggcaaggagt acaagtgcaa ggtctccaac aaagccctcc cagcccccat cgagaaaacc     1140
atctccaaag ccaaagggca gccccgagaa ccacaggtgt acaccctgcc cccatcccgg     1200
gatgagctga ccaagaacca ggtcagcctg acctgcctgg tcaaaggctt ctatccaagc     1260
gacatcgccg tggagtggga gagcaatggg cagccggaga acaactacaa gaccacgcct     1320
cccgtgctgg actccgacgg ctccttcttc ctctacagca agctcaccgt ggacaagagc     1380
aggtggcagc aggggaacgt cttctcatgc tccgtgatgc atgaggctct gcacaaccac     1440
tacacgcaga agagcctctc cctgtctccg ggtaaatga                            1479

<210> SEQ ID NO 22
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 22
```

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Ala Ser Gln
    130                 135                 140

Val Gln Leu Val Glu Ser Gly Gly Gly Val Val Gln Pro Gly Arg Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly

```
                        180                 185                 190
Asn Ile Asp Pro Tyr Tyr Gly Gly Thr Thr Tyr Asn Arg Lys Phe Lys
                195                 200                 205
Gly Gln Val Thr Ile Ser Ala Asp Lys Ser Ile Ser Thr Ala Tyr Leu
            210                 215                 220
Gln Trp Ser Ser Leu Lys Ala Ser Asp Thr Ala Met Tyr Tyr Cys Ala
225                 230                 235                 240
Arg Ser Val Gly Pro Met Asp Tyr Trp Gly Arg Gly Thr Leu Val Thr
                245                 250                 255
Val Ser Ser Ser Glu Pro Lys Ser Ser Asp Lys Thr His Thr Ser Pro
            260                 265                 270
Pro Cys Pro Ala Pro Glu Leu Leu Gly Gly Pro Ser Val Phe Leu Phe
        275                 280                 285
Pro Pro Lys Pro Lys Asp Thr Leu Met Ile Ser Arg Thr Pro Glu Val
            290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
                340                 345                 350
Val Leu His Gln Asp Trp Leu Asn Gly Lys Glu Tyr Lys Cys Lys Val
            355                 360                 365
Ser Asn Lys Ala Leu Pro Ala Pro Ile Glu Lys Thr Ile Ser Lys Ala
        370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
                420                 425                 430
Glu Asn Asn Tyr Lys Thr Thr Pro Pro Val Leu Asp Ser Asp Gly Ser
            435                 440                 445
Phe Phe Leu Tyr Ser Lys Leu Thr Val Asp Lys Ser Arg Trp Gln Gln
        450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys
                485                 490

<210> SEQ ID NO 23
<211> LENGTH: 1503
<212> TYPE: DNA
<213> ORGANISM: Artificial sequence
<220> FEATURE:
<223> OTHER INFORMATION: CD37 specific binding protein

<400> SEQUENCE: 23
atggaagcac cagcgcagct tctcttcctc ctgctactct ggctcccaga taccaccggt      60
gcggtccagc tgcagcagtc tggacctgag tcggaaaagc ctggcgcttc agtgaagatt     120
tcctgcaagg cttctggtta ctcattcact ggctacaata tgaactgggt gaagcagaat     180
aatggaaaga gccttgagtg gattggaaat attgatcctt attatggtgg tactacctac     240
aaccggaagt tcaagggcaa ggccacattg actgtagaca atcctccag cacagcctac     300
```

```
atgcagctca agagtctgac atctgaggac tctgcagtct attactgtgc aagatcggtc    360
ggccctatgg actactgggg tcaaggaacc tcagtcaccg tctcttctgg tggcggtggc    420
tcgggcggtg gtgggtcggg tggcggcgga tcaggaggag gcgggagtgc tagcgaaatt    480
gtgttgacac agtctccagc caccctgtct ttgtctccag gcgaaagagc caccctctcc    540
tgccgaacaa gtgaaaatgt ttacagctac ttagcctggt accaacagaa acctggccag    600
gctcctaggc tcctcatcta ttttgcaaaa accttagcag aaggaattcc agccaggttc    660
agtggcagtg gatccgggac agacttcact ctcaccatca gcagcctaga gcctgaagat    720
tttgcagttt attactgtca acatcattcc gataatccgt ggacattcgg ccaagggacc    780
aaggtggaaa tcaaaggctc gagcgagccc aaatcttctg acaaaactca cacatctcca    840
ccgtgcccag cacctgaact cctgggtgga ccgtcagtct tcctcttccc cccaaaaccc    900
aaggacaccc tcatgatctc ccggacccct gaggtcacat gcgtggtggt ggacgtgagc    960
cacgaagacc ctgaggtcaa gttcaactgg tacgtggacg gcgtggaggt gcataatgcc   1020
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aaccatctcc aaagccaaag gcagccccg agaaccacag    1200
gtgtacaccc tgcccccatc ccgggatgag ctgaccaaga accaggtcag cctgacctgc   1260
ctggtcaaag gcttctatcc aagcgacatc gccgtggagt gggagagcaa tgggcagccg   1320
gagaacaact acaagaccac gcctcccgtg ctggactccg acggctcctt cttcctctac   1380
agcaagctca ccgtggacaa gagcaggtgg cagcagggga acgtcttctc atgctccgtg   1440
atgcatgagg ctctgcacaa ccactacacg cagaagagcc tctccctgtc tccgggtaaa   1500
tga                                                                 1503

<210> SEQ ID NO 24
<211> LENGTH: 500
<212> TYPE: PRT
<213> ORGANISM: Artificial sequence
<220> FEATURE:
<223> OTHER INFORMATION: CD37 specific binding protein

<400> SEQUENCE: 24

Met Glu Ala Pro Ala Gln Leu Leu Phe Leu Leu Leu Leu Trp Leu Pro
1               5                   10                  15

Asp Thr Thr Gly Ala Val Gln Leu Gln Gln Ser Gly Pro Glu Ser Glu
            20                  25                  30

Lys Pro Gly Ala Ser Val Lys Ile Ser Cys Lys Ala Ser Gly Tyr Ser
        35                  40                  45

Phe Thr Gly Tyr Asn Met Asn Trp Val Lys Gln Asn Asn Gly Lys Ser
    50                  55                  60

Leu Glu Trp Ile Gly Asn Ile Asp Pro Tyr Tyr Gly Gly Thr Thr Tyr
65                  70                  75                  80

Asn Arg Lys Phe Lys Gly Lys Ala Thr Leu Thr Val Asp Lys Ser Ser
                85                  90                  95

Ser Thr Ala Tyr Met Gln Leu Lys Ser Leu Thr Ser Glu Asp Ser Ala
            100                 105                 110

Val Tyr Tyr Cys Ala Arg Ser Val Gly Pro Met Asp Tyr Trp Gly Gln
        115                 120                 125

Gly Thr Ser Val Thr Val Ser Ser Gly Gly Gly Ser Gly Gly Gly
    130                 135                 140
```

```
Gly Ser Gly Gly Gly Ser Gly Gly Gly Ser Ala Ser Glu Ile
145                 150                 155                 160

Val Leu Thr Gln Ser Pro Ala Thr Leu Ser Leu Ser Pro Gly Glu Arg
            165                 170                 175

Ala Thr Leu Ser Cys Arg Thr Ser Glu Asn Val Tyr Ser Tyr Leu Ala
        180                 185                 190

Trp Tyr Gln Gln Lys Pro Gly Gln Ala Pro Arg Leu Leu Ile Tyr Phe
    195                 200                 205

Ala Lys Thr Leu Ala Glu Gly Ile Pro Ala Arg Phe Ser Gly Ser Gly
210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln His His Ser Asp Asn Pro Trp Thr Phe
                245                 250                 255

Gly Gln Gly Thr Lys Val Glu Ile Lys Gly Ser Ser Glu Pro Lys Ser
            260                 265                 270

Ser Asp Lys Thr His Thr Ser Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
            500

<210> SEQ ID NO 25
<211> LENGTH: 1488
<212> TYPE: DNA
<213> ORGANISM: Artificial sequence
<220> FEATURE:
<223> OTHER INFORMATION: CD37 specific binding protein

<400> SEQUENCE: 25
```

```
atggattttc aagtgcagat tttcagcttc ctgctaatca gtgcttcagt cataattgcc      60
agaggagtcg aaattgtgtt gacacagtct ccagccaccc tgtctttgtc tccaggcgaa     120
agagccaccc tctcctgccg aacaagtgaa atgtttaca gctacttagc ctggtaccaa      180
cagaaacctg gccaggctcc taggctcctc atctattttg caaaaacctt agcagaagga     240
attccagcca ggttcagtgg cagtggatcc gggacagact tcactctcac catcagcagc     300
ctagagcctg aagattttgc agtttattac tgtcaacatc attccgataa tccgtggaca     360
ttcggccaag ggaccaaggt ggaaatcaaa ggtggcggtg gctcgggcgg tggtggatct     420
ggaggaggtg gagctagcgc ggtccagctg cagcagtctg gacctgagtc ggaaaagcct     480
ggcgcttcag tgaagatttc ctgcaaggct tctggttact cattcactgg ctacaatatg     540
aactgggtga agcagaataa tggaaagagc cttgagtgga ttggaaatat tgatccttat     600
tatggtggta ctacctacaa ccggaagttc aagggcaagg ccacattgac tgtagacaaa     660
tcctccagca cagcctacat gcagctcaag agtctgacat ctgaggactc tgcagtctat     720
tactgtgcaa gatcggtcgg ccctatggac tactggggtc aaggaacctc agtcaccgtc     780
tcctcgagcg agcccaaatc ttctgacaaa actcacacat ctccaccgtg cccagcacct     840
gaactcctgg gtggaccgtc agtcttcctc ttccccccaa aacccaagga caccctcatg     900
atctcccgga cccctgaggt cacatgcgtg gtggtggacg tgagccacga agaccctgag     960
gtcaagttca actggtacgt ggacggcgtg gaggtgcata atgccaagac aaagccgcgg    1020
gaggagcagt acaacagcac gtaccgtgtg gtcagcgtcc tcaccgtcct gcaccaggac    1080
tggctgaatg gcaaggagta caagtgcaag gtctccaaca agccctccc agcccccatc     1140
gagaaaacca tctccaaagc caagggcag ccccgagaac acaggtgta caccctgccc      1200
ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gtaaatga                 1488
```

<210> SEQ ID NO 26
<211> LENGTH: 495
<212> TYPE: PRT
<213> ORGANISM: Artificial sequence
<220> FEATURE:
<223> OTHER INFORMATION: CD37 specific binding protein

<400> SEQUENCE: 26

```
Met Asp Phe Gln Val Gln Ile Phe Ser Phe Leu Leu Ile Ser Ala Ser
1               5                   10                  15

Val Ile Ile Ala Arg Gly Val Glu Ile Val Leu Thr Gln Ser Pro Ala
                20                  25                  30

Thr Leu Ser Leu Ser Pro Gly Glu Arg Ala Thr Leu Ser Cys Arg Thr
            35                  40                  45

Ser Glu Asn Val Tyr Ser Tyr Leu Ala Trp Tyr Gln Gln Lys Pro Gly
        50                  55                  60

Gln Ala Pro Arg Leu Leu Ile Tyr Phe Ala Lys Thr Leu Ala Glu Gly
65                  70                  75                  80

Ile Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
```

|     |     |     |     |     | 100 |     |     |     | 105 |     |     |     |     | 110 |
| --- | --- | --- | --- | --- | --- | --- | --- | --- | --- | --- | --- | --- | --- | --- |

His His Ser Asp Asn Pro Trp Thr Phe Gly Gln Gly Thr Lys Val Glu
         115                    120                   125

Ile Lys Gly Gly Gly Ser Gly Gly Gly Ser Gly Gly Gly Gly
 130                    135                   140

Ala Ser Ala Val Gln Leu Gln Gln Ser Gly Pro Glu Ser Glu Lys Pro
145                 150                   155                 160

Gly Ala Ser Val Lys Ile Ser Cys Lys Ala Ser Gly Tyr Ser Phe Thr
                 165                   170                 175

Gly Tyr Asn Met Asn Trp Val Lys Gln Asn Asn Gly Lys Ser Leu Glu
         180                   185                 190

Trp Ile Gly Asn Ile Asp Pro Tyr Tyr Gly Gly Thr Thr Tyr Asn Arg
     195                   200                 205

Lys Phe Lys Gly Lys Ala Thr Leu Thr Val Asp Lys Ser Ser Ser Thr
 210                    215                 220

Ala Tyr Met Gln Leu Lys Ser Leu Thr Ser Glu Asp Ser Ala Val Tyr
225                 230                   235                 240

Tyr Cys Ala Arg Ser Val Gly Pro Met Asp Tyr Trp Gly Gln Gly Thr
             245                   250                 255

Ser Val Thr Val Ser Ser Ser Glu Pro Lys Ser Ser Asp Lys Thr His
         260                   265                 270

Thr Ser Pro Pro Cys Pro Ala Pro Glu Leu Leu Gly Gly Pro Ser Val
     275                   280                 285

Phe Leu Phe Pro Pro Lys Pro Lys Asp Thr Leu Met Ile Ser Arg Thr
 290                    295                 300

Pro Glu Val Thr Cys Val Val Asp Val Ser His Glu Asp Pro Glu
305                 310                   315                 320

Val Lys Phe Asn Trp Tyr Val Asp Gly Val Glu Val His Asn Ala Lys
             325                   330                 335

Thr Lys Pro Arg Glu Glu Gln Tyr Asn Ser Thr Tyr Arg Val Val Ser
         340                   345                 350

Val Leu Thr Val Leu His Gln Asp Trp Leu Asn Gly Lys Glu Tyr Lys
     355                   360                 365

Cys Lys Val Ser Asn Lys Ala Leu Pro Ala Pro Ile Glu Lys Thr Ile
 370                    375                 380

Ser Lys Ala Lys Gly Gln Pro Arg Glu Pro Gln Val Tyr Thr Leu Pro
385                 390                   395                 400

Pro Ser Arg Asp Glu Leu Thr Lys Asn Gln Val Ser Leu Thr Cys Leu
             405                   410                 415

Val Lys Gly Phe Tyr Pro Ser Asp Ile Ala Val Glu Trp Glu Ser Asn
         420                   425                 430

Gly Gln Pro Glu Asn Asn Tyr Lys Thr Thr Pro Pro Val Leu Asp Ser
     435                   440                 445

Asp Gly Ser Phe Phe Leu Tyr Ser Lys Leu Thr Val Asp Lys Ser Arg
 450                    455                 460

Trp Gln Gln Gly Asn Val Phe Ser Cys Ser Val Met His Glu Ala Leu
465                 470                   475                 480

His Asn His Tyr Thr Gln Lys Ser Leu Ser Leu Ser Pro Gly Lys
             485                   490                 495

<210> SEQ ID NO 27
<211> LENGTH: 1503
<212> TYPE: DNA
<213> ORGANISM: Artificial sequence
<220> FEATURE:
<223> OTHER INFORMATION: CD37 specific binding protein

<400> SEQUENCE: 27

| | | | | | |
|---|---|---|---|---|---|
| atggaagcac | cagcgcagct | tctcttcctc | ctgctactct | ggctcccaga | taccaccggt | 60 |
| gcggtccagc | tgcagcagtc | tggacctgag | tcggaaaagc | ctggcgcttc | agtgaagatt | 120 |
| tcctgcaagg | cttctggtta | ctcattcact | ggctacaata | tgaactgggt | gaagcagaat | 180 |
| aatgaaaga | gccttgagtg | gattggaaat | attgatcctt | attatggtgg | tactacctac | 240 |
| aaccggaagt | tcaagggcaa | ggccacattg | actgtagaca | atcctccag | cacagcctac | 300 |
| atgcagctca | gagtctgac | atctgaggac | tctgcagtct | attactgtgc | aagatcggtc | 360 |
| ggccctatgg | actactgggg | tcaaggaacc | tcagtcaccg | tctcttctgg | tggcggtggc | 420 |
| tcgggcggtg | gtgggtcggg | tggcggcgga | tcaggaggag | gcgggagtgc | tagcgaaatt | 480 |
| gtgttgacac | agtctccagc | caccctgtct | ttgtctccag | gcgaaagagc | caccctctcc | 540 |
| tgccgaacaa | gtgaaaatgt | ttacagctac | ttagcctggt | accaacagaa | acctggccag | 600 |
| gctcctaggc | tcctcatcta | ttttgcaaaa | accttagcag | aaggaattcc | agccaggttc | 660 |
| agtggcagtg | gatccgggac | agacttcact | ctcaccatca | gcagcctaga | gcctgaagat | 720 |
| tttgcagttt | attactgtca | acatcattcc | gataatccgt | ggacattcgg | ccaagggacc | 780 |
| aaggtggaaa | tcaaaggctc | gagcgagccc | aaatcttctg | acaaaactca | cacatgccca | 840 |
| ccgtgcccag | cacctgaact | cctgggtgga | ccgtcagtct | tcctcttccc | cccaaaaccc | 900 |
| aaggacaccc | tcatgatctc | ccggacccct | gaggtcacat | gcgtggtggt | ggacgtgagc | 960 |
| cacgaagacc | ctgaggtcaa | gttcaactgg | tacgtggacg | gcgtggaggt | gcataatgcc | 1020 |
| aagacaaagc | cgcgggagga | gcagtacaac | agcacgtacc | gtgtggtcag | cgtcctcacc | 1080 |
| gtcctgcacc | aggactggct | gaatggcaag | gagtacaagt | gcaaggtctc | caacaaagcc | 1140 |
| ctcccagccc | ccatcgagaa | aaccatctcc | aaagccaaag | gcagccccg | agaaccacag | 1200 |
| gtgtacaccc | tgcccccatc | ccgggatgag | ctgaccaaga | accaggtcag | cctgacctgc | 1260 |
| ctggtcaaag | gcttctatcc | aagcgacatc | gccgtggagt | gggagagcaa | tgggcagccg | 1320 |
| gagaacaact | acaagaccac | gcctcccgtg | ctggactccg | acggctcctt | cttcctctac | 1380 |
| agcaagctca | ccgtggacaa | gagcaggtgg | cagcagggga | acgtcttctc | atgctccgtg | 1440 |
| atgcatgagg | ctctgcacaa | ccactacacg | cagaagagcc | tctccctgtc | tccgggtaaa | 1500 |
| tga | | | | | | 1503 |

<210> SEQ ID NO 28
<211> LENGTH: 500
<212> TYPE: PRT
<213> ORGANISM: Artificial sequence
<220> FEATURE:
<223> OTHER INFORMATION: CD37 specific binding protein

<400> SEQUENCE: 28

Met Glu Ala Pro Ala Gln Leu Leu Phe Leu Leu Leu Leu Trp Leu Pro
1               5                   10                  15

Asp Thr Thr Gly Ala Val Gln Leu Gln Gln Ser Gly Pro Glu Ser Glu
            20                  25                  30

Lys Pro Gly Ala Ser Val Lys Ile Ser Cys Lys Ala Ser Gly Tyr Ser
        35                  40                  45

Phe Thr Gly Tyr Asn Met Asn Trp Val Lys Gln Asn Asn Gly Lys Ser
    50                  55                  60

-continued

```
Leu Glu Trp Ile Gly Asn Ile Asp Pro Tyr Tyr Gly Gly Thr Thr Tyr
 65                  70                  75                  80

Asn Arg Lys Phe Lys Gly Lys Ala Thr Leu Thr Val Asp Lys Ser Ser
                 85                  90                  95

Ser Thr Ala Tyr Met Gln Leu Lys Ser Leu Thr Ser Glu Asp Ser Ala
            100                 105                 110

Val Tyr Tyr Cys Ala Arg Ser Val Gly Pro Met Asp Tyr Trp Gly Gln
        115                 120                 125

Gly Thr Ser Val Thr Val Ser Ser Gly Gly Gly Ser Gly Gly Gly
    130                 135                 140

Gly Ser Gly Gly Gly Gly Ser Gly Gly Gly Gly Ser Ala Ser Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Thr Ser Glu Asn Val Tyr Ser Tyr Leu Ala
            180                 185                 190

Trp Tyr Gln Gln Lys Pro Gly Gln Ala Pro Arg Leu Leu Ile Tyr Phe
        195                 200                 205

Ala Lys Thr Leu Ala Glu Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln His His Ser Asp Asn Pro Trp Thr Phe
                245                 250                 255

Gly Gln Gly Thr Lys Val Glu Ile Lys Gly Ser Ser Glu Pro Lys Ser
            260                 265                 270

Ser Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
```

Ser Pro Gly Lys
        500

<210> SEQ ID NO 29
<211> LENGTH: 1479
<212> TYPE: DNA
<213> ORGANISM: Artificial sequence
<220> FEATURE:
<223> OTHER INFORMATION: CD37 specific binding protein

<400> SEQUENCE: 29

```
atggaagcac cagcgcagct tctcttcctc ctgctactct ggctcccaga taccaccggt      60
gaaattgtgt tgacacagtc tccagccacc ctgtctttgt ctccaggcga agagccacc     120
ctctcctgcc gaacaagtga aaatgtttac agctacttag cctggtacca acagaaacct     180
ggccaggctc ctaggctcct catctatttt gcaaaaacct agcagaagg aattccagcc     240
aggttcagtg gcagtggatc cgggacagac ttcactctca ccatcagcag cctagagcct     300
gaagattttg cagtttatta ctgtcaacat cattccgata tccgtggac attcggccaa     360
gggaccaagg tggaaatcaa aggtggcggt ggctcgggcg gtggtggatc tggaggaggt     420
ggagctagcg cggtccagct gcagcagtct ggacctgagt cggaaaagcc tggcgcttca     480
gtgaagattt cctgcaaggc ttctggttac tcattcactg ctacaatat gaactgggtg     540
aagcagaata atggaaagag ccttgagtgg attggaaata ttgatcctta ttatggtggt     600
actacctaca accggaagtt caagggcaag gccacattga ctgtagacaa atcctccagc     660
acagcctaca tgcagctcaa gagtctgaca tctgaggact ctgcagtcta ttactgtgca     720
agatcggtcg gccctatgga ctactgggt caaggaacct cagtcaccgt ctcctcgagc     780
gagcccaaat cttctgacaa aactcacaca tctccaccgt gcccagcacc tgaactcctg     840
ggtggaccgt cagtcttcct cttcccccca aaacccaagg acaccctcat gatctcccgg     900
accccctgagg tcacatgcgt ggtggtggac gtgagccacg aagaccctga ggtcaagttc     960
aactggtacg tggacggcgt ggaggtgcat aatgccaaga caaagccgcg ggaggagcag    1020
tacaacagca cgtaccgtgt ggtcagcgtc ctcaccgtcc tgcaccagga ctggctgaat    1080
ggcaaggagt acaagtgcaa ggtctccaac aaagccctcc cagcccccat cgagaaaacc    1140
atctccaaag ccaaagggca gccccgagaa ccacaggtgt acaccctgcc cccatcccgg    1200
gatgagctga ccaagaacca ggtcagcctg acctgcctgg tcaaaggctt ctatccaagc    1260
gacatcgccg tggagtggga gagcaatggg cagccggaga acaactacaa gaccacgcct    1320
cccgtgctgg actccgacgg ctccttcttc ctctacagca agctcaccgt ggacaagagc    1380
aggtggcagc aggggaacgt cttctcatgc tccgtgatgc atgaggctct gcacaaccac    1440
tacacgcaga agagcctctc cctgtctccg ggtaaatga                           1479
```

<210> SEQ ID NO 30
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 30

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser

-continued

```
                 20                  25                  30
Leu Ser Pro Gly Glu Arg Ala Thr Leu Ser Cys Arg Thr Ser Glu Asn
             35                  40                  45

Val Tyr Ser Tyr Leu Ala Trp Tyr Gln Gln Lys Pro Gly Gln Ala Pro
 50                  55                  60

Arg Leu Leu Ile Tyr Phe Ala Lys Thr Leu Ala Glu Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
            115                 120                 125

Gly Gly Gly Ser Gly Gly Gly Ser Gly Gly Gly Ala Ser Ala
            130                 135                 140

Val Gln Leu Gln Gln Ser Gly Pro Glu Ser Glu Lys Pro Gly Ala Ser
145                 150                 155                 160

Val Lys Ile Ser Cys Lys Ala Ser Gly Tyr Ser Phe Thr Gly Tyr Asn
                165                 170                 175

Met Asn Trp Val Lys Gln Asn Gly Lys Ser Leu Glu Trp Ile Gly
            180                 185                 190

Asn Ile Asp Pro Tyr Tyr Gly Gly Thr Thr Tyr Asn Arg Lys Phe Lys
            195                 200                 205

Gly Lys Ala Thr Leu Thr Val Asp Lys Ser Ser Thr Ala Tyr Met
            210                 215                 220

Gln Leu Lys Ser Leu Thr Ser Glu Asp Ser Ala Val Tyr Tyr Cys Ala
225                 230                 235                 240

Arg Ser Val Gly Pro Met Asp Tyr Trp Gly Gln Gly Thr Ser Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
            275                 280                 285

Pro Pro Lys Pro Lys Asp Thr Leu Met Ile Ser Arg Thr Pro Glu Val
            290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
            355                 360                 365

Ser Asn Lys Ala Leu Pro Ala Pro Ile Glu Lys Thr Ile Ser Lys Ala
            370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445
```

```
Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 31
<211> LENGTH: 1479
<212> TYPE: DNA
<213> ORGANISM: Artificial sequence
<220> FEATURE:
<223> OTHER INFORMATION: CD37 specific binding protein

<400> SEQUENCE: 31
atggaagcac cagcgcagct tctcttcctc ctgctactct ggctcccaga taccaccggt      60
gaaattgtgt tgacacagtc tccagccacc ctgtctttgt ctccaggcga aagagccacc     120
ctctcctgcc gaacaagtga aaatgtttac agctacttag cctggtacca acagaaacct     180
ggccaggctc ctaggctcct catctatttt gcaaaaacct tagcagaagg aattccagcc     240
aggttcagtg gcagtggatc cgggacagac ttcactctca ccatcagcag cctagagcct     300
gaagattttg cagtttatta ctgtcaacat cattccgata tccgtggac attcggccaa      360 gggaccaagg tggaaatcaa aggtggcggt ggctcgggcg gtggtggatc tggaggaggt     420
ggagctagcg cggtccagct gcagcagtct ggacctgagt cggaaaagcc tggcgcttca     480
gtgaagattt cctgcaaggc ttctggttac tcattcactg ctacaatat gaactgggtg      540 aagcagaata tggaaagag ccttgagtgg attggaaata ttgatcctta ttatggtggt      600
actacctaca accggaagtt caagggcaag gccacattga ctgtagacaa atcctccagc      660
acagcctaca tgcagctcaa gagtctgaca tctgaggact ctgcagtcta ttactgtgca     720
agatcggtcg gccctatgga ctactggggt caaggaacct cagtcaccgt ctcctcgagc      780
gagcccaaat cttctgacaa aactcacaca tgcccaccgt gcccagcacc tgaactcctg     840
ggtggaccgt cagtcttcct cttccccca aaacccaagg acaccctcat gatctcccgg      900
acccctgagg tcacatgcgt ggtggtggac gtgagccacg aagaccctga ggtcaagttc     960
aactggtacg tggacggcgt ggaggtgcat aatgccaaga caaagccgcg ggaggagcag    1020
tacaacagca cgtaccgtgt ggtcagcgtc ctcaccgtcc tgcaccagga ctggctgaat    1080
ggcaaggagt acaagtgcaa ggtctccaac aaagccctcc cagcccccat cgagaaaacc    1140
atctccaaag ccaaagggca gccccgagaa ccacaggtgt acaccctgcc cccatcccgg    1200
gatgagctga ccaagaacca ggtcagcctg acctgcctgg tcaaaggctt ctatccaagc    1260
gacatcgccg tggagtggga gagcaatggg cagccggaga caactacaa gaccacgcct     1320 cccgtgctgg actccgacgg ctccttcttc ctctacagca agctcaccgt ggacaagagc    1380
aggtggcagc aggggaacgt cttctcatgc tccgtgatgc atgaggctct gcacaaccac    1440
tacacgcaga agagcctctc cctgtctccg ggtaaatga                           1479

<210> SEQ ID NO 32
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 32
```

```
Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Ala
    130                 135                 140

Val Gln Leu Gln Gln Ser Gly Pro Glu Ser Glu Lys Pro Gly Ala Ser
145                 150                 155                 160

Val Lys Ile Ser Cys Lys Ala Ser Gly Tyr Ser Phe Thr Gly Tyr Asn
                165                 170                 175

Met Asn Trp Val Lys Gln Asn Asn Gly Lys Ser Leu Glu Trp Ile Gly
            180                 185                 190

Asn Ile Asp Pro Tyr Tyr Gly Gly Thr Thr Tyr Asn Arg Lys Phe Lys
        195                 200                 205

Gly Lys Ala Thr Leu Thr Val Asp Lys Ser Ser Ser Thr Ala Tyr Met
    210                 215                 220

Gln Leu Lys Ser Leu Thr Ser Glu Asp Ser Ala Val Tyr Tyr Cys Ala
225                 230                 235                 240

Arg Ser Val Gly Pro Met Asp Tyr Trp Gly Gln Gly Thr Ser Val Thr
                245                 250                 255

Val Ser Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415
```

```
Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
        450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
            485                 490
```

```
<210> SEQ ID NO 33
<211> LENGTH: 1479
<212> TYPE: DNA
<213> ORGANISM: Artificial sequence
<220> FEATURE:
<223> OTHER INFORMATION: CD37 specific binding protein

<400> SEQUENCE: 33
```

| | | |
|---|---|---|
| atggaagcac cagcgcagct tctcttcctc ctgctactct ggctcccaga taccaccggt | 60 |
| gaaattgtgt tgacacagtc tccagccacc ctgtctttgt ctccaggcga aagagccacc | 120 |
| ctctcctgcc gaacaagtga aaatgtttac agctactag cctggtacca acagaaacct | 180 |
| ggccaggctc ctaggctcct catctatttt gcaaaaacct tagcagaagg aattccagcc | 240 |
| aggttcagtg gcagtggatc cgggacagac ttcactctca ccatcagcag cctagagcct | 300 |
| gaagattttg cagtttatta ctgtcaacat cattccgata tccgtggac attcggccaa | 360 |
| gggaccaagg tggaaatcaa aggtggcggt ggctcgggcg tggtggatc tggaggaggt | 420 |
| ggagctagcc aggtgcagct ggtggagtct ggtggaggcg tggtccagcc tgggaggtcc | 480 |
| ctgagactct cctgtgcagc ctctggattc accttcagtg gctacaatat gaactgggtc | 540 |
| cgccagatgc ccgggaaagg cctggagtgg atgggcaata ttgatcctta ttatggtggt | 600 |
| actacctaca accggaagtt caagggccag gtcactatct ccgccgacaa gtccatcagc | 660 |
| accgcctacc tgcaatggag cagcctgaag gcctcggaca ccgccatgta ttactgtgca | 720 |
| cgctcagtcg gccctatgga ctactggggc cgcggcaccc tggtcactgt ctcctcgagc | 780 |
| gagcccaaat cttctgacaa aactcacaca tgcccaccgt gcccagcacc tgaactcctg | 840 |
| ggtggaccgt cagtcttcct cttccccccca aacccaagg acaccctcat gatctcccgg | 900 |
| acccctgagg tcacatgcgt ggtggtggac gtgagccacg aagaccctga ggtcaagttc | 960 |
| aactggtacg tggacggcgt ggaggtgcat aatgccaaga caaagccgcg ggaggagcag | 1020 |
| tacaacagca cgtaccgtgt ggtcagcgtc ctcaccgtcc tgcaccagga ctggctgaat | 1080 |
| ggcaaggagt acaagtgcaa ggtctccaac aaagccctcc cagcccccat cgagaaaacc | 1140 |
| atctccaaag ccaaagggca gccccgagaa ccacaggtgt acaccctgcc cccatcccgg | 1200 |
| gatgagctga ccaagaacca ggtcagcctg acctgcctgg tcaaaggctt ctatccaagc | 1260 |
| gacatcgccg tggagtggga gagcaatggg cagccggaga caactacaa gaccacgcct | 1320 |
| cccgtgctgg actccgacgg ctccttcttc ctctacagca agctcaccgt ggacaagagc | 1380 |
| aggtggcagc aggggaacgt cttctcatgc tccgtgatgc atgaggctct gcacaaccac | 1440 |
| tacacgcaga agagcctctc cctgtctccg ggtaaatga | 1479 |

```
<210> SEQ ID NO 34
<211> LENGTH: 492
<212> TYPE: PRT
```

<213> ORGANISM: Artificial sequence
<220> FEATURE:
<223> OTHER INFORMATION: CD37 specific binding protein

<400> SEQUENCE: 34

```
Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Ala Ser Gln
    130                 135                 140

Val Gln Leu Val Glu Ser Gly Gly Val Val Gln Pro Gly Arg Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
```

```
                385               390               395               400
Asp Glu Leu Thr Lys Asn Gln Val Ser Leu Thr Cys Leu Val Lys Gly
                405               410               415

Phe Tyr Pro Ser Asp Ile Ala Val Glu Trp Glu Ser Asn Gly Gln Pro
            420               425               430

Glu Asn Asn Tyr Lys Thr Thr Pro Pro Val Leu Asp Ser Asp Gly Ser
                435               440               445

Phe Phe Leu Tyr Ser Lys Leu Thr Val Asp Lys Ser Arg Trp Gln Gln
        450               455               460

Gly Asn Val Phe Ser Cys Ser Val Met His Glu Ala Leu His Asn His
465               470               475               480

Tyr Thr Gln Lys Ser Leu Ser Leu Ser Pro Gly Lys
                485               490

<210> SEQ ID NO 35
<211> LENGTH: 1479
<212> TYPE: DNA
<213> ORGANISM: Artificial sequence
<220> FEATURE:
<223> OTHER INFORMATION: CD37 specific binding protein

<400> SEQUENCE: 35
atggaagcac cagcgcagct tctcttcctc ctgctactct ggctcccaga taccaccggt      60
gaaattgtgt tgacacagtc tccagccacc ctgtctttgt ctccaggcga agagccacc      120
ctctcctgcc gaacaagtga aaatgtttac agctacttag cctggtacca acagaaacct     180
ggccaggctc ctaggctcct catctatttt gcaaaaacct agcagaagg aattccagcc      240
aggttcagtg gcagtggatc cgggacagac ttcactctca ccatcagcag cctagagcct    300
gaagattttg cagtttatta ctgtcaacat cattccgata tccgtggac attcggccaa     360
gggaccaagg tggaaatcaa aggtggcggt ggctcgggcg gtggtggatc tggaggaggt    420
ggagctagcc aggtgcagct ggtggagtct ggtggaggcg tggtccagcc tgggaggtcc    480
ctgagactct cctgtgcagc ctctggattc accttcagtg gctacaatat gaactgggtc    540
cgccagatgc ccgggaaagg cctggagtgg atgggcaata ttgatcctta ttatggtggt    600
actacctaca accggaagtt caagggccag gtcactatct ccgccgacaa gtccatcagc    660
accgcctacc tgcaatggag cagcctgaag gcctcggaca ccgccatgta ttactgtgca    720
cgctcagtcg gccctatgga ctactgggc cgcggcaccc tggtcactgt ctcctcgagc    780
gagcccaaat cttctgacaa aactcacaca tgcccaccgt gcccagcacc tgaactcctg    840
ggtggaccgt cagtcttcct cttcccccca aaacccaagg acaccctcat gatctcccgg    900
acccctgagg tcacatgcgt ggtggtggac gtgagccacg aagaccctga ggtcaagttc    960
aactggtacg tggacggcgt ggaggtgcat aatgccaaga caaagccgcg ggaggagcag   1020
tacaacagca cgtaccgtgt ggtcagcgtc ctcaccgtcc tgcaccagga ctggctgaat   1080
ggcaaggagt acaagtgcaa ggtctccaac aaagccctcc cagcccccat cgagaaaacc   1140
atctccaaag ccaaagggca gccccgagaa ccacaggtgt acaccctgcc cccatcccgg   1200
gatgagctga ccaagaacca ggtcagcctg acctgcctgg tcaaaggctt ctatccaagc   1260
gacatcgccg tggagtggga gagcaatggg cagccggaga caactacaa gaccacgcct    1320
cccgtgctgg actccgacgg ctccttcttc ctctacagca agctcaccgt ggacaagagc   1380
aggtggcagc aggggaacgt cttctcatgc tccgtgatgc atgaggctct gcacaaccac   1440
tacacgcaga agagcctctc cctgtctccg ggtaaatga                         1479
```

<210> SEQ ID NO 36
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 36

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Gln
    130                 135                 140

Val Gln Leu Val Glu Ser Gly Gly Val Val Gln Pro Gly Arg Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

```
Ser Asn Lys Ala Leu Pro Ala Pro Ile Glu Lys Thr Ile Ser Lys Ala
        370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
            405                 410                 415

Phe Tyr Pro Ser Asp Ile Ala Val Glu Trp Glu Ser Asn Gly Gln Pro
        420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
        450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
            485                 490
```

<210> SEQ ID NO 37
<211> LENGTH: 1476
<212> TYPE: DNA
<213> ORGANISM: Artificial sequence
<220> FEATURE:
<223> OTHER INFORMATION: CD37 specific binding protein

<400> SEQUENCE: 37

```
atggaagcac cagcgcagct tctcttcctc ctgctactct ggctcccaga taccaccggt      60
gaaattgtgt tgacacagtc tccagccacc ctgtctttgt ctccaggcga agagccacc     120 ctctcctgcc gaacaagtga aaatgtttac agctacttag cctggtacca acagaaacct     180
ggccaggctc ctaggctcct catctatttt gcaaaaacct agcagaagg aattccagcc     240 aggttcagtg gcagtggatc cgggacagac ttcactctca ccatcagcag cctagagcct     300
gaagattttg cagtttatta ctgtcaacat cattccgata tccgtggac attcggccaa     360 gggaccaagg tggaaatcaa aggtggcggt ggctcgggcg gtggtggatc tggaggaggt     420
ggggctagcg aggtgcagct ggtggagtct ggtggaggct tggtccagcc tggagggtcc     480
ctgagactct cctgtgcagc ctctggattc accttcagtg ctacaatat gaactgggtc     540 cgccagatgc ccgggaaagg cctggagtgg atgggcaata ttgatcctta ttatggtggt     600
actacctaca accggaagtt caagggccag gtcactatct ccgccgacaa gtccatcagc     660
accgcctacc tgcaatggag cagcctgaag gcctcggaca ccgccatgta ttactgtgca     720
cgctcagtcg gcctatgga ctactggggc cgcggcaccc tggtcactgt ctcctcgagc     780
gagcccaaat cttctgacaa aactcacaca tctccaccgt gcccagcacc tgaactcctg     840
ggtggaccgt cagtcttcct cttccccca aaacccaagg acaccctcat gatctcccgg     900 accccctgagg tcacatgcgt ggtggtggac gtgagccacg aagaccctga ggtcaagttc     960
aactggtacg tggacggcgt ggaggtgcat aatgccaaga caaagccgcg ggaggagcag    1020
tacaacagca cgtaccgtgt ggtcagcgtc ctcaccgtcc tgcaccagga ctggctgaat    1080
ggcaaggagt acaagtgcaa ggtctccaac aaagccctcc cagcccccat cgagaaaacc    1140
atctccaaag ccaaagggca gccccgagaa ccacaggtgt acaccctgcc cccatcccgg    1200
gatgagctga ccaagaacca ggtcagcctg acctgcctgg tcaaaggctt ctatccaagc    1260
gacatcgccg tggagtggga gagcaatggg cagccggaga caactacaa gaccacgcct    1320
```

```
cccgtgctgg actccgacgg ctccttcttc ctctacagca agctcaccgt ggacaagagc   1380
aggtggcagc aggggaacgt cttctcatgc tccgtgatgc atgaggctct gcacaaccac   1440
tacacgcaga agagcctctc cctgtctccg ggtaaa                             1476
```

<210> SEQ ID NO 38
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 38

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335
```

Arg Glu Glu Gln Tyr Asn Ser Thr Tyr Arg Val Val Ser Val Leu Thr
                340                 345                 350

Val Leu His Gln Asp Trp Leu Asn Gly Lys Glu Tyr Lys Cys Lys Val
            355                 360                 365

Ser Asn Lys Ala Leu Pro Ala Pro Ile Glu Lys Thr Ile Ser Lys Ala
        370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 39
<211> LENGTH: 1476
<212> TYPE: DNA
<213> ORGANISM: Artificial sequence
<220> FEATURE:
<223> OTHER INFORMATION: CD37 specific binding protein

<400> SEQUENCE: 39

| | | | | | |
|---|---|---|---|---|---|
| atggaagcac | cagcgcagct | tctcttcctc | ctgctactct | ggctcccaga | taccaccggt | 60 |
| gaaattgtgt | tgacacagtc | tccagccacc | ctgtctttgt | ctccaggcga | aagagccacc | 120 |
| ctctcctgcc | gaacaagtga | aaatgtttac | agctacttag | cctggtacca | acagaaacct | 180 |
| ggccaggctc | ctaggctcct | catctatttt | gcaaaaacct | tagcagaagg | aattccagcc | 240 |
| aggttcagtg | gcagtggatc | cgggacagac | ttcactctca | ccatcagcag | cctagagcct | 300 |
| gaagattttg | cagtttatta | ctgtcaacat | cattccgata | tccgtggaca | ttcggccaa | 360 |
| gggaccaagg | tggaaatcaa | aggtggcggt | ggctcgggcg | gtggtggatc | tggaggaggt | 420 |
| ggggctagcg | aggtgcagct | ggtggagtct | ggtggaggct | tggtccagcc | tggagggtcc | 480 |
| ctgagactct | cctgtgcagc | ctctggattc | accttcagtg | gctacaatat | gaactgggtc | 540 |
| cgccagatgc | ccgggaaagg | cctggagtgg | atgggcaata | ttgatcctta | ttatggtggt | 600 |
| actacctaca | accggaagtt | caagggccag | gtcactatct | ccgccgacaa | gtccatcagc | 660 |
| accgcctacc | tgcaatggag | cagcctgaag | gcctcggaca | ccgccatgta | ttactgtgca | 720 |
| cgctcagtcg | gcctatgga | ctactggggc | cgcggcaccc | tggtcactgt | ctcctcgagc | 780 |
| gagcccaaat | cttctgacaa | aactcacaca | tgcccaccgt | gcccagcacc | tgaactcctg | 840 |
| ggtggaccgt | cagtcttcct | cttcccccca | aaacccaagg | acaccctcat | gatctcccgg | 900 |
| acccctgagg | tcacatgcgt | ggtggtggac | gtgagccacg | aagaccctga | ggtcaagttc | 960 |
| aactggtacg | tggacggcgt | ggaggtgcat | aatgccaaga | caaagccgcg | ggaggagcag | 1020 |
| tacaacagca | cgtaccgtgt | ggtcagcgtc | ctcaccgtcc | tgcaccagga | ctggctgaat | 1080 |
| ggcaaggagt | acaagtgcaa | ggtctccaac | aaagccctcc | cagcccccat | cgagaaaacc | 1140 |
| atctccaaag | ccaaagggca | gccccgagaa | ccacaggtgt | acaccctgcc | cccatcccgg | 1200 |

```
gatgagctga ccaagaacca ggtcagcctg acctgcctgg tcaaaggctt ctatccaagc   1260
gacatcgccg tggagtggga gagcaatggg cagccggaga caactacaa gaccacgcct    1320 cccgtgctgg actccgacgg ctccttcttc ctctacagca agctcaccgt ggacaagagc   1380
aggtggcagc aggggaacgt cttctcatgc tccgtgatgc atgaggctct gcacaaccac   1440
tacacgcaga agagcctctc cctgtctccg ggtaaa                             1476
```

<210> SEQ ID NO 40
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 40

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Thr Ser Glu Asn
            35                  40                  45

Val Tyr Ser Tyr Leu Ala Trp Tyr Gln Gln Lys Pro Gly Gln Ala Pro
        50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Ala Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
```

```
                    305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
                340                 345                 350
Val Leu His Gln Asp Trp Leu Asn Gly Lys Glu Tyr Lys Cys Lys Val
                355                 360                 365
Ser Asn Lys Ala Leu Pro Ala Pro Ile Glu Lys Thr Ile Ser Lys Ala
            370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
                420                 425                 430
Glu Asn Asn Tyr Lys Thr Thr Pro Pro Val Leu Asp Ser Asp Gly Ser
                435                 440                 445
Phe Phe Leu Tyr Ser Lys Leu Thr Val Asp Lys Ser Arg Trp Gln Gln
        450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys
                485                 490

<210> SEQ ID NO 41
<211> LENGTH: 1476
<212> TYPE: DNA
<213> ORGANISM: Artificial sequence
<220> FEATURE:
<223> OTHER INFORMATION: CD37 specific binding protein

<400> SEQUENCE: 41
atggaagcac cagcgcagct tctcttcctc ctgctactct ggctcccaga taccaccggt      60
gaaattgtgt tgacacagtc tccagccacc ctgtctttgt ctccaggcga aagagccacc     120
ctctcctgcc gaacaagtga aaatgtttac agctacttag cctggtacca acagaaacct     180
ggccaggctc ctaggctcct catctatttt gcaaaaacct tagcagaagg aattccagcc     240
aggttcagtg gcagtggatc cgggacagac ttcactctca ccatcagcag cctagagcct     300
gaagattttg cagtttatta ctgtcaacat cattccgata tccgtggac attcggccaa     360 gggaccaagg tggaaatcaa aggtggcggt ggctcgggcg tggtggatc tggaggaggt     420 ggggctagcg aggtgcagct ggtggagtct ggtggaggct ctgtccagcc tggagggtcc     480
ctgagactct cctgtgcagc tctggattc accttcagtg gctacaatat gaactgggtc     540
cgccagatgc ccgggaaagg cctggagtgg atgggcaata ttgatcctta ttatggtggt     600
actacctaca accggaagtt caagggccag gtcactatct ccgccgacaa gtccatcagc     660
accgcctacc tgcaatggag cagcctgaag gcctcggaca ccgccatgta ttactgtgca     720
cgctcagtcg gccctatgga ctactggggc cgcggcaccc tggtcactgt ctcctcgagc     780
gagcccaaat cttctgacaa aactcacaca tctccaccgt gcccagcacc tgaactcctg     840
ggtggaccgt cagtcttcct cttcccccca aaacccaagg acaccctcat gatctcccgg     900
acccctgagg tcacatgcgt ggtggtggac gtgagccacg aagaccctga ggtcaagttc     960
aactggtacg tggacggcgt ggaggtgcat aatgccaaga caaagccgcg ggaggagcag    1020
```

-continued

```
tacaacagca cgtaccgtgt ggtcagcgtc ctcaccgtcc tgcaccagga ctggctgaat   1080
ggcaaggagt acaagtgcaa ggtctccaac aaagccctcc cagcccccat cgagaaaacc   1140
atctccaaag ccaaagggca gccccgagaa ccacaggtgt acaccctgcc cccatcccgg   1200
gatgagctga ccaagaacca ggtcagcctg acctgcctgg tcaaaggctt ctatccaagc   1260
gacatcgccg tggagtggga gagcaatggg cagccggaga caactacaa gaccacgcct   1320 cccgtgctgg actccgacgg ctccttcttc ctctacagca agctcaccgt ggacaagagc   1380
aggtggcagc aggggaacgt cttctcatgc tccgtgatgc atgaggctct gcacaaccac   1440
tacacgcaga agagcctctc cctgtctccg ggtaaa                              1476
```

<210> SEQ ID NO 42
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 42

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Glu Ser Gly Gly Ser Val Gln Pro Gly Gly Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285
```

```
Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
                340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 43
<211> LENGTH: 1476
<212> TYPE: DNA
<213> ORGANISM: Artificial sequence
<220> FEATURE:
<223> OTHER INFORMATION: CD37 specific binding protein

<400> SEQUENCE: 43
atggaagcac cagcgcagct tctcttcctc ctgctactct ggctcccaga taccaccggt     60
gaaattgtgt tgacacagtc tccagccacc ctgtctttgt ctccaggcga agagccacc    120 ctctcctgcc gaacaagtga aaatgtttac agctacttag cctggtacca acagaaacct    180
ggccaggctc ctaggctcct catctatttt gcaaaaacct agcagaagg aattccagcc    240 aggttcagtg gcagtggatc cgggacagac ttcactctca ccatcagcag cctagagcct    300
gaagattttg cagtttatta ctgtcaacat cattccgata tccgtggac attcggccaa    360 gggaccaagg tggaaatcaa aggtggcggt ggctcgggcg gtggtggatc tggaggaggt    420
ggggctagcg aggtgcagct ggtggagtct ggtggaggct ctgtccagcc tggagggtcc    480
ctgagactct cctgtgcagc ctctggattc accttcagtg gctacaatat gaactgggtc    540
cgccagatgc ccgggaaagg cctggagtgg atgggcaata ttgatcctta ttatggtggt    600
actacctaca accggaagtt caagggccag gtcactatct ccgccgacaa gtccatcagc    660
accgcctacc tgcaatggag cagcctgaag gcctcggaca ccgccatgta ttactgtgca    720
cgctcagtcg gcctatgga ctactggggc cgcggcaccc tggtcactgt ctcctcgagc    780
gagcccaaat cttctgacaa aactcacaca tgcccaccgt gcccagcacc tgaactcctg    840
ggtggaccgt cagtcttcct cttcccccca aaacccaagg acaccctcat gatctcccgg    900
```

```
acccctgagg tcacatgcgt ggtggtggac gtgagccacg aagaccctga ggtcaagttc    960
aactggtacg tggacggcgt ggaggtgcat aatgccaaga caaagccgcg ggaggagcag   1020
tacaacagca cgtaccgtgt ggtcagcgtc ctcaccgtcc tgcaccagga ctggctgaat   1080
ggcaaggagt acaagtgcaa ggtctccaac aaagccctcc cagcccccat cgagaaaacc   1140
atctccaaag ccaaagggca gccccgagaa ccacaggtgt acaccctgcc cccatcccgg   1200
gatgagctga ccaagaacca ggtcagcctg acctgcctgg tcaaaggctt ctatccaagc   1260
gacatcgccg tggagtggga gagcaatggg cagccggaga caactacaa gaccacgcct    1320 cccgtgctgg actccgacgg ctccttcttc ctctacagca agctcaccgt ggacaagagc   1380
aggtggcagc aggggaacgt cttctcatgc tccgtgatgc atgaggctct gcacaaccac   1440
tacacgcaga gagcctctc cctgtctccg ggtaaa                              1476
```

<210> SEQ ID NO 44
<211> LENGTH: 492
<212> TYPE: PRT
<213> ORGANISM: Artificial sequence
<220> FEATURE:
<223> OTHER INFORMATION: CD37 specific binding protein

<400> SEQUENCE: 44

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Ala Ser Glu
    130                 135                 140

Val Gln Leu Val Glu Ser Gly Gly Ser Val Gln Pro Gly Gly Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255
```

Val Ser Ser Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
            275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
            355                 360                 365

Ser Asn Lys Ala Leu Pro Ala Pro Ile Glu Lys Thr Ile Ser Lys Ala
        370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 45
<211> LENGTH: 1482
<212> TYPE: DNA
<213> ORGANISM: Artificial sequence
<220> FEATURE:
<223> OTHER INFORMATION: CD37 specific binding protein

<400> SEQUENCE: 45

| | |
|---|---|
| atggaagccc cagctcagct tctcttcctc ctgctactct ggctcccaga taccaccgga | 60 |
| gaaattgtgt tgacacagtc tccagccacc ctgtctttgt ctccaggcga aagagccacc | 120 |
| ctctcctgcc gagcaagtca aagtgtttac agctacttag cctggtacca acagaaacct | 180 |
| ggccaggctc ctaggctcct catctatttt gcaaaaacct agcagaagg aattccagcc | 240 |
| aggttcagtg gcagtggatc cgggacagac ttcactctca ccatcagcag cctagagcct | 300 |
| gaagattttg cagtttatta ctgtcaacat cattccgata tccgtggac attcggccaa | 360 |
| gggaccaagg tggaaatcaa aggtggcggt ggctcgggcg gtggtggatc tggaggaggt | 420 |
| gggaccggtg aggtgcagct ggtgcagtct ggagcagagg tgaaaaagcc cggagagtct | 480 |
| ctgaagattt cctgtaaggg atccggttac tcattcactg gctacaatat gaactgggtg | 540 |
| cgccagatgc ccgggaaagg cctcgagtgg atgggcaata ttgatcctta ttatggtggt | 600 |
| actacctaca accggaagtt caagggccag gtcactatct ccgccgacaa gtccatcagc | 660 |
| accgcctacc tgcaatggag cagcctgaag gcctcggaca ccgccatgta ttactgtgca | 720 |

-continued

```
cgctcagtcg gccctatgga ctactggggc cgcggcaccc tggtcactgt ctcctctgat      780
caggagccca atcttctga caaaactcac acatctccac cgtgcccagc acctgaactc       840
ctgggtggac cgtcagtctt cctcttcccc ccaaaaccca aggacaccct catgatctcc      900 cggaccctg aggtcacatg cgtggtggtg gacgtgagcc acgaagaccc tgaggtcaag       960
ttcaactggt acgtggacgg cgtggaggtg cataatgcca agacaaagcc gcgggaggag     1020
cagtacaaca gcacgtaccg tgtggtcagc gtcctcaccg tcctgcacca ggactggctg     1080
aatggcaagg agtacaagtg caaggtctcc aacaaagccc tcccagcccc catcgagaaa     1140
accatctcca aagccaaagg gcagccccga gaaccacagg tgtacaccct gcccccatcc     1200
cgggatgagc tgaccaagaa ccaggtcagc ctgacctgcc tggtcaaagg cttctatcca     1260
agcgacatcg ccgtggagtg ggagagcaat gggcagccgg agaacaacta caagaccacg     1320
cctcccgtgc tggactccga cggctccttc ttcctctaca gcaagctcac cgtggacaag     1380
agcaggtggc agcaggggaa cgtcttctca tgctccgtga tgcatgaggc tctgcacaac     1440
cactacacgc agaagagcct ctccctgtct ccgggtaaat ga                         1482
```

<210> SEQ ID NO 46
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 46

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
```

```
                225                 230                 235                 240
Arg Ser Val Gly Pro Met Asp Tyr Trp Gly Arg Gly Thr Leu Val Thr
                    245                 250                 255

Val Ser Ser Asp Gln Glu Pro Lys Ser Ser Asp Lys Thr His Thr Ser
                260                 265                 270

Pro Pro Cys Pro Ala Pro Glu Leu Leu Gly Gly Pro Ser Val Phe Leu
            275                 280                 285

Phe Pro Pro Lys Pro Lys Asp Thr Leu Met Ile Ser Arg Thr Pro Glu
        290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 47
<211> LENGTH: 1500
<212> TYPE: DNA
<213> ORGANISM: Artificial sequence
<220> FEATURE:
<223> OTHER INFORMATION: CD37 specific binding protein

<400> SEQUENCE: 47
aagcttgccg ccatggaagc cccagcgcag cttctcttcc tcctgctact ctggctccca    60
gataccaccg gagaaattgt gttgacacag tctccagcca ccctgtcttt gtctccaggc   120
gaaagagcca ccctctcctg ccagcaagt gaaaatgttt acagctactt agcctggtac   180
caacagaaac ctggccaggc tcctaggctc ctcatctatt ttgcaaaaac cttagcagaa   240
ggaattccag ccaggttcag tggcagtgga tccgggacag acttcactct caccatcagc   300
agcctagagc ctgaagattt tgcagtttat tactgtcaac atcattccga taatccgtgg   360
acattcggcc aagggaccaa ggtggaaatc aaaggtggcg gcggctcggg cggtggtgga   420
tctggaggag gtgggaccgg tgaggtgcag ctggtgcagt ctggagcaga ggtgaaaaag   480
cccggagagt ctctgaagat ttcctgtaag ggatccggtt actcattcac tggctacaat   540
atgaactggg tgcgccagat gcccgggaaa ggcctcgagt ggatgggcaa tattgatcct   600
```

```
tattatggtg gtactaccta caaccggaag ttcaagggcc aggtcactat ctccgccgac    660
aagtccatca gcaccgccta cctgcaatgg agcagcctga aggcctcgga caccgccatg    720
tattactgtg cacgctcagt cggccctttc gactactggg gccagggcac cctggtcact    780
gtctcctctg atcaggagcc caaatcttct gacaaaactc acacatctcc accgtgccca    840
gcacctgaac tcctgggtgg accgtcagtc ttcctcttcc ccccaaaacc caaggacacc    900
ctcatgatct cccggacccc tgaggtcaca tgcgtggtgg tggacgtgag ccacgaagac    960
cctgaggtca agttcaactg gtacgtggac ggcgtggagg tgcataatgc caagacaaag   1020
ccgcgggagg agcagtacaa cagcacgtac cgtgtggtca gcgtcctcac cgtcctgcac   1080
caggactggc tgaatggcaa ggagtacaag tgcaaggtct ccaacaaagc cctcccagcc   1140
cccatcgaga aaaccatctc caaagccaaa gggcagcccc gagaaccaca ggtgtacacc   1200
ctgcccccat cccgggatga gctgaccaag aaccaggtca gcctgacctg cctggtcaaa   1260
ggcttctatc caagcgacat cgccgtggag tgggagagca atgggcagcc ggagaacaac   1320
tacaagacca cgcctcccgt gctggactcc gacggctcct tcttcctcta cagcaagctc   1380
accgtggaca agagcaggtg gcagcagggg aacgtcttct catgctccgt gatgcatgag   1440
gctctgcaca accactacac gcagaagagc ctctccctgt ctccgggtaa atgatctaga   1500
```

<210> SEQ ID NO 48
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 48

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205
```

-continued

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Phe Asp Tyr Trp Gly Gln Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 49

<400> SEQUENCE: 49

000

<210> SEQ ID NO 50

<400> SEQUENCE: 50

000

<210> SEQ ID NO 51
<211> LENGTH: 1381
<212> TYPE: DNA
<213> ORGANISM: Artificial sequence
<220> FEATURE:
<223> OTHER INFORMATION: CD37 specific binding protein

<400> SEQUENCE: 51

```
aagcttgccg ccatggaagc cccagcgcag cttctcttcc tcctgctact ctggctccca      60
gataccaccg gagaaattgt gttgacacag tctccagcca ccctgtcttt gtctccaggc     120
gaaagagcca ccctctcctg ccgagcaagt gaaaatgttt acagctactt agcctggtac     180
caacagaaac ctggccaggc tcctaggctc ctcatctatt ttgcaaaaac cttagcagaa     240
ggaattccag ccaggttcag tggcagtgga tccgggacag acttcactct caccatcagc     300
agcctagagc ctgaagattt tgcagtttat tactgtcaac atcattccga taatccgtgg     360
acattcggcc aagggaccaa ggtggaaatc aaaggtggcg gtggctcggg cggtggtgga     420
tctggaggag gtgggaccgg tgaggtgcag ctggtgcagt ctggagcaga ggtgaaaaag     480
cccggagagt ctctgaagat ttcctgtaag ggatccggtt actcattcac tggctacaat     540
atgaactggg tgcgccagat gcccgggaaa ggcctcgagt ggatgggcaa tattgatcct     600
tattatggtg gtactaccta aaccggaagt tcaagggcc aggtcactat ctccgccgac     660
aagtccatca gcaccgccta cctgcaatgg agcagcctga aggcctcgga caccgccatg     720
tattactgtg cacgctcagt cggcccttc gactcctggg gccagggcac cctggtcact     780
gtctcctctg atcaggagcc caaatcttct gacaaaactc acacatctcc accgtgccca     840
gcacctgaac tcctgggtgg accgtcagtc ttcctcttcc ccccaaaacc caaggacacc     900
ctcatgatct cccggacccc tgaggtcaca tgcgtggtgg tggacgtgag ccacgaagac     960
cctgaggtca agttcaactg gtacgtggac ggcgtggagg tgcataatgc caagacaaag    1020
ccgcgggagg agcagtacaa cagcacgtac cgtgtggtca gcgtcctcac cgtcctgcac    1080
caggactggc tgaatggcaa ggagtacaag tgcaaggtct ccaacaaagc cctcccagcc    1140
cccatcgaga aaaccatctc caaagccaaa gggcagcccc gagaaccaca ggtgtacacc    1200
ctgcccccat cccgggatga gctgaccaag aaccaggtca gcctgacctg cctggtcaaa    1260
ggcttctatc caagcgacat cgccgtggag tgggagagca atgggcagcc ggagaacaac    1320
tacaagacca cgcctcccgt gctggactcc gacggctcct tcttcctcta cagcaagctc    1380
a                                                                    1381
```

<210> SEQ ID NO 52
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 52

```
Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Glu Asn
            35                  40                  45

Val Tyr Ser Tyr Leu Ala Trp Tyr Gln Gln Lys Pro Gly Gln Ala Pro
        50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110
```

```
Asp Asn Pro Trp Thr Phe Gly Gln Gly Thr Lys Val Glu Ile Lys Gly
            115                 120                 125
Gly Gly Gly Ser Gly Gly Gly Ser Gly Gly Gly Thr Gly Glu
130                 135                 140
Val Gln Leu Val Gln Ser Gly Ala Glu Val Lys Lys Pro Gly Glu Ser
145                 150                 155                 160
Leu Lys Ile Ser Cys Lys Gly Ser Gly Tyr Ser Phe Thr Gly Tyr Asn
                165                 170                 175
Met Asn Trp Val Arg Gln Met Pro Gly Lys Gly Leu Glu Trp Met Gly
            180                 185                 190
Asn Ile Asp Pro Tyr Tyr Gly Gly Thr Thr Tyr Asn Arg Lys Phe Lys
        195                 200                 205
Gly Gln Val Thr Ile Ser Ala Asp Lys Ser Ile Ser Thr Ala Tyr Leu
    210                 215                 220
Gln Trp Ser Ser Leu Lys Ala Ser Asp Thr Ala Met Tyr Tyr Cys Ala
225                 230                 235                 240
Arg Ser Val Gly Pro Phe Asp Ser Trp Gly Gln Gly Thr Leu Val Thr
                245                 250                 255
Val Ser Ser Asp Gln Glu Pro Lys Ser Ser Asp Lys Thr His Thr Ser
            260                 265                 270
Pro Pro Cys Pro Ala Pro Glu Leu Leu Gly Gly Pro Ser Val Phe Leu
        275                 280                 285
Phe Pro Pro Lys Pro Lys Asp Thr Leu Met Ile Ser Arg Thr Pro Glu
    290                 295                 300
Val Thr Cys Val Val Val Asp Val Ser His Glu Asp Pro Glu Val Lys
305                 310                 315                 320
Phe Asn Trp Tyr Val Asp Gly Val Glu Val His Asn Ala Lys Thr Lys
                325                 330                 335
Pro Arg Glu Glu Gln Tyr Asn Ser Thr Tyr Arg Val Val Ser Val Leu
            340                 345                 350
Thr Val Leu His Gln Asp Trp Leu Asn Gly Lys Glu Tyr Lys Cys Lys
        355                 360                 365
Val Ser Asn Lys Ala Leu Pro Ala Pro Ile Glu Lys Thr Ile Ser Lys
    370                 375                 380
Ala Lys Gly Gln Pro Arg Glu Pro Gln Val Tyr Thr Leu Pro Pro Ser
385                 390                 395                 400
Arg Asp Glu Leu Thr Lys Asn Gln Val Ser Leu Thr Cys Leu Val Lys
                405                 410                 415
Gly Phe Tyr Pro Ser Asp Ile Ala Val Glu Trp Glu Ser Asn Gly Gln
            420                 425                 430
Pro Glu Asn Asn Tyr Lys Thr Thr Pro Pro Val Leu Asp Ser Asp Gly
        435                 440                 445
Ser Phe Phe Leu Tyr Ser Lys Leu Thr Val Asp Lys Ser Arg Trp Gln
    450                 455                 460
Gln Gly Asn Val Phe Ser Cys Ser Val Met His Glu Ala Leu His Asn
465                 470                 475                 480
His Tyr Thr Gln Lys Ser Leu Ser Leu Ser Pro Gly Lys
                485                 490

<210> SEQ ID NO 53

<400> SEQUENCE: 53

000
```

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61
<211> LENGTH: 11
<212> TYPE: PRT
<213> ORGANISM: Artificial sequence
<220> FEATURE:
<223> OTHER INFORMATION: CDR

<400> SEQUENCE: 61

Arg Ala Ser Glu Asn Val Tyr Ser Tyr Leu Ala
1               5                   10

<210> SEQ ID NO 62
<211> LENGTH: 11
<212> TYPE: PRT
<213> ORGANISM: Artificial sequence
<220> FEATURE:
<223> OTHER INFORMATION: CDR

<400> SEQUENCE: 62

Arg Thr Ser Glu Asn Val Tyr Ser Tyr Leu Ala
1               5                   10

<210> SEQ ID NO 63
<211> LENGTH: 5
<212> TYPE: PRT

```
<213> ORGANISM: Artificial sequence
<220> FEATURE:
<223> OTHER INFORMATION: CDR

<400> SEQUENCE: 63

Gly Tyr Asn Met Asn
1               5

<210> SEQ ID NO 64
<211> LENGTH: 7
<212> TYPE: PRT
<213> ORGANISM: Artificial sequence
<220> FEATURE:
<223> OTHER INFORMATION: CDR

<400> SEQUENCE: 64

Phe Ala Lys Thr Leu Ala Glu
1               5

<210> SEQ ID NO 65
<211> LENGTH: 17
<212> TYPE: PRT
<213> ORGANISM: Artificial sequence
<220> FEATURE:
<223> OTHER INFORMATION: CDR

<400> SEQUENCE: 65

Asn Ile Asp Pro Tyr Tyr Gly Gly Thr Thr Tyr Asn Arg Lys Phe Lys
1               5                   10                  15
Gly

<210> SEQ ID NO 66
<211> LENGTH: 9
<212> TYPE: PRT
<213> ORGANISM: Artificial sequence
<220> FEATURE:
<223> OTHER INFORMATION: CDR

<400> SEQUENCE: 66

Gln His His Ser Asp Asn Pro Trp Thr
1               5

<210> SEQ ID NO 67
<211> LENGTH: 7
<212> TYPE: PRT
<213> ORGANISM: Artificial sequence
<220> FEATURE:
<223> OTHER INFORMATION: CDR

<400> SEQUENCE: 67

Ser Val Gly Pro Phe Asp Tyr
1               5

<210> SEQ ID NO 68
<211> LENGTH: 7
<212> TYPE: PRT
<213> ORGANISM: Artificial sequence
<220> FEATURE:
<223> OTHER INFORMATION: CDR

<400> SEQUENCE: 68

Ser Val Gly Pro Phe Asp Ser
1               5

<210> SEQ ID NO 69
<211> LENGTH: 7
```

```
<212> TYPE: PRT
<213> ORGANISM: Artificial sequence
<220> FEATURE:
<223> OTHER INFORMATION: CDR

<400> SEQUENCE: 69

Ser Val Gly Pro Met Asp Tyr
1               5

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79
<211> LENGTH: 1500
<212> TYPE: DNA
<213> ORGANISM: Artificial sequence
<220> FEATURE:
```

<223> OTHER INFORMATION: CD37 specific binding protein

<400> SEQUENCE: 79

```
aagcttgccg ccatggaagc cccagcgcag cttctcttcc tcctgctact ctggctccca      60
gataccaccg gagaaattgt gttgacacag tctccagcca ccctgtcttt gtctccaggc     120
gaaagagcca ccctctcctg ccgagcaagt gaaaatgttt acagctactt agcctggtac     180
caacagaaac ctggccaggc tcctaggctc ctcatctatt ttgcaaaaac cttagcagaa     240
ggaattccag ccaggttcag tggcagtgga tccgggacag acttcactct caccatcagc     300
agcctagagc ctgaagattt tgcagtttat tactgtcaac atcattccga taatccgtgg     360
acattcggcc aagggaccaa ggtggaaatc aaaggtggcg gtggctcggg cggtggtgga     420
tctggaggag gtgggaccgg tgaggtgcag ctggtgcagt ctggagcaga ggtgaaaaag     480
cccggagagt ctctgaagat ttcctgtaag ggatccggtt actcattcac tggctacaat     540
atgaactggg tgcgccagat gcccgggaaa ggcctcgagt ggatgggcaa tattgatcct     600
tattatggtg gtactaccta caaccggaag ttcaagggcc aggtcactat ctccgccgac     660
aagtccatca gcaccgccta cctgcaatgg agcagcctga aggcctcgga caccgccatg     720
tattactgtg cacgctcagt cggccctttc gacctctggg gcagaggcac cctggtcact     780
gtctcctctg atcaggagcc caaatcttct gacaaaactc acacatctcc accgtgccca     840
gcacctgaac tcctgggtgg accgtcagtc ttcctcttcc ccccaaaacc caaggacacc     900
ctcatgatct cccggacccc tgaggtcaca tgcgtggtgg tggacgtgag ccacgaagac     960
cctgaggtca agttcaactg gtacgtggac ggcgtggagg tgcataatgc caagacaaag    1020
ccgcgggagg agcagtacaa cagcacgtac cgtgtggtca gcgtcctcac cgtcctgcac    1080
caggactggc tgaatggcaa ggagtacaag tgcaaggtct ccaacaaagc cctcccagcc    1140
cccatcgaga aaaccatctc caaagccaaa gggcagcccc gagaaccaca ggtgtacacc    1200
ctgcccccat cccgggatga gctgaccaag aaccaggtca gcctgacctg cctggtcaaa    1260
ggcttctatc caagcgacat cgccgtggag tgggagagca atgggcagcc ggagaacaac    1320
tacaagacca cgcctcccgt gctggactcc gacggctcct tcttcctcta cagcaagctc    1380
accgtggaca agagcaggtg gcagcagggg aacgtcttct catgctccgt gatgcatgag    1440
gctctgcaca accactacac gcagaagagc ctctccctgt ctccgggtaa atgatctaga    1500
```

<210> SEQ ID NO 80
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 80

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80
```

```
Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Phe Asp Leu Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490
```

<210> SEQ ID NO 81
<211> LENGTH: 1494
<212> TYPE: DNA
<213> ORGANISM: Artificial sequence
<220> FEATURE:
<223> OTHER INFORMATION: CD37 specific binding protein

<400> SEQUENCE: 81

```
aagcttgccg ccatggaagc cccagctcag cttctcttcc tcctgctact ctggctccca      60
gataccaccg gagaaattgt gttgacacag tctccagcca ccctgtcttt gtctccaggc     120
gaaagagcca ccctctcctg ccgagcaagt gaaaatgttt acagctactt agcctggtac     180
caacagaaac ctggccaggc tcctaggctc ctcatctatt ttgcaaaaac cttagcagaa     240
ggaattccag ccaggttcag tggcagtgga tccgggacag acttcactct caccatcagc     300
agcctagagc ctgaagattt tgcagtttat tactgtcaac atcattccga taatccgtgg     360
acattcggcc aagggaccaa ggtggaaatc aaaggtggcg gtggctcggg cggtggtgga     420
tctggaggag gtgggctag cgaggtgcag ctggtgcagt ctggagcaga ggtgaaaaag     480
cccggagagt ctctgaagat ttcctgtaag ggatccggtt actcattcac tagctacaat     540
atgaactggg tgcgccagat gcccgggaaa ggcctgagt ggatgggcaa tattgatcct     600
tattatggtg gtactaacta cgcccagaag ttccagggcc aggtcactat ctccgccgac     660
aagtccatca gcaccgccta cctgcaatgg agcagcctga aggcctcgga caccgccatg     720
tattactgtg cacgctcagt cggccctatg gactactggg gccgcggcac cctggtcact     780
gtctcctctg atcaggagcc aaatcttct gacaaaactc acacatctcc accgtgccca     840
gcacctgaac tcctgggtgg accgtcagtc ttcctcttcc ccccaaaacc caaggacacc     900
ctcatgatct cccggacccc tgaggtcaca tgcgtggtgg tggacgtgag ccacgaagac     960
cctgaggtca agttcaactg gtacgtggac ggcgtggagg tgcataatgc caagacaaag    1020
ccgcgggagg agcagtacaa cagcacgtac cgtgtggtca gcgtcctcac cgtcctgcac    1080
caggactggc tgaatggcaa ggagtacaag tgcaaggtct ccaacaaagc cctcccagcc    1140
cccatcgaga aaaccatctc caaagccaaa gggcagcccc gagaaccaca ggtgtacacc    1200
ctgcccccat cccgggatga gctgaccaag aaccaggtca gcctgacctg cctggtcaaa    1260
ggcttctatc caagcgacat cgccgtggag tgggagagca atgggcagcc ggagaacaac    1320
tacaagacca cgcctcccgt gctggactcc gacggctcct tcttcctcta cagcaagctc    1380
accgtggaca gagcaggtg gcagcagggg aacgtcttct catgctccgt gatgcatgag    1440
gctctgcaca accactacac gcagaagagc ctctccctgt ctccgggtaa atga          1494
```

<210> SEQ ID NO 82
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 82

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
```

```
            50                  55                  60
Arg Leu Leu Ile Tyr Phe Ala Lys Thr Leu Ala Glu Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Ser Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Asn Tyr Ala Gln Lys Phe Gln
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480
```

His Tyr Thr Gln Lys Ser Leu Ser Leu Ser Pro Gly Lys
            485                 490

<210> SEQ ID NO 83
<211> LENGTH: 1476
<212> TYPE: DNA
<213> ORGANISM: Artificial sequence
<220> FEATURE:
<223> OTHER INFORMATION: CD37 specific binding protein

<400> SEQUENCE: 83

| | | | | |
|---|---|---|---|---|
| aagcttgccg | ccatggaagc | cccagcgcag | cttctcttcc | tcctgctact | ctggctccca | 60 |
| gataccaccg | gagaaattgt | gttgacacag | tctccagcca | ccctgtcttt | gtctccaggc | 120 |
| gaaagagcca | ccctctcctg | ccgagcaagt | gagaatgttt | acagctactt | agcctggtac | 180 |
| caacagaaac | ctggccaggc | tcctaggctc | ctcatctatt | ttgcaaaaac | cttagcagaa | 240 |
| gggattccag | ccagattcag | tggcagtggt | tccgggacag | acttcactct | caccatcagc | 300 |
| agcctagagc | ctgaagattt | tgcagtttat | tactgtcaac | atcattccga | taatccgtgg | 360 |
| acattcggcc | aagggaccaa | ggtggaaatc | aaaggtggcg | gtggctcggg | cggtggtgga | 420 |
| tctggaggag | tgggagcgg | aggaggagct | agcgaggtgc | agctggtgca | gtctggagca | 480 |
| gaggtgaaaa | agcccggaga | gtctctgaag | atttcctgta | agggatccgg | ttactcattc | 540 |
| actggctaca | atatgaactg | ggtgcgccag | atgcccggga | aaggcctcga | atggatgggc | 600 |
| aatattgatc | cttattatgg | tggtactacc | tacaaccgga | agttcaaggg | ccaggtcact | 660 |
| atctccgccg | acaagtccat | cagcaccgcc | tacctgcaag | gagcagcctg | aaggcctcgg | 720 |
| acaccgccat | gtattactgt | gcacgctcag | tcggcccttt | cgactcctgg | ggccagggca | 780 |
| ccctggtcac | tgtctcgagt | gtccaccgt | gcccagcacc | tgaactcctg | ggtggaccgt | 840 |
| cagtcttcct | cttcccccca | aaacccaagg | acaccctcat | gatctcccgg | acccctgagg | 900 |
| tcacatgcgt | ggtggtggac | gtgagccacg | aagaccctga | ggtcaagttc | aactggtacg | 960 |
| tggacggcgt | ggaggtgcat | aatgccaaga | caaagccgcg | ggaggagcag | tacaacagca | 1020 |
| cgtaccgtgt | ggtcagcgtc | ctcaccgtcc | tgcaccagga | ctggctgaat | ggcaaggagt | 1080 |
| acaagtgcaa | ggtctccaac | aaagccctcc | cagcccccat | cgagaaaacc | atctccaaag | 1140 |
| ccaaagggca | gccccgagaa | ccacaggtgt | acaccctgcc | cccatcccgg | gatgagctga | 1200 |
| ccaagaacca | ggtcagcctg | acctgcctgg | tcaaaggctt | ctatccaagc | gacatcgccg | 1260 |
| tggagtggga | gagcaatggg | cagccggaga | acaactacaa | gaccacgcct | cccgtgctgg | 1320 |
| actccgacgg | ctccttcttc | ctctacagca | agctcaccgt | ggacaagagc | aggtggcagc | 1380 |
| aggggaacgt | cttctcatgc | tccgtgatgc | atgaggctct | gcacaaccac | tacacgcaga | 1440 |
| agagcctctc | cctgtctccg | ggtaaatgac | tctaga | | | 1476 |

<210> SEQ ID NO 84
<211> LENGTH: 485
<212> TYPE: PRT
<213> ORGANISM: Artificial sequence
<220> FEATURE:
<223> OTHER INFORMATION: CD37 specific binding protein

<400> SEQUENCE: 84

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

-continued

```
Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
 50                  55                  60

Arg Leu Leu Ile Tyr Phe Ala Lys Thr Leu Ala Glu Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln His His Ser
                100                 105                 110

Asp Asn Pro Trp Thr Phe Gly Gln Gly Thr Lys Val Glu Ile Lys Gly
            115                 120                 125

Gly Gly Gly Ser Gly Gly Gly Gly Ser Gly Gly Gly Gly Ser Gly Gly
130                 135                 140

Gly Ala Ser Glu Val Gln Leu Val Gln Ser Gly Ala Glu Val Lys Lys
145                 150                 155                 160

Pro Gly Glu Ser Leu Lys Ile Ser Cys Lys Gly Ser Gly Tyr Ser Phe
                165                 170                 175

Thr Gly Tyr Asn Met Asn Trp Val Arg Gln Met Pro Gly Lys Gly Leu
            180                 185                 190

Glu Trp Met Gly Asn Ile Asp Pro Tyr Tyr Gly Gly Thr Thr Tyr Asn
        195                 200                 205

Arg Lys Phe Lys Gly Gln Val Thr Ile Ser Ala Asp Lys Ser Ile Ser
210                 215                 220

Thr Ala Tyr Leu Gln Trp Ser Ser Leu Lys Ala Ser Asp Thr Ala Met
225                 230                 235                 240

Tyr Tyr Cys Ala Arg Ser Val Gly Pro Phe Asp Ser Trp Gly Gln Gly
                245                 250                 255

Thr Leu Val Thr Val Ser Ser Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
370                 375                 380

Gln Val Tyr Thr Leu Pro Pro Ser Arg Asp Glu Leu Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445
```

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys
            485

<210> SEQ ID NO 85
<211> LENGTH: 1494
<212> TYPE: DNA
<213> ORGANISM: Artificial sequence
<220> FEATURE:
<223> OTHER INFORMATION: CD37 specific binding protein

<400> SEQUENCE: 85

| | | | | | |
|---|---|---|---|---|---|
| aagcttgccg | ccatggaagc | cccagctcag | cttctcttcc | tcctgctact | ctggctccca | 60 |
| gataccaccg | agaaaattgt | gttgacacag | tctccagcca | ccctgtcttt | gtctccaggc | 120 |
| gaaagagcca | ccctctcctg | ccgaacaagt | gaaaatgttt | acagctactt | agcctggtac | 180 |
| caacagaaac | ctggccaggc | tcctaggctc | ctcatctatt | ttgcaaaaac | cttagcagaa | 240 |
| ggaattccag | ccaggttcag | tggcagtgga | tccgggacag | acttcactct | caccatcagc | 300 |
| agcctagagc | ctgaagattt | tgcagtttat | tactgtcaac | atcattccga | taatccgtgg | 360 |
| acattcggcc | aagggaccaa | ggtggaaatc | aaaggtggcg | gtggctcggg | cggtggtgga | 420 |
| tctggaggag | gtgggaccgg | tgaggtgcag | ctggtgcagt | ctggagcaga | ggtgaaaaag | 480 |
| cccggagagt | ctctgaagat | ttcctgtaag | ggatccggtt | actcattcac | tggctacaat | 540 |
| atgaactggg | tgcgccagat | gcccgggaaa | ggcctggagt | ggatgggcaa | tattgatcct | 600 |
| tattatggtg | gtactaccta | caaccggaag | ttcaagggcc | aggtcactat | ctccgccgac | 660 |
| aagtccatca | gcaccgccta | cctgcaatgg | agcagcctga | aggcctcgga | caccgccatg | 720 |
| tattactgtg | cacgctcagt | cggccctatg | gactactggg | gccgcggcac | cctggtcact | 780 |
| gtctcctctg | atcaggagcc | caaatcttct | gacaaaactc | acacatctcc | accgtgccca | 840 |
| gcacctgaac | tcctggggtgg | accgtcagtc | ttcctcttcc | ccccaaaacc | caaggacacc | 900 |
| ctcatgatct | cccggacccc | tgaggtcaca | tgcgtggtgg | tggacgtgag | ccacgaagac | 960 |
| cctgaggtca | agttcaactg | gtacgtggac | ggcgtggagg | tgcataatgc | caagacaaag | 1020 |
| ccgcgggagg | agcagtacaa | cagcacgtac | cgtgtggtca | gcgtcctcac | cgtcctgcac | 1080 |
| caggactggc | tgaatggcaa | ggagtacaag | tgcaaggtct | ccaacaaagc | cctcccagcc | 1140 |
| cccatcgaga | aaaccatctc | caaagccaaa | gggcagcccc | gagaaccaca | ggtgtacacc | 1200 |
| ctgcccccat | cccgggatga | gctgaccaag | aaccaggtca | gcctgacctg | cctggtcaaa | 1260 |
| ggcttctatc | caagcgacat | cgccgtggag | tgggagagca | atgggcagcc | ggagaacaac | 1320 |
| tacaagacca | cgcctcccgt | gctggactcc | gacggctcct | tcttcctcta | cagcaagctc | 1380 |
| accgtggaca | agagcaggtg | gcagcagggg | aacgtcttct | catgctccgt | gatgcatgag | 1440 |
| gctctgcaca | accactacac | gcagaagagc | ctctccctgt | ctccgggtaa | atga | 1494 |

<210> SEQ ID NO 86
<211> LENGTH: 493
<212> TYPE: PRT
<213> ORGANISM: Artificial sequence
<220> FEATURE:
<223> OTHER INFORMATION: CD37 specific binding protein

<400> SEQUENCE: 86

```
Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
```

```
                420             425             430
       Pro Glu Asn Asn Tyr Lys Thr Thr Pro Pro Val Leu Asp Ser Asp Gly
               435             440             445

Ser Phe Phe Leu Tyr Ser Lys Leu Thr Val Asp Lys Ser Arg Trp Gln
           450             455             460

Gln Gly Asn Val Phe Ser Cys Ser Val Met His Glu Ala Leu His Asn
       465             470             475             480

His Tyr Thr Gln Lys Ser Leu Ser Leu Ser Pro Gly Lys
                       485             490

<210> SEQ ID NO 87
<211> LENGTH: 1494
<212> TYPE: DNA
<213> ORGANISM: Artificial sequence
<220> FEATURE:
<223> OTHER INFORMATION: CD37 specific binding protein

<400> SEQUENCE: 87
```

| | | | | | |
|---|---|---|---|---|---|
| aagcttgccg | ccatggaagc | cccagctcag | cttctcttcc | tcctgctact | ctggctccca | 60 |
| gataccaccg | tgaaattgtt | gttgacacag | tctccagcca | ccctgtcttt | gtctccaggc | 120 |
| gaaagagcca | ccctctcctg | ccgaacaagt | gaaaatgttt | acagctactt | agcctggtac | 180 |
| caacagaaac | ctggccaggc | tcctaggctc | ctcatctatt | ttgcaaaaac | cttagcagaa | 240 |
| ggaattccag | ccaggttcag | tggcagtgga | tccgggacag | acttcactct | caccatcagc | 300 |
| agcctagagc | ctgaagattt | tgcagtttat | tactgtcaac | atcattccga | taatccgtgg | 360 |
| acattcggcc | aagggaccaa | ggtggaaatc | aaaggtggcg | gtggctcggg | cggtggtgga | 420 |
| tctggaggag | gtggggctag | cgaggtgcag | ctggtgcagt | ctggagcaga | ggtgaaaaag | 480 |
| cccggagagt | ctctgaggat | ttcctgtaag | ggatccggtt | actcattcac | tggctacaat | 540 |
| atgaactggg | tgcgccagat | gcccgggaaa | ggcctggagt | ggatgggcaa | tattgatcct | 600 |
| tattatggtg | gtactaccta | caaccggaag | ttcaagggcc | aggtcactat | ctccgccgac | 660 |
| aagtccatca | gcaccgccta | cctgcaatgg | agcagcctga | aggcctcgga | caccgccatg | 720 |
| tattactgtg | cacgctcagt | cggccctatg | gactactggg | gccgcggcac | cctggtcact | 780 |
| gtctcctctg | atcaggagcc | caaatcttct | gacaaaactc | acacatctcc | accgtgccca | 840 |
| gcacctgaac | tcctgggtgg | accgtcagtc | ttcctcttcc | ccccaaaacc | caaggacacc | 900 |
| ctcatgatct | cccggacccc | tgaggtcaca | tgcgtggtgg | tggacgtgag | ccacgaagac | 960 |
| cctgaggtca | agttcaactg | gtacgtggac | ggcgtggagg | tgcataatgc | caagacaaag | 1020 |
| ccgcgggagg | agcagtacaa | cagcacgtac | cgtgtggtca | gcgtcctcac | cgtcctgcac | 1080 |
| caggactggc | tgaatggcaa | ggagtacaag | tgcaaggtct | ccaacaaagc | cctcccagcc | 1140 |
| cccatcgaga | aaaccatctc | caaagccaaa | gggcagcccc | gagaaccaca | ggtgtacacc | 1200 |
| ctgcccccat | cccgggatga | gctgaccaag | aaccaggtca | gcctgacctg | cctggtcaaa | 1260 |
| ggcttctatc | caagcgacat | cgccgtggag | tgggagagca | atgggcagcc | ggagaacaac | 1320 |
| tacaagacca | cgcctcccgt | gctggactcc | gacggctcct | tcttcctcta | cagcaagctc | 1380 |
| accgtggaca | agagcaggtg | gcagcagggg | aacgtcttct | catgctccgt | gatgcatgag | 1440 |
| gctctgcaca | accactacac | gcagaagagc | ctctccctgt | ctccgggtaa | atga | 1494 |

```
<210> SEQ ID NO 88
<211> LENGTH: 493
<212> TYPE: PRT
<213> ORGANISM: Artificial sequence
```

<220> FEATURE:
<223> OTHER INFORMATION: CD37 specific binding protein

<400> SEQUENCE: 88

| | | | | | | | | | | | | | | |
|---|---|---|---|---|---|---|---|---|---|---|---|---|---|---|

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
            85                  90                  95

Ser Leu Glu Pro Glu Asp Phe Ala Val Tyr Tyr Cys Gln His His Ser
        100                 105                 110

Asp Asn Pro Trp Thr Phe Gly Gln Gly Thr Lys Val Glu Ile Lys Gly
    115                 120                 125

Gly Gly Gly Ser Gly Gly Gly Gly Ser Gly Gly Gly Gly Ala Ser Glu
130                 135                 140

Val Gln Leu Val Gln Ser Gly Ala Glu Val Lys Lys Pro Gly Glu Ser
145                 150                 155                 160

Leu Arg Ile Ser Cys Lys Gly Ser Gly Tyr Ser Phe Thr Gly Tyr Asn
            165                 170                 175

Met Asn Trp Val Arg Gln Met Pro Gly Lys Gly Leu Glu Trp Met Gly
        180                 185                 190

Asn Ile Asp Pro Tyr Tyr Gly Gly Thr Thr Tyr Asn Arg Lys Phe Lys
    195                 200                 205

Gly Gln Val Thr Ile Ser Ala Asp Lys Ser Ile Ser Thr Ala Tyr Leu
210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
            245                 250                 255

Val Ser Ser Asp Gln Glu Pro Lys Ser Ser Asp Lys Thr His Thr Ser
        260                 265                 270

Pro Pro Cys Pro Ala Pro Glu Leu Leu Gly Gly Pro Ser Val Phe Leu
    275                 280                 285

Phe Pro Pro Lys Pro Lys Asp Thr Leu Met Ile Ser Arg Thr Pro Glu
290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
            325                 330                 335

Pro Arg Glu Glu Gln Tyr Asn Ser Thr Tyr Arg Val Val Ser Val Leu
        340                 345                 350

Thr Val Leu His Gln Asp Trp Leu Asn Gly Lys Glu Tyr Lys Cys Lys
    355                 360                 365

Val Ser Asn Lys Ala Leu Pro Ala Pro Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
            405                 410                 415

Gly Phe Tyr Pro Ser Asp Ile Ala Val Glu Trp Glu Ser Asn Gly Gln
        420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
            485                 490

<210> SEQ ID NO 89
<211> LENGTH: 45
<212> TYPE: DNA
<213> ORGANISM: Artificial sequence
<220> FEATURE:
<223> OTHER INFORMATION: Hinge region

<400> SEQUENCE: 89
gagcccaaat cttgtgacaa aactcacaca tgtccaccgt gccca                45

<210> SEQ ID NO 90
<211> LENGTH: 15
<212> TYPE: PRT
<213> ORGANISM: Artificial sequence
<220> FEATURE:
<223> OTHER INFORMATION: Hinge region

<400> SEQUENCE: 90

Glu Pro Lys Ser Cys Asp Lys Thr His Thr Cys Pro Pro Cys Pro
1               5                   10                  15

<210> SEQ ID NO 91
<211> LENGTH: 45
<212> TYPE: DNA
<213> ORGANISM: Artificial sequence
<220> FEATURE:
<223> OTHER INFORMATION: Hinge region

<400> SEQUENCE: 91
gagcccaaat cttctgacaa aactcacaca tgtccaccgt gccca                45

<210> SEQ ID NO 92
<211> LENGTH: 15
<212> TYPE: PRT
<213> ORGANISM: Artificial sequence
<220> FEATURE:
<223> OTHER INFORMATION: Hinge region

<400> SEQUENCE: 92

Glu Pro Lys Ser Ser Asp Lys Thr His Thr Cys Pro Pro Cys Pro
1               5                   10                  15

<210> SEQ ID NO 93
<211> LENGTH: 45
<212> TYPE: DNA
<213> ORGANISM: Artificial sequence
<220> FEATURE:
<223> OTHER INFORMATION: Hinge region

<400> SEQUENCE: 93

```
gagcccaaat cttctgacaa aactcacaca tgtccaccgt gctca          45
```

<210> SEQ ID NO 94
<211> LENGTH: 15
<212> TYPE: PRT
<213> ORGANISM: Artificial sequence
<220> FEATURE:
<223> OTHER INFORMATION: Hinge region

<400> SEQUENCE: 94

```
Glu Pro Lys Ser Ser Asp Lys Thr His Thr Cys Pro Pro Cys Ser
1               5                   10                  15
```

<210> SEQ ID NO 95
<211> LENGTH: 45
<212> TYPE: DNA
<213> ORGANISM: Artificial sequence
<220> FEATURE:
<223> OTHER INFORMATION: Hinge region

<400> SEQUENCE: 95

```
gagcccaaat cttgtgacaa aactcacaca tgtccaccga gctca          45
```

<210> SEQ ID NO 96
<211> LENGTH: 15
<212> TYPE: PRT
<213> ORGANISM: Artificial sequence
<220> FEATURE:
<223> OTHER INFORMATION: Hinge region

<400> SEQUENCE: 96

```
Glu Pro Lys Ser Ser Asp Lys Thr His Thr Cys Pro Pro Ser Ser
1               5                   10                  15
```

<210> SEQ ID NO 97
<211> LENGTH: 45
<212> TYPE: DNA
<213> ORGANISM: Artificial sequence
<220> FEATURE:
<223> OTHER INFORMATION: Hinge region

<400> SEQUENCE: 97

```
gagcccaaat cttctgacaa aactcacaca tctccaccga gccca          45
```

<210> SEQ ID NO 98
<211> LENGTH: 15
<212> TYPE: PRT
<213> ORGANISM: Artificial sequence
<220> FEATURE:
<223> OTHER INFORMATION: Hinge region

<400> SEQUENCE: 98

```
Glu Pro Lys Ser Ser Asp Lys Thr His Thr Ser Pro Pro Ser Pro
1               5                   10                  15
```

<210> SEQ ID NO 99
<211> LENGTH: 45
<212> TYPE: DNA
<213> ORGANISM: Artificial sequence
<220> FEATURE:
<223> OTHER INFORMATION: Hinge region

<400> SEQUENCE: 99

```
gagcccaaat cttctgacaa aactcacaca tctccaccga gctca          45
```

<210> SEQ ID NO 100

```
<211> LENGTH: 15
<212> TYPE: PRT
<213> ORGANISM: Artificial sequence
<220> FEATURE:
<223> OTHER INFORMATION: Hinge region

<400> SEQUENCE: 100

Glu Pro Lys Ser Ser Asp Lys Thr His Thr Ser Pro Pro Ser Ser
1               5                   10                  15

<210> SEQ ID NO 101
<211> LENGTH: 45
<212> TYPE: DNA
<213> ORGANISM: Artificial sequence
<220> FEATURE:
<223> OTHER INFORMATION: Hinge region

<400> SEQUENCE: 101
gagcccaaat cttgtgacaa aactcacaca tctccaccgt gccca           45

<210> SEQ ID NO 102
<211> LENGTH: 15
<212> TYPE: PRT
<213> ORGANISM: Artificial sequence
<220> FEATURE:
<223> OTHER INFORMATION: Hinge region

<400> SEQUENCE: 102

Glu Pro Lys Ser Cys Asp Lys Thr His Thr Ser Pro Pro Cys Pro
1               5                   10                  15

<210> SEQ ID NO 103
<211> LENGTH: 45
<212> TYPE: DNA
<213> ORGANISM: Artificial sequence
<220> FEATURE:
<223> OTHER INFORMATION: Hinge region

<400> SEQUENCE: 103
gagcccaaat cttgtgacaa aactcacaca tctccaccgt gctca            45

<210> SEQ ID NO 104
<211> LENGTH: 15
<212> TYPE: PRT
<213> ORGANISM: Artificial sequence
<220> FEATURE:
<223> OTHER INFORMATION: Hinge region

<400> SEQUENCE: 104

Glu Pro Lys Ser Cys Asp Lys Thr His Thr Ser Pro Pro Cys Ser
1               5                   10                  15

<210> SEQ ID NO 105
<211> LENGTH: 45
<212> TYPE: DNA
<213> ORGANISM: Artificial sequence
<220> FEATURE:
<223> OTHER INFORMATION: Hinge region

<400> SEQUENCE: 105
gagcccaaat cttctgacaa aactcacaca tctccaccgt gccca            45

<210> SEQ ID NO 106
<211> LENGTH: 15
<212> TYPE: PRT
<213> ORGANISM: Artificial sequence
<220> FEATURE:
```

<223> OTHER INFORMATION: Hinge region

<400> SEQUENCE: 106

Glu Pro Lys Ser Ser Asp Lys Thr His Thr Ser Pro Pro Cys Pro
1               5                   10                  15

<210> SEQ ID NO 107
<211> LENGTH: 45
<212> TYPE: DNA
<213> ORGANISM: Artificial sequence
<220> FEATURE:
<223> OTHER INFORMATION: Hinge region

<400> SEQUENCE: 107
gagcccaaat cttctgacaa aactcacaca tctccaccgt gctca          45

<210> SEQ ID NO 108
<211> LENGTH: 15
<212> TYPE: PRT
<213> ORGANISM: Artificial sequence
<220> FEATURE:
<223> OTHER INFORMATION: Hinge region

<400> SEQUENCE: 108

Glu Pro Lys Ser Ser Asp Lys Thr His Thr Ser Pro Pro Cys Ser
1               5                   10                  15

<210> SEQ ID NO 109
<211> LENGTH: 45
<212> TYPE: DNA
<213> ORGANISM: Artificial sequence
<220> FEATURE:
<223> OTHER INFORMATION: Hinge region

<400> SEQUENCE: 109
gagcccaaat cttgtgacaa aactcacaca tctccaccga gccca          45

<210> SEQ ID NO 110
<211> LENGTH: 15
<212> TYPE: PRT
<213> ORGANISM: Artificial sequence
<220> FEATURE:
<223> OTHER INFORMATION: Hinge region

<400> SEQUENCE: 110

Glu Pro Lys Ser Cys Asp Lys Thr His Thr Ser Pro Pro Ser Pro
1               5                   10                  15

<210> SEQ ID NO 111
<211> LENGTH: 45
<212> TYPE: DNA
<213> ORGANISM: Artificial sequence
<220> FEATURE:
<223> OTHER INFORMATION: Hinge region

<400> SEQUENCE: 111
gagcccaaat cttgtgacaa aactcacaca tctccaccga gctca          45

<210> SEQ ID NO 112
<211> LENGTH: 15
<212> TYPE: PRT
<213> ORGANISM: Artificial sequence
<220> FEATURE:
<223> OTHER INFORMATION: Hinge region

<400> SEQUENCE: 112

Glu Pro Lys Ser Cys Asp Lys Thr His Thr Ser Pro Pro Ser Ser
1               5                   10                  15

<210> SEQ ID NO 113

<400> SEQUENCE: 113

000

<210> SEQ ID NO 114

<400> SEQUENCE: 114

000

<210> SEQ ID NO 115
<211> LENGTH: 19
<212> TYPE: PRT
<213> ORGANISM: Artificial sequence
<220> FEATURE:
<223> OTHER INFORMATION: Hinge region

<400> SEQUENCE: 115

Val Pro Ser Thr Pro Pro Thr Pro Ser Pro Ser Thr Pro Pro Thr Pro
1               5                   10                  15

Ser Pro Ser

<210> SEQ ID NO 116
<211> LENGTH: 6
<212> TYPE: PRT
<213> ORGANISM: Artificial sequence
<220> FEATURE:
<223> OTHER INFORMATION: Hinge region

<400> SEQUENCE: 116

Val Pro Pro Pro Pro Pro
1               5

<210> SEQ ID NO 117
<211> LENGTH: 186
<212> TYPE: DNA
<213> ORGANISM: Artificial sequence
<220> FEATURE:
<223> OTHER INFORMATION: Hinge region

<400> SEQUENCE: 117
gagctcaaaa ctcctctcgg ggatacgacc catacgtgtc cccgctgtcc tgaaccgaag      60
tcctgcgata cgcctccgcc atgtccacgg tgcccagagc ccaaatcatg cgatacgccc     120
ccaccgtgtc cccgctgtcc tgaaccaaag tcatgcgata ccccaccacc atgtccaaga     180
tgccca                                                                186

<210> SEQ ID NO 118
<211> LENGTH: 62
<212> TYPE: PRT
<213> ORGANISM: Artificial sequence
<220> FEATURE:
<223> OTHER INFORMATION: Hinge region

<400> SEQUENCE: 118

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Pro Cys Pro Arg Cys Pro Glu
                35                  40                  45

Pro Lys Ser Cys Asp Thr Pro Pro Pro Cys Pro Arg Cys Pro
        50                  55                  60

<210> SEQ ID NO 119
<211> LENGTH: 45
<212> TYPE: DNA
<213> ORGANISM: Artificial sequence
<220> FEATURE:
<223> OTHER INFORMATION: Hinge region

<400> SEQUENCE: 119
gagcccaaat cttctgacac acctccccca tgcccacggt gcccc                45

<210> SEQ ID NO 120
<211> LENGTH: 15
<212> TYPE: PRT
<213> ORGANISM: Artificial sequence
<220> FEATURE:
<223> OTHER INFORMATION: Hinge region

<400> SEQUENCE: 120

Glu Pro Lys Ser Ser Asp Thr Pro Pro Pro Cys Pro Arg Cys Pro
1               5                   10                  15

<210> SEQ ID NO 121
<211> LENGTH: 45
<212> TYPE: DNA
<213> ORGANISM: Artificial sequence
<220> FEATURE:
<223> OTHER INFORMATION: Hinge region

<400> SEQUENCE: 121
gagcccaaat cttgtgacac acctccccca tccccacggt cccca                45

<210> SEQ ID NO 122
<211> LENGTH: 15
<212> TYPE: PRT
<213> ORGANISM: Artificial sequence
<220> FEATURE:
<223> OTHER INFORMATION: Hinge region

<400> SEQUENCE: 122

Glu Pro Lys Ser Cys Asp Thr Pro Pro Pro Ser Pro Arg Ser Pro
1               5                   10                  15

<210> SEQ ID NO 123
<211> LENGTH: 45
<212> TYPE: DNA
<213> ORGANISM: Artificial sequence
<220> FEATURE:
<223> OTHER INFORMATION: Hinge region

<400> SEQUENCE: 123
gagcccaaat cttctgacac acctccccca tccccacggt cccca                45

<210> SEQ ID NO 124
<211> LENGTH: 15
<212> TYPE: PRT
<213> ORGANISM: Artificial sequence
<220> FEATURE:
<223> OTHER INFORMATION: Hinge region

<400> SEQUENCE: 124

Glu Pro Lys Ser Ser Asp Thr Pro Pro Pro Ser Pro Arg Ser Pro

```
1               5                   10                  15
```

<210> SEQ ID NO 125
<211> LENGTH: 45
<212> TYPE: DNA
<213> ORGANISM: Artificial sequence
<220> FEATURE:
<223> OTHER INFORMATION: Hinge region

<400> SEQUENCE: 125
gagcccaaat cttgtgacac acctccccca tccccacggt gccca           45

<210> SEQ ID NO 126
<211> LENGTH: 15
<212> TYPE: PRT
<213> ORGANISM: Artificial sequence
<220> FEATURE:
<223> OTHER INFORMATION: Hinge region

<400> SEQUENCE: 126

Glu Pro Lys Ser Cys Asp Thr Pro Pro Pro Ser Pro Arg Cys Pro
1               5                   10                  15

<210> SEQ ID NO 127
<211> LENGTH: 58
<212> TYPE: PRT
<213> ORGANISM: Artificial sequence
<220> FEATURE:
<223> OTHER INFORMATION: Hinge region

<400> SEQUENCE: 127

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                      45

Glu Gln Glu Glu Arg Glu Thr Lys Thr Pro
    50                  55

<210> SEQ ID NO 128
<211> LENGTH: 11
<212> TYPE: PRT
<213> ORGANISM: Artificial sequence
<220> FEATURE:
<223> OTHER INFORMATION: CDR

<400> SEQUENCE: 128

Arg Thr Ser Gln Asn Val Tyr Ser Tyr Leu Ala
1               5                   10

<210> SEQ ID NO 129
<211> LENGTH: 11
<212> TYPE: PRT
<213> ORGANISM: Artificial sequence
<220> FEATURE:
<223> OTHER INFORMATION: CDR

<400> SEQUENCE: 129

Arg Thr Ser Glu Ser Val Tyr Ser Tyr Leu Ala
1               5                   10

<210> SEQ ID NO 130
<211> LENGTH: 11
<212> TYPE: PRT

```
<213> ORGANISM: Artificial sequence
<220> FEATURE:
<223> OTHER INFORMATION: CDR

<400> SEQUENCE: 130

Arg Ala Ser Gln Ser Val Tyr Ser Tyr Leu Ala
1               5                   10

<210> SEQ ID NO 131
<211> LENGTH: 11
<212> TYPE: PRT
<213> ORGANISM: Artificial sequence
<220> FEATURE:
<223> OTHER INFORMATION: CDR

<400> SEQUENCE: 131

Arg Ala Ser Gln Ser Val Ser Ser Tyr Leu Ala
1               5                   10

<210> SEQ ID NO 132
<211> LENGTH: 11
<212> TYPE: PRT
<213> ORGANISM: Artificial sequence
<220> FEATURE:
<223> OTHER INFORMATION: CDR

<400> SEQUENCE: 132

Arg Ala Ser Gln Ser Val Ser Tyr Tyr Leu Ala
1               5                   10

<210> SEQ ID NO 133
<211> LENGTH: 5
<212> TYPE: PRT
<213> ORGANISM: Artificial sequence
<220> FEATURE:
<223> OTHER INFORMATION: CDR

<400> SEQUENCE: 133

Ser Tyr Met Asn Met
1               5

<210> SEQ ID NO 134
<211> LENGTH: 5
<212> TYPE: PRT
<213> ORGANISM: Artificial sequence
<220> FEATURE:
<223> OTHER INFORMATION: CDR

<400> SEQUENCE: 134

Ser Tyr Trp Ile Gly
1               5

<210> SEQ ID NO 135
<211> LENGTH: 7
<212> TYPE: PRT
<213> ORGANISM: Artificial sequence
<220> FEATURE:
<223> OTHER INFORMATION: CDR

<400> SEQUENCE: 135

Ala Ala Ser Ser Leu Gln Ser
1               5

<210> SEQ ID NO 136
<211> LENGTH: 7
<212> TYPE: PRT
<213> ORGANISM: Artificial sequence
```

```
<220> FEATURE:
<223> OTHER INFORMATION: CDR

<400> SEQUENCE: 136

Gly Ala Ser Thr Arg Ala Thr
1               5

<210> SEQ ID NO 137
<211> LENGTH: 7
<212> TYPE: PRT
<213> ORGANISM: Artificial sequence
<220> FEATURE:
<223> OTHER INFORMATION: CDR

<400> SEQUENCE: 137

Asp Ala Ser Asn Arg Ala Thr
1               5

<210> SEQ ID NO 138
<211> LENGTH: 17
<212> TYPE: PRT
<213> ORGANISM: Artificial sequence
<220> FEATURE:
<223> OTHER INFORMATION: CDR

<400> SEQUENCE: 138

Ile Ile Tyr Pro Gly Asp Ser Asp Thr Arg Tyr Ser Pro Ser Phe Gln
1               5                   10                  15

Gly

<210> SEQ ID NO 139
<211> LENGTH: 17
<212> TYPE: PRT
<213> ORGANISM: Artificial sequence
<220> FEATURE:
<223> OTHER INFORMATION: CDR

<400> SEQUENCE: 139

Arg Ile Asp Pro Ser Asp Ser Tyr Thr Asn Tyr Ser Pro Ser Phe Gln
1               5                   10                  15

Gly

<210> SEQ ID NO 140
<211> LENGTH: 30
<212> TYPE: PRT
<213> ORGANISM: Artificial sequence
<220> FEATURE:
<223> OTHER INFORMATION: Framework region

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 141
<211> LENGTH: 30
<212> TYPE: PRT
<213> ORGANISM: Artificial sequence
<220> FEATURE:
<223> OTHER INFORMATION: Framework region

<400> SEQUENCE: 141

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser
            20                  25                  30

<210> SEQ ID NO 142

<400> SEQUENCE: 142

000

<210> SEQ ID NO 143
<211> LENGTH: 30
<212> TYPE: PRT
<213> ORGANISM: Artificial sequence
<220> FEATURE:
<223> OTHER INFORMATION: Framework region

<400> SEQUENCE: 143

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 144
<211> LENGTH: 30
<212> TYPE: PRT
<213> ORGANISM: Artificial sequence
<220> FEATURE:
<223> OTHER INFORMATION: Framework region

<400> SEQUENCE: 144

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 145
<211> LENGTH: 30
<212> TYPE: PRT
<213> ORGANISM: Artificial sequence
<220> FEATURE:
<223> OTHER INFORMATION: Framework region

<400> SEQUENCE: 145

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr
            20                  25                  30

<210> SEQ ID NO 146
<211> LENGTH: 30
<212> TYPE: PRT
<213> ORGANISM: Artificial sequence
<220> FEATURE:
<223> OTHER INFORMATION: Framework region

<400> SEQUENCE: 146

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 147
<211> LENGTH: 14
<212> TYPE: PRT
```

```
<213> ORGANISM: Artificial sequence
<220> FEATURE:
<223> OTHER INFORMATION: Framework region

<400> SEQUENCE: 147

Trp Val Arg Gln Ala Pro Gly Gln Gly Leu Glu Trp Met Gly
1               5                   10

<210> SEQ ID NO 148

<400> SEQUENCE: 148

000

<210> SEQ ID NO 149

<400> SEQUENCE: 149

000

<210> SEQ ID NO 150
<211> LENGTH: 14
<212> TYPE: PRT
<213> ORGANISM: Artificial sequence
<220> FEATURE:
<223> OTHER INFORMATION: Framework region

<400> SEQUENCE: 150

Trp Val Gln Gln Ala Pro Gly Lys Gly Leu Glu Trp Met Gly
1               5                   10

<210> SEQ ID NO 151
<211> LENGTH: 14
<212> TYPE: PRT
<213> ORGANISM: Artificial sequence
<220> FEATURE:
<223> OTHER INFORMATION: Framework region

<400> SEQUENCE: 151

Trp Val Arg Gln Met Pro Gly Lys Gly Leu Glu Trp Met Gly
1               5                   10

<210> SEQ ID NO 152

<400> SEQUENCE: 152

000

<210> SEQ ID NO 153

<400> SEQUENCE: 153

000

<210> SEQ ID NO 154
<211> LENGTH: 32
<212> TYPE: PRT
<213> ORGANISM: Artificial sequence
<220> FEATURE:
<223> OTHER INFORMATION: Framework region

<400> SEQUENCE: 154

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
                20                  25                  30
```

<210> SEQ ID NO 155
<211> LENGTH: 32
<212> TYPE: PRT
<213> ORGANISM: Artificial sequence
<220> FEATURE:
<223> OTHER INFORMATION: Framework region

<400> SEQUENCE: 155

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 156
<211> LENGTH: 32
<212> TYPE: PRT
<213> ORGANISM: Artificial sequence
<220> FEATURE:
<223> OTHER INFORMATION: Framework region

<400> SEQUENCE: 156

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 157
<211> LENGTH: 32
<212> TYPE: PRT
<213> ORGANISM: Artificial sequence
<220> FEATURE:
<223> OTHER INFORMATION: Framework region

<400> SEQUENCE: 157

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 158
<211> LENGTH: 32
<212> TYPE: PRT
<213> ORGANISM: Artificial sequence
<220> FEATURE:
<223> OTHER INFORMATION: Framework region

<400> SEQUENCE: 158

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 159
<211> LENGTH: 32
<212> TYPE: PRT
<213> ORGANISM: Artificial sequence
<220> FEATURE:
<223> OTHER INFORMATION: Framework region

<400> SEQUENCE: 159

His Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

```
<210> SEQ ID NO 160
<211> LENGTH: 32
<212> TYPE: PRT
<213> ORGANISM: Artificial sequence
<220> FEATURE:
<223> OTHER INFORMATION: Framework region

<400> SEQUENCE: 160

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 161
<211> LENGTH: 11
<212> TYPE: PRT
<213> ORGANISM: Artificial sequence
<220> FEATURE:
<223> OTHER INFORMATION: Framework region

<400> SEQUENCE: 161

Trp Gly Gln Gly Thr Leu Val Thr Val Ser Ser
1               5                   10

<210> SEQ ID NO 162
<211> LENGTH: 11
<212> TYPE: PRT
<213> ORGANISM: Artificial sequence
<220> FEATURE:
<223> OTHER INFORMATION: Framework region

<400> SEQUENCE: 162

Trp Gly Arg Gly Thr Leu Val Thr Val Ser Ser
1               5                   10

<210> SEQ ID NO 163
<211> LENGTH: 11
<212> TYPE: PRT
<213> ORGANISM: Artificial sequence
<220> FEATURE:
<223> OTHER INFORMATION: Framework region

<400> SEQUENCE: 163

Trp Gly Gln Gly Thr Met Val Thr Val Ser Ser
1               5                   10

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167
```

<400> SEQUENCE: 167

000

<210> SEQ ID NO 168
<211> LENGTH: 11
<212> TYPE: PRT
<213> ORGANISM: Artificial sequence
<220> FEATURE:
<223> OTHER INFORMATION: Framework region

<400> SEQUENCE: 168

Trp Gly Gln Gly Thr Thr Val Thr Val Ser Ser
1               5                   10

<210> SEQ ID NO 169
<211> LENGTH: 11
<212> TYPE: PRT
<213> ORGANISM: Artificial sequence
<220> FEATURE:
<223> OTHER INFORMATION: Framework region

<400> SEQUENCE: 169

Trp Gly Lys Gly Thr Thr Val Thr Val Ser Ser
1               5                   10

<210> SEQ ID NO 170
<211> LENGTH: 23
<212> TYPE: PRT
<213> ORGANISM: Artificial sequence
<220> FEATURE:
<223> OTHER INFORMATION: Framework region

<400> SEQUENCE: 170

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 171
<211> LENGTH: 23
<212> TYPE: PRT
<213> ORGANISM: Artificial sequence
<220> FEATURE:
<223> OTHER INFORMATION: Framework region

<400> SEQUENCE: 171

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 172
<211> LENGTH: 23
<212> TYPE: PRT
<213> ORGANISM: Artificial sequence
<220> FEATURE:
<223> OTHER INFORMATION: Framework region

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 173

<400> SEQUENCE: 173

000

<210> SEQ ID NO 174

<400> SEQUENCE: 174

000

<210> SEQ ID NO 175
<211> LENGTH: 23
<212> TYPE: PRT
<213> ORGANISM: Artificial sequence
<220> FEATURE:
<223> OTHER INFORMATION: Framework region

<400> SEQUENCE: 175

Asn Ile Gln Met Thr Gln Ser Pro Ser Ala Met Ser Ala Ser Val Gly
1               5                   10                  15

Asp Arg Val Thr Ile Thr Cys
            20

<210> SEQ ID NO 176

<400> SEQUENCE: 176

000

<210> SEQ ID NO 177
<211> LENGTH: 23
<212> TYPE: PRT
<213> ORGANISM: Artificial sequence
<220> FEATURE:
<223> OTHER INFORMATION: Framework region

<400> SEQUENCE: 177

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 178
<211> LENGTH: 23
<212> TYPE: PRT
<213> ORGANISM: Artificial sequence
<220> FEATURE:
<223> OTHER INFORMATION: Framework region

<400> SEQUENCE: 178

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 179
<211> LENGTH: 23
<212> TYPE: PRT
<213> ORGANISM: Artificial sequence
<220> FEATURE:
<223> OTHER INFORMATION: Framework region

<400> SEQUENCE: 179

```
Ala Ile Arg Met Thr Gln Ser Pro Phe Ser Leu Ser Ala Ser Val Gly
1               5                   10                  15

Asp Arg Val Thr Ile Thr Cys
            20
```

<210> SEQ ID NO 180
<211> LENGTH: 23
<212> TYPE: PRT
<213> ORGANISM: Artificial sequence
<220> FEATURE:
<223> OTHER INFORMATION: Framework region

<400> SEQUENCE: 180

```
Ala Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 181
<211> LENGTH: 23
<212> TYPE: PRT
<213> ORGANISM: Artificial sequence
<220> FEATURE:
<223> OTHER INFORMATION: Framework region

<400> SEQUENCE: 181

```
Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 182
<211> LENGTH: 15
<212> TYPE: PRT
<213> ORGANISM: Artificial sequence
<220> FEATURE:
<223> OTHER INFORMATION: Framework region

<400> SEQUENCE: 182

```
Trp Tyr Gln Gln Lys Pro Gly Gln Ala Pro Arg Leu Leu Ile Tyr
1               5                   10                  15
```

<210> SEQ ID NO 183

<400> SEQUENCE: 183

000

<210> SEQ ID NO 184
<211> LENGTH: 15
<212> TYPE: PRT
<213> ORGANISM: Artificial sequence
<220> FEATURE:
<223> OTHER INFORMATION: Framework region

<400> SEQUENCE: 184

```
Trp Tyr Gln Gln Lys Pro Gly Lys Ala Pro Lys Leu Leu Ile Tyr
1               5                   10                  15
```

<210> SEQ ID NO 185
<211> LENGTH: 15
<212> TYPE: PRT
<213> ORGANISM: Artificial sequence
<220> FEATURE:
<223> OTHER INFORMATION: Framework region

<400> SEQUENCE: 185

Trp Tyr Gln Gln Lys Pro Gly Lys Val Pro Lys Leu Leu Ile Tyr
1               5                   10                  15

<210> SEQ ID NO 186
<211> LENGTH: 15
<212> TYPE: PRT
<213> ORGANISM: Artificial sequence
<220> FEATURE:
<223> OTHER INFORMATION: Framework region

<400> SEQUENCE: 186

Trp Tyr Gln Gln Lys Pro Gly Lys Ala Pro Lys Arg Leu Ile Tyr
1               5                   10                  15

<210> SEQ ID NO 187
<211> LENGTH: 15
<212> TYPE: PRT
<213> ORGANISM: Artificial sequence
<220> FEATURE:
<223> OTHER INFORMATION: Framework region

<400> SEQUENCE: 187

Trp Phe Gln Gln Lys Pro Gly Lys Val Pro Lys His Leu Ile Tyr
1               5                   10                  15

<210> SEQ ID NO 188
<211> LENGTH: 15
<212> TYPE: PRT
<213> ORGANISM: Artificial sequence
<220> FEATURE:
<223> OTHER INFORMATION: Framework region

<400> SEQUENCE: 188

Trp Phe Gln Gln Lys Pro Gly Lys Ala Pro Lys Ser Leu Ile Tyr
1               5                   10                  15

<210> SEQ ID NO 189

<400> SEQUENCE: 189

000

<210> SEQ ID NO 190

<400> SEQUENCE: 190

000

<210> SEQ ID NO 191
<211> LENGTH: 15
<212> TYPE: PRT
<213> ORGANISM: Artificial sequence
<220> FEATURE:
<223> OTHER INFORMATION: Framework region

<400> SEQUENCE: 191

Trp Tyr Gln Gln Lys Pro Ala Lys Ala Pro Lys Leu Phe Ile Tyr
1               5                   10                  15

<210> SEQ ID NO 192

<400> SEQUENCE: 192

000

<210> SEQ ID NO 193

<400> SEQUENCE: 193

000

<210> SEQ ID NO 194
<211> LENGTH: 32
<212> TYPE: PRT
<213> ORGANISM: Artificial sequence
<220> FEATURE:
<223> OTHER INFORMATION: Framework region

<400> SEQUENCE: 194

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 195
<211> LENGTH: 32
<212> TYPE: PRT
<213> ORGANISM: Artificial sequence
<220> FEATURE:
<223> OTHER INFORMATION: Framework region

<400> SEQUENCE: 195

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 196
<211> LENGTH: 32
<212> TYPE: PRT
<213> ORGANISM: Artificial sequence
<220> FEATURE:
<223> OTHER INFORMATION: Framework region

<400> SEQUENCE: 196

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 197
<211> LENGTH: 32
<212> TYPE: PRT
<213> ORGANISM: Artificial sequence
<220> FEATURE:
<223> OTHER INFORMATION: Framework region

<400> SEQUENCE: 197

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 198
<211> LENGTH: 32
<212> TYPE: PRT
<213> ORGANISM: Artificial sequence
<220> FEATURE:
<223> OTHER INFORMATION: Framework region

<400> SEQUENCE: 198

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203
<211> LENGTH: 32
<212> TYPE: PRT
<213> ORGANISM: Artificial sequence
<220> FEATURE:
<223> OTHER INFORMATION: Framework region

<400> SEQUENCE: 203

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 204

<400> SEQUENCE: 204

000

<210> SEQ ID NO 205
<211> LENGTH: 32
<212> TYPE: PRT
<213> ORGANISM: Artificial sequence
<220> FEATURE:
<223> OTHER INFORMATION: Framework region

<400> SEQUENCE: 205

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 206
<211> LENGTH: 10
<212> TYPE: PRT
<213> ORGANISM: Artificial sequence

```
<220> FEATURE:
<223> OTHER INFORMATION: Framework region

<400> SEQUENCE: 206

Phe Gly Gln Gly Thr Lys Val Glu Ile Lys
1               5                   10

<210> SEQ ID NO 207
<211> LENGTH: 10
<212> TYPE: PRT
<213> ORGANISM: Artificial sequence
<220> FEATURE:
<223> OTHER INFORMATION: Framework region

<400> SEQUENCE: 207

Phe Gly Gln Gly Thr Lys Leu Glu Ile Lys
1               5                   10

<210> SEQ ID NO 208
<211> LENGTH: 10
<212> TYPE: PRT
<213> ORGANISM: Artificial sequence
<220> FEATURE:
<223> OTHER INFORMATION: Framework region

<400> SEQUENCE: 208

Phe Gly Pro Gly Thr Lys Val Asp Ile Lys
1               5                   10

<210> SEQ ID NO 209
<211> LENGTH: 10
<212> TYPE: PRT
<213> ORGANISM: Artificial sequence
<220> FEATURE:
<223> OTHER INFORMATION: Framework region

<400> SEQUENCE: 209

Phe Gly Gly Gly Thr Lys Val Glu Ile Lys
1               5                   10

<210> SEQ ID NO 210
<211> LENGTH: 10
<212> TYPE: PRT
<213> ORGANISM: Artificial sequence
<220> FEATURE:
<223> OTHER INFORMATION: Framework region

<400> SEQUENCE: 210

Phe Gly Gln Gly Thr Arg Leu Glu Ile Lys
1               5                   10

<210> SEQ ID NO 211
<211> LENGTH: 7
<212> TYPE: PRT
<213> ORGANISM: Artificial sequence
<220> FEATURE:
<223> OTHER INFORMATION: CDR

<400> SEQUENCE: 211

Ser Val Gly Pro Met Asp Tyr
1               5

<210> SEQ ID NO 212
<211> LENGTH: 7
<212> TYPE: PRT
<213> ORGANISM: Artificial sequence
<220> FEATURE:
```

<223> OTHER INFORMATION: CDR

<400> SEQUENCE: 212

Ser Val Gly Pro Phe Asp Tyr
1               5

<210> SEQ ID NO 213
<211> LENGTH: 7
<212> TYPE: PRT
<213> ORGANISM: Artificial sequence
<220> FEATURE:
<223> OTHER INFORMATION: CDR

<400> SEQUENCE: 213

Ser Val Gly Pro Met Asp Val
1               5

<210> SEQ ID NO 214
<211> LENGTH: 7
<212> TYPE: PRT
<213> ORGANISM: Artificial sequence
<220> FEATURE:
<223> OTHER INFORMATION: CDR

<400> SEQUENCE: 214

Ser Val Gly Pro Phe Asp Ser
1               5

<210> SEQ ID NO 215
<211> LENGTH: 7
<212> TYPE: PRT
<213> ORGANISM: Artificial sequence
<220> FEATURE:
<223> OTHER INFORMATION: CDR

<400> SEQUENCE: 215

Ser Val Gly Pro Phe Asp Pro
1               5

<210> SEQ ID NO 216
<211> LENGTH: 7
<212> TYPE: PRT
<213> ORGANISM: Artificial sequence
<220> FEATURE:
<223> OTHER INFORMATION: CDR

<400> SEQUENCE: 216

Ser Val Gly Pro Phe Gln His
1               5

<210> SEQ ID NO 217
<211> LENGTH: 7
<212> TYPE: PRT
<213> ORGANISM: Artificial sequence
<220> FEATURE:
<223> OTHER INFORMATION: CDR

<400> SEQUENCE: 217

Ser Val Gly Pro Phe Asp Val
1               5

<210> SEQ ID NO 218
<211> LENGTH: 7
<212> TYPE: PRT
<213> ORGANISM: Artificial sequence
<220> FEATURE:
<223> OTHER INFORMATION: CDR

<400> SEQUENCE: 218

Ser Val Gly Pro Phe Asp Ile
1               5

<210> SEQ ID NO 219
<211> LENGTH: 7
<212> TYPE: PRT
<213> ORGANISM: Artificial sequence
<220> FEATURE:
<223> OTHER INFORMATION: CDR

<400> SEQUENCE: 219

Ser Val Gly Pro Phe Asp Leu
1               5

<210> SEQ ID NO 220
<211> LENGTH: 9
<212> TYPE: PRT
<213> ORGANISM: Artificial sequence
<220> FEATURE:
<223> OTHER INFORMATION: CDR

<400> SEQUENCE: 220

Gln His His Ser Asp Asn Pro Trp Thr
1               5

<210> SEQ ID NO 221
<211> LENGTH: 1530
<212> TYPE: DNA
<213> ORGANISM: Artificial sequence
<220> FEATURE:
<223> OTHER INFORMATION: CD37 specific binding protein

<400> SEQUENCE: 221

| | |
|---|---|
| aagcttgccg ccatggaagc cccagctcag cttctcttcc tcctgctact ctggctccca | 60 |
| gataccaccg agaggtgca gctggtgcag tctggagcag aggtgaaaaa gcccggagag | 120 |
| tctctgaaga tttcctgtaa gggctccggt tactcattca ctggctacaa tatgaactgg | 180 |
| gtgcgccaga tgcccgggaa aggcctcgag tggatgggca atattgatcc ttattatggt | 240 |
| ggtactacct acaaccggaa gttcaagggc caggtcacta tctccgccga caagtccatc | 300 |
| agcaccgcct acctgcaatg gagcagcctg aaggcctcgg acaccgccat gtattactgt | 360 |
| gcacgctcag tcggccctt cgactcctgg ggccagggca cctggtcac tgtctcctct | 420 |
| gggggtggag gctctggtgg cggtggctct ggcggaggtg gatccggtgg cggcggatct | 480 |
| ggcggggtg gctctgaaat tgtgttgaca cagtctccag ccaccctgtc tttgtctcca | 540 |
| ggcgaaagag ccaccctctc ctgccgagca agtgaaaatg tttacagcta cttagcctgg | 600 |
| taccaacaga aacctggcca ggctcctagg ctcctcatct attttgcaaa aaccttagca | 660 |
| gaaggaattc cagccaggtt cagtggcagt ggctccggga cagacttcac tctcaccatc | 720 |
| agcagcctag agcctgaaga ttttgcagtt tattactgtc aacatcattc cgataatccg | 780 |
| tggacattcg gccaagggac caaggtggaa atcaaggtg atcaggagcc caaatcttct | 840 |
| gacaaaactc acacatctcc accgtgccca gcacctgaac tcctgggtgg accgtcagtc | 900 |
| ttcctcttcc ccccaaaacc caaggacacc ctcatgatct cccggacccc tgaggtcaca | 960 |
| tgcgtggtgg tggacgtgag ccacgaagac cctgaggtca agttcaactg gtacgtggac | 1020 |
| ggcgtggagg tgcataatgc caagacaaag ccgcgggagg agcagtacaa cagcacgtac | 1080 |
| cgtgtggtca gcgtcctcac cgtcctgcac caggactggc tgaatggcaa ggagtacaag | 1140 |

-continued

```
tgcaaggtct ccaacaaagc cctcccagcc cccatcgaga aaaccatctc caaagccaaa    1200
gggcagcccc gagaaccaca ggtgtacacc ctgcccccat cccgggatga gctgaccaag    1260
aaccaggtca gcctgacctg cctggtcaaa ggcttctatc caagcgacat cgccgtggag    1320
tgggagagca atgggcagcc ggagaacaac tacaagacca cgcctcccgt gctggactcc    1380
gacggctcct tcttcctcta cagcaagctc accgtggaca agagcaggtg gcagcagggg    1440
aacgtcttct catgctccgt gatgcatgag gctctgcaca accactacac gcagaagagc    1500
ctctccctgt ctccgggtaa atgatctaga                                    1530
```

<210> SEQ ID NO 222
<211> LENGTH: 503
<212> TYPE: PRT
<213> ORGANISM: Artificial sequence
<220> FEATURE:
<223> OTHER INFORMATION: CD37 specific binding protein

<400> SEQUENCE: 222

```
Met Glu Ala Pro Ala Gln Leu Leu Phe Leu Leu Leu Leu Trp Leu Pro
1               5                   10                  15

Asp Thr Thr Gly Glu Val Gln Leu Val Gln Ser Gly Ala Glu Val Lys
            20                  25                  30

Lys Pro Gly Glu Ser Leu Lys Ile Ser Cys Lys Gly Ser Gly Tyr Ser
        35                  40                  45

Phe Thr Gly Tyr Asn Met Asn Trp Val Arg Gln Met Pro Gly Lys Gly
    50                  55                  60

Leu Glu Trp Met Gly Asn Ile Asp Pro Tyr Tyr Gly Gly Thr Thr Tyr
65                  70                  75                  80

Asn Arg Lys Phe Lys Gly Gln Val Thr Ile Ser Ala Asp Lys Ser Ile
                85                  90                  95

Ser Thr Ala Tyr Leu Gln Trp Ser Ser Leu Lys Ala Ser Asp Thr Ala
            100                 105                 110

Met Tyr Tyr Cys Ala Arg Ser Val Gly Pro Phe Asp Ser Trp Gly Gln
        115                 120                 125

Gly Thr Leu Val Thr Val Ser Ser Gly Gly Gly Ser Gly Gly Gly
    130                 135                 140

Gly Ser Gly Gly Gly Ser Gly Gly Gly Ser Gly Gly Gly Gly
145                 150                 155                 160

Ser Glu Ile Val Leu Thr Gln Ser Pro Ala Thr Leu Ser Leu Ser Pro
                165                 170                 175

Gly Glu Arg Ala Thr Leu Ser Cys Arg Ala Ser Glu Asn Val Tyr Ser
            180                 185                 190

Tyr Leu Ala Trp Tyr Gln Gln Lys Pro Gly Gln Ala Pro Arg Leu Leu
        195                 200                 205

Ile Tyr Phe Ala Lys Thr Leu Ala Glu Gly Ile Pro Ala Arg Phe Ser
    210                 215                 220

Gly Ser Gly Ser Gly Thr Asp Phe Thr Leu Thr Ile Ser Ser Leu Glu
225                 230                 235                 240

Pro Glu Asp Phe Ala Val Tyr Tyr Cys Gln His His Ser Asp Asn Pro
                245                 250                 255

Trp Thr Phe Gly Gln Gly Thr Lys Val Glu Ile Lys Gly Asp Gln Glu
            260                 265                 270

Pro Lys Ser Ser Asp Lys Thr His Thr Ser Pro Pro Cys Pro Ala Pro
        275                 280                 285
```

-continued

```
Glu Leu Leu Gly Gly Pro Ser Val Phe Leu Phe Pro Pro Lys Pro Lys
290                 295                 300
Asp Thr Leu Met Ile Ser Arg Thr Pro Glu Val Thr Cys Val Val Val
305                 310                 315                 320
Asp Val Ser His Glu Asp Pro Glu Val Lys Phe Asn Trp Tyr Val Asp
            325                 330                 335
Gly Val Glu Val His Asn Ala Lys Thr Lys Pro Arg Glu Glu Gln Tyr
        340                 345                 350
Asn Ser Thr Tyr Arg Val Val Ser Val Leu Thr Val Leu His Gln Asp
    355                 360                 365
Trp Leu Asn Gly Lys Glu Tyr Lys Cys Lys Val Ser Asn Lys Ala Leu
370                 375                 380
Pro Ala Pro Ile Glu Lys Thr Ile Ser Lys Ala Lys Gly Gln Pro Arg
385                 390                 395                 400
Glu Pro Gln Val Tyr Thr Leu Pro Pro Ser Arg Asp Glu Leu Thr Lys
            405                 410                 415
Asn Gln Val Ser Leu Thr Cys Leu Val Lys Gly Phe Tyr Pro Ser Asp
        420                 425                 430
Ile Ala Val Glu Trp Glu Ser Asn Gly Gln Pro Glu Asn Asn Tyr Lys
    435                 440                 445
Thr Thr Pro Pro Val Leu Asp Ser Asp Gly Ser Phe Phe Leu Tyr Ser
450                 455                 460
Lys Leu Thr Val Asp Lys Ser Arg Trp Gln Gln Gly Asn Val Phe Ser
465                 470                 475                 480
Cys Ser Val Met His Glu Ala Leu His Asn His Tyr Thr Gln Lys Ser
            485                 490                 495
Leu Ser Leu Ser Pro Gly Lys
            500

<210> SEQ ID NO 223
<211> LENGTH: 23
<212> TYPE: PRT
<213> ORGANISM: Artificial Sequence
<220> FEATURE:
<223> OTHER INFORMATION: Linker sequence

<400> SEQUENCE: 223

Met Asp Phe Gln Val Gln Ile Phe Ser Phe Leu Leu Ile Ser Ala Ser
1               5                   10                  15
Val Ile Ile Ala Arg Gly Val
            20

<210> SEQ ID NO 224
<211> LENGTH: 20
<212> TYPE: PRT
<213> ORGANISM: Artificial Sequence
<220> FEATURE:
<223> OTHER INFORMATION: Linker sequence

<400> SEQUENCE: 224

Met Glu Ala Pro Ala Gln Leu Leu Phe Leu Leu Leu Leu Trp Leu Pro
1               5                   10                  15
Asp Thr Thr Gly
            20

<210> SEQ ID NO 225
<211> LENGTH: 16
<212> TYPE: PRT
<213> ORGANISM: Artificial Sequence
```

```
<220> FEATURE:
<223> OTHER INFORMATION: Linker sequence

<400> SEQUENCE: 225

Gly Gly Gly Gly Ser Gly Gly Gly Ser Gly Gly Gly Gly Ser Ser
 1               5                  10                  15

<210> SEQ ID NO 226
<211> LENGTH: 16
<212> TYPE: PRT
<213> ORGANISM: Artificial Sequence
<220> FEATURE:
<223> OTHER INFORMATION: Linker sequence

<400> SEQUENCE: 226

Gly Gly Gly Gly Ser Gly Gly Gly Gly Ser Gly Gly Gly Gly Ala Ser
 1               5                  10                  15

<210> SEQ ID NO 227
<211> LENGTH: 16
<212> TYPE: PRT
<213> ORGANISM: Artificial Sequence
<220> FEATURE:
<223> OTHER INFORMATION: Linker sequence

<400> SEQUENCE: 227

Gly Gly Gly Gly Ser Gly Gly Ser Gly Ser Gly Gly Gly Gly Ala Ser
 1               5                  10                  15

<210> SEQ ID NO 228
<211> LENGTH: 16
<212> TYPE: PRT
<213> ORGANISM: Artificial Sequence
<220> FEATURE:
<223> OTHER INFORMATION: Linker sequence

<400> SEQUENCE: 228

Gly Gly Gly Gly Ser Gly Gly Gly Gly Ser Gly Gly Gly Gly Thr Gly
 1               5                  10                  15

<210> SEQ ID NO 229
<211> LENGTH: 25
<212> TYPE: PRT
<213> ORGANISM: Artificial Sequence
<220> FEATURE:
<223> OTHER INFORMATION: Linker sequence

<400> SEQUENCE: 229

Gly Gly Gly Gly Ser Gly Gly Gly Gly Ser Gly Gly Gly Gly Ser Gly
 1               5                  10                  15

Gly Gly Gly Ser Gly Gly Gly Gly Ser
            20                  25

<210> SEQ ID NO 230
<211> LENGTH: 5
<212> TYPE: PRT
<213> ORGANISM: Artificial Sequence
<220> FEATURE:
<223> OTHER INFORMATION: Hinge sequence

<400> SEQUENCE: 230

Cys Pro Pro Cys Pro
 1               5

<210> SEQ ID NO 231
<211> LENGTH: 16
```

```
<212> TYPE: PRT
<213> ORGANISM: Artificial Sequence
<220> FEATURE:
<223> OTHER INFORMATION: Hinge sequence

<400> SEQUENCE: 231

Ser Glu Pro Lys Ser Ser Asp Lys Thr His Thr Ser Pro Pro Cys Pro
 1               5                  10                  15

<210> SEQ ID NO 232
<211> LENGTH: 17
<212> TYPE: PRT
<213> ORGANISM: Artificial Sequence
<220> FEATURE:
<223> OTHER INFORMATION: Hinge sequence

<400> SEQUENCE: 232

Asp Leu Glu Pro Lys Ser Ser Asp Lys Thr His Thr Ser Pro Pro Cys
 1               5                  10                  15
Pro

<210> SEQ ID NO 233
<211> LENGTH: 17
<212> TYPE: PRT
<213> ORGANISM: Artificial Sequence
<220> FEATURE:
<223> OTHER INFORMATION: Hinge sequence

<400> SEQUENCE: 233

Asp Gln Glu Pro Lys Ser Ser Asp Lys Thr His Thr Ser Pro Pro Cys
 1               5                  10                  15
Pro

<210> SEQ ID NO 234
<211> LENGTH: 18
<212> TYPE: PRT
<213> ORGANISM: Artificial Sequence
<220> FEATURE:
<223> OTHER INFORMATION: Hinge sequence

<400> SEQUENCE: 234

Gly Asp Gln Glu Pro Lys Ser Ser Asp Lys Thr His Thr Ser Pro Pro
 1               5                  10                  15
Cys Pro

<210> SEQ ID NO 235
<211> LENGTH: 18
<212> TYPE: PRT
<213> ORGANISM: Artificial Sequence
<220> FEATURE:
<223> OTHER INFORMATION: Hinge sequence

<400> SEQUENCE: 235

Gly Ser Ser Glu Pro Lys Ser Ser Asp Lys Thr His Thr Ser Pro Pro
 1               5                  10                  15
Cys Pro

<210> SEQ ID NO 236
<211> LENGTH: 107
<212> TYPE: PRT
<213> ORGANISM: Artificial Sequence
<220> FEATURE:
<223> OTHER INFORMATION: variable light chain region

<400> SEQUENCE: 236
```

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys
            100                 105

<210> SEQ ID NO 237
<211> LENGTH: 107
<212> TYPE: PRT
<213> ORGANISM: Artificial Sequence
<220> FEATURE:
<223> OTHER INFORMATION: variable light chain region

<400> SEQUENCE: 237

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Phe Ala Lys Thr Leu Ala Glu Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His His Ser Asp Asn Pro Trp
                85                  90                  95

Thr Phe Gly Gln Gly Thr Lys Val Glu Ile Lys
            100                 105

<210> SEQ ID NO 238
<211> LENGTH: 107
<212> TYPE: PRT
<213> ORGANISM: Artificial Sequence
<220> FEATURE:
<223> OTHER INFORMATION: variable light chain region

<400> SEQUENCE: 238

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Phe Ala Lys Thr Leu Ala Glu Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His His Ser Asp Asn Pro Trp

```
                     85                  90                  95

Thr Phe Gly Gln Gly Thr Lys Val Glu Ile Lys
                100                 105

<210> SEQ ID NO 239
<211> LENGTH: 107
<212> TYPE: PRT
<213> ORGANISM: Artificial Sequence
<220> FEATURE:
<223> OTHER INFORMATION: variable light chain region

<400> SEQUENCE: 239

Glu Ile Val Leu Thr Gln Ser Pro Ala Thr Leu Ser Leu Ser Pro Gly
  1               5                  10                  15

Glu Arg Ala Thr Leu Ser Cys Arg Thr Ser Gln Asn Val Tyr Ser Tyr
                 20                  25                  30

Leu Ala Trp Tyr Gln Gln Lys Pro Gly Gln Ala Pro Arg Leu Leu Ile
             35                  40                  45

Tyr Phe Ala Lys Thr Leu Ala Glu Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His His Ser Asp Asn Pro Trp
                 85                  90                  95

Thr Phe Gly Gln Gly Thr Lys Val Glu Ile Lys
                100                 105

<210> SEQ ID NO 240
<211> LENGTH: 107
<212> TYPE: PRT
<213> ORGANISM: Artificial Sequence
<220> FEATURE:
<223> OTHER INFORMATION: variable light chain region

<400> SEQUENCE: 240

Glu Ile Val Leu Thr Gln Ser Pro Ala Thr Leu Ser Leu Ser Pro Gly
  1               5                  10                  15

Glu Arg Ala Thr Leu Ser Cys Arg Thr Ser Gln Ser Val Tyr Ser Tyr
                 20                  25                  30

Leu Ala Trp Tyr Gln Gln Lys Pro Gly Gln Ala Pro Arg Leu Leu Ile
             35                  40                  45

Tyr Phe Ala Lys Thr Leu Ala Glu Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His His Ser Asp Asn Pro Trp
                 85                  90                  95

Thr Phe Gly Gln Gly Thr Lys Val Glu Ile Lys
                100                 105

<210> SEQ ID NO 241
<211> LENGTH: 116
<212> TYPE: PRT
<213> ORGANISM: Artificial Sequence
<220> FEATURE:
<223> OTHER INFORMATION: variable heavy chain region

<400> SEQUENCE: 241

Ala Val Gln Leu Gln Gln Ser Gly Pro Glu Ser Glu Lys Pro Gly Ala
  1               5                  10                  15
```

Ser Val Lys Ile Ser Cys Lys Ala Ser Gly Tyr Ser Phe Thr Gly Tyr
            20                  25                  30

Asn Met Asn Trp Val Lys Gln Asn Gly Lys Ser Leu Glu Trp Ile
        35                  40                  45

Gly Asn Ile Asp Pro Tyr Tyr Gly Gly Thr Thr Tyr Asn Arg Lys Phe
 50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
            85                  90                  95

Ala Arg Ser Val Gly Pro Met Asp Tyr Trp Gly Gln Gly Thr Ser Val
            100                 105                 110

Thr Val Ser Ser
        115

<210> SEQ ID NO 242
<211> LENGTH: 116
<212> TYPE: PRT
<213> ORGANISM: Artificial Sequence
<220> FEATURE:
<223> OTHER INFORMATION: variable heavy chain region

<400> SEQUENCE: 242

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Gly Tyr
            20                  25                  30

Asn Met Asn Trp Val Arg Gln Met Pro Gly Lys Gly Leu Glu Trp Met
        35                  40                  45

Gly Asn Ile Asp Pro Tyr Tyr Gly Gly Thr Thr Tyr Asn Arg Lys Phe
 50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Ser Val Gly Pro Met Asp Tyr Trp Gly Gln Gly Thr Leu Val
            100                 105                 110

Thr Val Ser Ser
        115

<210> SEQ ID NO 243
<211> LENGTH: 116
<212> TYPE: PRT
<213> ORGANISM: Artificial Sequence
<220> FEATURE:
<223> OTHER INFORMATION: variable heavy chain region

<400> SEQUENCE: 243

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Gly Tyr
            20                  25                  30

Asn Met Asn Trp Val Arg Gln Met Pro Gly Lys Gly Leu Glu Trp Met
        35                  40                  45

Gly Asn Ile Asp Pro Tyr Tyr Gly Gly Thr Thr Tyr Asn Arg Lys Phe
 50                  55                  60

Lys Gly Gln Val Thr Ile Ser Ala Asp Lys Ser Ile Ser Thr Ala Tyr

```
                65                  70                  75                  80
Leu Gln Trp Ser Ser Leu Lys Ala Ser Asp Thr Ala Met Tyr Tyr Cys
                85                  90                  95

Ala Arg Ser Val Gly Pro Met Asp Val Trp Gly Gln Gly Thr Leu Val
                100                 105                 110

Thr Val Ser Ser
        115

<210> SEQ ID NO 244
<211> LENGTH: 116
<212> TYPE: PRT
<213> ORGANISM: Artificial Sequence
<220> FEATURE:
<223> OTHER INFORMATION: variable heavy chain region

<400> SEQUENCE: 244

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
                20                  25                  30

Asn Met Asn Trp Val Arg Gln Met Pro Gly Lys Gly Leu Glu Trp Met
                35                  40                  45

Gly Asn Ile Asp Pro Tyr Tyr Gly Gly Thr Thr Tyr Asn Arg Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Val Gly Pro Phe Asp Tyr Trp Gly Gln Gly Thr Leu Val
                100                 105                 110

Thr Val Ser Ser
        115

<210> SEQ ID NO 245
<211> LENGTH: 116
<212> TYPE: PRT
<213> ORGANISM: Artificial Sequence
<220> FEATURE:
<223> OTHER INFORMATION: variable heavy chain region

<400> SEQUENCE: 245

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
                20                  25                  30

Asn Met Asn Trp Val Arg Gln Met Pro Gly Lys Gly Leu Glu Trp Met
                35                  40                  45

Gly Asn Ile Asp Pro Tyr Tyr Gly Gly Thr Thr Tyr Asn Arg Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Val Gly Pro Phe Asp Ser Trp Gly Gln Gly Thr Leu Val
                100                 105                 110

Thr Val Ser Ser
        115
```

<210> SEQ ID NO 246
<211> LENGTH: 217
<212> TYPE: PRT
<213> ORGANISM: Artificial Sequence
<220> FEATURE:
<223> OTHER INFORMATION: human IgG1 CH2 and CH3 regions

<400> SEQUENCE: 246

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 247
<211> LENGTH: 473
<212> TYPE: PRT
<213> ORGANISM: Artificial Sequence
<220> FEATURE:
<223> OTHER INFORMATION: CD37 specific binding protein

<400> SEQUENCE: 247

Asp Ile Gln Met Thr Gln Ser Pro Ala Ser Leu Ser Ala Ser Val Gly
 1               5                  10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys Gly Gly Gly Ser
                100                 105                 110

Gly Gly Gly Gly Ser Gly Gly Gly Ser Ser Ala Val Gln Leu Gln
            115                 120                 125

Gln Ser Gly Pro Glu Ser Glu Lys Pro Gly Ala Ser Val Lys Ile Ser
130                 135                 140

Cys Lys Ala Ser Gly Tyr Ser Phe Thr Gly Tyr Asn Met Asn Trp Val
145                 150                 155                 160

Lys Gln Asn Asn Gly Lys Ser Leu Glu Trp Ile Gly Asn Ile Asp Pro
                165                 170                 175

Tyr Tyr Gly Gly Thr Thr Tyr Asn Arg Lys Phe Lys Gly Lys Ala Thr
            180                 185                 190

Leu Thr Val Asp Lys Ser Ser Thr Ala Tyr Met Gln Leu Lys Ser
        195                 200                 205

Leu Thr Ser Glu Asp Ser Ala Val Tyr Tyr Cys Ala Arg Ser Val Gly
        210                 215                 220

Pro Met Asp Tyr Trp Gly Gln Gly Thr Ser Val Thr Val Ser Ser Asp
225                 230                 235                 240

Leu Glu Pro Lys Ser Ser Asp Lys Thr His Thr Ser Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470

<210> SEQ ID NO 248
<211> LENGTH: 473
<212> TYPE: PRT
<213> ORGANISM: Artificial Sequence
<220> FEATURE:

<223> OTHER INFORMATION: CD37 specific binding protein

<400> SEQUENCE: 248

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Phe Ala Lys Thr Leu Ala Glu Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His His Ser Asp Asn Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Thr Gly Glu Val Gln Leu Val
        115                 120                 125

Gln Ser Gly Ala Glu Val Lys Lys Pro Gly Glu Ser Leu Lys Ile Ser
130                 135                 140

Cys Lys Gly Ser Gly Tyr Ser Phe Thr Gly Tyr Asn Met Asn Trp Val
145                 150                 155                 160

Arg Gln Met Pro Gly Lys Gly Leu Glu Trp Met Gly Asn Ile Asp Pro
                165                 170                 175

Tyr Tyr Gly Gly Thr Thr Tyr Asn Arg Lys Phe Lys Gly Gln Val Thr
            180                 185                 190

Ile Ser Ala Asp Lys Ser Ile Ser Thr Ala Tyr Leu Gln Trp Ser Ser
        195                 200                 205

Leu Lys Ala Ser Asp Thr Ala Met Tyr Tyr Cys Ala Arg Ser Val Gly
210                 215                 220

Pro Met Asp Tyr Trp Gly Arg Gly Thr Leu Val Thr Val Ser Ser Asp
225                 230                 235                 240

Gln Glu Pro Lys Ser Ser Asp Lys Thr His Thr Ser Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400
```

```
Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 249
<211> LENGTH: 473
<212> TYPE: PRT
<213> ORGANISM: Artificial Sequence
<220> FEATURE:
<223> OTHER INFORMATION: CD37 specific binding protein

<400> SEQUENCE: 249

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Phe Ala Lys Thr Leu Ala Glu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His His Ser Asp Asn Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Thr Gly Glu Val Gln Leu Val
        115                 120                 125

Gln Ser Gly Ala Glu Val Lys Lys Pro Gly Glu Ser Leu Lys Ile Ser
    130                 135                 140

Cys Lys Gly Ser Gly Tyr Ser Phe Thr Gly Tyr Asn Met Asn Trp Val
145                 150                 155                 160

Arg Gln Met Pro Gly Lys Gly Leu Glu Trp Met Gly Asn Ile Asp Pro
                165                 170                 175

Tyr Tyr Gly Gly Thr Thr Tyr Asn Arg Lys Phe Lys Gly Gln Val Thr
            180                 185                 190

Ile Ser Ala Asp Lys Ser Ile Ser Thr Ala Tyr Leu Gln Trp Ser Ser
        195                 200                 205

Leu Lys Ala Ser Asp Thr Ala Met Tyr Tyr Cys Ala Arg Ser Val Gly
    210                 215                 220

Pro Phe Asp Tyr Trp Gly Gln Gly Thr Leu Val Thr Val Ser Ser Asp
225                 230                 235                 240

Gln Glu Pro Lys Ser Ser Asp Lys Thr His Thr Ser Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285
```

```
Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Thr Ile Ser Lys Ala Lys Gly Gln
                355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 250
<211> LENGTH: 473
<212> TYPE: PRT
<213> ORGANISM: Artificial Sequence
<220> FEATURE:
<223> OTHER INFORMATION: CD37 specific binding protein

<400> SEQUENCE: 250

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Phe Ala Lys Thr Leu Ala Glu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His His Ser Asp Asn Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Thr Gly Glu Val Gln Leu Val
        115                 120                 125

Gln Ser Gly Ala Glu Val Lys Lys Pro Gly Glu Ser Leu Lys Ile Ser
130                 135                 140

Cys Lys Gly Ser Gly Tyr Ser Phe Thr Gly Tyr Asn Met Asn Trp Val
145                 150                 155                 160

Arg Gln Met Pro Gly Lys Gly Leu Glu Trp Met Gly Asn Ile Asp Pro
                165                 170                 175
```

```
Tyr Tyr Gly Gly Thr Thr Tyr Asn Arg Lys Phe Lys Gly Gln Val Thr
                180                 185                 190

Ile Ser Ala Asp Lys Ser Ile Ser Thr Ala Tyr Leu Gln Trp Ser Ser
        195                 200                 205

Leu Lys Ala Ser Asp Thr Ala Met Tyr Tyr Cys Ala Arg Ser Val Gly
    210                 215                 220

Pro Phe Asp Ser Trp Gly Gln Gly Thr Leu Val Thr Val Ser Ser Asp
225                 230                 235                 240

Gln Glu Pro Lys Ser Ser Asp Lys Thr His Thr Ser Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 251
<211> LENGTH: 480
<212> TYPE: PRT
<213> ORGANISM: Artificial Sequence
<220> FEATURE:
<223> OTHER INFORMATION: CD37 specific binding protein

<400> SEQUENCE: 251

Ala Val Gln Leu Gln Gln Ser Gly Pro Glu Ser Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Gly Lys Ser Leu Glu Trp Ile
        35                  40                  45

Gly Asn Ile Asp Pro Tyr Tyr Gly Gly Thr Thr Tyr Asn Arg Lys Phe
    50                  55                  60
```

```
Lys Gly Lys Ala Thr Leu Thr Val Asp Lys Ser Ser Thr Ala Tyr
 65                  70                  75                  80

Met Gln Leu Lys Ser Leu Thr Ser Glu Asp Ser Ala Val Tyr Tyr Cys
                 85                  90                  95

Ala Arg Ser Val Gly Pro Met Asp Tyr Trp Gly Gln Gly Thr Ser Val
            100                 105                 110

Thr Val Ser Ser Gly Gly Gly Ser Gly Gly Gly Ser Gly Gly
            115                 120                 125

Gly Gly Ser Gly Gly Gly Ser Ala Ser Glu Ile Val Leu Thr Gln
        130                 135                 140

Ser Pro Ala Thr Leu Ser Leu Ser Pro Gly Glu Arg Ala Thr Leu Ser
145                 150                 155                 160

Cys Arg Thr Ser Glu Asn Val Tyr Ser Tyr Leu Ala Trp Tyr Gln Gln
                165                 170                 175

Lys Pro Gly Gln Ala Pro Arg Leu Leu Ile Tyr Phe Ala Lys Thr Leu
            180                 185                 190

Ala Glu Gly Ile Pro Ala Arg Phe Ser Gly Ser Gly Ser Gly Thr Asp
            195                 200                 205

Phe Thr Leu Thr Ile Ser Ser Leu Glu Pro Glu Asp Phe Ala Val Tyr
        210                 215                 220

Tyr Cys Gln His His Ser Asp Asn Pro Trp Thr Phe Gly Gln Gly Thr
225                 230                 235                 240

Lys Val Glu Ile Lys Gly Ser Ser Glu Pro Lys Ser Ser Asp Lys Thr
                245                 250                 255

His Thr Ser Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Asp Val Ser His Glu Asp Pro
            290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
        370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
            435                 440                 445

Arg Trp Gln Gln Gly Asn Val Phe Ser Cys Ser Val Met His Glu Ala
            450                 455                 460

Leu His Asn His Tyr Thr Gln Lys Ser Leu Ser Leu Ser Pro Gly Lys
465                 470                 475                 480
```

<210> SEQ ID NO 252
<211> LENGTH: 472
<212> TYPE: PRT
<213> ORGANISM: Artificial Sequence
<220> FEATURE:
<223> OTHER INFORMATION: CD37 specific binding protein

<400> SEQUENCE: 252

```
Glu Ile Val Leu Thr Gln Ser Pro Ala Thr Leu Ser Leu Ser Pro Gly
 1               5                  10                  15

Glu Arg Ala Thr Leu Ser Cys Arg Thr Ser Glu Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Phe Ala Lys Thr Leu Ala Glu Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His His Ser Asp Asn Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ala Ser Ala Val Gln Leu Gln
        115                 120                 125

Gln Ser Gly Pro Glu Ser Glu Lys Pro Gly Ala Ser Val Lys Ile Ser
130                 135                 140

Cys Lys Ala Ser Gly Tyr Ser Phe Thr Gly Tyr Asn Met Asn Trp Val
145                 150                 155                 160

Lys Gln Asn Asn Gly Lys Ser Leu Glu Trp Ile Gly Asn Ile Asp Pro
                165                 170                 175

Tyr Tyr Gly Gly Thr Thr Tyr Asn Arg Lys Phe Lys Gly Lys Ala Thr
            180                 185                 190

Leu Thr Val Asp Lys Ser Ser Thr Ala Tyr Met Gln Leu Lys Ser
        195                 200                 205

Leu Thr Ser Glu Asp Ser Ala Val Tyr Tyr Cys Ala Arg Ser Val Gly
210                 215                 220

Pro Met Asp Tyr Trp Gly Gln Gly Thr Ser Val Thr Val Ser Ser Ser
225                 230                 235                 240

Glu Pro Lys Ser Ser Asp Lys Thr His Thr Ser Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
```

```
                370                 375                 380
Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Lys
465                 470

<210> SEQ ID NO 253
<211> LENGTH: 483
<212> TYPE: PRT
<213> ORGANISM: Artificial Sequence
<220> FEATURE:
<223> OTHER INFORMATION: CD37 specific binding protein

<400> SEQUENCE: 253

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
                20                  25                  30

Asn Met Asn Trp Val Arg Gln Met Pro Gly Lys Gly Leu Glu Trp Met
            35                  40                  45

Gly Asn Ile Asp Pro Tyr Tyr Gly Gly Thr Thr Tyr Asn Arg Lys Phe
        50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Val Gly Pro Phe Asp Ser Trp Gly Gln Gly Thr Leu Val
                100                 105                 110

Thr Val Ser Ser Gly Gly Gly Ser Gly Gly Gly Ser Gly Gly
            115                 120                 125

Gly Gly Ser Gly Gly Gly Ser Gly Gly Gly Ser Glu Ile Val
        130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Glu Asn Val Tyr Ser Tyr Leu Ala Trp
                165                 170                 175

Tyr Gln Gln Lys Pro Gly Gln Ala Pro Arg Leu Leu Ile Tyr Phe Ala
                180                 185                 190

Lys Thr Leu Ala Glu Gly Ile Pro Ala Arg Phe Ser Gly Ser Gly Ser
                195                 200                 205

Gly Thr Asp Phe Thr Leu Thr Ile Ser Ser Leu Glu Pro Glu Asp Phe
        210                 215                 220

Ala Val Tyr Tyr Cys Gln His Ser Asp Asn Pro Trp Thr Phe Gly
225                 230                 235                 240

Gln Gly Thr Lys Val Glu Ile Lys Gly Asp Gln Glu Pro Lys Ser Ser
                245                 250                 255

Asp Lys Thr His Thr Ser Pro Pro Cys Pro Ala Pro Glu Leu Leu Gly
```

-continued

```
                260                 265                 270
Gly Pro Ser Val Phe Leu Phe Pro Pro Lys Pro Lys Asp Thr Leu Met
            275                 280                 285
Ile Ser Arg Thr Pro Glu Val Thr Cys Val Val Val Asp Val Ser His
        290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
                325                 330                 335
Arg Val Val Ser Val Leu Thr Val Leu His Gln Asp Trp Leu Asn Gly
            340                 345                 350
Lys Glu Tyr Lys Cys Lys Val Ser Asn Lys Ala Leu Pro Ala Pro Ile
        355                 360                 365
Glu Lys Thr Ile Ser Lys Ala Lys Gly Gln Pro Arg Glu Pro Gln Val
    370                 375                 380
Tyr Thr Leu Pro Pro Ser Arg Asp Glu Leu Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Lys Leu Thr Val
        435                 440                 445
Asp Lys Ser Arg Trp Gln Gln Gly Asn Val Phe Ser Cys Ser Val Met
    450                 455                 460
His Glu Ala Leu His Asn His Tyr Thr Gln Lys Ser Leu Ser Leu Ser
465                 470                 475                 480
Pro Gly Lys

<210> SEQ ID NO 254
<211> LENGTH: 473
<212> TYPE: PRT
<213> ORGANISM: Artificial Sequence
<220> FEATURE:
<223> OTHER INFORMATION: CD37 specific binding protein

<400> SEQUENCE: 254

Glu Ile Val Leu Thr Gln Ser Pro Ala Thr Leu Ser Leu Ser Pro Gly
  1               5                  10                  15
Glu Arg Ala Thr Leu Ser Cys Arg Ala Ser Glu Asn Val Tyr Ser Tyr
                 20                  25                  30
Leu Ala Trp Tyr Gln Gln Lys Pro Gly Gln Ala Pro Arg Leu Leu Ile
             35                  40                  45
Tyr Phe Ala Lys Thr Leu Ala Glu Gly Ile Pro Ala Arg Phe Ser Gly
         50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln His His Ser Asp Asn Pro Trp
                 85                  90                  95
Thr Phe Gly Gln Gly Thr Lys Val Glu Ile Lys Gly Gly Gly Gly Ser
                100                 105                 110
Gly Gly Gly Gly Ser Gly Gly Gly Thr Gly Glu Val Gln Leu Val
             115                 120                 125
Gln Ser Gly Ala Glu Val Lys Lys Pro Gly Glu Ser Leu Lys Ile Ser
         130                 135                 140
```

```
Cys Lys Gly Ser Gly Tyr Ser Phe Thr Gly Tyr Asn Met Asn Trp Val
145                 150                 155                 160

Arg Gln Met Pro Gly Lys Gly Leu Glu Trp Met Gly Asn Ile Asp Pro
                165                 170                 175

Tyr Tyr Gly Gly Thr Thr Tyr Asn Arg Lys Phe Lys Gly Gln Val Thr
            180                 185                 190

Ile Ser Ala Asp Lys Ser Ile Ser Thr Ala Tyr Leu Gln Trp Ser Ser
        195                 200                 205

Leu Lys Ala Ser Asp Thr Ala Met Tyr Tyr Cys Ala Arg Ser Val Gly
    210                 215                 220

Pro Met Asp Val Trp Gly Gln Gly Thr Thr Val Thr Val Ser Ser Asp
225                 230                 235                 240

Gln Glu Pro Lys Ser Ser Asp Lys Thr His Thr Ser Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 255
<211> LENGTH: 15
<212> TYPE: PRT
<213> ORGANISM: Artificial Sequence
<220> FEATURE:
<223> OTHER INFORMATION: Hinge region

<400> SEQUENCE: 255

Glu Pro Lys Ser Cys Asp Lys Thr His Thr Cys Pro Pro Ser Pro
1               5                   10                  15

<210> SEQ ID NO 256
```

```
<211> LENGTH: 15
<212> TYPE: PRT
<213> ORGANISM: Artificial Sequence
<220> FEATURE:
<223> OTHER INFORMATION: Hinge region

<400> SEQUENCE: 256

Glu Pro Lys Ser Cys Asp Lys Thr His Thr Cys Pro Pro Ser Ser
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Hinge region

<400> SEQUENCE: 257

Glu Pro Lys Ser Ser Asp Lys Thr His Thr Cys Pro Pro Ser Pro
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Hinge region

<400> SEQUENCE: 258

Glu Pro Lys Ser Cys Asp Thr Pro Pro Pro Cys Pro Arg Cys Pro
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Hinge region

<400> SEQUENCE: 259

Glu Pro Lys Ser Cys Asp Thr Pro Pro Pro Cys Pro Arg Ser Pro
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Hinge region

<400> SEQUENCE: 260

Glu Pro Lys Ser Cys Asp Thr Pro Pro Ser Pro Arg Cys Pro
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Hinge region

<400> SEQUENCE: 261

Glu Pro Lys Ser Cys Asp Thr Pro Pro Cys Pro Arg Ser Pro
1               5                   10                  15

<210> SEQ ID NO 262
<211> LENGTH: 493
```

```
<212> TYPE: PRT
<213> ORGANISM: Artificial Sequence
<220> FEATURE:
<223> OTHER INFORMATION: CD37 specific binding protein

<400> SEQUENCE: 262

Met Glu Ala Pro Ala Gln Leu Leu Phe Leu Leu Leu Leu Trp Leu Pro
 1               5                  10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Ser Gly Gly Gly Ala Ser Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Ser Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Thr Gly Tyr Ala Gln Lys Phe Gln
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380
```

```
Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 263
<211> LENGTH: 10
<212> TYPE: PRT
<213> ORGANISM: Homo sapiens

<400> SEQUENCE: 263

Glu Pro Lys Ser Cys Asp Lys Thr His Thr
1               5                   10

<210> SEQ ID NO 264
<211> LENGTH: 4
<212> TYPE: PRT
<213> ORGANISM: Homo sapiens

<400> SEQUENCE: 264

Cys Pro Pro Cys
1

<210> SEQ ID NO 265
<211> LENGTH: 4
<212> TYPE: PRT
<213> ORGANISM: Homo sapiens

<400> SEQUENCE: 265

Gly Thr Cys Tyr
1

<210> SEQ ID NO 266
<211> LENGTH: 473
<212> TYPE: PRT
<213> ORGANISM: Artificial Sequence
<220> FEATURE:
<223> OTHER INFORMATION: CD37 specific binding protein

<400> SEQUENCE: 266

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Phe Ala Lys Thr Leu Ala Glu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln His His Ser Asp Asn Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Thr Gly Glu Val Gln Leu Val
            115                 120                 125

Gln Ser Gly Ala Glu Val Lys Lys Pro Gly Glu Ser Leu Lys Ile Ser
        130                 135                 140

Cys Lys Gly Ser Gly Tyr Ser Phe Thr Gly Tyr Asn Met Asn Trp Val
145                 150                 155                 160

Arg Gln Met Pro Gly Lys Gly Leu Glu Trp Met Gly Asn Ile Asp Pro
                165                 170                 175

Tyr Tyr Gly Gly Thr Thr Tyr Asn Arg Lys Phe Lys Gly Gln Val Thr
            180                 185                 190

Ile Ser Ala Asp Lys Ser Ile Ser Thr Ala Tyr Leu Gln Trp Ser Ser
        195                 200                 205

Leu Lys Ala Ser Asp Thr Ala Met Tyr Tyr Cys Ala Arg Ser Val Gly
    210                 215                 220

Pro Phe Asp Pro Trp Gly Gln Gly Thr Leu Val Thr Val Ser Ser Asp
225                 230                 235                 240

Gln Glu Pro Lys Ser Ser Asp Lys Thr His Thr Ser Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 267
<211> LENGTH: 473
<212> TYPE: PRT
```

<213> ORGANISM: Artificial Sequence
<220> FEATURE:
<223> OTHER INFORMATION: CD37 specific binding protein

<400> SEQUENCE: 267

| Glu | Ile | Val | Leu | Thr | Gln | Ser | Pro | Ala | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Glu | Asn | Val | Tyr | Ser | Tyr |
| | | | 20 | | | | | 25 | | | | | 30 | | |

| Leu | Ala | Trp | Tyr | Gln | Gln | Lys | Pro | Gly | Gln | Ala | Pro | Arg | Leu | Leu | Ile |
| | | | 35 | | | | | 40 | | | | | 45 | | |

| Tyr | Phe | Ala | Lys | Thr | Leu | Ala | Glu | Gly | Ile | Pro | Ala | Arg | Phe | Ser | Gly |
| | 50 | | | | | 55 | | | | | 60 | | | | |

| Ser | Gly | Ser | Gly | Thr | Asp | Phe | Thr | Leu | Thr | Ile | Ser | Ser | Leu | Glu | Pro |
| 65 | | | | | 70 | | | | | 75 | | | | | 80 |

| Glu | Asp | Phe | Ala | Val | Tyr | Tyr | Cys | Gln | His | Ser | Asp | Asn | Pro | Trp |
| | | | | 85 | | | | 90 | | | | | 95 | |

| Thr | Phe | Gly | Gln | Gly | Thr | Lys | Val | Glu | Ile | Lys | Gly | Gly | Gly | Ser |
| | | | 100 | | | | | 105 | | | | | 110 | |

| Gly | Gly | Gly | Gly | Ser | Gly | Gly | Gly | Thr | Gly | Glu | Val | Gln | Leu | Val |
| | 115 | | | | | 120 | | | | | 125 | | | |

| Gln | Ser | Gly | Ala | Glu | Val | Lys | Lys | Pro | Gly | Glu | Ser | Leu | Lys | Ile | Ser |
| 130 | | | | | 135 | | | | | 140 | | | | | |

| Cys | Lys | Gly | Ser | Gly | Tyr | Ser | Phe | Thr | Gly | Tyr | Asn | Met | Asn | Trp | Val |
| 145 | | | | | 150 | | | | | 155 | | | | | 160 |

| Arg | Gln | Met | Pro | Gly | Lys | Gly | Leu | Glu | Trp | Met | Gly | Asn | Ile | Asp | Pro |
| | | | | 165 | | | | | 170 | | | | | 175 | |

| Tyr | Tyr | Gly | Gly | Thr | Thr | Tyr | Asn | Arg | Lys | Phe | Lys | Gly | Gln | Val | Thr |
| | | | 180 | | | | | 185 | | | | | 190 | | |

| Ile | Ser | Ala | Asp | Lys | Ser | Ile | Ser | Thr | Ala | Tyr | Leu | Gln | Trp | Ser | Ser |
| | | 195 | | | | | 200 | | | | | 205 | | | |

| Leu | Lys | Ala | Ser | Asp | Thr | Ala | Met | Tyr | Tyr | Cys | Ala | Arg | Ser | Val | Gly |
| | 210 | | | | | 215 | | | | | 220 | | | | |

| Pro | Met | Glu | His | Trp | Gly | Gln | Gly | Thr | Leu | Val | Thr | Val | Ser | Ser | Asp |
| 225 | | | | | 230 | | | | | 235 | | | | | 240 |

| Gln | Glu | Pro | Lys | Ser | Ser | Asp | Lys | Thr | His | Thr | Ser | Pro | Pro | Cys | Pro |
| | | | 245 | | | | | 250 | | | | | 255 | | |

| Ala | Pro | Glu | Leu | Leu | Gly | Gly | Pro | Ser | Val | Phe | Leu | Phe | Pro | Pro | Lys |
| | | 260 | | | | | 265 | | | | | 270 | | | |

| Pro | Lys | Asp | Thr | Leu | Met | Ile | Ser | Arg | Thr | Pro | Glu | Val | Thr | Cys | Val |
| | 275 | | | | | 280 | | | | | 285 | | | | |

| Val | Val | Asp | Val | Ser | His | Glu | Asp | Pro | Glu | Val | Lys | Phe | Asn | Trp | Tyr |
| 290 | | | | | 295 | | | | | 300 | | | | | |

| Val | Asp | Gly | Val | Glu | Val | His | Asn | Ala | Lys | Thr | Lys | Pro | Arg | Glu | Glu |
| 305 | | | | | 310 | | | | | 315 | | | | | 320 |

| Gln | Tyr | Asn | Ser | Thr | Tyr | Arg | Val | Val | Ser | Val | Leu | Thr | Val | Leu | His |
| | | | | 325 | | | | | 330 | | | | | 335 | |

| Gln | Asp | Trp | Leu | Asn | Gly | Lys | Glu | Tyr | Lys | Cys | Lys | Val | Ser | Asn | Lys |
| | | | 340 | | | | | 345 | | | | | 350 | | |

| Ala | Leu | Pro | Ala | Pro | Ile | Glu | Lys | Thr | Ile | Ser | Lys | Ala | Lys | Gly | Gln |
| | | 355 | | | | | 360 | | | | | 365 | | | |

| Pro | Arg | Glu | Pro | Gln | Val | Tyr | Thr | Leu | Pro | Pro | Ser | Arg | Asp | Glu | Leu |
| | 370 | | | | | 375 | | | | | 380 | | | | |

| Thr | Lys | Asn | Gln | Val | Ser | Leu | Thr | Cys | Leu | Val | Lys | Gly | Phe | Tyr | Pro |

```
385                 390                 395                 400
Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470

<210> SEQ ID NO 268
<211> LENGTH: 473
<212> TYPE: PRT
<213> ORGANISM: Artificial Sequence
<220> FEATURE:
<223> OTHER INFORMATION: CD37 specific binding protein

<400> SEQUENCE: 268

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Asn Val Tyr Ser Tyr
            20                  25                  30

Leu Ala Trp Tyr Gln Gln Lys Pro Gly Gln Ala Pro Arg Leu Leu Ile
        35                  40                  45

Tyr Phe Ala Lys Thr Leu Ala Glu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His His Ser Asp Asn Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Thr Gly Glu Val Gln Leu Val
        115                 120                 125

Gln Ser Gly Ala Glu Val Lys Lys Pro Gly Glu Ser Leu Lys Ile Ser
    130                 135                 140

Cys Lys Gly Ser Gly Tyr Ser Phe Thr Gly Tyr Asn Met Asn Trp Val
145                 150                 155                 160

Arg Gln Met Pro Gly Lys Gly Leu Glu Trp Met Gly Asn Ile Asp Pro
                165                 170                 175

Tyr Tyr Gly Gly Thr Thr Tyr Asn Arg Lys Phe Lys Gly Gln Val Thr
            180                 185                 190

Ile Ser Ala Asp Lys Ser Ile Ser Thr Ala Tyr Leu Gln Trp Ser Ser
        195                 200                 205

Leu Lys Ala Ser Asp Thr Ala Met Tyr Tyr Cys Ala Arg Ser Val Gly
    210                 215                 220

Pro Phe Asp Val Trp Gly Gln Gly Thr Met Val Thr Val Ser Ser Asp
225                 230                 235                 240

Gln Glu Pro Lys Ser Ser Asp Lys Thr His Thr Ser Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
```

```
                275                 280                 285
Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 269
<211> LENGTH: 473
<212> TYPE: PRT
<213> ORGANISM: Artificial Sequence
<220> FEATURE:
<223> OTHER INFORMATION: CD37 specific binding protein

<400> SEQUENCE: 269

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Glu Asn Val Tyr Ser Tyr
             20                  25                  30

Leu Ala Trp Tyr Gln Gln Lys Pro Gly Gln Ala Pro Arg Leu Leu Ile
         35                  40                  45

Tyr Phe Ala Lys Thr Leu Ala Glu Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His His Ser Asp Asn Pro Trp
                 85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Thr Gly Glu Val Gln Leu Val
        115                 120                 125

Gln Ser Gly Ala Glu Val Lys Lys Pro Gly Glu Ser Leu Lys Ile Ser
    130                 135                 140

Cys Lys Gly Ser Gly Tyr Ser Phe Thr Gly Tyr Asn Met Asn Trp Val
145                 150                 155                 160

Arg Gln Met Pro Gly Lys Gly Leu Glu Trp Met Gly Asn Ile Asp Pro
```

```
                    165                 170                 175
Tyr Tyr Gly Gly Thr Thr Tyr Asn Arg Lys Phe Lys Gly Gln Val Thr
            180                 185                 190

Ile Ser Ala Asp Lys Ser Ile Ser Thr Ala Tyr Leu Gln Trp Ser Ser
            195                 200                 205

Leu Lys Ala Ser Asp Thr Ala Met Tyr Tyr Cys Ala Arg Ser Val Gly
            210                 215                 220

Pro Phe Asp Ile Trp Gly Gln Gly Thr Met Val Thr Val Ser Ser Asp
225                 230                 235                 240

Gln Glu Pro Lys Ser Ser Asp Lys Thr His Thr Ser Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 270
<211> LENGTH: 116
<212> TYPE: PRT
<213> ORGANISM: Artificial Sequence
<220> FEATURE:
<223> OTHER INFORMATION: Consensus heavy chain sequence
<220> FEATURE:
<221> NAME/KEY: VARIANT
<222> LOCATION: 1, 16
<223> OTHER INFORMATION: Xaa = Ala or Glu
<220> FEATURE:
<221> NAME/KEY: VARIANT
<222> LOCATION: 5
<223> OTHER INFORMATION: Xaa = Gln or Val
<220> FEATURE:
<221> NAME/KEY: VARIANT
<222> LOCATION: 9
<223> OTHER INFORMATION: Xaa = Pro or Ala
<220> FEATURE:
```

-continued

```
<221> NAME/KEY: VARIANT
<222> LOCATION: 11
<223> OTHER INFORMATION: Xaa = Ser or Val
<220> FEATURE:
<221> NAME/KEY: VARIANT
<222> LOCATION: 12
<223> OTHER INFORMATION: Xaa = Glu or Lys
<220> FEATURE:
<221> NAME/KEY: VARIANT
<222> LOCATION: 18
<223> OTHER INFORMATION: Xaa = Val or Leu
<220> FEATURE:
<221> NAME/KEY: VARIANT
<222> LOCATION: 24
<223> OTHER INFORMATION: Xaa = Ala or Gly
<220> FEATURE:
<221> NAME/KEY: VARIANT
<222> LOCATION: 38
<223> OTHER INFORMATION: Xaa = Lys or Arg
<220> FEATURE:
<221> NAME/KEY: VARIANT
<222> LOCATION: 40
<223> OTHER INFORMATION: Xaa = Asn or Met
<220> FEATURE:
<221> NAME/KEY: VARIANT
<222> LOCATION: 41
<223> OTHER INFORMATION: Xaa = Asn or Pro
<220> FEATURE:
<221> NAME/KEY: VARIANT
<222> LOCATION: 44
<223> OTHER INFORMATION: Xaa = Ser or Gly
<220> FEATURE:
<221> NAME/KEY: VARIANT
<222> LOCATION: 48
<223> OTHER INFORMATION: Xaa = Ile or Met
<220> FEATURE:
<221> NAME/KEY: VARIANT
<222> LOCATION: 67
<223> OTHER INFORMATION: Xaa = Lys or Gln
<220> FEATURE:
<221> NAME/KEY: VARIANT
<222> LOCATION: 68, 72
<223> OTHER INFORMATION: Xaa = Ala or Val
<220> FEATURE:
<221> NAME/KEY: VARIANT
<222> LOCATION: 70
<223> OTHER INFORMATION: Xaa = Leu or Ile
<220> FEATURE:
<221> NAME/KEY: VARIANT
<222> LOCATION: 71, 91
<223> OTHER INFORMATION: Xaa = Thr or Ser
<220> FEATURE:
<221> NAME/KEY: VARIANT
<222> LOCATION: 76
<223> OTHER INFORMATION: Xaa = Ser or Ile
<220> FEATURE:
<221> NAME/KEY: VARIANT
<222> LOCATION: 81
<223> OTHER INFORMATION: Xaa = Met or Leu
<220> FEATURE:
<221> NAME/KEY: VARIANT
<222> LOCATION: 83
<223> OTHER INFORMATION: Xaa = Leu or Trp
<220> FEATURE:
<221> NAME/KEY: VARIANT
<222> LOCATION: 84
<223> OTHER INFORMATION: Xaa = Lys or Ser
<220> FEATURE:
<221> NAME/KEY: VARIANT
<222> LOCATION: 87
<223> OTHER INFORMATION: Xaa = Thr or Lys
<220> FEATURE:
<221> NAME/KEY: VARIANT
<222> LOCATION: 88
<223> OTHER INFORMATION: Xaa = Ser or Ala
<220> FEATURE:
<221> NAME/KEY: VARIANT
<222> LOCATION: 89
<223> OTHER INFORMATION: Xaa = Glu or Ser
```

```
<220> FEATURE:
<221> NAME/KEY: VARIANT
<222> LOCATION: 93
<223> OTHER INFORMATION: Xaa = Val or Met
<220> FEATURE:
<221> NAME/KEY: VARIANT
<222> LOCATION: 103
<223> OTHER INFORMATION: Xaa = Met or Phe
<220> FEATURE:
<221> NAME/KEY: VARIANT
<222> LOCATION: 105
<223> OTHER INFORMATION: Xaa = Tyr or Ser
<220> FEATURE:
<221> NAME/KEY: VARIANT
<222> LOCATION: 111
<223> OTHER INFORMATION: Xaa = Ser or Leu

<400> SEQUENCE: 270

Xaa Val Gln Leu Xaa Gln Ser Gly Xaa Glu Xaa Xaa Lys Pro Gly Xaa
 1               5                  10                  15

Ser Xaa Lys Ile Ser Cys Lys Xaa Ser Gly Tyr Ser Phe Thr Gly Tyr
            20                  25                  30

Asn Met Asn Trp Val Xaa Gln Xaa Gly Lys Xaa Leu Glu Trp Xaa
        35                  40                  45

Gly Asn Ile Asp Pro Tyr Tyr Gly Gly Thr Thr Tyr Asn Arg Lys Phe
 50                  55                  60

Lys Gly Xaa Xaa Thr Xaa Xaa Xaa Asp Lys Ser Xaa Ser Thr Ala Tyr
 65                  70                  75                  80

Xaa Gln Xaa Xaa Ser Leu Xaa Xaa Xaa Asp Xaa Ala Xaa Tyr Tyr Cys
            85                  90                  95

Ala Arg Ser Val Gly Pro Xaa Asp Xaa Trp Gly Gln Gly Thr Xaa Val
            100                 105                 110

Thr Val Ser Ser
        115

<210> SEQ ID NO 271
<211> LENGTH: 107
<212> TYPE: PRT
<213> ORGANISM: Artificial Sequence
<220> FEATURE:
<223> OTHER INFORMATION: Consensus light chain sequence
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 3
<223> OTHER INFORMATION: Xaa = Gln or Val
<220> FEATURE:
<221> NAME/KEY: VARIANT
<222> LOCATION: 4
<223> OTHER INFORMATION: Xaa = Met or Leu
<220> FEATURE:
<221> NAME/KEY: VARIANT
<222> LOCATION: 13
<223> OTHER INFORMATION: Xaa = Ala or Leu
<220> FEATURE:
<221> NAME/KEY: VARIANT
<222> LOCATION: 15
<223> OTHER INFORMATION: Xaa = Val or Pro
<220> FEATURE:
<221> NAME/KEY: VARIANT
<222> LOCATION: 18
<223> OTHER INFORMATION: Xaa = Thr or Arg
<220> FEATURE:
<221> NAME/KEY: VARIANT
<222> LOCATION: 19
<223> OTHER INFORMATION: Xaa = Val or Ala
<220> FEATURE:
```

```
<221> NAME/KEY: VARIANT
<222> LOCATION: 21
<223> OTHER INFORMATION: Xaa = Ile or Leu
<220> FEATURE:
<221> NAME/KEY: VARIANT
<222> LOCATION: 22, 72
<223> OTHER INFORMATION: Xaa = Thr or Ser
<220> FEATURE:
<221> NAME/KEY: VARIANT
<222> LOCATION: 25
<223> OTHER INFORMATION: Xaa = Thr or Ala
<220> FEATURE:
<221> NAME/KEY: VARIANT
<222> LOCATION: 40
<223> OTHER INFORMATION: Xaa = Gln or Pro
<220> FEATURE:
<221> NAME/KEY: VARIANT
<222> LOCATION: 42
<223> OTHER INFORMATION: Xaa = Lys or Gln
<220> FEATURE:
<221> NAME/KEY: VARIANT
<222> LOCATION: 43, 60
<223> OTHER INFORMATION: Xaa = Ser or Ala
<220> FEATURE:
<221> NAME/KEY: VARIANT
<222> LOCATION: 45
<223> OTHER INFORMATION: Xaa = Gln or Arg
<220> FEATURE:
<221> NAME/KEY: VARIANT
<222> LOCATION: 48, 58
<223> OTHER INFORMATION: Xaa = Val or Ile
<220> FEATURE:
<221> NAME/KEY: VARIANT
<222> LOCATION: 49
<223> OTHER INFORMATION: Xaa = Ser or Tyr
<220> FEATURE:
<221> NAME/KEY: VARIANT
<222> LOCATION: 70
<223> OTHER INFORMATION: Xaa = Gln or Asp
<220> FEATURE:
<221> NAME/KEY: VARIANT
<222> LOCATION: 74
<223> OTHER INFORMATION: Xaa = Lys or Thr
<220> FEATURE:
<221> NAME/KEY: VARIANT
<222> LOCATION: 79
<223> OTHER INFORMATION: Xaa = Gln or Glu
<220> FEATURE:
<221> NAME/KEY: VARIANT
<222> LOCATION: 83
<223> OTHER INFORMATION: Xaa = Ser or Phe
<220> FEATURE:
<221> NAME/KEY: VARIANT
<222> LOCATION: 84
<223> OTHER INFORMATION: Xaa = Gly or Ala
<220> FEATURE:
<221> NAME/KEY: VARIANT
<222> LOCATION: 85
<223> OTHER INFORMATION: Xaa = Ser or Val
<220> FEATURE:
<221> NAME/KEY: VARIANT
<222> LOCATION: 87
<223> OTHER INFORMATION: Xaa = Phe or Tyr
<220> FEATURE:
<221> NAME/KEY: VARIANT
<222> LOCATION: 100
<223> OTHER INFORMATION: Xaa = Gly or Gln
<220> FEATURE:
<221> NAME/KEY: VARIANT
<222> LOCATION: 103
<223> OTHER INFORMATION: Xaa = Glu or Lys
<220> FEATURE:
<221> NAME/KEY: VARIANT
<222> LOCATION: 104
<223> OTHER INFORMATION: Xaa = Leu or Val

<400> SEQUENCE: 271

Xaa Ile Xaa Xaa Thr Gln Ser Pro Ala Thr Leu Ser Xaa Ser Xaa Gly
```

```
                1               5                   10                  15
Glu Xaa Xaa Thr Xaa Xaa Cys Arg Xaa Ser Glu Asn Val Tyr Ser Tyr
                20                  25                  30

Leu Ala Trp Tyr Gln Gln Lys Xaa Gly Xaa Xaa Pro Xaa Leu Leu Xaa
                35                  40                  45

Xaa Phe Ala Lys Thr Leu Ala Glu Gly Xaa Pro Xaa Arg Phe Ser Gly
        50                  55                  60

Ser Gly Ser Gly Thr Xaa Phe Xaa Leu Xaa Ile Ser Ser Leu Xaa Pro
 65                 70                  75                  80

Glu Asp Xaa Xaa Xaa Tyr Xaa Cys Gln His His Ser Asp Asn Pro Trp
                85                  90                  95

Thr Phe Gly Xaa Gly Thr Xaa Xaa Glu Ile Lys
                100                 105
```

<210> SEQ ID NO 272
<211> LENGTH: 5
<212> TYPE: PRT
<213> ORGANISM: Artificial Sequence
<220> FEATURE:
<223> OTHER INFORMATION: Linker peptide

<400> SEQUENCE: 272

```
Gly Gly Gly Gly Ser
 1               5
```

<210> SEQ ID NO 273
<211> LENGTH: 10
<212> TYPE: PRT
<213> ORGANISM: Artificial Sequence
<220> FEATURE:
<223> OTHER INFORMATION: Linker peptide

<400> SEQUENCE: 273

```
Gly Gly Gly Gly Ser Gly Gly Gly Gly Ser
 1               5                   10
```

<210> SEQ ID NO 274
<211> LENGTH: 15
<212> TYPE: PRT
<213> ORGANISM: Artificial Sequence
<220> FEATURE:
<223> OTHER INFORMATION: Linker peptide

<400> SEQUENCE: 274

```
Gly Gly Gly Gly Ser Gly Gly Gly Gly Ser Gly Gly Gly Gly Ser
 1               5                   10                  15
```

<210> SEQ ID NO 275
<211> LENGTH: 20
<212> TYPE: PRT
<213> ORGANISM: Artificial Sequence
<220> FEATURE:
<223> OTHER INFORMATION: Linker peptide

<400> SEQUENCE: 275

```
Gly Gly Gly Gly Ser Gly Gly Gly Gly Ser Gly Gly Gly Gly Ser Gly
 1               5                   10                  15

Gly Gly Gly Ser
            20
```

<210> SEQ ID NO 276
<211> LENGTH: 4
<212> TYPE: PRT

```
<213> ORGANISM: Artificial Sequence
<220> FEATURE:
<223> OTHER INFORMATION: Linker peptide

<400> SEQUENCE: 276

Gly Ser Gly Ser
1

<210> SEQ ID NO 277
<211> LENGTH: 6
<212> TYPE: PRT
<213> ORGANISM: Artificial Sequence
<220> FEATURE:
<223> OTHER INFORMATION: Linker peptide

<400> SEQUENCE: 277

Gly Ser Gly Ser Gly Ser
1               5

<210> SEQ ID NO 278
<211> LENGTH: 8
<212> TYPE: PRT
<213> ORGANISM: Artificial Sequence
<220> FEATURE:
<223> OTHER INFORMATION: Linker peptide

<400> SEQUENCE: 278

Gly Ser Gly Ser Gly Ser Gly Ser
1               5

<210> SEQ ID NO 279
<211> LENGTH: 10
<212> TYPE: PRT
<213> ORGANISM: Artificial Sequence
<220> FEATURE:
<223> OTHER INFORMATION: Linker peptide

<400> SEQUENCE: 279

Gly Ser Gly Ser Gly Ser Gly Ser Gly Ser
1               5                   10

<210> SEQ ID NO 280
<211> LENGTH: 6
<212> TYPE: PRT
<213> ORGANISM: Artificial Sequence
<220> FEATURE:
<223> OTHER INFORMATION: Linker peptide

<400> SEQUENCE: 280

Gly Gly Ser Gly Gly Ser
1               5

<210> SEQ ID NO 281
<211> LENGTH: 9
<212> TYPE: PRT
<213> ORGANISM: Artificial Sequence
<220> FEATURE:
<223> OTHER INFORMATION: Linker peptide

<400> SEQUENCE: 281

Gly Gly Ser Gly Gly Ser Gly Gly Ser
1               5

<210> SEQ ID NO 282
<211> LENGTH: 12
<212> TYPE: PRT
<213> ORGANISM: Artificial Sequence
```

```
<220> FEATURE:
<223> OTHER INFORMATION: Linker peptide

<400> SEQUENCE: 282

Gly Gly Ser Gly Gly Ser Gly Gly Ser Gly Gly Ser
1               5                   10

<210> SEQ ID NO 283
<211> LENGTH: 15
<212> TYPE: PRT
<213> ORGANISM: Artificial Sequence
<220> FEATURE:
<223> OTHER INFORMATION: Linker peptide

<400> SEQUENCE: 283

Gly Gly Ser Gly Gly Ser Gly Gly Ser Gly Gly Ser Gly Gly Ser
1               5                   10                  15

<210> SEQ ID NO 284
<211> LENGTH: 4
<212> TYPE: PRT
<213> ORGANISM: Artificial Sequence
<220> FEATURE:
<223> OTHER INFORMATION: Linker peptide

<400> SEQUENCE: 284

Gly Gly Gly Ser
1

<210> SEQ ID NO 285
<211> LENGTH: 8
<212> TYPE: PRT
<213> ORGANISM: Artificial Sequence
<220> FEATURE:
<223> OTHER INFORMATION: Linker peptide

<400> SEQUENCE: 285

Gly Gly Gly Ser Gly Gly Gly Ser
1               5

<210> SEQ ID NO 286
<211> LENGTH: 12
<212> TYPE: PRT
<213> ORGANISM: Artificial Sequence
<220> FEATURE:
<223> OTHER INFORMATION: Linker peptide

<400> SEQUENCE: 286

Gly Gly Gly Ser Gly Gly Gly Ser Gly Gly Gly Ser
1               5                   10

<210> SEQ ID NO 287
<211> LENGTH: 16
<212> TYPE: PRT
<213> ORGANISM: Artificial Sequence
<220> FEATURE:
<223> OTHER INFORMATION: Linker peptide

<400> SEQUENCE: 287

Gly Gly Gly Ser Gly Gly Gly Ser Gly Gly Gly Ser Gly Gly Gly Ser
1               5                   10                  15

<210> SEQ ID NO 288
<211> LENGTH: 20
<212> TYPE: PRT
<213> ORGANISM: Artificial Sequence
<220> FEATURE:
```

```
<223> OTHER INFORMATION: Linker peptide

<400> SEQUENCE: 288

Gly Gly Gly Ser Gly Gly Gly Ser Gly Gly Gly Ser Gly Gly Gly Ser
1               5                   10                  15

Gly Gly Gly Ser
            20

<210> SEQ ID NO 289
<211> LENGTH: 6
<212> TYPE: PRT
<213> ORGANISM: Artificial Sequence
<220> FEATURE:
<223> OTHER INFORMATION: Linker peptide

<400> SEQUENCE: 289

Gly Gly Gly Gly Gly Ser
1               5

<210> SEQ ID NO 290
<211> LENGTH: 12
<212> TYPE: PRT
<213> ORGANISM: Artificial Sequence
<220> FEATURE:
<223> OTHER INFORMATION: Linker peptide

<400> SEQUENCE: 290

Gly Gly Gly Gly Gly Ser Gly Gly Gly Gly Gly Ser
1               5                   10

<210> SEQ ID NO 291
<211> LENGTH: 18
<212> TYPE: PRT
<213> ORGANISM: Artificial Sequence
<220> FEATURE:
<223> OTHER INFORMATION: Linker peptide

<400> SEQUENCE: 291

Gly Gly Gly Gly Gly Ser Gly Gly Gly Gly Gly Ser Gly Gly Gly Gly
1               5                   10                  15

Gly Ser

<210> SEQ ID NO 292
<211> LENGTH: 24
<212> TYPE: PRT
<213> ORGANISM: Artificial Sequence
<220> FEATURE:
<223> OTHER INFORMATION: Linker peptide

<400> SEQUENCE: 292

Gly Gly Gly Gly Gly Ser Gly Gly Gly Gly Gly Ser Gly Gly Gly Gly
1               5                   10                  15

Gly Ser Gly Gly Gly Gly Gly Ser
            20

<210> SEQ ID NO 293
<211> LENGTH: 30
<212> TYPE: PRT
<213> ORGANISM: Artificial Sequence
<220> FEATURE:
<223> OTHER INFORMATION: Linker peptide
```

<400> SEQUENCE: 293

```
Gly Gly Gly Gly Gly Ser Gly Gly Gly Gly Ser Gly Gly Gly Gly
 1               5                  10                  15

Gly Ser Gly Gly Gly Gly Gly Ser Gly Gly Gly Gly Gly Ser
        20                  25                  30
```